United States Patent
O'Heeron et al.

(10) Patent No.: US 12,233,094 B2
(45) Date of Patent: Feb. 25, 2025

(54) INTERACTION OF FIBROBLASTS AND IMMUNE CELLS FOR ACTIVATION AND USES THEREOF

(71) Applicant: SPINALCYTE LLC, Houston, TX (US)

(72) Inventors: Pete O'Heeron, Houston, TX (US); Thomas Ichim, San Diego, CA (US)

(73) Assignee: Spinalcyte, LLC, Houston, TX (US)

( * ) Notice: Subject to any disclaimer, the term of this patent is extended or adjusted under 35 U.S.C. 154(b) by 386 days.

(21) Appl. No.: 16/765,060

(22) PCT Filed: Nov. 29, 2018

(86) PCT No.: PCT/US2018/063001
§ 371 (c)(1),
(2) Date: May 18, 2020

(87) PCT Pub. No.: WO2019/108756
PCT Pub. Date: Jun. 6, 2019

(65) Prior Publication Data
US 2021/0393700 A1    Dec. 23, 2021

Related U.S. Application Data

(60) Provisional application No. 62/591,858, filed on Nov. 29, 2017.

(51) Int. Cl.
| | |
|---|---|
| *A61K 35/33* | (2015.01) |
| *A61K 35/17* | (2015.01) |
| *A61K 38/18* | (2006.01) |
| *A61K 38/20* | (2006.01) |
| *A61K 38/21* | (2006.01) |
| *A61K 45/06* | (2006.01) |
| *A61P 21/00* | (2006.01) |
| *A61P 37/06* | (2006.01) |
| *C12N 5/0783* | (2010.01) |
| *C12N 5/0786* | (2010.01) |

(52) U.S. Cl.
CPC ............ *A61K 35/33* (2013.01); *A61K 35/17* (2013.01); *A61K 38/1825* (2013.01); *A61K 38/1841* (2013.01); *A61K 38/1866* (2013.01); *A61K 38/20* (2013.01); *A61K 38/21* (2013.01); *A61K 45/06* (2013.01); *A61P 21/00* (2018.01); *A61P 37/06* (2018.01); *C12N 5/0637* (2013.01); *C12N 5/0645* (2013.01)

(58) Field of Classification Search
None
See application file for complete search history.

(56) References Cited

U.S. PATENT DOCUMENTS

| | | |
|---|---|---|
| 5,032,508 A | 7/1991 | Naughton et al. |
| 7,491,388 B1 | 2/2009 | McIntosh et al. |
| 2002/0127216 A1 | 9/2002 | Kiss |
| 2005/0202035 A1 | 9/2005 | Subjeck et al. |
| 2007/0059824 A1 | 3/2007 | Zhao et al. |
| 2007/0072291 A1 | 3/2007 | Kremer et al. |
| 2008/0063652 A1* | 3/2008 | Pykett ............... A61P 43/00 435/375 |
| 2010/0003272 A1 | 1/2010 | Sieweke |
| 2011/0033434 A1 | 2/2011 | Ratcliffe et al. |
| 2011/0123572 A1 | 5/2011 | Bizik et al. |
| 2012/0251563 A1 | 10/2012 | Nicchitta et al. |
| 2014/0314869 A1 | 10/2014 | Caplan |
| 2014/0356361 A1 | 12/2014 | Maldonado et al. |
| 2015/0366909 A1* | 12/2015 | Faustman ........... A61P 17/06 435/372.3 |
| 2017/0121378 A1 | 5/2017 | Lin et al. |
| 2017/0196951 A1 | 7/2017 | Wagner et al. |
| 2017/0283769 A1* | 10/2017 | Xiao ............... C12N 5/0603 |
| 2018/0305665 A1 | 10/2018 | Cho et al. |

FOREIGN PATENT DOCUMENTS

| | | |
|---|---|---|
| CN | 1234417 | 1/2006 |
| CN | 102596223 | 7/2012 |
| CN | 101861167 | 8/2013 |
| CN | 106659743 | 5/2017 |
| JP | 2002-529508 | 9/2002 |
| JP | 2013-507945 | 3/2013 |
| JP | 2014-534957 | 12/2014 |
| WO | WO 2000/029001 | 5/2000 |
| WO | 2002/022573 A2 | 3/2002 |
| WO | 2007/035843 A2 | 3/2007 |
| WO | WO 2011/048222 | 4/2011 |

(Continued)

OTHER PUBLICATIONS

Shevach (2012, Trends Immunol. 33(12):626-632).*
Da Silva et al. (May 2017, Int. J. Clin. Exp. Med. 10(5):7533-7542).*
Curran et al. (2014, Immunology 219:17-24).*
Huber et al. (2016, Blood 128(22):3849; pp. 1-3).*
Li et al. (2008, Stem Cells and Development 17:391-395).*
Lee et al. Abstract of "Identification of a distinct subpopulation of fibroblasts from murine dermis: CD73(-) CD105(+) as potential marker of dermal fibroblasts subset with multipotency," Cell Biology International, Jul. 11, 2016 (Jul. 11, 2016), vol. 40, No. 9, pp. 1008-1016.

(Continued)

*Primary Examiner* — Elizabeth C. Kemmerer
(74) *Attorney, Agent, or Firm* — Norton Rose Fulbright US LLP

(57) ABSTRACT

The present disclosure is directed to systems, methods, and compositions for functional interaction of fibroblasts with one or more types of immune cells such that the interaction results in modification to the fibroblasts, the one or more types of immune cells, or both. In some embodiments, one or more certain agents are also utilized during the interaction or in lieu of one of the types of cells. In specific embodiments, cells to be used in cellular transplantation therapy are modified to have reduced immunogenicity.

13 Claims, 34 Drawing Sheets

(56) References Cited

FOREIGN PATENT DOCUMENTS

| WO | WO 2013/050792 | 4/2013 |
| WO | WO 2014/139883 | 9/2014 |
| WO | WO 2016/068217 | 5/2016 |
| WO | 2017/069512 A1 | 4/2017 |

OTHER PUBLICATIONS

Toraya-Brown et al. "Local hyperthermia treatment of tumors induces CO8+ T cell-mediated resistance against distal and secondary tumors," Nanomedicine, Feb. 22, 2014 (Feb. 22, 2014), vol. 10, No. 6, pp. 1273-1285.

Cheng, J.-T et al: "Hepatic carcinoma-associated fibroblasts induce IDO-producing regulatory dendritic cells through L-6-mediated STAT3 activation", Oncogenesis, vol. 5, No. 2, Feb. 1, 2016 (Feb. 1, 2016), pp. eI98-eI98.

Denu, Ryan et al: "Mesenchymal Stromal/Stem Cells Are Phenotypically Indistinguishable", Acta Haematologica, vol. 136, No. 2, Jan. 1, 2016 (Jan. 1, 2016), pp. 85-97.

Saalbach et al: "Dermal Fibroblasts Promote the Migration of Dendritic Cells", Journal of Investigative Dermatology, vol. 130, No. 2, Feb. 1, 2010 (Feb. 1, 2010), pp. 444-454.

Polchert et al: "Fibroblasts and Mesenchymal Stromal/Stem Cells Are Phenotypically Indistinguishable", European Journal of Immunology, vol. 38, No. 6, May 20, 2008 (May 20, 2008), pp. 1745-1755.

Smith T J: "Insights into the role of fibroblasts in human autoimmune diseases", Clinical and Experimental Immunology, vol. 141, No. 3, May 23, 2005 (May 23, 2005), pp. 388-397, Wiley-Blackwell Publishing Ltd, GB.

English Translation of Office Communication issued in Japanese Patent Application No. 2020-529293, dated Oct. 14, 2022.

Cui et al., "Role of cytokines in wound healing," Hebei Medical Journal, 18(2):89-90, 1996. (Partial English Translation).

English translation of Office Communication issued in Chinese Patent Application No. 201880086376.5, dated Feb. 14, 2023.

Nie et al., Fibroblasts function as "sentinel cells" in inflammatory reaction, Chinese Journal of Pathophysiology, 16(4):368-370, 2000. (English abstract).

English translation of Office Communication issued in Chinese Patent Application No. 201880086376.5, dated Aug. 16, 2023.

Ferrer et al., "Dermal fibroblasts promote alternative macrophage activation improving impaired wound healing," Journal of Investigative Dermatology, 137(4):941-950, 2016.

He et al., "Effect of IFN2-$\gamma$ and IL-6 on ICAM-1 expression in orbital fibroblasts," China Opthal. Res., 24(2):119-121, 2006. (English abstract).

Liu et al., "Research progress of tumor-associated macrophages in angiogenesis and lymphangiogenesis," Chin. J. Cell. Mol. Immunol., 32(2):280-283, 2016. (English abstract).

Miao et al., "Macrophage activation and would healing," Journal of Shanghai Jiaotong University (Medical Edition), 31(8):1189-1193, 2011. (English abstract).

Yin et al., "Adipose-derived stem cells promote the polarization from M1 macrophages to M2 macrophages," Chin. J. Cell. Mol. Immunol., 32(3):332-338, 2016. (English abstract).

Zhang et al., "Research progress on the polarization-related mechanisms of macrophages," China J. Cell. Mol. Immunol., 32(11):1570-1573, 2016. (English abstract).

English translation of Office Communication issued in Japanese Patent Application No. 2023-137037, dated Nov. 12, 2024.

\* cited by examiner

INTERACTION OF FIBROBLASTS AND IMMUNE CELLS FOR ACTIVATION AND USES THEREOF

This application is a national phase application under 35 U.S.C. § 371 that claims priority to International Application No. PCT/US2018/063001 filed Nov. 29, 2018, which claims priority to U.S. Provisional Patent Application Ser. No. 62/591,858, filed Nov. 29, 2017, all of which are incorporated by reference herein in their entirety.

TECHNICAL FIELD

Embodiments of the disclosure concern at least the fields of cell biology, molecular biology, immunology, and medicine.

BACKGROUND

Transplantation of cellular therapies, particularly allotransplantation, allows for the utilization of "universal donor" approaches. The possibility of allotransplanting cells allows for utilization of cells that are optimized for therapeutic activity. For example, in the case of autologous bone marrow therapies, the cellular fraction possessing angiogenic or trophic activity decreases with age and is further compounded by co-morbidities of the patient, such as diabetes or peripheral artery disease. The possibility of utilizing allogeneic cells allows for administration of a cellular product that is optimized for efficiency.

Allogeneic cellular products have the disadvantage of rejection by the immune system of the host. There are two types of rejection processes that are known to occur. Direct rejection is stimulated by engagement of recipient T cell receptors with donor MHC II molecules, as is classically mediated by CD4+ T cells. Indirect rejection occurs when recipient antigen presenting cells engulf donor cells and present them on MHC I, thus stimulating CD8+ T cells. It is known that in the rejection of allogeneic cells that both the direct and indirect pathways of antigen presentation are involved in immune-mediated destruction. Current means of inhibiting cellular rejection include use of calcineurin inhibitors, such as cyclosporine, or inhibitors of mTOR, such as rapamycin and everolimus.

While cellular therapy trials have been performed using a variety of allogeneic cells, a variety of trials required the use of continued immune suppression. Whether fetal-derived stem cells, pancreatic islets, or embryonic derived tissues, the use of continual immune suppression has been utilized. Unfortunately, continual immune suppression predisposes the individual to increased risk of infections, neoplasia, and organ failure, particularly renal failure in the case of calcineurin inhibitor-containing regimens.

Thus, there is a need in the art for decreasing immunogenicity of cells that are to be utilized for therapeutic purposes. In addition, there is a need in the art for improved cellular therapies for a variety of medical conditions.

BRIEF SUMMARY

Embodiments of the disclosure encompass compositions, methods, and systems for modifying cells and for cellular therapy. In particular embodiments the disclosure concerns interaction of a first type of cells with a second type of cells and/or certain agent(s) and includes modification(s) to the first and/or second type of cells as a result of the interaction. In specific embodiments, the disclosure includes compositions, methods, and systems in which fibroblasts are modified upon exposure to certain cells and/or certain agent(s). In specific embodiments, the disclosure concerns compositions, methods, and systems in which certain cells are modified upon exposure to fibroblasts and/or certain agent(s) produced from fibroblasts. In particular embodiments, the interaction of fibroblasts with one or more other types of cells (and optionally that interaction also includes one or more certain agent(s)) results in modification of the fibroblasts and/or the other type of cells. In specific embodiments, the other types of cells includes at least immune cells.

In certain embodiments, exposure of fibroblasts to one or more types of immune cells results in modifications to the fibroblasts and/or to the immune cells. In certain aspects, exposure of fibroblasts and/or agents produced therefrom result in modifications to one or more types of immune cells and/or exposure of one or more types of immune cells and/or agents produced therefrom result in modification to the fibroblasts. In specific embodiments, one or more agents are also included in the exposure and may or may not be exogenously provided, such as in other cases where they are endogenous to an environment and/or cell and/or tissue.

In specific embodiments, methods of the disclosure occur ex vivo, such as in a culture. In particular cases, the methods occur by the hand of man and do not encompass ordinary or random occurrences in a body. The methods of the disclosure are non-natural, in particular aspects. In specific embodiments, the concentrations of cells used in a method of exposing one type of cells to another type of cells does not occur in nature and does not happen randomly in nature. In specific embodiments, the concentration of one or more agents used in a method of exposing the one or more agents to one or more types of cells does not occur in nature and does not happen randomly in nature. The modification of any types of cells encompassed by the disclosure that occurs ex vivo or in vitro does not occur in vivo naturally in the same manner.

The disclosure encompasses therapeutic uses of cells, including fibroblasts, immune cells, and mixtures thereof. In at least some cases the fibroblasts have been modified prior to their exposure to the immune cells, such as activated, or exposed to conditions that are not normally found in the body, and in other cases immune cells, or their derivatives, have been modified, such as activated, prior to their exposure to the fibroblasts.

In some embodiments, the present disclosure is directed to systems, methods, and compositions for reducing the immunogenicity of cells to be used in cellular transplantation therapy. In general embodiments, a population of cells is subjected to one or more compositions comprising one or more types of media and/or one or more agents capable of reducing the immunogenicity of the population of cells. In particular embodiments of the disclosure, methods are directed to a population of cells wherein the cells comprise at least fibroblasts, which may be of any type.

In certain embodiments, the disclosure pertains to the use of one or more agents to decrease immunogenicity of fibroblasts, such as in order to allow for transplantation, including at least allotransplantation of fibroblasts without rejection occurring (or xenogeneic or syngeneic transplantation). In at least some cases, the agent(s) are capable of downregulating expression of one or more immunogenic molecules in the fibroblasts.

Embodiments of the disclosure provide means of utilizing fibroblasts as allogeneic (or xenogeneic or syngeneic) therapeutic cells through modification of culture conditions in order to decrease immunogenicity of the fibroblasts. In one embodiment of the disclosure, fibroblasts are extracted from sources with lower immunogenicity (e.g. placental fibroblasts, omental tissue derived fibroblasts, cord blood derived fibroblasts, etc.). In another embodiment, fibroblasts of any level of immunogenicity are subjected to interferon gamma (IFN-gamma), such as upon culture ex vivo, which without being restricted to mechanism has been demonstrated by the inventors to reduce immunogenicity. The reduction in immunogenicity is exemplified by inhibiting the ability of the fibroblasts to evoke alloreactive T cell responses, in specific embodiments. In specific embodiments of the disclosure, these modified fibroblast cells are referred to as "universal donor" fibroblasts, meaning that they may be administered to any individual, including in a manner that does not evoke a deleterious immune response in the recipient individual. In some cases, fibroblasts that are extracted from sources with lower immunogenicity are also subjected to sufficient amounts of IFN-gamma to reduce immunogenicity further.

In one embodiment of the disclosure, fibroblasts are cultured ex vivo for preserving viability and proliferative ability of fibroblasts. The disclosure provides for the modification of known culture techniques to decrease recognition of fibroblasts by the recipient immune system. In one embodiment fibroblasts are cultured in conditions that lack xenogeneic components, such as xenogeneic-free medium; in some cases the media is free of fetal calf serum, for example. In specific embodiments, the disclosure encompasses the substitution of fetal calf serum with one or more other agents, such as those that facilitate reduction of immunogenicity of fibroblasts, for example, human platelet rich plasma, platelet lysate, umbilical cord blood serum, autologous serum, and/or one or more defined cytokines, such as fibroblast growth factor 1-18, epidermal growth factor, leukemia inhibitory factor, insulin like growth factor, angiopoietin, and vascular endothelial growth factor.

In one embodiment of the disclosure, effective amounts of fibroblasts as prepared in methods encompassed by the disclosure are administered to an individual for a therapy or prevention of one or more medical conditions. In specific embodiments, the fibroblasts are administered to stimulate new blood vessel formation, a process termed angiogenesis. In other situations, the fibroblasts administered are utilized to repair a blood vessel defect. Exemplary defects include loss of endothelial responsiveness, reduction in elasticity, and/or reduction in prothrombogenicity. Although the fibroblasts may stimulate new blood vessel formation directly or indirectly, in some embodiments stimulation of angiogenesis is accomplished by one or more growth factors released by the fibroblasts and/or interaction between the fibroblasts and one or more types of cells in the recipient individual(s).

Specific embodiments of the disclosure provide methods for therapy of angiogenesis. In the art, angiogenesis therapy has previously been limited to stem cells; however embodiments of the disclosure provide methods of angiogenesis therapy performed with fibroblasts. In the art, angiogenesis therapy has been described as a "biological bypass," the underlying idea being that through administration of agent(s) capable of inducing collateralization; a more natural type of "bypass" can be achieved. In the art, it has been observed that ischemic muscles secrete angiogenic factors in response to hypoxia and that to some extent natural angiogenesis does occur in animal models of critical limb ischemia (CLI) and in humans (Milkiewicz et al., 2004; van Weel et al., 2007). In one embodiment of the disclosure, an effective amount of universal donor fibroblasts are administered to a subject, for example by injection, such as intramuscular injection, in hypoxic areas or any area in need of new blood vessel formation or repair.

Embodiments of the disclosure provide methods for co-administration of universal donor fibroblasts with one or more agents that stimulate angiogenesis. In a specific embodiment of the disclosure, methods are provided for co-administration of universal donor fibroblasts with VEGF, as an example. In one embodiment of the disclosure, universal donor fibroblasts derived from fibroblasts that have been treated under conditions to reduce immunogenicity are utilized to stimulate VEGF production from endogenous cells of the individual.

In a specific embodiment of the disclosure, methods are provided for co-administration of universal donor fibroblasts with FGF-1, for example. In the art it is known that cytokine FGF-1 is "upstream" of VEGF, hence it is believed to stimulate numerous angiogenic processes so as to result in creation of more mature vessels (McDonnell et al., 2005). HIF-1alpha may be co-administered as an alternative or in addition to FGF-1 and/or VEGF with the fibroblasts to the individual as well, in certain embodiments.

In particular embodiments of the disclosure, one or more angiogenic agent(s) are expressed in universal donor fibroblasts via one or more recombinant expression vectors operable in eukaryotic cells, and the expression of the angiogenic agent(s) may be regulated by a constitutive promoter or an inducible promoter or a tissue-specific promoter, for example. In specific embodiments, the vector is a viral vector, such as a retrovirus, lentivirus, adenovirus, adeno-associated virus, or herpes simplex virus, or the vector is a non-viral vector, such as naked DNA or plasmid DNA or minicircle DNA, for example.

Embodiments of the disclosure provide methods of reducing immunogenicity of particular types of fibroblasts. Fibroblasts may be derived from various tissues or organs, such as skin, heart, blood vessels, bone marrow, skeletal muscle, liver, pancreas, brain, foreskin, which can be obtained by biopsy (where appropriate) or upon autopsy. In some aspects, the cells comprise fibroblasts, which can be from a fetal, neonatal, adult origin, or a combination thereof.

Fibroblasts for use in any methods of the disclosure may be exposed to certain medium component(s), in specific embodiments. For example, fibroblasts may be re-suspended in ex vivo culture in medium supplemented with (a) one or more agents to decrease immunogenicity, (2) serum, and/or (3) serum-replacement. Serum can be of any source including fetal bovine serum, human serum or serum replacement. In some embodiments serum replacement refers to cytokine/growth factor-comprising media, in which case the cytokines/growth factors are provided at concentrations similar to those found in serum, and therefore capable of allowing for cellular growth and activity in a manner similar to that provided by serum based media. Examples of serum replacement media are described in the following U.S. patent Nos. and incorporated by reference: U.S. Pat. Nos. 9,637,721; 9,580,687; 6,162,643; 6,103,529; 6,048,728; 7,709,229; 4,560,655; and 5,324,666. In some embodiments, human serum or serum replacement is utilized in order to provide a xenogeneic-free environment for the cells, such as foreskin feeder cells. In specific embodiments, subsequent to culture, the human foreskin feeder cells of the present disclosure are capable of forming monolayers when attached to a solid phase such as a tissue culture plate [Dugdale and Siddall (1969) J. Med. Lab. Technol. 26: 31-5]. In particular embodiments, this characteristic of the human foreskin feeder cells of the present disclosure renders these cells as suitable universal donors because of high replicative ability and responsiveness to treatment with IFN-gamma with respect to reduction of immunogenicity. In one embodiment, the fibroblasts are treated with certain concentrations of interferon gamma. One of skill in the art will appreciate that fibroblasts from different sources may possess different levels of reduction of immunogenicity at differing concentrations of interferon gamma. In specific embodiments, the disclosure provides methods for assessment of immunogenicity to be performed, e.g. quantifying the ability to modulate mixed lymphocyte reaction. Such an assessment of the immunogenicity by mixed lymphocyte reaction may be considered in determining whether or not to use such a certain population of fibroblasts.

Mixed lymphocyte reaction may be performed by co-culturing fibroblasts that have been treated with interferon gamma together with allogeneic lymphocytes. Proliferative indexes of the allogeneic lymphocytes are usually taken to represent the degree of immunogenicity of stimulator fibroblast cells. In some embodiments of the disclosure, fibroblasts are mitotically inactivated before culture with lymphocytes. Mitotic inactivation may be performed by treatment with mitomycin C or other agents that block proliferation without reducing viability. When chemical agents are utilized for mitotic inactivation, the chemical agents may be washed off of the cells in order to prevent inhibition of responding lymphocytes.

In some embodiments of the disclosure, assessment of cytokine production by responding lymphocytes may be performed. Cytokines that may be assessed include interleukin (IL)-1, which is involved in stimulation of inflammatory processes and macrophage; IL 2, which is associated with T cell and NK cell activation; interferon gamma, which activates macrophages, as well as assists in Th1 polarization; and IL-12 and IL-18, which activate NK cells and are associated with development of cellular cytotoxic responses. In specific embodiments for the practice of the methods of the disclosure it is useful that responding lymphocytes in mixed lymphocyte reaction produce less inflammatory cytokines. Conversely, assessment of immune suppressive or anti-inflammatory cytokines may also be performed within the context of the disclosure. Examples of cytokines include IL-4, which stimulates Th2 cells, IL10, which stimulates, intra alia, T regulatory cells, and TGF-B which inhibits inflammation.

In some embodiments of the disclosure, genetic modification of fibroblasts is utilized to cause reduction of immunogenicity of the fibroblasts. One method provides for genetic modification that includes cytoplasmic transfer with cells possessing reduced immunogenicity, such as immature dendritic cells. In another embodiment, gene editing is utilized to selectively excise inflammation evoking genes, such as HLA, CD80, CD86, CD40, CD5, TNF-alpha, IL-6, IL-8, IL-12, IL-15, IL-18, IL-17, IL-21, IL-23, and/or IL-27.

In particular embodiments of the disclosure, one or more immunomodulatory agent(s) are expressed in the universal donor fibroblasts, for example via a recombinant expression vector operable in eukaryotic cells, and the expression of the immunomodulatory agent(s) may be regulated by a constitutive promoter or an inducible promoter or a tissue-specific promoter. In specific embodiments, the vector is a viral vector, such as a retrovirus, lentivirus, adenovirus, adeno-associated virus, or herpes simplex virus, or the vector is a non-viral vector, such as naked DNA or plasmid DNA or minicircle DNA. Immunomodulatory agents for transfection include at least the following: Fas ligand, TGF-beta, IL-4, IL-10, HLA-G, indolamine 2,3 deoxygenase (IDO), galectin family members, Galectin 3, arginase, and/or IL-20, as examples.

Embodiments of the disclosure include methods of inducing dendritic cell maturation by exposing immature dendritic cells to stressed fibroblast cells, and in some cases the fibroblast cells are stressed with hyperthermia and/or serum deprivation.

In some embodiments, there are methods of generating angiogenic macrophages and the methods may include the steps of a) obtaining a monocyte and/or monocyte progenitor cell; and b) contacting the monocyte and/or monocytic progenitor cell with fibroblast cells under conditions to endow the monocyte and/or monocytic progenitor cell with an ability to stimulate angiogenesis.

In certain embodiments, there are methods provided for treating virally-induced hepatic failure in an individual by administering to the individual an effective amount of a population of fibroblast cells that have been preconditioned with one or more stress-inducing stimuli.

Various quality control means are known in the art for practitioners of the disclosure to perform clinical administration of the cells. Examples of criteria for qualification of the cells includes marker identification using means such as flow cytometry, viability, endotoxin content, as well as assessment for microbial and mycoplasma contamination.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 10A) and aspartate aminotransferase (AST; FIG. 10B).

DETAILED DESCRIPTION

I. Examples of Definitions

Figure 1:
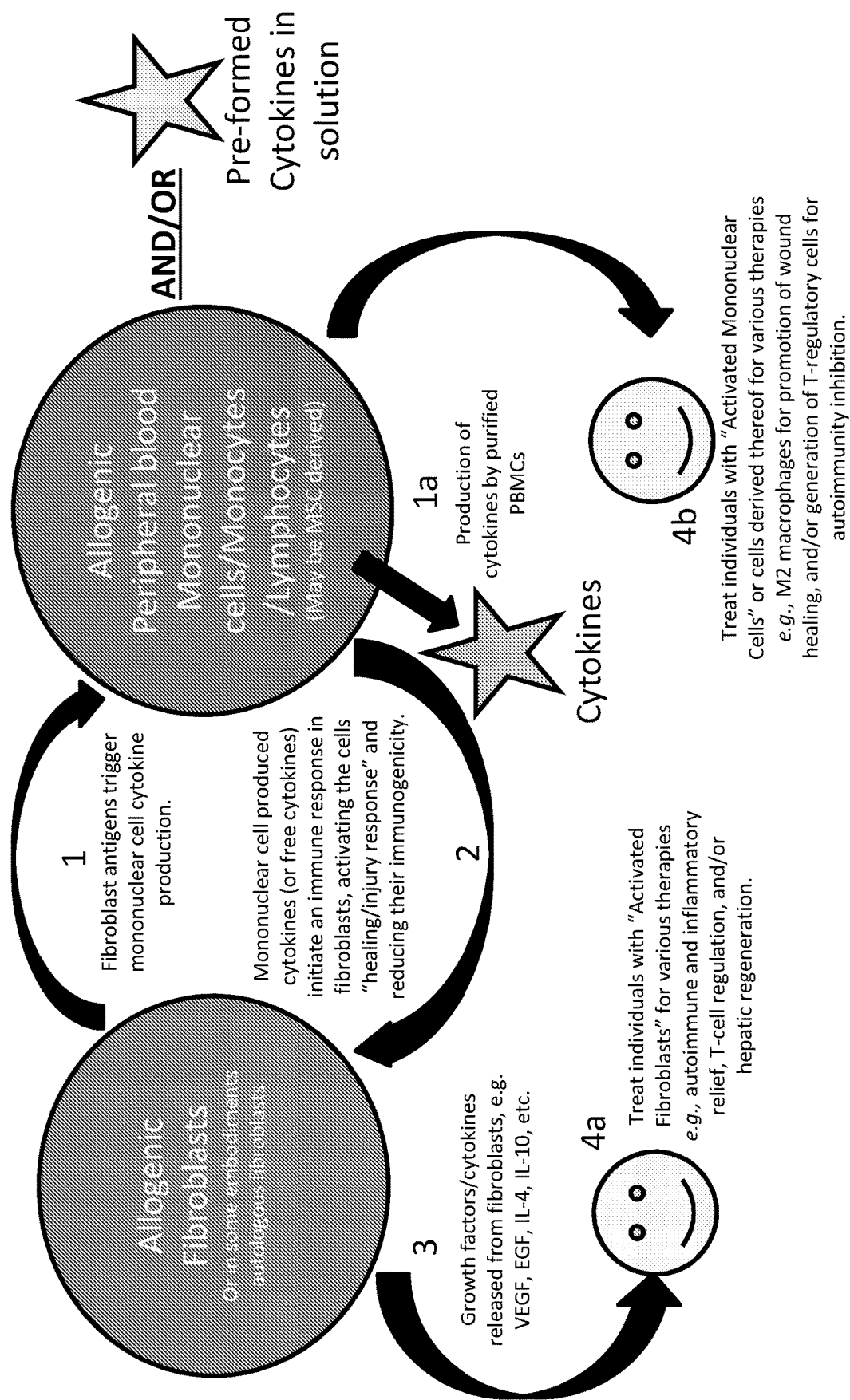
FIG. 1 illustrates specific examples of interactions of fibroblasts and/or one or more agents produced therefrom with one or more types of immune cells and/or one or more agents produced therefrom.

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%. With respect to biological systems or processes, the term can mean within an order of magnitude, preferably within 5-fold, and more preferably within 2-fold, of a value. Unless otherwise stated, the term 'about' means within an acceptable error range for the particular value.

As used herein, the term "activated fibroblasts" refers to fibroblasts treated with one or more stimuli capable of inducing one or more alterations in the cell: metabolic, immunological, growth factor-secreting, surface marker expression, and/or production of microvesicles.

As used herein, the term "activated immune cells" refers to immune cells treated with one or more stimuli capable of inducing one or more alterations in the cell: metabolic, immunological, growth factor secreting, surface marker expression, and production of microvesicals.

The term "administered" or "administering", as used herein, refers to any method of providing a composition to an individual such that the composition has its intended effect on the patient. For example, one method of administering is by an indirect mechanism using a medical device such as, but not limited to a catheter, applicator gun, syringe etc. A second exemplary method of administering is by a direct mechanism such as, local tissue administration, oral ingestion, transdermal patch, topical, inhalation, suppository etc.

As used herein, "allogeneic" refers to tissues or cells from another body that in a natural setting are immunologically incompatible or capable of being immunologically incompatible, although from one or more individuals of the same species.

As used herein, the term "allotransplantation" refers to the transplantation of organs, tissues, and/or cells from a donor to a recipient, where the donor and recipient are different individuals, but of the same species. Tissue transplanted by such procedures is referred to as an allograft or allotransplant.

As used herein, the terms "allostimulatory" and "alloreactive" refer to stimulation and reaction of the immune system in response to an allologous antigens, or "alloantigens" or cells expressing a dissimilar HLA haplotype.

As used herein, the term "angiogenesis" refers to a physiological process involving the growth of new blood vessels from pre-existing vessels and includes initiating angiogenesis, the formation of new blood vessel by initiating from existing ones, and splitting angiogenesis (intussusception: the formation of new blood vessel by splitting off existing ones).

As used herein, the term "autoimmunity" refers to the system of immune responses of an organism against its own healthy cells and tissues.

As used herein, "autologous" refers to tissues or cells that are derived or transferred from the same individual's body (i.e., autologous blood donation; an autologous bone marrow transplant).

As used herein, the term "autotransplantation" refers to the transplantation of organs, tissues, and/or cells from one part of the body in an individual to another part in the same individual, i.e., the donor and recipient are the same individual. Tissue transplanted by such "autologous" procedures is referred to as an autograft or autotransplant.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frame-shift mutation). Complementation is achieved by transfecting cells that lack protein activity with an expression vector that expresses the protein, a derivative thereof, or a portion thereof. In other cases, a fragment of a gene product (such as a protein) may be considered biologically active (or it may be referred to as functionally active) if it retains the activity of the full-length gene product, although it may be at a reduced but detectable level of the activity of the full-length gene product.

"Cell culture" is an artificial in vitro system containing viable cells, whether quiescent, senescent or (actively) dividing. In a cell culture, cells are grown and maintained at an appropriate temperature, typically a temperature of 37° C. and under an atmosphere typically containing oxygen and $CO_2$. Culture conditions may vary widely for each cell type though, and variation of conditions for a particular cell type can result in different phenotypes being expressed. The most commonly varied factor in culture systems is the growth medium. Growth media can vary in concentration of nutrients, growth factors, and the presence of other components. The growth factors used to supplement media are often derived from animal blood, such as calf serum.

"Chronic wound" means a wound that has not completely closed in twelve weeks since the occurrence of the wound in a patient having a condition, disease or therapy associated with defective healing. Conditions, diseases or therapies associated with defective healing include, for example, diabetes, arterial insufficiency, venous insufficiency, chronic steroid use, cancer chemotherapy, radiotherapy, radiation exposure, and malnutrition. A chronic wound includes defects resulting in inflammatory excess (e.g., excessive production of IL-6, tumor necrosis factor-alpha (TNF-alpha), and MMPs), a deficiency of important growth factors needed for proper healing, bacterial overgrowth and senescence of fibroblasts. A chronic wound has an epithelial layer that fails to cover the entire surface of the wound and is subject to bacterial colonization.

As used herein, the term "collateralization" refers to the growth of a blood vessel or several blood vessels that serve the same end organ or vascular bed as another blood vessel that cannot adequately supply that end organ or vascular bed sufficiently Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The term "drug", "agent" or "compound" as used herein, refers to any pharmacologically active substance capable of being administered that achieves a desired effect. Drugs or compounds can be synthetic or naturally occurring, non-peptide, proteins or peptides, oligonucleotides, or nucleotides (DNA and/or RNA), polysaccharides or sugars.

"Growth factor" can be a naturally occurring, endogenous or exogenous protein, or recombinant protein, capable of stimulating cellular proliferation and/or cellular differentiation and/or cellular migration.

The term "individual", as used herein, refers to a human or animal that may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants. It is not intended that the term "individual" connote a need for medical treatment, therefore, an individual may voluntarily or involuntarily be part of experimentation whether clinical or in support of basic science studies. The term "subject" or "individual" may be used interchangeably and refers to any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals.

As used herein, the term "ischemia" or "ischemic condition" refers to an inadequate blood supply to an organ or part of the body. Such conditions may comprise cardiac ischemia, ischemic colitis, mesenteric ischemia, ischemic stroke, brain ischemia, renal ischemia, and limb ischemia.

"Mesenchymal stem cell" or "MSC" refers to cells that are (1) adherent to plastic, (2) express CD73, CD90, and CD105 antigens, while being CD14, CD34, CD45, and HLA-DR negative, and (3) possess ability to differentiate to osteogenic, chondrogenic and adipogenic lineage, for example. In specific embodiments, mesenchymal stem cells do not express substantial (such as more than 50% compared to baseline) levels of HLA-DR, CD117, CD45, or a combination thereof. As used herein, "mesenchymal stromal cell" (which may also be referred to as "mesenchymal stem cell") or "MSC" can be derived from any tissue including, but not limited to, bone marrow, adipose tissue, amniotic fluid, endometrium, trophoblast-derived tissues, cord blood, Wharton jelly, placenta, amniotic tissue, derived from pluripotent stem cells, and tooth. As used herein, "mesenchymal stromal cell" or "MSC" includes cells that are CD34 positive upon initial isolation from tissue but are similar to cells described about phenotypically and functionally. As used herein, "MSC" includes cells that are isolated from tissues using cell surface markers selected from the list comprised of NGF-R, PDGF-R, EGF-R, IGF-R, CD29, CD49a, CD56, CD63, CD73, CD105, CD106, CD140b, CD146, CD271, MSCA-1, SSEA4, STRO-1 and STRO-3 or any combination thereof, and satisfy the ISCT criteria either before or after expansion. As used herein, "mesenchymal stromal cell" or "MSC" includes cells described in the literature as bone marrow stromal stem cells (BMSSC), marrow-isolated adult multipotent inducible cells (MIAMI) cells, multipotent adult progenitor cells (MAPC), mesenchymal adult stem cells (MASCS), MultiStem®, Prochymal®, remestemcel-L, Mesenchymal Precursor Cells (MPCs), Dental Pulp Stem Cells (DPSCs), PLX cells, PLX-PAD, AlloStem®, Astrostem®, Ixmyelocel-T, MSC-NTF, NurOwn™, Stemedyne™-MSC, Stempeucel®, StempeucelCLI, StempeucelOA, HiQCell, Hearticellgram-AMI, Revascor®, Cardiorel®, Cartistem®, Pneumostem®, Promostem®, Homeo-GH, AC607, PDA001, SB623, CX601, AC607, Endometrial Regenerative Cells (ERC), adipose-derived stem and regenerative cells (ADRCs).

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

"Therapeutic agent" means to have "therapeutic efficacy" in modulating angiogenesis and/or wound healing and an amount of the therapeutic is said to be a "angiogenic modulatory amount", if administration of that amount of the therapeutic is sufficient to cause a significant modulation (i.e., increase or decrease) in angiogenic activity when administered to a subject (e.g., an animal model or human patient) needing modulation of angiogenesis.

As used herein, the term "therapeutically effective amount" is synonymous with "effective amount", "therapeutically effective dose", and/or "effective dose" and refers to the amount of compound that will elicit the biological, cosmetic or clinical response being sought by the practitioner in an individual in need thereof. As one example, an effective amount is the amount sufficient to reduce immunogenicity of a group of cells. As a non-limiting example, an effective amount is an amount sufficient to promote formation of a blood supply sufficient to support the transplanted tissue. As another non-limiting example, an effective amount is an amount sufficient to promote formation of new blood vessels and associated vasculature (angiogenesis) and/or an amount sufficient to promote repair or remodeling of existing blood vessels and associated vasculature. The appropriate effective amount to be administered for a particular application of the disclosed methods can be determined by those skilled in the art, using the guidance provided herein. For example, an effective amount can be extrapolated from in vitro and in vivo assays as described in the present specification. One skilled in the art will recognize that the condition of the individual can be monitored throughout the course of therapy and that the effective amount of a compound or composition disclosed herein that is administered can be adjusted accordingly.

As used herein, the term "transplantation" refers to the process of taking living tissue or cells and implanting it in another part of the body or into another body.

"Treatment," "treat," or "treating" means a method of reducing the effects of a disease or condition. Treatment can also refer to a method of reducing the disease or condition itself rather than just the symptoms. The treatment can be any reduction from pre-treatment levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression, including reduction in the severity of at least one symptom of the disease. For example, a disclosed method for reducing the immunogenicity of cells is considered to be a treatment if there is a detectable reduction in the immunogenicity of cells when compared to pre-treatment levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition. In specific embodiments, treatment refers to the lessening in severity or extent of at least one symptom and may alternatively or in addition refer to a delay in the onset of at least one symptom.

II. Functional Interaction of Fibroblasts and Immune Cells

In particular embodiments of the present disclosure, there is biological, functional cross-talk between first and second non-identical types of cells, and that integration results (directly or indirectly) in at least one of the two types of cells to have one or more modifications such that is may be utilized for a particular therapeutic purpose. In some cases, there is biological, functional cross-talk between a first and second type of cells and that interaction causes each type of the cells to have one or more modifications such that both types of cells may be utilized for respective therapeutic purposes. In some embodiments, exposure of fibroblasts to immune cells (including monocytes, monocyte progenitor cells, PBMCs, MSCs, and so forth) or other cells render the respective fibroblasts and immune or other cells capable of expressing one or more agents and/or harboring one or more activities that the respective cells were not capable of in the absence of the exposure. In particular embodiments, the fibroblast cells and the immune or other cells are allogeneic with respect to one another, although in other embodiments they are autologous to one another.

In particular embodiments, the disclosure concerns an in vitro method of producing activated fibroblasts or activated immune cells or activated immune cell derivatives, comprising the step of exposing fibroblasts to immune cells under conditions such that one or more agents from the immune cells activates the fibroblasts to become activated fibroblasts. In specific embodiments, in addition to this one or more antigens from the fibroblasts triggers production of one or more cytokines from the immune cells to produce activated immune cells. In certain embodiments there is an in vitro method of producing activated fibroblasts or activated immune cells or activated immune cell derivatives by exposing fibroblasts to one or more growth factors and/or one or more cytokines under conditions such that the one or more growth factors and/or one or more cytokines activates the fibroblasts to become activated fibroblasts.

Embodiments of this scheme are illustrated in FIG. 1. For the sake of brevity, hereafter in the example of FIG. 1 the term "monocytes" will serve merely as a representative of peripheral blood mononuclear cells such as immune lymphocytes or other cells including MSCs, for example; dendritic cells may be utilized. In element 1 of FIG. 1, fibroblasts (from any source) and monocytes are exposed to and/or are in contact with one another, for example in a liquid media capable of maintaining cell viability and allowing for interaction of molecules and extracellular vesicles. As a result, fibroblast antigens trigger cytokine production from the monocytes. In some cases, cytokines and/or growth factors in solution are exposed to the fibroblasts in lieu of or in addition to exposing the fibroblasts to the monocytes. The monocytes or free cytokines activate an immune response in the fibroblast cells, thereby activating the fibroblast cells for a "healing/injury response" and reducing the immunogenicity of the fibroblast cells (element 2), in at least some cases. This reduction in immunogenicity facilitates the use of the fibroblasts in individuals from which the fibroblasts were not originally sourced, in at least some cases.

The resultant activated fibroblasts may now express one or more certain activation markers and/or produce one or more growth factors and/or one or more cytokines (e.g. VEGF, EGF, IL-4, IL-10, etc.)(element 3) such that these factors are useful for numerous therapeutic interventions (e.g. angiogenesis, reduction in inflammatory response, etc.), in particular embodiments (element 4a). In element 4a, individuals suffering from an array of maladies can be given activated fibroblast cell therapy for the alleviation of one or more of their symptoms, e.g., endogenous autoimmune activity, chronic inflammation, T-cell hyperactivity, or hepatic regeneration, for example.

Additionally or alternatively, the co-cultured mononuclear cells (or cells produced therefrom) following exposure to the fibroblasts can be used for the treatment of one or more other maladies, e.g. using M1-to-M2 activated macrophages for the promotion of wound healing and/or the generation of T-regulatory cells to inhibit autoimmunity, for example (element 4b).

In one embodiment of the disclosure, universal donor fibroblasts are administered to an individual to stimulate new blood vessel formation, a process termed angiogenesis. In some embodiments stimulation of angiogenesis is accomplished by one or more growth factors released by fibroblasts, and/or interaction between fibroblasts and cells of the recipient. In particular embodiments, such fibroblasts have been exposed at least to IFN-gamma.

Specific embodiments of the disclosure provide methods for angiogenesis therapy. Embodiments of the disclosure provide methods of angiogenesis therapy performed with fibroblasts. In certain embodiments of the disclosure, a therapeutically effective amount of universal donor fibroblasts are administered to a subject for the purpose of stimulating angiogenesis. In some cases, the fibroblasts are provided to the individual without the intended purpose to stimulate angiogenesis but the fibroblasts still stimulate angiogenesis. Embodiments of the disclosure provide methods for co-administration of universal donor fibroblasts with one or more agents, including one or more agents that stimulate angiogenesis.

In a specific embodiment of the disclosure, methods are provided for co-administration of universal donor fibroblasts with a therapeutically effective amount of one or more growth factors, such as VEGF, including purified VEGF. Other growth factors include the following: HGF, FGF-1, FGF-2, FGF-5, EGF, BDNF, PDGF, and/or angiopoietin. In one embodiment of the disclosure, universal donor fibroblasts are utilized to stimulate growth factor(s) (such as VEGF) production from cells of the individual. In a specific embodiment of the disclosure, methods are provided for co-administration of universal donor fibroblasts with a therapeutically effective amount of FGF-1, such as purified FGF-1 as an example.

In particular embodiments of the disclosure, one or more angiogenic agent(s) are expressed in the universal donor fibroblasts of the disclosure via a recombinant expression vector operable in eukaryotic cells, and the expression of the angiogenic agent(s) may be regulated by a constitutive promoter or an inducible promoter or a tissue-specific promoter. In specific embodiments, the vector is a viral vector, such as a retrovirus, lentivirus, adenovirus, adeno-associated virus, or herpes simplex virus, or the vector is a non-viral vector, such as naked DNA or plasmid DNA or minicircle DNA. In specific cases, the recombinantly expressed angiogenic agent(s) may comprise VEGF, FGF-1, FGF-2, FGF-5, EGF, angiopoietin, HIF-1-alpha, PDGF, HGF, or combinations thereof.

Although in specific embodiments there is cross-talk between two types of cells and/or one or more agents thereof, in some cases a first type of cells is modified by a second type of cells when the second type of cells is not concomitantly modified by a first type of cells.

The following examples illustrate certain applications for use of fibroblasts and/or immune cells following their concomitant exposure to each other (and/or exposure to certain agents) and modifications of the respective cell type(s) thereafter.

A. Reducing Cellular Immunogenicity of Ex Vivo Cultured Cells

In some embodiments of the disclosure, there are methods of reducing the immunogenicity of a cell population, wherein the population is subjected to a composition comprising IFN-gamma and optionally one or more additional agent(s) and/or condition(s).

In general embodiments, a population of cells is subjected to one or more compositions comprised of one or more particular media and/or one or more agents such that the composition(s) are capable of reducing the immunogenicity of the population of cells. In particular embodiments of the disclosure, methods are directed to a population of cells wherein the cells are fibroblasts of any type and the fibroblasts become modified such that they have reduced immunogenicity and may be utilized in a therapeutic capacity. In certain embodiments, the fibroblasts may be of any kind, including placental fibroblasts or foreskin fibroblasts, for example. In other embodiments, cells other than fibroblasts are modified such that they have reduced immunogenicity compared to in the absence of the method, such that the cells may be pancreatic beta cells, pancreatic islets, hepatocytes, neurons, chondrocytes, pluripotent stem cells, or derivatives thereof; such cells may or may not be in a mixture with one or more types of fibroblasts. In embodiments wherein the cells are pluripotent stem cells, the stem cells may comprise inducible pluripotent stem cells, stress induced stem cells, parthenogenic derived stem cells, embryonic stem cells, somatic cell nuclear transfer derived stem cells, or derivatives thereof, for example. In certain cases, methods of the disclosure are directed to autologous cells. In other cases, methods of the disclosure are directed to allogeneic cells, xenogeneic cells, or syngeneic cells.

Embodiments of the disclosure provide means of utilizing fibroblasts (or other types of cells, as noted above) as allogeneic therapeutic cells through modification of culture conditions in order to decrease immunogenicity of the fibroblasts. In one embodiment of the disclosure, fibroblasts are extracted from sources with lower immunogenicity (e.g. placental fibroblasts, etc.). In another embodiment, fibroblasts are cultured ex vivo and subjected to interferon gamma (IFN-gamma), which without being restricted to mechanism, has been demonstrated by the inventors to reduce immunogenicity. The reduction in immunogenicity may be exemplified by inhibiting the ability of the fibroblasts to evoke alloreactive T cell responses.

In specific embodiments, the disclosure provides methods for assessment of immunogenicity to be performed, e.g., quantifying the ability to modulate mixed lymphocyte reaction. Mixed lymphocyte reactions are well known in the art. Typically, mixed lymphocyte reaction is performed by co-culturing fibroblasts (in this case, that have been treated with interferon gamma) together with allogeneic lymphocytes. In certain embodiments, parameters of the mixed lymphocyte reaction that indicate modulation in immunogenicity comprise T cell proliferation, cytokine secretion, and cytotoxicity. Methods for quantifying T cell proliferation, cytokine secretion, and cytotoxicity are well known in the art. In certain embodiments, modulation of immunogenicity can be determined by quantifying the secretion of one or more cytokines comprising TNF-alpha, Interferon gamma, interleukin (IL)-1, IL-2, IL-6, IL-7, IL-8, IL-12, IL-15, IL-17, IL-33, or a combination thereof.

In specific embodiments, the disclosure provides methods that pertain to the administration of cells with reduced immunogenicity to an individual in need thereof. The population of cells with reduced immunogenicity may be administered as desired. Depending upon the response desired, the manner of administration, the life of the cells, and/or the number of cells present, various protocols may be employed.

B. Cellular Transplantation Therapy for Immunomodulation

Autoimmune diseases are characterized by an excessive reaction of the immune system against endogenous tissue. The immune system erroneously recognizes endogenous tissue as foreign bodies to be combated. This results in severe inflammatory reactions, which lead to damage to organs affected by them. An important part in distinguishing between endogenous and exogenous structures is played by T lymphocytes or T cells, which are "trained" in the thymus to dock only onto endogenous cell surface molecules, the so-called MEW molecules, and thus to tolerate endogenous structures.

In autoimmune diseases, a group of T cells behaves abnormally. In addition to the still functioning defense from exogenous molecules and organisms, they now also attack endogenous structure. Organs or tissues are perceived as exogenous. There can be various consequences: if vital structures are affected, an autoimmune disease will take a fatal course. The immune system directs its defense against these structures, cellular and also humoral defense reactions are set in motion, and autoantibodies are formed, as a result of which the organs affected in the course of time cease to function. Most commonly, the immune system is weakened and the body becomes susceptible to all kinds of diseases. Under some circumstances, recognition of the exogenous is also disrupted, and as a result the spreading of degenerated cancer cells (for example) can no longer be effectively prevented, and those affected are more susceptible to infectious diseases. In the course of the disease, cells of the immune system destroy the endogenous structures, while the body's repair mechanisms attempt as far as possible to regenerate the damaged organ parts. As a rule, without treatment this erroneous attack of the defensive system continues throughout life or until the complete destruction of the target structure.

Autoimmune diseases are treated according to the organ affected. In this, the basic principle of the causal therapy is to suppress the activity of the immune system by administration of immunosuppressants, e.g., cortisone. These substances are characterized by multiple systemic side-effects and interactions, owing to which attempts have been made to develop new drugs which specifically influence the mechanisms involved in the disease event.

In one embodiment of the disclosure, modified fibroblasts are administered to an individual for treatment of an autoimmunity or inflammatory disorder. In some embodiments of the disclosure, fibroblast cells are cultured ex vivo and subjected to conditions that reduce their immunogenicity, and then the fibroblasts are utilized to stimulate anti-inflammatory and/or immunomodulatory properties. Additional embodiments are directed to methods of administration of the cells to an individual in need thereof for the purpose of treating an autoimmune and/or inflammatory condition.

The present disclosure is directed to systems, methods, and compositions for reducing the immunogenicity of cells to be used in cellular transplantation therapy. In general embodiments, a population of cells is subjected to one or more compositions comprising one or more types of media and/or one or more agents capable of reducing the immunogenicity of the population of cells. In particular embodiments of the disclosure, methods are directed to a population of cells wherein the cells comprise at least fibroblasts.

Embodiments of the disclosure provide means of utilizing fibroblasts as allogeneic therapeutic cells through modification of culture conditions in order to decrease immunogenicity of the fibroblasts. In one embodiment of the disclosure, fibroblasts are extracted from sources with lower immunogenicity (e.g. placental fibroblasts, etc.). In another embodiment, fibroblasts are subjected to interferon gamma (IFN-gamma), such as upon culture ex vivo, which without being restricted to mechanism, has been demonstrated by the inventors to reduce immunogenicity. The reduction in immunogenicity is exemplified by inhibiting the ability of the fibroblasts to evoke alloreactive T cell responses, in specific embodiments. In specific embodiments of the disclosure, these modified fibroblast cells are universal donor fibroblasts.

Certain methods of the disclosure are directed to reducing the immunogenicity of fibroblasts of any kind, including foreskin fibroblasts as an example. In certain embodiments, fibroblasts are re-suspended in ex vivo culture in medium, such as medium supplemented with serum or serum-replacement. Serum can be of any source including fetal bovine serum, human serum or serum replacement. In certain embodiments human serum or serum replacement is utilized in order to provide a xenogeneic-free environment for the fibroblasts (for example, foreskin feeder cells). In one embodiment, the fibroblasts are treated with one or more certain concentrations of IFN-γ.

Embodiments of the present disclosure are directed to systems and methods for the use of fibroblast cells, either autologous or allogeneic, for treatment of inflammatory and autoimmune conditions. Methods and compositions of the disclosure encompass certain manipulated cells for the treatment of inflammatory and autoimmune conditions. In particular, the cells include at least fibroblasts of any kind. Means of manipulation of fibroblasts are disclosed, as well as fibroblasts of different tissue origins, which actively inhibit inflammatory and/or autoimmune processes. In one embodiment of the disclosure, fibroblasts are utilized for their ability to inhibit immune responses and also utilized as a cellular therapy for prevention and/or treatment of autoimmune conditions. In one embodiment, fibroblasts are generated or manipulated and utilized in mixed lymphocyte reactions to assess their ability to suppress immune activation. In a specific embodiment, fibroblasts are treated with one or more particular agents and/or conditions to be able to directly or indirectly treat inflammatory and/or autoimmune processes. In particular embodiments, the agent comprises interferon gamma and/or platelet rich plasma, and in some cases at least interferon gamma and/or platelet rich plasma (and/or platelet rich lysate) can endow the ability of the fibroblasts to directly or indirectly actively suppress immune responses. Fibroblasts cultured under these conditions are administered into individuals suffering from autoimmune or inflammatory disorders or at risk thereof. The route of administration, dosage and frequency is determined as a function of the disease process, as well as stage of the disease, and can be optimized per routine practices in medicine.

In one embodiment, allogeneic (or xenogeneic or syngeneic) fibroblasts are administered to an individual in a non-manipulated manner (for example, without prior exposure to one or more particular agents, such as interferon gamma) but selected from sources naturally characterized by immune modulatory activity, such as placental fibroblasts or adipose tissue-associated fibroblasts, for example. In other embodiments of the disclosure, any fibroblasts are cultured under conditions capable of inducing retro-differentiation so as to endow an immature phenotype for the fibroblasts, wherein the immature phenotype correlates with enhanced anti-inflammatory and/or immune modulatory potential. For example, fibroblasts may be cultured in the presence of one or more histone deacetylase inhibitors, such as valproic acid (Moon et al., 2008; Huang et al., 2011). In addition to HDAC inhibitors, other means of inducing dedifferentiation of the fibroblasts may also be utilized in the context of the current disclosure, such as 8-Br-cAMP (Wang et al., 2011); M-CSF treatment (Li et al., 2016); exposure to reveresine (Li et al., 2016); and/or exposure to stem cell extracts (Xiong et al., 2014). Characterization of fibroblast dedifferentiation can be performed by assessment of extracellular markers, such as CXCR4, VEGFR-2, CD34, and/or CD133, as well as intracellular markers such as SOX-2, NANOG, and/or OCT-4.

In some embodiments of the disclosure, fibroblast cells that have been dedifferentiated may be utilized for immunomodulation express one or more markers selected from the group consisting of Telomerase, Nanog, Sox2, beta-III-Tubulin, NF-M, MAP2, APP, GLUT, NCAM, NeuroD, Nurr1, GFAP, NG2, Olig1, Alkaline Phosphatase, Vimentin, Osteonectin, Osteoprotegrin, Osterix, Adipsin, Erythropoietin, SM22-alpha, HGF, c-MET, alpha-1-Antriptrypsin, Ceruloplasmin, AFP, PEPCK 1, BDNF, NT-4/5, TrkA, BMP2, BMP4, FGF2, FGF4, PDGF, PGF, TGFalpha, TGF-beta, VEGF and a combination thereof.

In one embodiment of the disclosure, fibroblasts are administered together with one or more agents that possess immune-modulatory properties. Such agents include the following examples: 1) hydroxychloroquine, which acts in part as a toll like receptor (TLR) 7/9 antagonist, thus decreasing innate immune activation (Sun et al., 2007); 2) leflunomide, an antimetabolite that inhibits pyrimidine synthesis and protein tyrosine kinase activity (Chong et al., 1999), which results in suppression of T cell responses (Dimitrova et al., 2002), and has been also demonstrated to inhibit dendritic cell (DC) activation (Kirsch et al., 2005); 3) injectable gold compounds (such as auranofin) which directly or through metabolites such as dicyanogold (i) have been demonstrated to inhibit T cell and antigen presenting cell activation (Tepperman et al., 1999; Han et al., 2008), as well as cause Th2 deviation (Kim et al., 2001); 4) sulfasalazine, which has been used since 1950, acts primarily through inhibition of cycloxygenase and lipoxygenase (Taggart et al., 1987); and 5) methotrexate, an antifolate that inhibits T cell activation and proliferation and that has been one of the golden standards for RA (Bansard et al., 2009). Typically, combinations of disease-modifying anti-rheumatic drugs (DMARDs) with glucocorticoids are used, or alternatively one or more pulses of high dose glucocorticoids are administered to cause a general inhibition of inflammation (Bijlsma et al., 2006). Concentrations of fibroblasts used are dependent on stage of the disease, as well as patient history and responsiveness to prior therapy.

In one embodiment of the disclosure, fibroblasts to be used for immunomodulation are genetically engineered, for example to express: a) one or more autoantigens; and/or b) one or more immune modulatory proteins. The engineered cells are subsequently used for induction of immunological tolerance. The characteristics of the individual and disease may dictate which genes are to be used for engineering of fibroblasts, in at least some cases. For example, in situations of type 1 diabetes, numerous autoantigens are known in the field, for example IGRP (Fuchs et al., 2017), IA-2 (Guerra et al., 2016), Proinsulin-2 (Babon et al., 2016), and GAD65 (Phelps et al., 2016). In these cases, the autoantigen may be transfected into the fibroblasts in polynucleotide form and the fibroblasts are either cultured to allow for immune modulation or transfected with genes allowing for immune modulation. Genes of particular interest for transfection to induce immune modulation include at least the following: Fas ligand, TGF-beta, IL-4, IL-10, HLA-G, indolamine 2,3 deoxygenase, galectin family members, Galectin 3, arginase, and/or IL-20 (de Jesus et al., 2016; Wang et al., 2011; Zhao et al., 2010; Min et al., 2001; Cancedda et al., 2001). Any of the genes described herein or active portions thereof may be cloned into mammalian expression constructs comprising promoter sequences enabling expression in fibroblast cells such as the CMV promoter [Artuc et al., Exp. Dermatol. 1995, 4:317-21]. Examples of suitable constructs include, but are not limited to pcDNA3, pcDNA3.1 (+/−), pGL3, PzeoSV2 (+/−), pDisplay, pEF/myc/cyto, pCMV/myc/cyto (each of which is commercially available from Invitrogen, for example), or the pSH expression vector that enables a regulated polynucleotide expression in human foreskin cells [Ventura and Villa, 1993, Biochem. Biophys. Commun. 192: 867-9]. Examples of retroviral vector and packaging systems are those commercially available from Clontech, San Diego, Calif., USA, including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter. After completing plasmid transfection fibroblasts are harvested by a means allowing for detachment from tissue culture plates, for example, by trypsinization and transferred to either a 6-well (Nunc, Denmark) or a 24-well plate (Nunc) for proliferation. Approximately 3 days post-transfection, the cell media is changed to media suitable for proliferation and expansion of modified fibroblasts. One example is Neurobasal A (NBA) proliferation medium comprising Neurobasal-A (Invitrogen), 1% D-glucose (Sigma Aldrich), 1% Penicillin/Streptomycin/Glutamine (Invitrogen), 2% B27 supplement with Retinoic acid (Invitrogen), 0.2% EGF (Peprotech, USA), 0.08% FGF-2 (Peprotech), 0.2% Heparin (Sigma Aldrich, USA) and Valproic acid (Sigma Aldrich) to a concentration of 1 µM. The media is then subsequently changed, such as thrice weekly, and cells are re-plated regularly (for example, 2-8 times up to a maximum of weekly re-plating, becoming more regular as colonies began to develop) to remove non-reprogrammed cells until widespread colony formation is achieved. Various quality control means are known in the art for practitioners of the disclosure to perform clinical administration of the cells. Example criteria for qualification of the cells includes marker identification using means such as flow cytometry, viability, endotoxin content, as well as assessment for microbial and mycoplasma contamination.

In one embodiment of the disclosure, fibroblasts are cultured ex vivo using means known in the art for preserving viability and proliferative ability of fibroblasts. The disclosure provides for the modification of known culture techniques to decrease recognition of fibroblasts by the recipient immune system. In one embodiment fibroblasts are cultured in conditions that lack xenogeneic components, such as fetal calf serum. Xenogeneic components are known to trigger immunological reactions, including elicitation of antibody and T cell reactions (Selvaggi et al., 1997; Mackensen et al., 2000; Kadri et al., 2007; Forni et al., 1976; Lauer et al., 1983). In many individuals, natural antibodies of the IgM isotype exist to fetal calf serum associated components (Irie et al., 1974), causing rejection, inflammation or anaphylaxis subsequent to administration of cells grown in the presence of fetal calf serum (Macy et al., 1989). In specific embodiments, the disclosure encompasses the substitution of fetal calf serum with human platelet rich plasma, platelet lysate, umbilical cord blood serum, autologous serum, and/or defined cytokine mixes as an additional feature to reduce the immunogenicity of fibroblasts. Means of culturing tissues in xenogeneic-free medium are known in the art for other cell types and are incorporated by reference (Riordan et al., 2015).

Embodiments of the disclosure provide methods of reducing immunogenicity of particular types of fibroblasts. Fibroblasts may be derived from various tissues or organs, such as skin, heart, blood vessels, bone marrow, skeletal muscle, liver, pancreas, brain, and/or foreskin, which can be obtained by biopsy (where appropriate) or upon autopsy. In some aspects, the cells comprise fibroblasts, which can be from a fetal, neonatal, adult origin, or a combination thereof.

Foreskin fibroblasts may be re-suspended in ex vivo culture in medium supplemented with one or more agents to decrease immunogenicity, serum and/or serum-replacement. Serum can be of any source including fetal bovine serum, human serum or serum replacement (for example, replacement with human platelet lysate (Riordan et al., 2007; Schallmoser et al., 2007; Capelli et al., 2007; Carrancio et al., 2008; Salvade et al., 2010; Bieback et al., 2009))). In some embodiments, human serum or serum replacement is utilized in order to provide a xenogeneic-free environment for the foreskin feeder cells. Subsequent to culture the human foreskin feeder cells of the present disclosure are capable of forming monolayers when attached to a solid phase such as a tissue culture plate [Dugdale and Siddall (1969) J. Med. Lab. Technol. 26: 31-5]. This characteristic of the human foreskin feeder cells of the present disclosure makes these cells suitable universal donors because of high replicative ability and responsiveness to treatment with IFN-gamma with respect to reduction of immunogenicity. One of skill in the art will appreciate that fibroblasts from different sources may possess different reduction of immunogenicity at differing concentrations of interferon gamma. In specific embodiments the disclosure provides methods for assessment of immunogenicity to be performed, e.g. quantifying the ability to modulate mixed lymphocyte reaction.

Typically, to measure the immunogenicity of the fibroblasts, mixed lymphocyte reaction is performed by co-culturing fibroblasts that have been treated with interferon gamma together with allogeneic lymphocytes. Proliferative indexes of the allogeneic lymphocytes are usually taken to represent the degree of immunogenicity of stimulator fibroblast cells. In some embodiments of the disclosure, fibroblasts are mitotically inactivated before culture with lymphocytes. Mitotic inactivation may be performed by treatment with one or more agents, such as mitomycin C or other agents, that block proliferation without reducing viability. When chemical agents are utilized for mitotic inactivation, the chemical agents are washed off the cells in order to prevent inhibition of responding lymphocytes.

In other embodiments of the disclosure, the treated fibroblast cells are characterized for their level of immunogenicity, such as assessment of cytokine production by responding lymphocytes. Examples of cytokines of note include IL-1, which is involved in stimulation of inflammatory processes and macrophages; IL-2, which is associated with T cell and NK cell activation; interferon gamma, which activates macrophages, as well as assists in Th1 polarization; and/or IL-12 and/or IL-18, which activate NK cells and are associated with development of cellular cytotoxic responses. It is desirable for the practice of the disclosure that responding lymphocytes in a mixed lymphocyte reaction produce less inflammatory cytokines. Thus, in particular embodiments fibroblasts are selected for use when they elicit in responding lymphocytes the production of IL-2, IFN-gamma, IL-12, and/or IL-18. Conversely, assessment of immune suppressive or anti-inflammatory cytokines may also be performed within the context of the disclosure. The cytokines include interleukin 4, which stimulates Th2 cells; interleukin 10, which stimulates, intra alia, T regulatory cells; and TGF-B that inhibits inflammation.

In some embodiments of the disclosure, genetic modification of fibroblasts is performed to cause reduction of immunogenicity of the fibroblasts. One method provides for genetic modification that includes cytoplasmic transfer with cells possessing reduced immunogenicity, such as immature dendritic cells. In another embodiment, gene editing is utilized to selectively excise inflammation-evoking genes, such as HLA or costimulatory molecules such as CD40, CD80, CD86, TNF-alpha, HMGB-1, IFN-gamma, IL-1 beta, IL-17, FAP, IL-18, IL-33, or a combination thereof.

In particular embodiments of the disclosure, one or more immunomodulatory agent(s) are expressed in universal donor fibroblasts via a recombinant expression vector operable in eukaryotic cells, and the expression of the immunomodulatory agent(s) may be regulated by a constitutive promoter or an inducible promoter or a tissue-specific promoter. In specific embodiments, the vector is a viral vector, such as a retrovirus, lentivirus, adenovirus, adeno-associated virus, or herpes simplex virus, or the vector is a non-viral vector, such as naked DNA or plasmid DNA or minicircle DNA. Polynucleotides of particular interest for transfection into the fibroblasts include at least the following: Fas ligand, TGF-beta, IL-4, IL-10, HLA-G, indolamine 2,3 deoxygenase (IDO), galectin family members, Galectin 3, arginase, IL-20, HGF, PDGF-BB, EGF, IGF, GDF-5, GDF-11, Angiopoietin, FGF-1, FGF-2, FGF-5, FGF-15, or a combination thereof. In specific cases, recombinantly expressed angiogenic agent(s) may comprise FAS ligand, IL-2, IL-4, IL-10, IL-20, IL-35, HLA-G, I-309, IDO, iNOS, CD200, Galectin 3, arginase, PGE-2, TGF-beta, CTLA-4, PD-L1, IFN-gamma, or a combination thereof.

Various quality control means are known in the art for practitioners of the disclosure to perform clinical administration of the cells. Example criteria for qualification of the cells includes marker identification using means such as flow cytometry, viability, and/or endotoxin content, as well as assessment for microbial and mycoplasma contamination.

In one embodiment of the disclosure, universal donor fibroblasts are administered to an individual for treatment of an autoimmunity or inflammatory disorder. In some embodiments of the disclosure, cells are cultured ex vivo and subjected to conditions that reduce immunogenicity and stimulate anti-inflammatory and/or immunomodulatory properties. Additional embodiments are directed to methods of administration of the cells to an individual in need thereof for the purpose of treating an autoimmune and/or inflammatory condition.

Particular embodiments of the disclosure provide a method for treating one or more autoimmune or inflammatory condition(s) such as Acute Disseminated Encephalomyelitis, Acute necrotizing hemorrhagic leukoencephalitis, Addison's disease, adhesive capsulitis, Agammaglobulinemia, Alopecia areata, Amyloidosis, Ankylosing spondylitis, Anti-GBM nephritis, Antiphospholipid syndrome (APS), Anti-TBM nephritis, arthofibrosis, atrial fibrosis, autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune neutropenia, autoimmune oophoritis, autoimmune pancreatitis, autoimmune retinopathy, autoimmune thrombocytopenic purpura (ATP), autoimmune thyroid disease, autoimmune urticarial, axonal and neuronal neuropathies, Balo disease, Behcet's disease, benign mucosal pemphigold, bullous pemphigoid, cardiomyopathy, Castleman disease, Celiac disease, Chagas disease, chronic fatigue syndrome, Chronic inflammatory demyelinating polyneuropathy (CIDP), chronic Lyme disease, Chronic recurrent multifocal ostomyelitis (CRMO), Churg-Strauss syndrome, cicatricial pemphigold, cirrhosis, Cogans syndrome, cold agglutinin disease, congenital heart block, Coxsackie myocarditis, CREST disease, Crohn's disease, Cystic Fibrosis, deficiency of the interleukin-1 receptor antagonist, demyelinating neuropathies, dermatitis herpetiformis, dermatomyosis, Devic's disease (neuromyelitis optica), discoid lupus, Dressler's syndrome, Dupuytren's contracture, endometriosis, endomyocardial fibrosis, eosinophilic esophagitis, eosinophilic facsciitis, erythema nodosum, essential mixed cryoglobulinemia, Evans syndrome, experimental allergic encephalomyelitis, Familial Mediterranean Fever, Fibromyalgia Fibrosing alveolitis, Giant cell arteritis (temporal arteritis), giant cell myocarditis, glomerulonephritis, Glomerulonephritis, Goodpasture's syndrome, Graft-versus-host disease (GVHD), granulomatosus with polyangitis, Graves' disease, Guillain-Barre syndrome, Hashimoto's encephalitis, Hashimoto's thyroiditis, hemolytic anemia, Henoch-Schonlein purpura, hepatitis, herpes gestationis, hypogammaglobulinemia, idiopathic pulmonary fibrosis, Idiopathic thrombocytopenic purpura (ITP), IgA nephropathy, IgG4-related sclerosing disease, Immunoregulatory lipoproteins, inclusion body myositis, inflammatory bowel disorders, interstitial cystitis, juvenile arthritis, Juvenile diabetes (Type 1 diabetes), juvenile myositis, Kawasaki syndrome, keloid, Lambert-Eaton syndrome, leukocytoclastic vasculitis, lichen planus, lichen sclerosis, ligneous conjunctivitis, linear IgA disease, Lupus (SLE), Lyme disease, mediastinal fibrosis, Meniere's disease, microscopic polyangitis, Mixed connective tissue disease (MCTD), Mooren's ulcer, Mucha-Habermann disease, Multiple Sclerosis (MS), Myasthenia gravis, myelofibrosis, Myositis, narcolepsy, Neonatal Onset Multisystem Inflammatory Disease, nephrogenic systemic fibrosis, Neuromyelitis optica (Devic's), neutropenia, nonalcoholic fatty liver disease, nonalcoholic steatohepatitis (NASH), ocular-cicatricial pemphigold, optic neuritis, palindromic rheumatism, paraneoplastic cerebellar degeneration, Paroxysmal nocturnal hemoglobinuria (PNH), Parry Romberg syndrome, Pars planitis (peripheral uveitis), Parsonnage-Turner syndrome, Pediatric Autoimmune Neuropsychiatric Disorders Associated with *Streptococcus* (PANDAS), Pemphigus, Peripheral neuropathy, Perivenous encephalomyelitis, Pernicious anemia, Peyronie's disease, POEMS syndrome, polyarteritis nodosa, polymyalgia rhematica, polymyositis, postmyocardial infarction syndrome, postpericardiotomy syndrome, primary biliary cirrhosis, primary sclerosing cholangitis, progesterone dermatitis, progressive massive fibrosis, psoriasis, psoriatic arthritis, pure red cell aplasia, pyoderma gangrenosum, Raynauds phenomenon, reactic arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, systemic lupus erythematosus (SLE), Takayasu's arteritis, temporal arteritis, Thrombocytopenic purpura (TTP), Tolosa-Hunt syndrome, transverse myelitis, Tumor Necrosis Factor Receptor-associated Periodic Syndrome, Type 1 diabetes, Type I autoimmune polyglandular syndrome, Type II autoimmune polyglandular syndrome, Type III autoimmune polyglandular syndrome, ulcerative colitis, undifferentiated connective tissue disease, uveitis, vasculitis, vesiculobullous dermatosis, Vitiligo, and Wegener's granulomatosis (now termed Granulomatosis with Polyangitis (GPA).

Certain methods of the disclosure are directed to reducing the immunogenicity of fibroblasts, including at least foreskin fibroblasts. In certain embodiments, fibroblasts are re-suspended in ex vivo culture in medium supplemented with serum or serum-replacement. Serum can be of any source including fetal bovine serum, human serum and/or serum replacement. In certain embodiments human serum or serum replacement is utilized in order to provide a xenogeneic-free environment for the foreskin feeder cells. In one embodiment the foreskin fibroblasts are treated with concentrations of IFN-gamma ranging from 0.1-500 Units per milliliter (IU/ml), including ranges of concentrations described elsewhere herein.

In certain embodiments a therapeutically effective amount of modified cells are co-administered with one or more immunomodulatory agents(s) to an individual. Exemplary immunomodulatory agents may comprise FAS ligand, IL-2R, IL-1 Ra, IL-2, IL-4, IL-8, IL-10, IL-20, IL-35, HLA-G, PD-L1, I-309, IDO, iNOS, CD200, Galectin 3, sCR1, arginase, PGE-2, aspirin, atorvastatin, fluvastatin, lovastatin, pravastatin, rosuvastatin, simvastatin, pitavastatin, n-acetylcysteine, rapamycin, IVIG, naltrexone, TGF-beta, VEGF, PDGF, CTLA-4, anti-CD45RB antibody, hydroxychloroquine, leflunomide, auranofin, dicyanogold, sulfasalazine, methotrexate, glucocorticoids, etanercept, adalimumab, abatacept, anakinra, certolizumab, Etanercept-szzs, golimumab, infliximab, rituximab, tocilizumab, cyclosporine, IFN-gamma, everolimus, rapamycin, or combinations thereof.

Particular embodiments of the disclosure provide a method for treating or preventing one or more autoimmune or inflammatory condition(s) comprising: Acute Disseminated Encephalomyelitis, Acute necrotizing hemorrhagic leukoencephalitis, Addison's disease, adhesive capsulitis, Agammaglobulinemia, Alopecia areata, Amyloidosis, Ankylosing spondylitis, Anti-GBM nephritis, Antiphospholipid syndrome (APS), Anti-TBM nephritis, arthofibrosis, atrial fibrosis, autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune neutropenia, autoimmune oophoritis, autoimmune pancreatitis, autoimmune retinopathy, autoimmune thrombocytopenic purpura (ATP), autoimmune thyroid disease, autoimmune urticarial, axonal and neuronal neuropathies, Balo disease, Behcet's disease, benign mucosal pemphigold, bullous pemphigoid, cardiomyopathy, Castleman disease, Celiac disease, Chagas disease, chronic fatigue syndrome, Chronic inflammatory demyelinating polyneuropathy (CIDP), chronic Lyme disease, Chronic recurrent multifocal ostomyelitis (CRMO), Churg-Strauss syndrome, cicatricial pemphigold, cirrhosis, Cogans syndrome, cold agglutinin disease, congenital heart block, Coxsackie myocarditis, CREST disease, Crohn's disease, Cystic Fibrosis, deficiency of the interleukin-1 receptor antagonist, demyelinating neuropathies, dermatitis herpetiformis, dermatomyositis, Devic's disease (neuromyelitis optica), discoid lupus, Dressler's syndrome, Dupuytren's contracture, endometriosis, endomyocardial fibrosis, eosinophilic esophagitis, eosinophilic facsciitis, erythema nodosum, essential mixed cryoglobulinemia, Evans syndrome, experimental allergic encephalomyelitis, Familial Mediterranean Fever, Fibromyalgia Fibrosing alveolitis, Giant cell arteritis (temporal arteritis), giant cell myocarditis, glomerulonephritis, Glomerulonephritis, Goodpasture's syndrome, Graft-versus-host disease (GVHD), granulomatosus with polyangitis, Graves' disease, Guillain-Barre syndrome, Hashimoto's encephalitis, Hashimoto's thyroiditis, hemolytic anemia, Henoch-Schonlein purpura, hepatitis, herpes gestationis, hypogammaglobulinemia, idiopathic pulmonary fibrosis, Idiopathic thrombocytopenic purpura (ITP), IgA nephropathy, IgG4-related sclerosing disease, Immunoregulatory lipoproteins, inclusion body myositis, inflammatory bowel disorders, interstitial cystitis, juvenile arthritis, Juvenile diabetes (Type 1 diabetes), juvenile myositis, Kawasaki syndrome, keloid, Lambert-Eaton syndrome, leukocytoclastic vasculitis, lichen planus, lichen sclerosis, ligneous conjunctivitis, linear IgA disease, Lupus (SLE), Lyme disease, mediastinal fibrosis, Meniere's disease, microscopic polyangitis, Mixed connective tissue disease (MCTD), Mooren's ulcer, Mucha-Habermann disease, Multiple Sclerosis (MS), Myasthenia gravis, myelofibrosis, Myositis, narcolepsy, Neonatal Onset Multisystem Inflammatory Disease, nephrogenic systemic fibrosis, Neuromyelitis optica (Devic's), neutropenia, non-alcoholic fatty liver disease, nonalcoholic steatohepatitis (NASH), ocular-cicatricial pemphigold, optic neuritis, palindromic rheumatism, paraneoplastic cerebellar degeneration, Paroxysmal nocturnal hemoglobinuria (PNH), Parry Romberg syndrome, Pars planitis (peripheral uveitis), Parsonnage-Turner syndrome, Pediatric Autoimmune Neuropsychiatric Disorders Associated with Streptococcus (PANDAS), Pemphigus, Peripheral neuropathy, Perivenous encephalomyelitis, Pernicious anemia, Peyronie's disease, POEMS syndrome, polyarteritis nodosa, polymyalgia rhematica, polymyositis, postmyocardial infarction syndrome, postpericardiotomy syndrome, primary biliary cirrhosis, primary sclerosing cholangitis, progesterone dermatitis, progressive massive fibrosis, psoriasis, psoriatic arthritis, pure red cell aplasia, pyoderma gangrenosum, Raynauds phenomenon, reactic arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, systemic lupus erythematosus (SLE), Takayasu's arteritis, temporal arteritis, Thrombocytopenic purpura (TTP), Tolosa-Hunt syndrome, transverse myelitis, Tumor Necrosis Factor Receptor-associated Periodic Syndrome, Type 1 diabetes, Type I autoimmune polyglandular syndrome, Type II autoimmune polyglandular syndrome, Type III autoimmune polyglandular syndrome, ulcerative colitis, undifferentiated connective tissue disease, uveitis, vasculitis, vesiculobullous dermatosis, Vitiligo, and Granulomatosis with Polyangitis (GPA).

Growth of fibroblasts for immune modulation may be performed in a variety of tissue culture media, for example. In one embodiment of the disclosure, one medium for the culturing of the cells comprises Dulbecco's Modified Essential Media (DMEM), including DMEM-low glucose (DMEM-LG) (Invitrogen, Carlsbad, CA). The DMEM-LG may be supplemented with serum, such as fetal bovine serum and/or human serum. Typically, 15% (v/v) fetal bovine serum (e.g. defined fetal bovine serum, Hyclone, Logan Utah) is added, along with antibiotics/antimycotics ((preferably 100 Unit/milliliter penicillin, 100 milligrams/milliliter streptomycin, and 0.25 microgram/milliliter amphotericin B; Invitrogen, Carlsbad, Calif.)), and 0.001% (v/v) 2-mercaptoethanol (Sigma, St. Louis MO). In some cases, different growth media are used, or different supplementations are provided, and these are normally indicated in the text as supplementations to Growth Medium. In certain chemically-defined media, the cells may be grown without serum present at all. In such cases, the cells may require certain growth factors, which can be added to the medium to support and sustain the cells. Certain factors to be added for growth on serum-free media include one or more of bFGF, EGF, IGF-I, and PDGF, in some cases. In some embodiments, two, three or all four of the factors are added to serum-free or chemically defined media. In other embodiments, LIF is added to serum-free medium to support or improve growth of the cells.

C. Expansion of Regulatory T Cells in Ex Vivo Culture

The present example provides a solution for a long-felt need in the art for expanding particular T cells.

T regulatory cells are an essential component of the immune system protecting the body against autoimmune attack. This is illustrated by early studies in which neonatally thymectomized mice suffered from systemic autoimmunity, which were rescued by transfer of CD4 cells (Hori et al., 2003). Subsequent studies identified the T regulatory (Treg) phenotype as possessing the IL-2 receptor CD25, which is somewhat problematic given that this receptor is found on activated T cells as well. Peripheral blood contains a small population of T cell lymphocytes that express the T regulatory phenotype ("Treg"), i.e., positive for both CD4 and CD25 antigens. There are several subsets of Treg cells. One subset of regulatory cells develops in the thymus. Thymic-derived Treg cells function by a cytokine-independent mechanism, which involves cell to cell contact. They are essential for the induction and maintenance of self-tolerance and for the prevention of autoimmunity (Shevach et al., 2000). These regulatory cells prevent the activation and proliferation of autoreactive T cells that have escaped thymic deletion or recognize extrathymic antigens, thus they are critical for homeostasis and immune regulation, as well as for protecting the host against the development of autoimmunity. Thus, immune regulatory $CD4^+$ $CD25^+$ T cells are often referred to as "professional suppressor cells." Suppression of immunity by Treg cells occurs through several mechanisms. One is direct lysis of activated T cells (Onishi et al., 2008; Gondek et al., 2005), another one is inhibition of dendritic cell maturation (Miyara et al., 2007), thus inhibiting ability of the antigen presenting cell arm of the immune system to initiate or perpetuate T cell responses.

Naturally arising $CD4^+$ $CD25^+$ Treg cells (nTregs) are a distinct cell population of cells that are positively selected on high affinity ligands in the thymus and that have been shown to play an important role in the establishment and maintenance of immunological tolerance to self antigens (Sakaguchi et al., 2009). Deficiencies in the development and/or function of these cells have been associated with severe autoimmunity in humans and various animal models of congenital or induced autoimmunity.

Treg cells manifest their tolerogenic effects directly via cell-to-cell contact or indirectly via soluble factors. Although the suppressive mechanisms of these cells remain to be fully elucidated, blockade of IL-2 expression in effector T cells (Teff), physical elimination of Teff cells, induction of tolerogenic dendritic cells (DCs) via CTLA-4/B7 axis, and inhibition of Teff cells via TGF-beta and IL-10 are some of the mechanisms that have been implicated to date. It also has been shown that reverse signaling through CTLA-4/CD80 into Teff cells plays an important role in their inhibition by Treg cells. Similarly, interactions between CTLA-4 on Treg cells and CD80 on DCs can result in reverse signaling and upregulation of the indoleamine dioxygenase enzyme that is involved in tolerance via the regulation of tryptophan metabolism.

Embodiments of the disclosure provide compositions and methods for providing or improving cell therapy to an individual in need thereof. Embodiments encompass both therapies and methods of generating therapies for individuals in need of cell therapy, such as individuals with one or more autoimmune or other diseases.

In particular embodiments, there are methods and compositions for expanding Tregs, including nTregs, such that the Tregs can be used for a therapy for an individual. In specific embodiments, the Tregs are expanded without the subsequent reversion of the cells to an undesired type, such as reversion of nTregs to T effector cells. Accordingly, such an expansion methodology allows for the establishment of a cell bank useful for stimulation of immune modulatory properties, such as immune suppressor properties.

In one aspect of the present disclosure, nTreg expansion can be performed by isolating nTregs from a desired cell source and subsequently expanding the cells in culture in the presence of a primary signal and a co-stimulatory signal found on fibroblasts (or combination of fibroblasts with other agents). Agents useful for stimulating a primary signal and an a co-stimulatory signal on Tregs may be used in soluble form, attached to the surface of a fibroblast cell, and/or immobilized on a surface as described herein.

In one embodiment both primary and co-stimulatory agents are co-immobilized on a surface, for example a substrate (such as a bead) or an engineered cell. In one embodiment, the molecule providing the primary activation signal, such as a CD3 ligand (crosslinking antibody or a lectin, for example), and the co-stimulatory molecule, such as a CD28 ligand, are coupled to or loaded on the same substrate, for example, a particle, bead or an engineered cell. Upon expansion, the cells can be administered alone or with other immune regulatory cells to treat one or more autoimmune diseases.

In another embodiment, the disclosure provides a method of expanding Tregs, such as nTregs, to significant numbers using a repetitive stimulation procedure. As an example, allogeneic naïve cells, such as CD4 cells, are cultured together with interferon gamma and/or platelet rich plasma-cultured fibroblasts. In one embodiment, the method of expanding nTregs comprises repeatedly stimulating nTregs, for example based upon cell size. In specific cases, nTregs exhibiting a cell size about the size of a resting nTreg are chosen for repeated stimulation. In some instances, the size of a resting nTreg is about 8.5 µm. That is, the invention encompasses the discovery that cell size is a parameter that contributes to the success of expanding nTregs without losing nTreg phenotype and suppressor activity. In another embodiment, the method of expanding nTregs comprises repeatedly stimulating nTregs in the presence of a particular agent (such as Rapamycin or everolimus, or any other inhibitor of the mammalian target of rapamycin (mTOR)) In certain cases, nTregs isolated from peripheral blood are re-stimulated in the presence of Rapamycin. That is, the invention encompasses the embodiment that Rapamycin contributes to the success of expanding nTregs isolated from peripheral blood without losing nTreg phenotype and suppressor activity in cases wherein fibroblast cells are added to the co-culture. In particular embodiments, the expanded cells produced by methods of the disclosure maintain Foxp3 profile indicative of nTregs. In one embodiment, the population of expanded nTregs expresses specific natural Treg markers, such as Foxp3 and Latency Associated Peptide (LAP); display Treg-specific demethylation in the Foxp3 gene, and contain very few IL-2-, IFN-gamma-, IL-17- secreting cells. The expanded cells of the disclosure also are able to suppress autoimmunity, as observed in an exemplary collagen-induced arthritis model. In other embodiments, at least a portion of the active cell population may be stored for later implantation/infusion. The population may be divided into more than one aliquot or unit such that part of the population of nTregs is retained for later application while part is applied immediately to the patient. Moderate to long-term storage of all or part of the cells in a cell bank is also within the scope of this disclosure. For the purpose of the disclosure, Treg and nTreg may be utilized in the context of the methods.

In one embodiment of the disclosure, Treg cells that are generated, either in vitro or in vivo, are further augmented in activity by modulation of the host microbiome. Modulation of microbiome may be performed by administration of either probiotics and/or prebiotics. It is known in the art that the intestinal microbiota drives host immune homeostasis by regulating the differentiation and expansion of Treg, Th1, and Th2 cells. It has been demonstrated that Foxp3$^+$ Treg cell deficiency results in gut microbial dysbiosis and autoimmunity. Means of remodeling the microbiome include administration of *Lactobacillus reuteri*, which is associated in animal models of autoimmunity with prolonged survival and reduced multi-organ inflammation. In one embodiment of the disclosure, *L. reuteri* is administered to change the metabolomic profile disrupted by Treg cell deficiency and/or to restore levels of the purine metabolite inosine. Accordingly, in one embodiment of the disclosure administration of inosine together with generation of Treg cells is utilized to stimulate enhanced suppressive activity and thereby treatment of autoimmunity. Means of administering inosine and modulation of microbiome for augmentation of Treg cells are described in the following papers, which are incorporated by reference: He et al., 2017; Hrdy et al., 2016; Thakur et al., 2016; Haileselassie et al., 2016; Liu et al., 2014; Kim et al., 2014; Narushima et al., 2014; Mercadante et al., 2014; Yoshida et al., 2013; Barletta et al., 2013; Smelt et al., 2013; Atarashi et al., 2013; Smelt et al., 2013; Qiu et al., 2013; Liu et al., 2013; Zhao et al., 2013; Jeon et al., 2012; Jang et al., 2012; Lopez et al., 2012; Lopez et al., 2012; Fink et al., 2010; Lavasani et al., 2010; Lyons et al., 2010; de Rooks et al., 2010; Karimi et al., 2009; and Feleszko et al., 2007.

In one embodiment, Treg cells are generated by the activation of mature, peripheral CD4$^+$ T cells in the presence of fibroblasts. In some embodiments, fibroblasts are cultured under conditions associated with immune modulation. Studies have indicated that peripherally derived Treg cells mediate their inhibitory activities by producing immunosuppressive cytokines, such as transforming growth factor-beta (TGF-beta) and IL-10. Accordingly, in one embodiment co-culture of fibroblasts and T cells are performed at various concentrations and levels of TGF-beta and IL-10 and are assessed as a marker to select optimum Treg generating conditions. Assessment of tolerogenic activities based on production of IL-10 and TGF-beta are described in the following papers and incorporated by reference: Kingsley et al., 2002 J. Immunol. 168: 1080; Nakamura et al., 2001 J. Exp. Med. 194: 629-644). In any event, embodiments of the disclosure include methods wherein fibroblasts and/or T cells are exposed to TGF-beta and/or IL-10 to effectively produce Tregs.

In one embodiment of the disclosure, existing methods of expanding Treg cells in vitro are utilized with the adaptation of utilizing fibroblast cells as feeder layers. Concentrations of fibroblasts useful for the practice of the disclosure typically range from 1 fibroblast for every 1 T cell to 100 T cells for every 1 fibroblast (or approximations thereof). In more particular embodiments, the fibroblast to T cell ratios are approximately 1, 2, 3, 4, 5, 6, 7, 8, 9, 10, or more fibroblasts for every T cell. In some embodiments addition of one or more growth factors, such as IL-2, are added for exposure of the fibroblasts and/or T cells to be expanded. Means of culturing Treg cells in absence of fibroblasts are provided by Trenado et al. who reported the first evaluation of the therapeutic efficacy of ex vivo activated and expanded CD4$^+$ CD25$^+$ regulatory cells in an in vivo mouse model of disease (Trenado et al., 2002 J. Clin. Invest. 112(11): 1688-1696).

In one embodiment of the disclosure, treated fibroblasts are used to replace mesenchymal stem cells for in vitro or in vivo expansion of Treg cells, although in some cases both are utilized. Means to induce Treg generation in vitro using mesenchymal stem cells (MSC) are replaced by techniques that according to the current disclosure can be adaptive by substituting mesenchymal stem cells with fibroblasts (see Chen et al., 2017, incorporated by reference herein). Previous studies have demonstrated that mesenchymal stem cells are capable of producing growth factors associated with cellular proliferation, such as FGF (Lai et al., 2011; Coutu et al., 2011), VEGF (Kinnaird et al., 2004; Kinnarid et al., 2004; Kwon et al., 2014), IGF-1 (Montes et al., 2009) and HGF (Shen et al., 2015). In fact, MSC feeder layers have previously been used to expand hematopoietic (Walenda et al., 2011; Fong et al., 2012), and pluripotent stem cells (Zou et al., 2016; Silva et al., 2014) while maintaining these cells in an undifferentiated state. Furthermore, MSC have been demonstrated to promote generation of Treg cells in vitro (Cahill et al., 2015; Wang et al., 2015; Kwon et al., 2014; Luz-Crawford et al., 2013; Erkers et al., 2013; Engela et al., 2013), and in vivo (Bai et al., 2012; Lee et al., 2015; Treacy et al., 2014). In one embodiment of the disclosure, fibroblasts are utilized as a substitute for MSC.

General embodiments of the disclosure provide improved methods, systems and compositions directed to the expansion of immune cells following exposure to one or more agents and/or exposure to fibroblasts, including modified fibroblasts. In specific embodiments, provided herein are methods of expanding a population of T regulatory cells, for example in ex vivo culture, upon exposure to fibroblasts that have been exposed to IFN-gamma, platelet rich plasma (including human), or a combination thereof.

In certain embodiments, T cells, such as regulatory T cells to be utilized in therapeutic or preventative methods of the disclosure, are isolated from tissues comprising them, such as thymus, peripheral blood, menstrual blood, adipose tissue, bone marrow, placenta, cord blood, cerebral spinal fluid, or a combination thereof, and in specific cases the T cells are isolated from an individual that will be receiving the T cells upon their expansion using methods of the disclosure. In specific cases, the T cells are obtained from the tissues of one individual, the cells are expanded using methods of the disclosure, and then are provided to a different individual. In other cases the T cells to be subjected to the fibroblasts may be otherwise obtained, such as commercially.

In specific embodiments the population of T cells is subjected one or more times to one or more compositions comprising fibroblast cells, including modified fibroblast cells and, optionally, one or more additional agent(s) and/or condition(s). In specific embodiments modified fibroblast cells are fibroblasts that have been exposed at least to IFN-gamma. The exposure of the fibroblast cells may occur ex vivo or may occur in vivo when the fibroblast cells and/or the IFN-gamma are provided to the individual exogenously (as opposed to fibroblasts being exposed in the body to IFN-gamma in an unmodified, natural setting). In particular embodiments, the fibroblasts are manipulated by the hand of man in at least one step of the method.

In certain embodiments the fibroblasts may be derived from tissues comprising skin, heart, blood vessels, bone marrow, skeletal muscle, liver, pancreas, brain, and/or foreskin. In specific embodiments, the fibroblasts are placental, fetal, neonatal or adult or mixtures thereof. In additional embodiments, the ratio of fibroblast cells to T cells in culture comprises a ratio of 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 200:1, 300:1, and so forth. In particular embodiments, the ratio of fibroblast to T cell in co-culture is 2:1. In alternative embodiments, the ratio of T cells to fibroblasts in culture comprises a ratio of 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 200:1, 300:1, and so forth.

In particular embodiments, the co-culture comprising the T cells and modified fibroblasts (and/or one or more additional agents and/or conditions) composition may comprise one or more additional agents including a CD3 ligand (crosslinking antibody or a lectin, for example), a CD28 ligand (CD80 or CD86 or a crosslinking antibody, for example), rapamycin, IL-10, TGF-beta, IL-2, hCG, PGE-2, estrogen, progesterone, salicylic acid, everolimus, or a combination thereof. In specific embodiments, the one or more additional agents are in solution with the fibroblasts, attached to the surface of a fibroblast cell, immobilized on a bead, immobilized on the surface of an engineered cell (for example, fibroblast or CHO cell engineered to express one or more costimulatory molecules and/or one or more crosslinking antibodies and/or more or more engineered receptors, such as chimeric antigen receptors or T cell receptors) and/or being expressed within the fibroblasts.

In specific embodiments, the regulatory T cells are derived from allogeneic naïve $CD4^+$ T cells, CD8 cells, gamma delta T cells, or a mixture thereof.

In additional embodiments, a composition to which fibroblasts are exposed to includes human platelet rich plasma at a concentration of at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of volume of the composition.

In specific embodiments, the population of regulatory T cells is selected to have a diameter of about 7-12, 7-11, 7-10, 7-9, 7-8, 8-12, 8-11, 8-10, 8-9, 9-12, 9-11, 9-10, 10-12, 10-11, or 11-12 μm. The diameter may be 7, 8, 9, 10, 11, or 12 μm. In particular cases, the majority of the population of regulatory T cells has a diameter of about 8.5 μm. In other cases, at least about 50%, 60%, 70%, 80%, 90%, or more of the cells in the population have a diameter of about 7-12 μm.

Following expansion of Treg cells upon exposure to modified fibroblasts, produced regulatory T cell populations may be utilized or may be stored for later use. Additional embodiments provide means for dividing the population of cells into two or more aliquots such that at least one aliquot is preserved for later use and at least one aliquot is administered to an individual to treat an autoimmune or inflammatory condition.

Additional embodiments are directed to methods wherein the regulatory T cells are administered to an individual to treat at least one autoimmune or inflammatory condition. In some cases, a fraction of the prepared T cell population is provided to one individual for the treatment of one condition, whereas another fraction of the prepared T cell population is provided to another individual for the treatment of the same or a different autoimmune or inflammatory condition.

In particular embodiments, a prepared T cell population is provided to an individual with an autoimmune or inflammatory condition, such as Acute Disseminated Encephalomyelitis, Acute necrotizing hemorrhagic leukoencephalitis, Addison's disease, adhesive capsulitis, Agammaglobulinemia, Alopecia areata, Amyloidosis, Ankylosing spondylitis, Anti-GBM nephritis, Antiphospholipid syndrome (APS), Anti-TBM nephritis, arthofibrosis, atrial fibrosis, autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune neutropenia, autoimmune oophoritis, autoimmune pancreatitis, autoimmune retinopathy, autoimmune thrombocytopenic purpura (ATP), autoimmune thyroid disease, autoimmune urticarial, axonal and neuronal neuropathies, Balo disease, Behcet's disease, benign mucosal pemphigold, bullous pemphigoid, cardiomyopathy, Castleman disease, Celiac disease, Chagas disease, chronic fatigue syndrome, Chronic inflammatory demyelinating polyneuropathy (CIDP), chronic Lyme disease, Chronic recurrent multifocal ostomyelitis (CRMO), Churg-Strauss syndrome, cicatricial pemphigold, cirrhosis, Cogans syndrome, cold agglutinin disease, congenital heart block, Coxsackie myocarditis, CREST disease, Crohn's disease, Cystic Fibrosis, deficiency of the interleukin-1 receptor antagonist, demyelinating neuropathies, dermatitis herpetiformis, dermatomyosis, Devic's disease (neuromyelitis optica), discoid lupus, Dressler's syndrome, Dupuytren's contracture, endometriosis, endomyocardial fibrosis, eosinophilic esophagitis, eosinophilic facsciitis, erythema nodosum, essential mixed cryoglobulinemia, Evans syndrome, experimental allergic encephalomyelitis, Familial Mediterranean Fever, Fibromyalgia Fibrosing alveolitis, Giant cell arteritis (temporal arteritis), giant cell myocarditis, glomerulonephritis, Glomerulonephritis, Goodpasture's syndrome, Graft-versus-host disease (GVHD), granulomatosus with polyangitis, Graves' disease, Guillain-Barre syndrome, Hashimoto's encephalitis, Hashimoto's thyroiditis, hemolytic anemia, Henoch-Schonlein purpura, hepatitis, herpes gestationis, hypogammaglobulinemia, idiopathic pulmonary fibrosis, Idiopathic thrombocytopenic purpura (ITP), IgA nephropathy, IgG4-related sclerosing disease, Immunoregulatory lipoproteins, inclusion body myositis, inflammatory bowel disorders, interstitial cystitis, juvenile arthritis, Juvenile diabetes (Type 1 diabetes), juvenile myositis, Kawasaki syndrome, keloid, Lambert-Eaton syndrome, leukocytoclastic vasculitis, lichen planus, lichen sclerosis, ligneous conjunctivitis, linear IgA disease, Lupus (SLE), Lyme disease, mediastinal fibrosis, Meniere's disease, microscopic polyangitis, Mixed connective tissue disease (MCTD), Mooren's ulcer, Mucha-Habermann disease, Multiple Sclerosis (MS), Myasthenia gravis, myelofibrosis, Myositis, narcolepsy, Neonatal Onset Multisystem Inflammatory Disease, nephrogenic systemic fibrosis, Neuromyelitis optica (Devic's), neutropenia, non-alcoholic fatty liver disease, nonalcoholic steatohepatitis (NASH), ocular-cicatricial pemphigold, optic neuritis, palindromic rheumatism, paraneoplastic cerebellar degeneration, Paroxysmal nocturnal hemoglobinuria (PNH), Parry Romberg syndrome, Pars planitis (peripheral uveitis), Parsonnage-Turner syndrome, Pediatric Autoimmune Neuropsychiatric Disorders Associated with Streptococcus (PANDAS), Pemphigus, Peripheral neuropathy, Perivenous encephalomyelitis, Pernicious anemia, Peyronie's disease, POEMS syndrome, polyarteritis nodosa, polymyalgia rheumatica, polymyositis, postmyocardial infarction syndrome, postpericardiotomy syndrome, primary biliary cirrhosis, primary sclerosing cholangitis, progesterone dermatitis, progressive massive fibrosis, psoriasis, psoriatic arthritis, pure red cell aplasia, pyoderma gangrenosum, Raynauds phenomenon, reactic arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, systemic lupus erythematosus (SLE), Takayasu's arteritis, temporal arteritis, Thrombocytopenic purpura (TTP), Tolosa-Hunt syndrome, transverse myelitis, Tumor Necrosis Factor Receptor-associated Periodic Syndrome, Type 1 diabetes, Type I autoimmune polyglandular syndrome, Type II autoimmune polyglandular syndrome, Type III autoimmune polyglandular syndrome, ulcerative colitis, undifferentiated connective tissue disease, uveitis, vasculitis, vesiculobullous dermatosis, Vitiligo, or Wegener's granulomatosis (now termed Granulomatosis with Polyangitis (GPA), for example In particular embodiments the regulatory T cells are administered to an individual with one or more additional immune regulatory cells, such as immature dendritic cells, NKT cells, TR1 cells, gamma delta T cells, CD5 B cells, or a mixture thereof.

In additional embodiments, the regulatory T cells may be co-administered to an individual with one or more immunomodulatory agents, such as inosine, FAS ligand, IL-2R, IL-1 Ra, IL-2, IL-4, IL-8, IL-10, IL-20, IL-35, HLA-G, PD-L1, I-309, IDO, iNOS, CD200, Galectin 3, sCR1, arginase, PGE-2, aspirin, atorvastatin, fluvastatin, lovastatin, pravastatin, rosuvastatin, simvastatin, pitavastatin, n-acetylcysteine, rapamycin, IVIG, naltrexone, TGF-beta, VEGF, PDGF, CTLA-4, anti-CD45RB antibody, hydroxychloroquine, leflunomide, auranofin, dicyanogold, sulfasalazine, methotrexate, glucocorticoids, etanercept, adalimumab, abatacept, anakinra, certolizumab, Etanercept-szzs, golimumab, infliximab, rituximab, tocilizumab, cyclosporine, IFN-gamma, everolimus, rapamycin, or a combination thereof.

Specific embodiments of the disclosure include modification of the administered regulatory T cells (in some cases in addition to the modified fibroblasts) by modulation of the microbiome of the individual to which the cells are provided ("the host"). In particular embodiments, the host microbiome is modulated by a composition comprising one or more prebiotics and/or one or more probiotics. The host microbiome may be modified prior to, during, and/or after delivery of the expanded T cells by the fibroblasts, and the microbiome modification in the host can occur through oral consumption of one or more microbes, rectal implantation, and/or fecal transplantation, and so forth. In specific embodiments, the host microbiome is modified by addition of one or more bacteria to the host.

In particular embodiments, a composition is provided to the host that comprises one or more probiotics, wherein probiotics comprise, consist of, or consist essentially of *Acetanaerobacterium, Acetivibrio, Alicyclobacillus, Alkaliphilus, Anaerofustis, Anaerosporobacter, Anaerostipes, Anaerotruncus, Anoxybacillus, Bacillus, Bacteroides, Blautia, Brachyspira, Brevibacillus, Bryantella, Bulleidia, Butyricicoccus, Butyrivibrio, Catenibacterium, Chlamydiales, Clostridiaceae, Clostridiales, Clostridium, Collinsella, Coprobacillus, Coprococcus, Coxiella, Deferribacteres, Desulfitobacterium, Desulfotomaculum, Dorea, Eggerthella, Erysipelothrix, Erysipelotrichaceae, Ethanoligenens, Eubacterium, Faecalibacterium, Filifactor, Flavonifractor, Flexistipes, Fulvimonas, Fusobacterium, Gemmiger, Geobacillus, Gloeobacter, Holdemania, Hydrogenoanaerobacterium, Kocuria, Lachnobacterium, Lachnospira, Lachnospiraceae, Lactobacillus, Lactonifactor, Leptospira, Lutispora, Lysinibacillus, Mollicutes, Moorella, Nocardia, Oscillibacter, Oscillospira, Paenibacillus, Papillibacter, Pseudoflavonifractor, Robinsoniella, Roseburia, Ruminococcaceae, Ruminococcus, Saccharomonospora, Sarcina, Solobacterium, Sporobacter, Sporolactobacillus, Streptomyces, Subdoligranulum, Sutterella, Syntrophococcus, Thermoanaerobacter, Thermobifida, Turicibacter, Acetonema, Amphibacillus, Ammonifex, Anaerobacter, Caldicellulosiruptor, Caloramator, Candidatus, Carboxydibrachium, Carboxydothermus, Cohnella, Dendrosporobacter Desulfitobacterium, Desulfosporosinus, Halobacteroides, Heliobacterium, Heliophilum, Heliorestis, Lachnoanaerobaculum, Oceanobacillus, Orenia (S.), Oxalophagus, Oxobacter, Pelospora, Pelotomaculum, Propionispora, Sporohalobacter, Sporomusa, Sporosarcina, Sporotomaculum, Symbiobacterium, Syntrophobotulus, Syntrophospora, Terribacillus, Thermosinus* or a combination thereof. In particular embodiments, the composition of probiotics comprises *Lactobacillus reuteri.*

In certain embodiments the probiotic composition may comprise, consist of, or consist essentially of no more than 1, no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20, no more than 50, or no more than 100 probiotics. In certain embodiments the probiotic composition may comprise, consist of, or consist essentially of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 50, or at least 100 probiotics.

In particular embodiments the composition may comprise, consist of, or consist essentially of between 1 and 100; 1 and 50; 1 and 20; 1 and 10; 2 and 10; 3 and 10; 4 and 10; 5 and 10; 6 and 10; 7 and 10; 8 and 10; 9 and 10; 1 and 9; 2 and 9; 3 and 9; 4 and 9; 5 and 9; 6 and 9; 7 and 9; 8 and 9; 1 and 8; 2 and 8; 3 and 8; 4 and 8; 5 and 8; 6 and 8; 7 and 8; 1 and 7; 2 and 7; 3 and 7; 4 and 7; 5 and 7; 6 and 7; 1 and 6; 2 and 6; 3 and 6; 4 and 6; 5 and 6; 1 and 5; 2 and 5; 3 and 5; 4 and 5; 1 and 4; 2 and 4; 3 and 4; 1 and 3; 2 and 3; or 1 and 2; or, there is only 1 type of probiotics.

In some embodiments a probiotic composition comprises, consists of, or consists essentially of one type of probiotic present in amounts of at least or no more than 2, 5, 10, 25, 50, 75, 100 or more than 100 times greater than any other type of probiotics present in the composition to be delivered to the host.

In particular embodiments, the majority of probiotics in a probiotic composition are *Lactobacillus reuteri*. In select embodiments, *Lactobacillus reuteri* comprises at least or no more than 25, 30, 35, 40, 45, 50, 55, 60, 65, 70, 75, 80, 85, 90, 95, 96, 97, 98, 99, or greater than 99% of the probiotics in the probiotic composition.

In certain embodiments, the relative presence of probiotics in the composition is expressed as a ratio of a first type of probiotic to a second type of probiotic comprising, consisting of, or consisting essentially of 1:1 or a ratio of 1:2, 1:3, 1:4, 1:5, 1:6, 1:7, 1:8, 1:9, 1:10, 1:15, 1:20, 1:25; 1:50; 1:75, 1:100, 1:200, 1:500, 1:1000, 1:10,000, 1:100,000 or greater than 1:100,000.

In particular embodiments, one or more prebiotics are given to an individual receiving the fibroblast-expanded T cells. The prebiotics of a prebiotic composition may comprise, consist of, or consist essentially of a monomer or polymer selected from the group consisting of arabinoxylan, xylose, soluble fiber dextran, soluble corn fiber, polydextrose, lactose, N-acetyl-lactosamine, glucose, galactose, fructose, rhamnose, mannose, uronic acids, 3'-fucosyllactose, 3' sialylactose, 6'-sialyllactose, lacto-N-neotetraose, 2'-2'-fucosyllactose, arabinose, fructose, fucose, lactose, galactose, glucose, mannose, D-xylose, xylitol, ribose, xylobiose, sucrose, maltose, lactose, lactulose, trehalose, cellobiose, and a combination thereof.

In certain embodiments the composition may comprise, consist of, or consist essentially of no more than 1, no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20, no more than 25, no more than 30, or no more than 35 type(s) of prebiotics. In certain embodiments the composition may comprise, consist of, or consist essentially of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, or at least 35 type(s) of prebiotics.

In additional embodiments a prebiotic composition may comprise, consist of, or consist essentially of between 1 and 35; 1 and 30; 1 and 25; 1 and 20; 1 and 10; 2 and 10; 3 and 10; 4 and 10; 5 and 10; 6 and 10; 7 and 10; 8 and 10; 9 and 10; 1 and 9; 2 and 9; 3 and 9; 4 and 9; 5 and 9; 6 and 9; 7 and 9; 8 and 9; 1 and 8; 2 and 8; 3 and 8; 4 and 8; 5 and 8; 6 and 8; 7 and 8; 1 and 7; 2 and 7; 3 and 7; 4 and 7; 5 and 7; 6 and 7; 1 and 6; 2 and 6; 3 and 6; 4 and 6; 5 and 6; 1 and 5; 2 and 5; 3 and 5; 4 and 5; 1 and 4; 2 and 4; 3 and 4; 1 and 3, 2 and 3; or 1 and 2; or there is one type of prebiotic.

In particular embodiments a prebiotic composition may comprise, consist of, or consist essentially of at least one type of prebiotic present in an amount of at least or no more than 2, 5, 10, 25, 50, 75, 100 or more than 100 times greater than any other type of prebiotic(s) present in the composition.

In some embodiments one of more prebiotics in the composition are present at a concentration of at least 1 µM, or at least 2 µM, or at least 3 µM, or at least 4 µM, or at least 5 µM, or at least 6 µM, or at least 7 µM, or at least 8 µM, or at least 9 µM, or at least 10 µM, or at least 20 µM, or at least 30 µM, or at least 40 µM, or at least 50 µM, or at least 60 µM, or at least 70 µM, or at least 80 µM, or at least 90 µM, or at least 100 µM, or at least 150 µM, or at least 200 µM, or at least 250 µM, or at least 300 µM, or at least 350 µM, or at least 400 µM, or at least 450 µM, or at least 500 µM, or at least 550 µM, or at least 600 µM, or at least 650 µM, or at least 700 µM, or at least 750 µM, or at least 800 µM, or at least 850 µM, or at least 900 µM, or at least 950 µM, or at least 1 mM, or at least 2 mM, or at least 3 mM, or at least 4 mM, or at least 5 mM, or at least 6 mM, or at least 7 mM, or at least 8 mM, or at least 9 mM, or at least 10 mM.

D. Treatment of Liver Medical Conditions

Embodiments of the disclosure pertain to the field of treatment or prevention of liver medical conditions, such as liver failure, including for augmenting liver regenerative processes in an individual in need thereof. More particularly, the disclosure pertains to utilization of fibroblast cells that have been endowed with immune modulatory properties to stimulate liver regeneration and, at least in some cases, while at the same time reducing liver fibrosis.

Liver failure is a major burden on the health care system and the 7$^{th}$ largest cause of death in industrialized countries. To date the only cure for liver failure is transplantation, which is severely limited by lack of donors and adverse effects of chronic immune suppression. Although stem cell therapies are currently in development for treatment of liver failure, these possess numerous shortcomings. Embryonic and iPS derived stem cells are all difficult to grow in large quantities and possess the possibility of carcinogenesis or teratoma formation. Additionally, ectopic tissue differentiation in the hepatic microenvironment could have devastating consequences. Adult stem cells offer the possibility of inducing some clinical benefit, however responses to date have not been profound. This is in part because of the inability of adult stem cells to fully take over hepatic tissue. The present disclosure encompasses immune modulation, whether by adult stem cells, or by immunocytes, for example, as a means of inhibiting liver failure and inducing regression of disease.

In some embodiments, there is a method of treating liver failure in an individual by providing to the individual an effective amount of a fibroblast cell population that has been exposed to immune cells; mesenchymal stem cells, CD34+ cells; very small embryonic like stem cells; Sertoli cells; or a mixture thereof.

In one aspect of the disclosure, fibroblasts that have been primed with enhanced hepatogenic activity are provided to an individual with or at risk for a liver medical condition, such as to accelerate the process of normal liver regeneration, or to protect the process of normal liver regeneration from fibrosis. It has been demonstrated that up to 70% resection of the liver results in complete regeneration (Fausto et al., 2006; Michalopoulos, 2011). However this is in situations where there is no inhibition of hepatocyte proliferation. In these situations, the liver depends on proliferation of oval cells.

In one aspect of the disclosure, primed fibroblasts are administered in order to allow individuals to undergo procedures such as living donor transplantation, two-stage hepatectomies, and/or split liver transplantation, which would be impossible for certain individuals with various liver pathologies or fibrosis.

There are three phases to liver regeneration in which an intervention can be made through the use of fibroblasts that have been pre-activated or "primed" according to this disclosure, the three phases being the following: a) Priming; b) Proliferation; and c) Termination (Fausto et al., 2006). It is important to note that hepatocytes are not terminally differentiated cells but cells that reside in a state of proliferative quiescence. Specifically, they share features with other regenerative cells, such hematopoietic stem cells, in that they are normally in the G0 phase of cell cycle. This is altered during liver regeneration$_{[NRF1]}$. While classical liver regeneration is mediated by hepatocytes (Fausto et al., 2006; Miyaoka and Miyajima, 2013) in certain situations, such as in liver failure, the ability of the hepatocytes to mediate regeneration is limited and liver progenitor cells (LPCs) must carry out the process.

Given the potent regenerative nature of the liver, combined with the possibility that extrahepatic cellular sources may contribute to regeneration, numerous attempts have been made to utilize cellular therapy for treatment of liver failure. The original hepatic cellular therapies involved the administration of allogeneic hepatocytes, which was attempted in animal models more than 30 years ago and is experimentally used clinically. Unfortunately, major hurdles exist that block this procedures from routine use. In specific embodiments of the disclosure stimulation of LPC may be performed by administration of immune cells that provide growth factor support for these cells. In particular embodiments, this includes administration of cord blood mononuclear cells or monocytes that have been cultured to possess augmented HGF and other hepatogenic growth factors.

It is known in the art that MSC are capable of possessing some activity against liver failure, however these have not been harnessed properly in the clinical setting. In embodiments of the disclosure, MSC are manipulated immunologically to induce optimized therapeutic effects for the treatment of liver failure. Although in terms of clinical translation bone marrow MSC are the most advanced, several other sources of MSC are known that possess various properties that may be useful for specific conditions. Bone marrow is also a source for hematopoietic stem cells (HSCs), which have also been used for liver regeneration. Likewise, human placenta is an easily accessible source of abundant MSCs, which can be differentiated in vitro. Finally, MSCs with tissue regenerative abilities can also be isolated from adipose tissue and induced to hepatocytes in large numbers.

Adipose tissue is an attractive alternative to bone marrow as a source of stem cells for treatment of degenerative conditions in general and liver failure specifically (Ishikawa et al., 2010; Puglisi et al., 2011), for the following reasons: a) extraction of adipose derived cells is a simpler procedure that is much less invasive than bone marrow extraction; b) adipose tissue contains a higher content of mesenchymal stem cells (MSC) as compared to bone marrow, therefore shorter in vitro expansion times are needed; and c) MSC from adipose tissue do not decrease in number with aging (Strioga et al., 2012; Yi and Song, 2012; Mosna et al., 2010).

MSCs utilized in methods of the disclosure may be sourced from any tissue, including adipose, hepatic, placenta-derived, umbilical-derived, menstrual blood derived, peripheral blood derived, placental derived and so forth. In one embodiment of the invention, MSC are utilized together with endothelial cells and/or endothelial progenitor cells to accelerate the process of liver regeneration and/or to induce regression of fibrotic tissues.

Indeed it is within the context of the current disclosure to transfect adipose tissue MSCs (AT-MSC) with immune modulatory genes to use them for immune modulation. Selected genes that are useful for the practice of the methods of the disclosure are dependent on the phase of liver regeneration where modulation is sought. For example if increased priming is sought, MSC may be transfected with IL-6, complement components C1q, C1r, C1s, C3a and/or C3b, or TLR activators such as BCG, imiquimod, beta-glucan, hsp65, hsp90, HMGB-1, lipopolysaccharide, Pam3CSK4, Poly I: Poly C, Flagellin, MALP-2, Imidazoquinoline Resiquimod, CpG oligonucleotides, zymozan, peptidoglycan, lipoteichoic acid, lipoprotein from gram-positive bacteria, lipoarabinomannan from mycobacteria, Polyadenylic-polyuridylic acid, monophosphoryl lipid A, single stranded RNA, double stranded RNA, 852A, rintatolimod, Gardiquimod, and lipopolysaccharide peptides. If augmentation of the proliferative phase is sought, MSC may be transfected with growth factors such as HGF, VEGF, or PDGF, for example. If stimulation of antifibrotic mechanisms is required, cells may be transfected with various MMPs, such as MMP-1, MMP-3, MMP-9.

In specific embodiments, bone marrow mononuclear cells (BMMCs) that are used are utilized in the methods encompassed by the disclosure. In particular embodiments, BMMCs are CD133-positive and/or CD34-positive. MMPs are important in liver regeneration not only because of their ability to cleave through fibrotic tissue in order to alter the local environment but also because of their role in angiogenesis, which is important for liver regeneration (Bellayr et al., 2009; Malemud, 2006; Kawai et al., 2012). Accordingly, the combination of agents that stimulate MMP expression together with MSC within the context of this embodiment is as a therapeutic mixture.

Various populations of mesenchymal stem cells may be used for the practice of embodiments of the disclosure. In addition to bone marrow, adipose, or umbilical cord derived mesenchymal stem cells, amniotic membrane mesenchymal stem cells may be utilized as immune modulatory cells. In one specific embodiment, 8×8 cm$^2$ sections of amniotic membrane are obtained. They were washed with 1.0 M phosphate-buffered saline (PBS; pH 7.2) containing 300 IU/ml penicillin and 300 mg/ml streptomycin (Gibco, Grand Island, NY, USA), and are immediately immersed in Dulbecco's modified Eagle's medium (DMEM)-high glucose (Gibco), supplemented with 10% fetal bovine serum (FBS; Gibco), 300 IIU/ml penicillin and 300 mg/ml streptomycin. All samples are processed within 12-15 h after collection. The amniotic membranes are treated with 0.1% collagenase I (Sigma-Aldrich, St Louis, MO, USA) in 1.0M PBS (pH 7.2) and are incubated at 37° C. for 20 min. Each amniotic membrane is washed three times with low-glucose DMEM (Gibco), and the detached cells are harvested after a gentle massage of the amniotic membrane. The cells are centrifuged at 300 g for 10 min at 37° C., and subsequently resuspended in RPMI 1640 medium with 10% FBS, then grown in 25 cm$^2$ flasks at a density of 1×10$^6$ cells/ml. After 24 h incubation, nonadherent cells are removed. The culture medium is replaced every 3 days. Adherent cells are cultured until they reached 80-90% confluence. Cells are subsequently selected based on quality control procedures including purity (eg>90% CD90 and CD105 positive), sterility (e.g., lack of endotoxin and *mycoplasma*/bacterial contamination) and potency (e.g. ability to immune modulate in vitro by suppressing production of inflammatory cytokines such as IFN-gamma). Cells may subsequently be utilized for perilymphatic or intralymphatic administration. The present disclosure contemplates the collection and delivery of a naturally occurring population of MSC derived from i, placental/umbilical cord, bone marrow, skin, or tooth pulp tissue. In accordance with the disclosure, the MSCs may generally be an adherent cell population expressing markers CD90 and CD105 (>90%) and lacking expression of CD34 and CD45 and MHC class II (<5%) as detected by flow cytometry, although other markers described herein may be utilized.

Cell expansion for cells originating from any of the abovementioned tissues above may occur in clean room facilities purposely built for cell therapy manufacture and meeting GMP clean room classification. In a sterile class II biologic safety cabinet located in a class 10,000 clean production suite, cells were thawed under controlled conditions and washed in a 15 mL conical tube with 10 ML of complete DMEM-low glucose media (cDMEM) (Gibco-BRL, Grand Island, N.Y.) supplemented with 20% Fetal Bovine Serum (Atlas) from dairy cattle confirmed to have no BSE % Fetal Bovine Serum specified to have Endotoxin level less than or equal to 100 EU/mL (with levels routinely less than or equal to 10 EU/mL) and hemoglobin level less than or equal to 30 mg/dl (levels routinely less than or equal to 25 mg/dl). The serum lot used is sequestered and one lot was used for all experiments. Cells are subsequently placed in a T-225 flask containing 45 mL of cDMEM and cultured for 24 hours at 37° C. at 5% $CO_2$ in a fully humidified atmosphere. This allowed the MSC to adhere. Non-adherent cells were washed off using cDMEM by gentle rinsing of the flask. This resulted in approximately 6 million cells per initiating T-225 flask. The cells of the first flask were then split into 4 flasks. Cells were grown for 4 days after which approximately 6 million cells per flask were present (24 million cells total). This scheme was repeated but cells were not expanded beyond 10 passages, and were then banked in 6 million cell aliquots in sealed vials for delivery. All processes in the generation, expansion, and product production were performed under conditions and testing that was compliant with current Good Manufacturing Processes and appropriate controls, as well as Guidances issued by the FDA in 1998 Guidance for Industry: Guidance for Human Somatic Cell Therapy and Gene Therapy; the 2008 Guidance for FDA Reviewers and Sponsors Content and Review of Chemistry, Manufacturing, and Control (CMC) Information for Human Somatic Cell Therapy Investigational New Drug Applications (INDs); and the 1993 FDA points-to-consider document for master cell banks were all followed for the generation of the cell products described. Donor cells are collected in sterile conditions, shipped to a contract manufacturing facility, assessed for lack of contamination and expanded. The expanded cells are stored in cryovials of approximately 6 million cells/vial, with approximately 100 vials per donor. At each step of the expansion quality control procedures were in place to ensure lack of contamination or abnormal cell growth.

In specific embodiments, mesenchymal stem cells are optimized to possess heightened immune modulatory properties. In one embodiment this may be performed by exposure of mesenchymal stem cells to hypoxic conditions; specifically, hypoxic conditions can comprise an oxygen level of lower than 10%. In some embodiments, hypoxic conditions comprise up to about 7% oxygen. For example, hypoxic conditions can comprise up to about 7%, up to about 6%, up to about 5%, up to about 4%, up to about 3%, up to about 2%, or up to about 1% oxygen. As another example, hypoxic conditions can comprise up to 7%, up to 6%, up to 5%, up to 4%, up to 3%, up to 2%, or up to 1% oxygen. In some embodiments, hypoxic conditions comprise about 1% oxygen up to about 7% oxygen. For example, hypoxic conditions can comprise about 1% oxygen up to about 7% oxygen; about 2% oxygen up to about 7% oxygen; about 3% oxygen up to about 7% oxygen; about 4% oxygen up to about 7% oxygen; about 5% oxygen up to about 7% oxygen; or about 6% oxygen up to about 7% oxygen. As another example, hypoxic conditions can comprise 1% oxygen up to 7% oxygen; 2% oxygen up to 7% oxygen; 3% oxygen up to 7% oxygen; 4% oxygen up to 7% oxygen; 5% oxygen up to 7% oxygen; or 6% oxygen up to 7% oxygen. As another example, hypoxic conditions can comprise about 1% oxygen up to about 7% oxygen; about 1% oxygen up to about 6% oxygen; about 1% oxygen up to about 5% oxygen; about 1% oxygen up to about 4% oxygen; about 1% oxygen up to about 3% oxygen; or about 1% oxygen up to about 2% oxygen. As another example, hypoxic conditions can comprise 1% oxygen up to 7% oxygen; 1% oxygen up to 6% oxygen; 1% oxygen up to 5% oxygen; 1% oxygen up to 4% oxygen; 1% oxygen up to 3% oxygen; or 1% oxygen up to 2% oxygen. As another example, hypoxic conditions can comprise about 1% oxygen up to about 7% oxygen; about 2% oxygen up to about 6% oxygen; or about 3% oxygen up to about 5% oxygen. As another example, hypoxic conditions can comprise 1% oxygen up to 7% oxygen; 2% oxygen up to 6% oxygen; or 3% oxygen up to 5% oxygen. In some embodiments, hypoxic conditions can comprise no more than about 2% oxygen. For example, hypoxic conditions can comprise no more than 2% oxygen. In specific cases, hypoxic conditions include <5%, <4%, <3%, <2%, <1%, or 0%.

E. In Vitro and In Vivo Reprogramming of Macrophages to an M2 Phenotype Using Fibroblasts Certain embodiments of the disclosure encompass cellular preparations useful for inhibition of inflammation and/or stimulation of angiogenesis in an individual in need thereof. In specific embodiments, cells generated by methods of the disclosure are utilized for inhibition of inflammation and/or stimulation of angiogenesis in an individual in need thereof. In one embodiment, culture of fibroblast cells (and/or one or more agents) with monocytes and/or monocytic progenitors results in immune cells useful for inhibition of inflammation and/or stimulation of angiogenesis. In one embodiment, M2 macrophages are generated by culture of certain cells with fibroblast cells and utilized as therapeutic cells for stimulating angiogenesis and inhibition of inflammation and characterized. In certain embodiments, the therapeutic cells are denoted by expression of arginase and/or having reduced ability to produce nitric oxide (NO). Although in some cases the cells produced by the method are tested for expression of arginase and/or a reduction in the ability to produce NO prior to delivery to the individual, in other cases they are not.

Certain embodiments pertain to the matter of angiogenesis stimulation, and in specific embodiments the disclosure pertains to generation of angiogenesis using macrophages produced from culture of monocytes and/or monocytic progenitor cells with fibroblast populations, including certain fibroblasts.

In one embodiment, fibroblasts are used to enhance generation of M2 macrophages when the fibroblasts are co-cultured with monocytes and/or monocytic precursors (which may also referred to as monocytic progenitors), and thereafter M2 macrophages produced from the monocytes and/or monocytic precursors are useful in a variety of settings therapeutically. For example, M2 macrophages may be utilized for reduced myocardial injury after infarction, and such M2 macrophages may suppress inflammation, they may stimulate angiogenesis, and/or they may inhibit M1 macrophage formation (M1 macrophages are associated with pathological cardiac remodeling and progression to heart failure (Liu et al., 2015; He et al., 2015). Accordingly, in one aspect of the disclosure, M2 macrophages are generated in vitro and are administered systemically or locally into an individual suffering from myocardial infarction or at risk thereof.

In some embodiments of the disclosure, fibroblast-cultured M2 cells are administered into an area in an individual in need of cardiac repair together with one or more angiogenic growth factors, such as TPO, SCF, IL-1, IL-3, IL-6, IL-7, IL-11, flt-3L, G-CSF, GM-CSF, Epo, FGF-1, FGF-2, FGF-4, FGF-20, IGF, EGF, NGF, LIF, PDGF, BMPs, activin-A, VEGF, or a combination thereof.

In some embodiments of the disclosure, fibroblasts are co-cultured with immune cells of any kind (including monocytes, monocyte progenitor cells, PBMCs, MSCs, and so forth) in the presence of at least PGE-2. In further embodiments, the concentration of PGE-2 exposed to the cells is approximately between 1-10,000 ng/mL, 7500 ng/mL, 1-5000 ng/mL, 1-2500 ng/mL, 1,000 ng/mL, 1-750 ng/mL, 1-500 ng/mL, 250-10000 ng/mL, 250-7500 ng/mL, 250-5000 ng/mL, 500-10000 ng/mL, 500-5000 ng/mL, 500-2500 ng/mL, 1000-10000 ng/mL, 1000-7500 ng/mL, 1000-5000 ng/mL, 5000-10000 ng/mL, 5000-7500 ng/mL, and so forth. In some embodiments, the concentration of PGE-2 is approximately 1 ng/mL, 5 ng/mL, 10 ng/mL, 20 ng/mL, 25 ng/mL, 50 ng/mL, 75 ng/mL, 100 ng/mL, 125 ng/mL, 150 ng/mL, 200 ng/mL, 250 ng/mL, 500 ng/mL, 750 ng/mL, 1,000 ng/mL, 2,000 ng/mL, 2,500 ng/mL, 5,000 ng/mL, 7,500 ng/mL, or 10,000 ng/mL. In specific embodiments, the fibroblasts are co-cultured with immune cells in the presence of PGE-2 for a period of at least or no more than or no less than 1-72, 1-50, 1-25, 25-72, 25-50, or 50-72 hours, for example. In some embodiments, the fibroblasts are co-cultured with immune cells in the presence of PGE-2 for a period of approximately 1 hour, 2 hours, 3 hours, 4 hours, 5 hours, 6 hours, 7 hours, 8 hours, 9 hours, 10 hours, 12 hours, 14 hours, 16 hours, 18 hours, 20 hours, 22 hours, 24 hours, 26 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours. In certain embodiments the co-culturing of fibroblasts and immune cells with PGE-2 endows the combined culture the ability to generate synergistic amounts of VEGF, PDGF-BB, and/or EGF, which is beneficial for cardiac regeneration in at least some aspects. In another embodiment, the co-culture of fibroblasts and immune cells in the presence of PGE-2 generates a therapeutic population of M2 macrophages that synergize with the fibroblasts to induce cardiac regeneration. In certain embodiments, the combination of cultured fibroblasts and immune cells are administered to the patient of at least or no more than 3 days to 15 days after the patient suffers myocardial infarction. In certain embodiments, the combination of cultured fibroblasts and immune cells are administered to the patient approximately 3 days, 4 days, 5 days, 6 days, 7 days, 8 days, 9 days, 10 days, 11 days, 12 days, 13 days, 14 days, or 15 days after the patient suffers myocardial infarction.

Certain embodiments provide methods of treating a patient subsequent to a myocardial infarct comprising the steps of optionally obtaining fibroblasts; culturing fibroblasts with immune cells in order to gain cardiac-reparative properties; and administering the fibroblast-immune cell combination into a patient having suffered an infarct or suspected to have had or be having or will have an infarct. The cells could be from an autologous or allogeneic source with respect to an individual. The fibroblasts could be derived from tissue selected from the group consisting of adipose, dermal, umbilical cord, foreskin, placental, omental, and a combination thereof. In some embodiments, culturing the fibroblast-immune cell combination comprises culturing in the presence of at least PGE-2. In further embodiments, the concentration of PGE-2 supplied to the cells is approximately between 1-10,000 ng/mL. In further embodiments, the concentration of PGE-2 is between 1-1, 000 ng/mL. In some embodiments, the concentration of PGE-2 is approximately 1 ng/mL, 5 ng/mL, 10 ng/mL, 20 ng/mL, 25 ng/mL, 50 ng/mL, 75 ng/mL, 100 ng/mL, 125 ng/mL, 150 ng/mL, 200 ng/mL, 250 ng/mL, 500 ng/mL, 750 ng/mL, 1,000 ng/mL, 2,000 ng/mL, 2,500 ng/mL, 5,000 ng/mL, 7,500 ng/mL, or 10,000 ng/mL. In specific embodiments, the fibroblasts are co-cultured with immune cells in the presence of PGE-2 for a period of at least or no more than 1 hour to 72 hours. In some embodiments, the fibroblasts are co-cultured with immune cells in the presence of PGE-2 for a period of approximately 1 hour, 2 hours, 3 hours, 4 hours, 5 hours, 6 hours, 7 hours, 8 hours, 9 hours, 10 hours, 12 hours, 14 hours, 16 hours, 18 hours, 20 hours, 22 hours, 24 hours, 26 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, or 72 hours. In certain embodiments the co-culturing of fibroblasts and immune cells with PGE-2 endows the combined culture the ability to generate synergistic amounts of VEGF, PDGF-BB, and EGF, which is beneficial for cardiac regeneration. In another embodiment, the co-culture of fibroblasts and immune cells in the presence of PGE-2 generates a therapeutic population of M2 macrophages that synergize with the fibroblasts to induce cardiac regeneration. In certain embodiments, the combination of cultured fibroblasts and immune cells are administered to the patient of at least or no more than 3 days and 15 days after the patient suffers myocardial infarction. In certain embodiments, the combination of cultured fibroblasts and immune cells are administered to the patient approximately 3 days, 4 days, 5 days, 6 days, 7 days, 8 days, 9 days, 10 days, 11 days, 12 days, 13 days, 14 days, or 15 days after the patient suffers myocardial infarction.

The disclosure encompasses the co-culture of fibroblasts with immune cells that allows for M2 macrophage cells to be generated, however, optimal generation may be apparent after culture in the presence of at least PGE-2, in at least some cases. The uses of the fibroblast-immune co-cultured cells can be applied to areas in which M2 cells have been applied. For example, it has been shown that mechanistically, M2 macrophages are associated with reduced myocardial injury after infarction by stimulation of angiogenesis (Dayan et al., 2011), and this is incorporated by reference. Elegant studies in mice genetically deficient for the M2 stimulatory cytokine interleukin 13 have shown increased infarct size and reduction in post-infarct healing in mice deficient of M2 macrophages. These results were replicated in another study in which depletion of M2 macrophages was accomplished by deficiency in the CSF-1 receptor signaling pathway. Treatments that exacerbate heart failure post-infarct decrease M2 macrophage accumulation. Additionally, therapies that induce acceleration of healing and angiogenesis have been shown in many contexts to stimulate generation of M2 macrophage. For example, administration of mesenchymal stem cells has been shown to induce a decrease in M1 macrophages and an increase in M2 macrophages, which correlates with improvement in post infarct recovery by stimulation of angiogenesis. Mechanistically, M2 macrophages are known to suppress inflammation, as well as to stimulation angiogenesis, which is an important aspect of post-infarct healing. Additionally, M2 macrophages inhibit M1 macrophage formation. This is important as M1 macrophages are associated with pathological cardiac remodeling and progression to heart failure. Accordingly, in one aspect of the invention, M2 macrophages are generated in vitro and administered systemically, or locally into a patient suffering from myocardial infarction.

Embodiments of the disclosure encompass methods of treating or preventing or delaying the onset and/or severity of a myocardial infarction for an individual in need thereof. Methods may comprise delivering a therapeutically effective amount of fibroblasts to the individual, including locally to the heart. In some cases, the fibroblasts have been modified. In specific embodiments, fibroblasts are exposed to a sufficient amount of immune cells, such as monocytes (autologous or allogeneic, for example) under conditions to endow the fibroblasts and/or the immune cells monocytes with cardiac-reparative properties; in specific cases the fibroblasts and/or immune cells are provided to an individual in need thereof. The individual may be in need for having had a myocardial infarction, presently having a myocardial infarction, or at risk of having a myocardial infarction because of personal or family history of heart disease including having had a myocardial infarction. In cases wherein the individual has already had a myocardial infarction, the fibroblasts and/or immune cells may be provided to repair the heart from the damage cause in the first myocardial infarction and/or to prevent or reduce in severity (or delay the onset of) a second or more myocardial infarction(s).

In cases wherein fibroblasts and/or immune cells (whether or not they have been exposed to one another in culture as described herein) are provided to an individual for a cardiac condition, they may be administered intramyocardially, administered into the infarct related artery by balloon catheter, or administered in retrograde using balloon collusion to the coronary sinus, for example.

In particular embodiments, the immune cells for the culture may be monocytes that are obtained by plastic adherence, obtained by flow cytometric purification for the marker CD14, or obtained by magnetic activated sorting (MACS) purification for the marker CD14. The fibroblasts and monocytes may be cultured at a ratio of approximately 1 to 1. The monocytes may express arginase activity after tissue culture with the fibroblasts.

Certain embodiments of the disclosure provide methods and compositions, including therapeutic compositions, for treating inflammation of any kind in the body. Particular embodiments provide methods and therapeutic compositions for treating myocardial infarction and/or acceleration of post-infarction healing processes by inducing an M2 polarization of macrophages. Methods include those comprising administering a composition comprising fibroblasts to one or more sites of the inflammation and/or macrophages, and the composition may further comprise one or more proteins selected from the group consisting of interleukin-4, interleukin-10, IL-1Ra, TGF-beta, sTNF-RII, IGF-I, EGF, HGF, PDGF-AB, PDGF-BB, VEGF, and sIL-1RII, and a combination thereof. In specific embodiments, the concentration of each protein in the composition is greater than the concentration of the protein in normal blood, together with the presence of fibroblasts. In specific embodiments, the concentration of the protein in the composition is greater than the concentration of the protein in normal blood, and in particular aspects the protein(s) are administered in the presence of fibroblasts. The compositions may also comprise white blood cells, platelets, concentrated plasma, bone marrow aspirate, adipose tissue, fractions thereof, and a combination thereof. In specific embodiments, a protein solution is generated by obtaining a cytokine cell suspension from a subject in need of treatment and fractionating the cytokine cell suspension to produce an autologous protein solution comprising IL-4, IL-10, IL-1Ra, and/or TGF-beta, which are administered together with fibroblasts. The fibroblasts may be allogeneic to the recipient individual or they may be autologous to the individual. The composition may then be administered to the site of inflammation in a human or other animal subject. In a specific case, fractionating comprises placing blood in a container with a separator operable to separate the blood into two or more fractions; and centrifuging the separator to generate a platelet-rich plasma fraction. The platelet-rich plasma may be contacted with a solid extraction material.

F. Stimulation of Angiogenesis and/or Acceleration of Wound Healing with Fibroblast-Reprogrammed Autologous T Cells Disclosed are methods of stimulating angiogenesis and/or acceleration of wound healing by administration of certain cells to an individual in need thereof. In particular embodiments, the individual receives an effective amount of autologous T cells that are reprogrammed by fibroblasts (including allogeneic, for example) under conditions capable of endowing the T cells with an inhibition of Th1 cytokine profile and augmentation of Th2/Th3 profiles, as well as inducing a genetic program in the T cells to allow the responding T cells to initiate expression of a pro-angiogenic gene program, wherein the pro-angiogenic gene program comprises at least in some cases of nuclear translocation of HIF-1 alpha, in some cases. In one embodiment, novel means of treating one or more ischemic conditions in the body are provided.

In particular embodiments regarding the field of angiogenesis, the disclosure pertains to stimulation of angiogenesis using immune cells, including endowing T cells of the immune system with the ability to stimulate angiogenesis by a prior co-culturing of the T cells with fibroblast cells (for example, allogeneic cells). Such T cells may be referred to as activated T cells.

Embodiments of the disclosure encompass the use of allogeneic fibroblasts to endow a proangiogenic phenotype to T cells by means of a co-culture system. In some embodiments, the co-culture comprises fibroblast cells, including adherent fibroblast cells, together with non-adherent cellular populations that comprise T cells or with purified T cells. In one embodiment of the disclosure, fibroblasts are cultured in a suitable tissue culture media, which may be selected from known media such as Roswell Park Memorial Institute (RPMI-1640), Dublecco's Modified Essential Media (DMEM), Eagle's Modified Essential Media (EMEM), Optimem, Iscove's Media, or combinations thereof together with fetal calf serum, and/or platelet lysate and/or platelet rich plasma, at a concentration of approximately 10% by volume. In some cases, the fibroblasts are allowed to adhere to a substrate (that may occur naturally), and subsequently T cells are added. In one particular embodiment the T cells are part of a population of peripheral blood mononuclear cells. The fibroblasts and T cells are cultured together for a particular time period, such as between 1 hour to two weeks. In specific embodiments they are cultured together for at least about or no more than about 1, 2, 3, 4, 5, 6, 7, 8, 9, 10, 11, 12, 13, 14, 15, 16, 17, 18, 19, 20, 21, 22, 23, or 24 hours or 1, 2, 3, 4, 5, 6, 7 days or 1 or 2 weeks. In specific embodiments the fibroblasts and T cells are cultured together for about 48 hours. Subsequently, non-adherent T cells and cellular populations comprising T cells are extracted and utilized for administration for stimulation of angiogenesis. Without being restricted to mechanism, the T cells that have been produced by tissue culture with fibroblasts may stimulate angiogenesis through directly acting as mitogens for endothelial cells and/or may stimulate angiogenesis by inducing production of pro-angiogenic cytokines in cells of the body, for example, in cells of the blood.

In some embodiments, T cells are extracted from co-culture with the fibroblasts by removal of non-adherent cells and, in the absence of further processing, in some cases T cells are further purified by one or more assays. In some cases, the non-adherent cells are further purified with the use of magnetic activated cell sorting (MACS). In situations where MACS is used, selection for one or more T cell markers is performed. In one embodiment, the T cell marker CD25 is used to select activated T cells, following which the CD25+ T cells are administered for treatment of a medical condition, such as ischemic disease, wounds, etc., in an individual in need thereof. In a particular embodiment, treatment of ischemic disease is performed by intramuscular administration of the T cells following culture of the T cells with fibroblasts. Ischemic disease includes at least critical limb ischemia, cardiac ischemia, lumbar ischemia, and intestinal ischemia. In other embodiments, T cells are administered to accelerate wound healing in an individual with a wound, such as a burn, cut, abrasion, laceration, puncture, avulsion, or a combination thereof.

In some embodiments, following exposure to fibroblasts the T cells are administered to an individual as part of a biodegradable implant, although in alternative embodiments the implant is not biodegradable or the T cells are administered in the absence of an implant. In specific embodiments, the implant comprises T cells and one or more angiogenic factors released by the T cells (including following implantation of the implant). In this type of an embodiment, the implant may comprise a carrier that may be chosen so as to remain within the implanted site for a prolonged period and slowly release the angiogenic factor(s) from the T cells contained therein to the surrounding environment. This mode of delivery allows the angiogenic factor(s) to remain in therapeutically effective amounts within the site for a prolonged period. By providing the angiogenic factor(s) within a carrier, the advantage of releasing the angiogenic factor(s) directly into the target area is realized. In some embodiments, the carrier for the implant is provided in an injectable form. Injectability allows the carrier to be delivered in a minimally invasive method, and the delivery may be percutaneous, intramuscular, subcutaneous, intraomental, intraventricular, and/or intrathecal, for example. In some embodiments, the injectable carrier is a gel. In others, the injectable carrier comprises hyaluronic acid (HA), as an example.

In some embodiments for the T cell graft, or implant, the carrier comprises a porous matrix having an average pore size of at least 25 micrometers. In certain embodiments, the porous matrix has an average pore size of between 25 micrometers and 110 micrometers. When the average pore size is in this range, in specific embodiments the porous matrix will also act as a scaffold for in-migrating of cells, such as monocytes, endothelial progenitor cells, myeloid progenitor cells, and/or mesenchymal stem cells, capable of becoming cells that stimulate angiogenesis in the targeted area. Numerous examples of organic materials that can be used to form the porous matrix are known to one of skill in the art, including but not limited to, collagen, polyamino acids, or gelatin. The collagen source may be artificial (i.e., recombinant), or autologous, or allogenic, or xenogeneic relative to the mammal receiving the implant. The collagen may also be in the form of an a telopeptide or telopeptide collagen. Additionally, collagens from sources associated with high level of angiogenesis, such as placental-derived collagen, may be used. Examples of synthetic polymers that can be used to form the matrix include, but are not limited to, polylactic acids, polyglycolic acids, or a combination of polylactic/polyglycolic acids. The matrix material may be comprised of one or more resorbable polymers and/or one or more non-resorbable polymers. One of skill in the art will appreciate that the terms porous or semi-porous refer to the varying density of the pores in the matrix. Scaffold structures may be used in some embodiments for anchoring or enhancing or substantially causing adhesion between the implant and anatomical structures (such anatomical structures may be bone, cartilage, nerve, tendon, and/or ligament, for example). In some embodiments the means of adhering the implant to the anatomical structure(s) may be a gel. The gel together with the implant can be injected to the graft site, in some embodiments under arthroscopic fluid conditions. The gel can be a biological or synthetic gel formed from a bioresorbable or bioabsorbable material that in at least some cases has the ability to resorb in a timely fashion in the body environment. Suitable scaffold agents are also known to one of skill in the art and may include hyaluronic acid, fibrin glue, fibrin clot, collagen gel, alginate gel, gelatin-resorcin-formalin adhesive, mussel-based adhesive, dihydroxyphenylalanine-based adhesive, chitosan, transglutaminase, poly (amino acid)-based adhesive, cellulose-based adhesive, polysaccharide-based adhesive, synthetic acrylate-based adhesives, platelet rich plasma (PRP) gel, platelet poor plasma (PPP) gel, clot of PRP, clot of PPP, Matrigel, Monostearoyl Glycerol co-Succinate. (MGSA), Monostearoyl Glycerol co-Succinate/polyethylene glycol (MGSA/PEG) copolymers, laminin, elastin, proteoglycans, poly(N-isopropylacrylamide), poly(oxyalkylene), a copolymer of poly(ethylene oxide)-poly(propylene oxide), poly(vinyl alcohol) and a combination thereof.

In some embodiments, a pliable scaffold is utilized so as to allow the scaffold to adjust to the dimensions of the target site of implantation. For instance, the scaffold can comprise a gel-like material or an adhesive material, as well as a foam or mesh structure. In certain embodiments, the scaffold is a bioabsorbable material. The scaffold can be formed from a polymeric foam component having pores with an open cell pore structure. The pore size can vary, but in particular cases the pores are sized to allow tissue or angiogenic ingrowth. In some embodiment, the pore size is in the range of about 40 to 900 micrometers. The polymeric foam component can, optionally, comprise a reinforcing component, such as for example, woven, knitted, warped knitted (i.e., lace-like), non-woven, and/or braided structures. In some embodiments, where the polymeric foam component comprises a reinforcing component, the foam component can be integrated with the reinforcing component such that the pores of the foam component penetrate the mesh of the reinforcing component and interlock with the reinforcing component. In some embodiments, one or more angiogenic growth factor(s) are predominantly released from a sustained delivery device by its diffusion through a sustained delivery device (such as through a polymer). In others, the angiogenic factor(s) are predominantly released from a sustained delivery device by the biodegradation of the sustained delivery device (such as biodegradation of a polymer). In some embodiments, the implant comprises a bioresorbable material whose gradual erosion causes the gradual release of the angiogenic factors. In some embodiments, the implant comprises a bioresorbable polymer. In particular embodiments, the bioresorbable polymer has a half-life of at least one month. Accordingly, in some embodiments, the implant comprises the co-polymer poly-DL-lactide-co-glycolide (PLG) admixed with one or more angiogenic factor(s).

In some embodiments, the implant is comprised of a hydrogel, including consisting of or consisting essentially of a hydrogel. Hydrogels can also be used to deliver one or more angiogenic factor(s) in a time-release manner to one or more areas of hypoperfusion. A "hydrogel", as defined herein, is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels may rapidly solidify to keep the angiogenic factor(s) in proximity to either the blood vessel causative of hypoperfusion or the area associated with hypoperfusion. In some embodiments, the hydrogel is a fine, powdery synthetic hydrogel. Suitable hydrogels exhibit an optimal combination of such properties as compatibility with the matrix polymer of choice, and biocompatibility. The hydrogel can include one or more of the following: polysaccharides, proteins, polyphosphazenes, poly(oxyethylene)-poly(oxypropylene) block polymers, poly(oxyethylene)-poly(oxypropylene) block polymers of ethylene diamine, poly(acrylic acids), poly(methacrylic acids), copolymers of acrylic acid and methacrylic acid, poly(vinyl acetate), and/or sulfonated polymers.

In particular embodiments, the disclosure includes T cells capable of producing one or more angiogenic growth factors. In certain embodiments, the T cells (including CD4, CD8, gamma delta, NK T cells, or mixtures thereof) may be generated by the steps comprising a) providing a fibroblast population (placental, fetal, neonatal or adult or mixtures thereof, for example); b) contacting the fibroblast population with an allogeneic population of cells, the population comprising T cells; and c) culturing the allogeneic fibroblasts with the allogeneic cell population comprising T cells for a time sufficient and under sufficient conditions to endow the T cells with one or more angiogenic characteristics, such as the ability to produce one or more angiogenic growth factors, including an ability that is lacking in T cells that were not previously exposed to fibroblasts. Examples of angiogenic growth factors include at least (a) PDGF-BB; (b) angiopoietin; (c) VEGF; (d) EGF; (e) FGF-1; (f) FGF-2; (g) FGF-5; (h) MMP3; (i) MMP9; and/or (j) stromelysin.

In some cases, the co-culture of the fibroblasts and T cells comprises one or more other agents, such as one or more immunomodulatory agents. In specific embodiments, the immunomodulatory agent comprises FAS ligand, IL-2R, IL-1 Ra, IL-2, IL-4, IL-8, IL-10, IL-20, IL-35, HLA-G, PD-L1, I-309, IDO, iNOS, CD200, Galectin 3, sCR1, arginase, PGE-2, aspirin, atorvastatin, fluvastatin, lovastatin, pravastatin, rosuvastatin, simvastatin, pitavastatin, n-acetylcysteine, rapamycin, IVIG, naltrexone, TGF-beta, VEGF, PDGF, CTLA-4, anti-CD45RB antibody, hydroxychloroquine, leflunomide, auranofin, dicyanogold, sulfasalazine, methotrexate, glucocorticoids, etanercept, adalimumab, abatacept, anakinra, certolizumab, Etanercept-szzs, golimumab, infliximab, rituximab, tocilizumab, cyclosporine, IFN-gamma, everolimus, rapamycin, or a combination thereof.

In specific embodiments, the fibroblasts and the population comprising T cells are cultured in a liquid media, such as Roswell Park Memorial Institute (RPMI-1640), Dublecco's Modified Essential Media (DMEM), Eagle's Modified Essential Media (EMEM), Optimem, Iscove's Media, or combinations thereof. In specific cases, one or more additional agents are added to the media, such as human platelet rich plasma, platelet lysate, umbilical cord blood serum, autologous serum, human serum, serum replacement, or combinations thereof. In some cases, the serum replacement comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of the volume of a media composition. In specific embodiments, human platelet rich plasma comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of the volume of a media composition. In some cases, platelet lysate comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of the volume of a media composition. In some cases, umbilical cord blood serum comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of the volume of a media composition. In certain cases, autologous serum comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of the volume of a media composition. In particular cases, human serum comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of the volume of a media composition.

In particular embodiments, IL-2, IL-3, IL-7, and/or IL-15 are included in the tissue culture with the fibroblasts and a population of cells that comprises T cells (for example, PBMCs) to enhance T cell proliferation, and in specific cases IL-2 may be added at a concentration ranging from about 10 picograms per ml of tissue culture media to about 1 microgram per ml of tissue culture media.

In some cases, one or more certain agents are exposed to the tissue culture to induce expression of one or more particular gene products in the T cells. For example, in some cases anti-CD3 and/or anti-CD28 antibodies are exposed to the T cells to induce expression of CD25 in the T cells. In specific cases, anti-CD3 and/or anti-CD28 antibodies are immobilized to a solid surface such as beads and/or tissue culture flasks, for example, and also exposed to the tissue culture media at a concentration and time sufficient to induce T cell expression of CD25, CD69, and/or CTLA4.

G. Optimization of Dendritic Cell Maturation Using Stressed Fibroblasts

In some embodiments, the disclosure pertains to the field of immunotherapy, more specifically, the disclosure pertains to the use of antigen presenting cells for induction of immunity towards specific antigens, more specifically, the disclosure pertains to the use of stressed fibroblasts (stressed being any condition that is not physiological) for augmenting immunogenicity of dendritic cells. Specific embodiments of the disclosure utilize properties of stressed fibroblasts to induce dendritic cell maturation.

Methods of increasing antigen presenting ability of dendritic cells are provided in which certain cells are cultured with fibroblasts that have already been stressed (although the fibroblasts may be stressed in the presence of the dendritic cells). In one embodiment of the disclosure, monocytes are cultured under conditions suitable for dendritic cell differentiation, and subsequently cultured with stressed fibroblasts, for example to induce maturation and optimized antigen presenting activity of dendritic cells produced from the monocytes. In one embodiment the dendritic cells are allogeneic to the fibroblasts. In another embodiment, the dendritic cells are autologous to the fibroblasts, although they may be allogeneic in specific cases.

The present embodiment provides the use of stressed fibroblast cells for stimulation of dendritic cell maturation. Stimulation of dendritic cell maturation includes enhancement of expression in the dendritic cells of costimulatory molecules such as CD40, CD80, and CD86, as well as enhancement of the ability to increase activation of T cells, in at least some cases. In one embodiment, the disclosure encompasses exposure of fibroblasts to nonphysiological conditions for sufficient duration to induce expression of one or more heat shock proteins and/or alter growth factor production activity of the fibroblasts, and exemplary growth factors include EGF, FGF-1, FGF-2, FGF-5, VEGF, PDGF, PDGF-BB, angiopoietin, IGF-1 and/or HGF. In one embodiment the fibroblasts are allogeneic to the dendritic cells, and in another embodiment the fibroblasts are autologous to the dendritic cells.

Exposure to stress for the fibroblasts may be performed using various means known in the art. In one embodiment, fibroblasts are exposed to hyperthermia, and the hyperthermia may comprise an elevation of temperature for at least or no more than 1 to 8 hours, and in some cases the elevation in temperature is at least or no more than 39, 40, 41, or 42° Celsius. In specific cases, cells are exposed to hyperthermia for about 4 hours at a temperature of approximately 40° Celsius. In some embodiments, dendritic cells are generated from peripheral blood mononuclear cells (PBMC) of individuals and CD8 cells are purified using magnetic activated cell sorting (MACS) from PBMC (for example). In other embodiments, CD8 T cells are extracted from tumor infiltrating lymphocytes.

In one aspect of the disclosure, dendritic cells are isolated according to conventional protocols and are exposed to stressed fibroblasts. In specific embodiments, a mechanism(s) behind stimulating dendritic cell activation is to generate the fibroblast in a manner to mimic innate immune system-activating signals, which are described as "danger" signals, such as toll like receptor (TLR) agonists that are associated with tissue injury or pathogenic threat. The present embodiment focuses on the activation of dendritic cells because, in contrast to other antigen presenting cells such as the macrophage or the B cell, dendritic cells exhibit magnitudes of higher ability to stimulate T cell responses both in antigen specific systems as well as in polyclonal experiments, such as in mixed lymphocyte reaction (Banchereau and Steinman, 1998). It is known that in peripheral tissues (outside of lymph nodes), DCs capture antigens through several complementary mechanisms including phagocytosis and receptor mediated endocytosis. Immature DC are known to possess high degree of phagocytic activity and low levels of antigen presenting activity. Normally, DCs in peripheral tissues are immature. These immature DCs have the ability to efficiently capture antigens; they can accumulate MHC class II molecules in that late endosome-lysosomal compartment; they can express low levels of co-stimulatory molecules; they can express a unique set of chemokine receptors (such as CCR7) that allow their migration to lymphoid tissues; and they have a limited capacity for secreting cytokines (Trombette and Mellman, 2005). The disclosure encompasses means of mimicking the natural process of DC activation that occurs in vivo, but in the disclosure encompasses the induction of this ex vivo.

The disclosure provides means of generating activated DC, such as by exposure to one or more stimulatory signals that are expressed on stressed fibroblasts, such as a toll like receptor agonists, including heat shock protein, for example hsp90 and/or hsp70. The exposure to the stressed fibroblasts causes DC to possess decreased phagocytic activity and allows the DC to then migrate into the draining lymph nodes through the afferent lymphatics, in at least some cases. During the trafficking process, DC degrade ingested proteins into peptides that bind to both MHC class I molecules and MHC class II molecules. This allows the DC to: a) perform cross presentation in that they ingest exogenous antigens but present peptides in the MHC I pathway; and b) activate both CD8 (via MHC I) and CD4 (via MHC II). Interestingly, lipid antigens are processed via different pathways and are loaded onto non-classical MHC molecules of the CD1 family (Itano and Jenkins, 2003).

The disclosure encompasses means of inducing maturation of DC, and in some cases the maturation is associated with the downregulation of antigen-capture activity, the increased expression of surface MHC class II molecules and costimulatory molecules, the ability to secrete cytokines, as well as the acquisition of CCR7, which allows migration of the DC into the draining lymph node. The ligation of the costimulatory receptor CD40 (also known as TNFRSF5) is an essential signal for the differentiation of immature DCs into fully mature DCs that are able to launch adaptive T cell-mediated immunity (Caux et al., 1994). However, DC maturation alone does not result in a unique DC phenotype. Instead, the different signals that are provided by different microbes or viruses either directly or through the surrounding immune cells induce DCs to acquire distinct phenotypes that eventually contribute to different immune responses. Indeed, DC maturation varies according to different microbes because microbes express different pathogen associated molecular patterns (PAMPs) that trigger distinct DC molecular sensors, which are called pattern recognition receptors (PPRs). Strikingly, although most microbes activate DCs, a few can block DC maturation through various pathways (Pulendran et al., 2001). Tissue-localized DCs can also be polarized into distinct phenotypes by the products released from surrounding immune cells that respond to injury. For example, γd-T cells and NK cells release interferon-γ (IFNγ), mast cells release pre-formed IL-4 and TNF, pDCs secrete IFNa, stromal cells secrete IL-15 and thymic stromal lymphopoietin (TSLP). Accordingly, in one aspect of the disclosure, stressed fibroblast/immature dendritic cell progenitors are cultured in the presence of additional cells and/or cell-produced factors such as IFN-gamma, IL-4 TNF, IFN-alpha, IL-15 and/or TSLP to mimic an in vivo immune response.

These cytokines induce the differentiation of progenitor cells or of precursor cells such as monocytes into distinct inflammatory DCs that yield unique types of T cells. On interaction of CD4 and CD8 T cells with DC, these cells can subsequently differentiate into antigen-specific effector T cells with different functions. CD4 T cells can become T helper 1 (TH1) cells, TH2 cells, TH17 cells or T follicular helper (T) cells that help B cells to differentiate into antibody-secreting cells, as well as Treg cells. Naive CD8 T cells can give rise to effector cytotoxic T lymphocytes (CTLs). An interesting activity of DC is that in addition to stimulating immune responses through the activation of naïve T cells, DC are also able to act as inhibitory cells. This is either directly, through inhibition of T cell activation and/or induction of T cell anergy (Lutz et al., 2000), as well as indirectly through stimulation of T regulatory (Treg) cells (Turnquist and Thomson, 20908; Pletinckx et al, 2011). It is interesting that not only Treg cells, but also anergic T cells are capable of inhibiting DC activation (Frasca et al., 2002; Vendetti et al., 2000; Veldhoen et al., 2006), thus possibly stimulating a self-maintaining immune regulatory feedback loop. In fact, such a scenario has been previously reported where Treg stimulate immature DC and the immature DC in turn stimulate production of new Treg cells (Guillot et al., 2003; Roelofs-Haarhuis et al., 2003).

Numerous types of DC-based therapies may be generated upon exposure of stressed fibroblasts to increase activation of DC. Such therapies include Provenge (sipuleucel-T), which is approved by the FDA for treatment of androgen resistant prostate cancer and is a cellular product derived from autologous peripheral blood mononuclear cell (PBMC) derived dendritic cells that have been grown using a chimeric protein comprised of GM-CSF and the prostate specific antigen, prostatic acid phosphatase (Sternberg et al., 2014; Gomela et al., 2014); DCs pulsed with particular peptides, such as PSM-P1, or -P2; DC that were pulsed with a GM-CSF-PAP fusion protein; PSA protein pulsed DC (Barrou et al., 2004); DCs loaded with antigenic peptides derived from prostate stem cell antigen (PSCA(14-22)), prostatic acid phosphatase (PAP(299-307)), prostate-specific membrane antigen (PSMA(4-12)), and/or prostate-specific antigen (PSA(154-163)) (Waeckerle-Men et al., 2006), and so forth.

In one embodiment of the disclosure, there are methods of inducing dendritic cell maturation (mature dendritic cells such as myeloid dendritic cells or lymphoid dendritic cells), comprising the steps of (a) obtaining a dendritic cell in an immature state (myeloid dendritic cells or lymphoid dendritic cells); and (b) culturing the immature dendritic cell in the presence of a fibroblast cell population that has been stressed (the fibroblasts may be obtained from any tissue, including at least dermis, penile foreskin, adipose tissue, placental tissue, and so forth). In specific embodiments, myeloid dendritic cells in an immature state express high levels of CD83 and/or IL-10 and/or express low levels of IL-12, CD40, CD80, and/or CD86. In specific embodiments, immature myeloid dendritic cell expresses high levels, such as more than 50% compared to an erythrocyte, of CD83, IL-10, or both. In specific embodiments, immature dendritic cells are a poor stimulator of mixed lymphocyte reaction and/or a poor stimulator of T cell activation. In specific embodiments the CD8 T cells are autologous or allogeneic to the dendritic cells and/or the fibroblasts. In specific cases, the immature dendritic cell includes monocytes or myeloid progenitor cells.

The fibroblasts may be exposed to one or more stressors to result in stressed fibroblasts, and any suitable stressor may be utilized. In specific embodiments, the stressor is hyperthermia, and in some cases, the hyperthermia includes exposure to an elevated temperature for a duration capable of inducing expression of heat shock protein 90. The hyperthermia may be elicited upon exposure to a temperature of 40° Celsius for at least or no more than about 1, 2, 3, 4, 5, 6, 7, or 8 hours. In some cases hyperthermia and another stressor are utilized, such as serum deprivation, although in some cases serum deprivation is used without hyperthermia. In specific embodiments, the stressor includes exposure to serum deprivation for at least or no more than about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours. In specific cases, the stressor is exposure to serum deprivation for 24 hours or exposure to serum deprivation for 12-48 hours.

H. Methods of Expanding CD8 T Cells Using Allogeneic Fibroblast Feeder Cells T cells, originally derived from the thymus, have been shown to play a critical role in functioning of the immune system. Broadly speaking, T cells are divided into T helper cells, with express the marker CD4 and T cytotoxic cells, which express the marker CD8. In the field of cancer immunotherapy, studies have shown that infiltration of CD8 T cells into the tumor correlates with increased survival. Unfortunately, tumors protect themselves from immune mediated destruction through the secretion of immunosuppressive factors (Wile et al., 1984; Medoff et al., 1986; Stratton and DiSaia et al., 1982; O'Mahony et al., 1993; Spellman et al., 1996; Avradopoulos et al., 1997; Young et al., 1997; Pope, 1985; Pope, 1985b, Pillay et al., 1986; Kppi and Halliday, 1983). Stimulating immune cells ex vivo (outside of the body) is much easier than in vivo, since in the former they are maintained in the absence of tumor-secreted immunosuppressive factors, thus making activation easier. Some researchers have tried to activate host immune cells in vivo by "flooding" the patient with immunomodulators. However, these protocols were problematic because the large quantities of cytokines needed to achieve proper activation would induce toxicity. A well-known example is the interleukin-2 (IL-2) trials in which the dosage needed to attain immune activation was so high that many patients had to cease therapy due to toxicities (Atkins et al., 1999; Rubin et al., 1989; Rosenberg et al., 1987; Lotze et al., 1986; Rosenberg et al., 1986; Bruton and Koieller, 1994; Richards et al., 1988; Du Bois et al., 1995; Shulman et al., 1996). Several groups are presently attempting to lower IL-2 toxicity by co-administering it with various agents including dexamethasone (Mier et al., 1990), pentoxifylline (Edwards et al., 1991), indomethacin (Mertens et al., 1993) and melatonin (Lissoni et al., 1996). Stimulating the immune cells ex vivo is less toxic than systemic immunomodulation and is also less expensive since a smaller amount of immunostimulant is used.

Ex vivo stimulation approaches began in mouse studies where immunity to tumors could be passed from a resistant mouse to a control mouse through the transfer of splenocytes (Takeichi and Boone, 1975; Ting, 1976; Ting, 1978; Igarashi et al., 1979; Ting et al., 1979; Rodrigues and Ting, 1981;

Mule et al., 1979; Whitney et al., 1975). Further analysis revealed that for the optimal transfer of protection CD4 and CD8 T cells had to be transferred together (Peng et al., 1997; Peng et al., 2000; Kjaergaard et al., 2001; Li et al., 1994). These mouse studies however, were not truly ex vivo experiments since stimulation of the lymphocytes occurred inside the mice. The question was "can we activate immune cells nonspecifically ex vivo?" or even better, "can we activate ex vivo T cells specific to the cancer?" The latter approach is superior to the former since nonspecific ex vivo activation can result in reactivation of autoreactive immune cells that can trigger autoimmunity. Early attempts did in fact activate patient cells nonspecifically by taking out leukocytes, adding the polyclonal T cell mitogen PHA ex vivo and then reinfusing the activated cells back into the host. The success of this therapy was not superior to conventional treatments such as chemotherapy or radiation and therefore it was abandoned (Cheema nd hersh, 1972; Garovoy et al., 1973).

The other ex vivo stimulation approach had a stronger success rate. This approach involved purifying peripheral blood mononuclear cells (i.e., lymphocytes), activating them with the immunostimulant interleukin 2, and reinfusing the activated lymphocytes back into the autologous patient. In contrast to the first approach that aimed at nonspecifically activating T cells, this approach activated natural killer (NK) cells and a subset of T-cells with NK-like ability called lymphokine activated killer (LAK) cells (Lindemann et al., 1989; Glassman, 1989; Grimm, 1986). These cells possess the ability to kill tumor cells expressing abnormal levels of MHC (Timonen and helander, 1997), and target cells not expressing empty MHC class 1 (R G Miller, personal communication).

Another immunotherapeutic approach that activates immune cells ex vivo involves using tumor infiltrating lymphocytes (TIL) against solid tumors. TILs have been noticed in a variety of tumors and are correlated with a favorable prognosis in certain cancers including liver carcinoma (Kaata et al., 1992), melanoma (Miwa, 1984; Lipponen et al., 1992), bladder cancer (Lipponen et al., 1992), colorectal cancer (Ropponen et al., 1997), and ovarian cancer (Ma and Gu, 1991; Tomsova et al., 2008). It is the belief of many tumor immunologists that TILs infiltrate tumors to induce their eradication, however, this does not occur in vivo because tumor-secreted immunosuppressive factors inhibit immune activation. TIL therapy involves surgically extricating a tumor mass, separating the TILs from the tumor cells on a density gradient, expanding the lymphocytes in immunostimulatory in vitro conditions and reinfusing the activated killer cells back into the patient (Filgueira et al., 1993; Topalian et al., 1988). Mouse models contrasting the antitumor efficacy of TIL therapy to LAK therapy showed that TIL therapy had approximately a one hundred fold greater tumoricidal effect (Spiess et al., 1987; Yang et al., 1990. A possible reason why TILs had an augmented tumor eradicating effect is that this therapy activates only lymphocytes that have recognized the tumor and are reacting to it. This is in contrast to LAK therapy that activates a plethora of cells, of which only a fraction are specific to the tumor. In the clinic, results using TIL have been fair, with reproducible responses in approximately 20% of melanoma patients (Whiteside, 1991). A means of augmenting the efficacy of TILs is to enhance their killing potential by transfecting them with cDNA to TNF (Rosenberg et al., 1993).

Perhaps one of the most potent and clinically successful examples of adoptive T cell therapy is the use of chimeric antigen receptor (CAR) T cells. One example of this is a recent publication in which T cells with reactivity against the ovarian cancer-associated antigen alpha-folate receptor (FR) were generated by genetic modification of autologous T cells with a chimeric gene incorporating an anti-FR single-chain antibody linked to the signaling domain of the Fc receptor gamma chain. Patients were assigned to one of two cohorts in the study. Eight patients in cohort 1 received a dose escalation of T cells in combination with high-dose interleukin-2, and six patients in cohort 2 received dual-specific T cells (reactive with both FR and allogeneic cells) followed by immunization with allogeneic peripheral blood mononuclear cells. Five patients in cohort 1 experienced some grade 3 to 4 treatment-related toxicity that was probably due to interleukin-2 administration, which could be managed using standard measures. Patients in cohort 2 experienced relatively mild side effects with grade 1 to 2 symptoms. No reduction in tumor burden was seen in any patient. Tracking 111In-labeled adoptively transferred T cells in cohort 1 revealed a lack of specific localization of T cells to tumor except in one patient where some signal was detected in a peritoneal deposit. PCR analysis showed that gene-modified T cells were present in the circulation in large numbers for the first 2 days after transfer, but these quickly declined to be barely detectable 1 month later in most patients (Kershaw et al., 2006). Similar CAR-T clinical studies have been reported for neuroblastoma (Park et al., 2007; Louis et al., 2011), B cell malignancies (Park and Brentjens, 2010; Kochenderfer et al., 2010; Porter et al., 2011; Kalos et al., 2011; Brentjens et al., 2011; Kebriaei et al., 2012; Kochenderfer et al., 2012; Till et al., 2012; Brentjens et al., 2013; Kochenderfer and Rosenberg, 2013; Davila and Brentjens, 2013; Cruz et al., 2013; Kochenderer et al., 2013) melanoma (Wu et al., 2012), ovarian cancer (Kandalaft et al., 2012), renal cancer (Lamers et al., 2013), mesothelioma (Schuberth et al., 2013), and head and neck cancer (van Schalwyk et al., 2013).

Embodiments of the disclosure address deficiencies in the art and include methods of enhancing activities of CD8 T cells by ex vivo culture. Embodiments of the disclosure pertain to the field of expanding T cells of the CD8 lineage and endowing the T cells with one or more abilities, such as to produce cytokines, to proliferate, and/or to cause cytotoxicity. In particular embodiments, the CD8 T cells are engineered such that they express non-endogenous receptors, including non-endogenous CARs, T cell receptors, $\alpha\beta$ receptors, and so forth.

In particular embodiments of the disclosure, fibroblast cells are exposed to one or more stressors and following this they are cultured with T cells of the CD8 lineage; the stressed fibroblasts are able to then potently expand proliferation, increase cytokine production, and increase cytotoxic activity of the CD8 T cells. In one embodiment, the fibroblasts are exposed to the one or more stressors, such as serum deprivation for approximately 24 hours. In another embodiment, the fibroblasts are exposed to one or more stressors including hyperthermia, for example for 4 hours of approximately 40 degrees Celsius.

The disclosure provides the use of "stressed" fibroblast cells as feeder cells for stimulation of CD8 T cells. Stimulation of CD8 T cells includes enhancement of proliferation ability, cytokine secretion augmentation, increased cytotoxic activity, and/or reduced costimulatory requirements. In one embodiment the disclosure, there is exposure of fibroblasts to unphysiological conditions for sufficient duration to induce expression of heat shock proteins and to alter growth factor production activity of the fibroblasts. At the same time as the fibroblasts being stressed, or subsequent to the fibroblasts being stressed, the fibroblasts are subjected to the CD8 T cells. In one embodiment, the fibroblasts are allogeneic to the CD8 T cells, and in another embodiment the fibroblasts are autologous with the CD8 T cells.

Exposure to stress for the fibroblasts may be performed using various means known in the art. In one embodiment, fibroblasts are exposed to hyperthermia, and the hyperthermia may comprise elevation of temperature for 1 to 8 hours, and the elevation in temperature may be between 39-42 Celsius. In a specific case, cells are exposed to hyperthermia for 4 hours at a temperature of approximately 40 Celsius. In some embodiments, T cells are isolated from peripheral blood mononuclear cells (PBMC) of patients and CD8 cells are purified using magnetic activated cell sorting (MACS). In other embodiments, CD8 T cells are extracted from tumor infiltrating lymphocytes. Methods of isolating tumor infiltrating lymphocytes are known in the art and incorporated by reference (Igarashi et al., 2002).

In one embodiment, the population of CD8 T cells are obtained from a blood sample from a subject, e.g., obtained by apheresis. In one embodiment, the immune effector cells collected by apheresis are washed to remove the plasma fraction and, optionally, the cells are provided in an appropriate buffer or media for subsequent processing steps. In one embodiment, the cells are washed with a buffer such as, e.g., phosphate buffered saline (PBS). In an embodiment, the cells are washed in a wash solution that lacks one or more divalent cations, such as calcium and/or magnesium. In one embodiment, the immune effector cells are washed in a buffer that has substantially no divalent cations.

In one embodiment, the method comprises generating a population of siRNA-engineered T cells transiently expressing exogenous siRNA from the population of immune effector cells. The method comprises introducing an in vitro-transcribed siRNA or synthetic siRNA into the immune cells prior to or following exposure to the fibroblasts. The siRNA transfection can be done before or after extraction of the CD8 T cells from the immune cells. In specific cases, the siRNA targets an immune inhibitory molecule, such as an immunological checkpoint. Numerous immunological checkpoints are known in the art, including CTLA-4, STATE, IL-10, and/or PD-1, for example. In one embodiment the siRNA is introduced into the immune effector cells by electroporation. In one embodiment, at least at least 80%, 85%, 86%, 87%, 88%, 89%, 90%, 91%, 92%, 93%, 94%, 95%, 96%, 97%, 98%, 99% or 100% of the immune effector cells express the siRNA. In one embodiment, the immune effector cells are expanded and/or activated by culturing the immune effector cells in the presence of a ligand, e.g., a cognate antigen molecule or an anti-idiotype antibody. In one embodiment, the immune effector cells are contacted with the cognate antigen molecule or anti-idiotype antibody at least, 2, 3, 4, 5, 6, 7, 8, 9, 10, 11, 12, 13, 14, 15, 16, 17, 18, 19, 20, 21, 22, 23, 24, 28, 32, 36, 36, or 48 hours after the siRNA is introduced into the immune effector cells. In one embodiment, the immune effector cells are contacted with the cognate antigen molecule or an anti-idiotype antibody less than 24, 15, 12, 10, or 8 hours after RNA is introduced into the immune effector cells. In specific embodiments, the immune effector cells are contacted with a cognate antigen molecule or anti-idiotype antibody at least a certain number of hours after the siRNA is introduced into the immune effector cells in which case the CD8 cells have yet to be extracted and the immune effectors are activated; subsequently, the CD8 cells are extracted.

In some embodiments of the disclosure, antigens that are capable of stimulating T cell proliferation are added to a stressed fibroblast/T cell culture. Antigens may be added as proteins, peptides, and/or altered peptide ligands into the culture, or any of them may be genetically engineered into the fibroblasts. In a situation of expansion of CD8 cells for use in tumor immunotherapy, tumor antigens may be utilized. Exemplary tumor antigens include CD19, CD123, CD22, CD30, CD171, CS-1, CLL-1 (CLECL1), CD33, EGFRvIII, GD2, GD3, BCMA, Tn Ag, PSMA, ROR1, FLT3, TAG72, CD38, CD44v6, CEA, EPCAM, B7H3, KIT, IL-13Ra2, Mesothelin, IL-11R.alpha., PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, FAP, IGF-I receptor, CAIX, LMP2, gp100, bcr-abl, tyrosinase, EphA2, Fucosyl GM1, sLe, GM3, TGSS, HMWMAA, o-acetyl-GD2, Folate receptor beta, TEM1/CD248, TEM7R, CLDN6, TSHR, GPRCSD, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, legumain, HPV E6, E7, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and/or IGLL1, for example.

In one embodiment, the culture of fibroblasts and CD8 T cells, with or without antigen(s), further comprises one or more factors for enhancing proliferation and/or viability, including serum (e.g., fetal bovine or human serum), e.g., one, two, three, four, five or more of the following: interleukin-2 (IL-2), insulin, IFN-gamma, IL-4, IL-7, GM-CSF, IL-10, IL-12, IL-15, IL-21, TGF-beta, and TNF-alpha or any other additives for the growth of cells. In one embodiment, the reaction mixture further comprises IL-15 and/or IL-7. In one embodiment, the cells are expanded in the presence of IL-2.

In one embodiment fibroblasts that have been stressed act as antigen presenting cells, in other embodiments, antigen presenting cells are added to the culture.

Embodiments of the disclosure include methods of enhancing activities of a CD8 T cell comprising: a) exposing a population of fibroblasts to one or more stressors; b) culturing the fibroblasts in combination with a T cell of the CD8 lineage; c) extracting the CD8 T cells from the culture. In specific embodiments, the stressor is hyperthermia, such as exposure to an elevated temperature for a duration capable of inducing expression of heat shock protein 90. The hyperthermia may be exposure to a temperature of 40 degree Celsius for 1, 2, 3, 4, 5, 6, 7, or 8 hours or any range there between. The stressor may comprise exposure to serum deprivation for 12, 13, 14, 15, 16, 1, 7, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours, or any range there between, including 12-48 hours.

In particular embodiments, following exposure of the CD8 T cells to stressed fibroblasts, one or more activities of the CD8 T cells are altered compared to the activities of the CD8 T cells in the absence of exposure to the stressed fibroblasts. Such activities include at least activities selected from the group consisting of a) proliferation; b) cytokine production; c) cytotoxicity; and d) a combination thereof. Cytokine production may comprise increased secretion of IL-2, IL-7, and/or IL-15. In specific embodiments, proliferation is enhanced in response to cytokine administration, and such cytokines may be selected from the group consisting of: a) IL-2; b) IL-7; c) IL-15; and d) a combination thereof. In certain cases for the CD8 T cells, following exposure of the CD8 T cells to stressed fibroblasts, their proliferation is enhanced, including in response to T cell receptor ligation (for example accomplished by an antigen or a mitogen). In particular embodiments, following exposure of the CD8 T cells to stressed fibroblasts, the CD8 T cells have enhanced cytotoxicity, including the ability to kill a target cell, increased perforin production; and/or increased granzyme production.

Embodiments of the disclosure include enhanced activity following exposure of the CD8 T cells to stressed fibroblasts, including the ability of the CD8 T cells to: a) proliferate; b) produce cytokines; and/or c) induce cytotoxicity with a lower requirement for costimulatory molecules compared to a CD8 T cell that has not been cultured in the presence of the fibroblasts exposed to the stressors. Such costimulatory molecules include CD80; CD86; CD40; ligation of CD28; IL-2; and/or IL-12.

I. Treatment of Graft Versus Host Disease by Fibroblasts and Populations Thereof In particular embodiments, the disclosure pertains to cellular therapeutics, more particularly to transplantation of organs and/or cellular grafts capable of transferring cellular elements possessing the potential of stimulating Graft Versus Host Disease. In specific embodiments, the disclosure concerns the utilization of cellular therapies for preventing, suppressing, and reversing Graft Versus Host Disease. In specific embodiments, fibroblasts are utilized for suppression of Graft Versus Host Disease (GVHD) in an individual.

The present embodiment addresses donor cells in a graft that stimulate GVHD. In particular cases these donor cells are donor T lymphocytes that are present in the donor cells or tissue (for example, a stem cell inoculum) and are required to mount an effective immune response. Although a functional immune system is able to reject T cells from a foreign donor, when a recipient's immune system is compromised through the use of various immune-ablative agents (chemotherapy and/or radiotherapy), the recipient is incapable of rejecting the transplanted cells. In particular embodiments, tissue antigens that differ in donor and recipient are major and minor human leukocyte antigens (HLA), and their expression on cell surfaces is crucial for the activation of allogenic T cells and initiation of disease.

In one embodiment, cells of the fibroblastic lineage are utilized for preventing and/or treating a graft versus host reaction for an individual in need thereof. In one embodiment of the disclosure, fibroblasts are administered under suitable conditions to a recipient of a graft, such as an allogeneic cellular graft, tissue graft, or organ graft. In specific cases, such fibroblasts prevent donor lymphocytes from inciting an immunological reaction against recipient tissue. In specific embodiments, allogeneic dermal fibroblasts are administered to a recipient of an allogeneic cellular graft in order to prevent donor lymphocytes from inciting an immunological reaction against recipient tissue.

In one specific embodiment, fibroblasts are selected for the ability to suppress production of TNF-alpha from monocytes stimulated by TLR4 agonists (such as lipopolysaccharide or HMBG-1). The fibroblasts may be isolated based on expression of one or more markers associated with an ability to inhibit dendritic cell maturation, including secretion of IL-10, human chorionic gonadotrophin, and/or IL-20, as examples.

The invention teaches a previously unexpected ability of allogeneic fibroblasts to reduce production of inflammatory cytokines in chronic conditions without inducing systemic immune suppression. Specifically the invention teaches that in inflammatory conditions, such as tumor associated cachexia, the introduction of fibroblasts of allogeneic sources results in reduction of inflammation and restoration of immunological parameters.

In one specific embodiment administration of allogeneic fibroblasts are utilized to reduce GVHD in the context of hematopoietic stem cell transplantation. In other embodiments recipient and/or donor fibroblasts are administered before and/or after introduction of cellular grafts such as bone marrow, pancreatic islet or other single cell or composite cell grafts.

Fibroblastic cells may be derived from a variety of tissues. In one embodiment isolated cells express very little or no SSEA-1 marker. The useful cells of the invention also expressed high levels of the cell surface antigens that are normally found on human mesenchymal stem cells, but not normally on human stem cells, there comprise of CD56 (99.6%), aminopeptidase N, CD44 (99.7%) hyaluronic acid-binding receptor, CD49b (99.8%) collagen/laminin-binding integrin alpha2, and CD105 (97%) endoglin. The presence of both the embryonic stem cell markers and the proprietary markers on the fibroblast cell cultures indicates that fibroblast cells, grown and propagated as described here, represent a novel class of regenerative cells.

In some embodiments of the disclosure, at least about 90%, 91%, 92%, 93%, 94%, 95%, 96%, 97%, 98%, 99%, or 100% of the cells in the culture express CD56. In additional embodiments, at least about 90%, 91%, 92%, 93%, 94%, 95%, 96%, 97%, 98%, 99%, or 100% of the cells in the culture express CD37. In some embodiments of the invention, a range from at least about 90%, 91%, 92%, 93%, 94%, 95%, 96%, 97%, 98%, 99%, or 100% of the cells in the culture express CD127. In further embodiments of the invention, a range from at least about 90%, 91%, 92%, 93%, 94%, 95%, 96%, 97%, 98%, 99%, or 100% of the cells in the culture express CD127.

In one particular embodiment of the disclosure, the regenerative cells are fibroblasts that may be propagated for an indefinite period of time in continuous culture in an undifferentiated state. The term "undifferentiated" refers to cells that have not become specialized cell types. A "nutrient medium" is a medium for culturing cells containing nutrients that promote proliferation. The nutrient medium may contain any of the following in an appropriate combination: isotonic saline, buffer, amino acids, antibiotics, serum or serum replacement, and exogenously added factors. The Amniotic fluid fibroblast cells may be grown in an undifferentiated state for as long as desired (and optionally stored as described above), and can then be cultured under certain conditions to allow progression to a differentiated state. While it is known that once sufficient cellular mass is achieved, cells can be differentiated into endodermal, mesodermal and ectodermal derived tissues in vitro and in vivo. This planned, specialized differentiation from undifferentiated cells towards a specific cell type or tissue type is termed "directed differentiation." Exemplary cell types that may be prepared from regenerative cells using directed differentiation toward anti-inflammatory phenotype include but are not limited to derivation of cells possessing CD105 associated with cells selected from a group comprising of: fat cells, cardiac muscle cells, epithelial cells, liver cells, brain cells, blood cells, neurons, glial cells, pancreatic cells, and the like.

In certain embodiments, there is a method of treating or preventing GVHD by delivering a therapeutically effective amount of fibroblasts cells to an individual in need thereof. The method may in some cases also include the steps of obtaining a fibroblast population; and expanding the fibroblast population ex vivo. The individual may be in need of treating or preventing GVHD because they have received, are receiving, and/or will receive a therapy (such as an immunotherapy) that may elicit a deleterious immune reaction. The administration of the fibroblasts may delay the onset of and/or reduce the severity of GVHD.

J. Treatment of Post-Infarct Remodeling by Administration of Fibroblast Monocyte Mixtures In some embodiments, there are compositions of matter, treatments, and protocols useful for repairing post-infarct cardiac damage by administration of autologous monocytes cultured in the presence of fibroblasts. In one embodiment, co-culture of fibroblasts and monocytes in the presence of prostaglandin-E2 generates a cellular composition capable of inducing myocardial regeneration and suppressing pathological post-infarct remodeling.

The disclosure encompasses the unexpected synergy of growth factor production and anti-inflammatory effects that is obtained by culture of fibroblasts together with monocytes, for example in the presence of PGE-2. The properties endowed by this culture induce myocardial regeneration in animal models, as well as preserve cardiac volume post infarct.

In one embodiment the disclosure, various concentrations of PGE-2 endow the ability of the joint culture of monocytes and fibroblasts to generate synergistic amounts of VEGF, PDGF-BB, and EGF, which is beneficial for cardiac regeneration. In another embodiment, the disclosure provides means of generating a therapeutic population of M2 cells that synergize with fibroblasts and endow the fibroblasts to have the ability to induce cardiac regeneration.

The disclosure encompasses administration of the co-culture of monocytes with fibroblasts to allow for M2 cells to be generated, however, in some cases PGE2 is utilized for optimal generation. The uses of the fibroblast-monocyte co-cultured cells can be applied to areas in which M2 cells have been applied. For example, it has been shown that mechanistically, M2 macrophages are associated with reduced myocardial injury after infarction by stimulation of angiogenesis, this is incorporated by reference (Dayan et al., 2011). Elegant studies in mice genetically deficient for the M2 stimulatory cytokine interleukin 13 have shown increased infarct size and reduction in post-infarct healing in mice deficient in M2 macrophages (Hofmann et al., 2014). These results where replicated in another study in which depletion of M2 macrophages was accomplished by deficiency in the CSF-1 receptor signaling pathway (Leblond et al., 2015). Treatments that exacerbate heart failure post-infarct decrease M2 macrophage accumulation (Wan et al., 2015). Additionally, therapies which induce acceleration of healing and angiogenesis have been shown in many contexts to stimulate generation of M2 macrophage (Ben-Mordechai et al., 2013; Hall and Wei, 2014; Courties et al., 2014; Weirather et al., 2014; Rafatian et al., 2014; Di Filippo et al., 2014; Zhou et al., 2015; Singla et al., 2015; Yabluchanskiy et al., 2016; Tian et al., 2015; Gross et al., 2016). For example, administration of mesenchymal stem cells has been shown to induce a decrease in M1 macrophages and an increase in M2 macrophages, which correlates with improvement in post infarct recovery by stimulation of angiogenesis (Cho et al., 2014; Zhang et al., 2015). Mechanistically, M2 macrophages are known to suppress inflammation, as well as to stimulation angiogenesis (Barbay et al., 2015), which is an important aspect of post-infarct healing. Additionally, M2 macrophages inhibit M1 macrophage formation. This is important since M1 macrophages are associated with pathological cardiac remodeling and progression to heart failure (Liu et al., 2015; He et al., 2015). Accordingly, in one aspect of the disclosure, M2 macrophages are generated in vitro and administered systemically, or locally into a patient suffering from myocardial infarction.

In some embodiments, there are methods of treating an individual subsequent to a myocardial infarct comprising the steps of: a) obtaining a fibroblast population; b) culturing the fibroblast population together with monocytes (autologous, allogeneic, or xenogeneic with respect to the individual being treated) for a period and concentration sufficient to endow the fibroblasts and/or the monocytes with cardiac-reparative properties, thereby producing a population of fibroblasts and/or the monocytes with cardiac-reparative properties; and c) administering the population to the individual. The fibroblasts may be obtained from an autologous source, allogeneic source, or xenogeneic source. The fibroblasts may be of any kind, including fibroblasts derived from a tissue selected from the group consisting of: a) adipose fibroblasts; b) dermal fibroblasts; c) umbilical cord fibroblasts; d) foreskin fibroblasts; e) placental fibroblasts; f) omental fibroblasts; and g) a combination thereof.

In such methods, the monocytes may be obtained by plastic adherence. The monocytes may be obtained by flow cytometric purification, including for the marker CD14. In specific embodiments, the monocytes are obtained by magnetic activated sorting (MACS) purification for the marker CD14.

When the fibroblasts and monocytes are co-cultured, they may be co-cultured in any suitable conditions and in any suitable ratio. In specific embodiments, the fibroblasts and monocytes are cultured at a ratio of approximately 1:1, 2:1, 5:1, 10:1, 50:1, 100:1, 1:2, 1:5, 1:10, 1:50, 1:100, and so forth. Fibroblasts and monocytes may be cultured in the presence of PGE 2 for a period of approximately 1-72, 1-60, 1-50, 1-48, 1-36, 1-24, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2, 2-72, 2-60, 2-50, 2-48, 2-36, 2-24, 2-19, 2-18, 2-17, 2-16, 2-15, 2-14, 2-13, 2-12, 2-11, 2-10, 2-9, 2-8, 2-7, 2-6, 2-5, 2-4, 2-3, 6-72, 6-60, 6-50, 6-48, 6-36, 6-24, 6-18, 6-12, 6-10, 10-72, 10-60, 10-50, 10-48, 10-36, 10-24, 10-18, 10-12, 18-72, 18-60, 18-50, 18-48, 18-36, 18-24, 18-20, 20-72, 20-60, 20-50, 20-40, 20-30, 24-72, 24-48, 24-36, 24-28, 30-72, 30-60, 30-48, 30-36, 48-72, 48-60, 48-50, 50-72, 50-60, or 60-72 hours. Fibroblasts and monocytes may be cultured in the presence of PGE 2 fora period of approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, or more hours.

The amount of prostaglandin E2 in the culture may be approximately 1-10000, 1-7500, 1-5000, 1-1000, 1-500, 1-250, 1-100, 1-50, 50-10000, 50-7500, 50-5000, 50-1000, 50-500, 50-100, 100-10000, 100-7500, 100-5000, 100-2500, 100-1000, 100-500, 500-10000, 500-7500, 500-5000, 500-2500, 500-1000, 500-750, 750-10000, 750-7500, 750-5000, 750-2500, 750-2000, 750-1000, 1000-10000, 1000-7500, 1000-5000, 1000-2500, 2500-10000, 2500-5000, 5000-10000, or 7500-10000 nanograms per ml. The amount of prostaglandin E2 in the culture may be approximately 1, 50, 75, 100, 250, 500, 1000, 1250, 1500, 1750, 2000, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 950, 9750, or 10000 or more nanograms per ml.

In specific embodiments, the monocytes express arginase activity after tissue culture with the fibroblasts.

Following co-culture of the monocytes and the fibroblasts, they may be administered to the individual about 3-15, 3-14, 3-13, 3-12, 3-11, 3-10, 3-9, 3-8, 3-7, 3-6, 3-5, 3-4, 4-15, 4-14, 4-13, 4-12, 4-11, 4-10, 4-9, 4-8, 4-7, 4-6, 4-5, 5-15, 5-14, 5-13, 5-12, 5-11, 5-10, 5-9, 5-8, 5-7, 5-6, 6-15, 6-14, 6-13, 6-12, 6-11, 6-10, 6-9, 6-8, 6-9, 7-15, 7-14, 7-13, 7-12, 7-11, 7-10, 7-9, 7-8, 8-15, 8-14, 8-13, 8-12, 8-11, 8-10, 8-9, 9-15, 9-14, 9-13, 9-12, 9-11, 9-10, 10-15, 10-14, 10-13, 10-12, 10-11, 11-15, 11-14, 11-13, 11-12, 12-15, 12-14, 12-13, 13-15, 13-14, or 14-15 days post infarct. In some cases, the co-culture of the monocytes and the fibroblasts are delivered less than 3 days after infarct, such as 1-2 days.

The combination of the co-cultured monocytes and fibroblasts may be administered by any suitable route, including intramyocardially. The may be administered into an infarct-related artery by balloon catheter, for example. In specific cases, the combination of cultured monocytes and fibroblasts are administered in retrograde using balloon collusion to the coronary sinus.

K. Treatment of Multiple Sclerosis by Fibroblast Cell Administration

In this embodiment, there are means of stimulating immunological processes capable of inhibiting development of multiple sclerosis in an individual. In one particular embodiment the disclosure, there is administration of fibroblasts (including intravenously) for inhibition of multiple sclerosis and/or stimulation of regeneration in multiple sclerosis. Particular other treatment methodologies include administration of fibroblasts followed by interleukin-2 at low doses to enhance T regulatory cells that are specific for myelin basic protein, and antigenic fragments thereof.

Embodiments of the disclosure include methods of treatment multiple sclerosis comprising administering an fibroblasts to an individual in need thereof. The administration may or may not be intravenous, for example. In specific embodiments, fibroblasts are derived from a) omnentum; b) skin; c) cord blood; d) placenta; e) Wharton's Jelly; f) peripheral blood; or g) adipose tissue. In specific cases, the fibroblasts express markers selected from the group consisting of CD73, CD105, CD90, and a combination thereof. The fibroblasts may lack expression of one or more markers selected from the group consisting of CD14, CD34, CD45, and a combination thereof. The fibroblasts may be adherent to plastic. The fibroblasts may be autologous, allogeneic, or xenogeneic with respect to the individual. The fibroblasts may possess the ability to inhibit a mixed lymphocyte reaction by >50% when added to an ongoing mixed lymphocyte reaction. In specific embodiments of the method, the proliferation of responding lymphocytes is assessed. The production of interferon gamma from responding lymphocytes may be assessed.

In particular embodiments, fibroblasts are administered at a concentration of about 10,000-2,000,000/kg per dose, such as per infusion. The dose may be 10,000-2,000,000; 10,000-1,000,000; 10,000-500,000; 10,000-250,000; 10,000-100,000; 100,000-2,000,000; 100,000-1,000,000; 100,000-500,000; 100,000-250,000; 250,000-2,000,000; 250,000-1,000,000; 250,000-500,000; 500,000-2,000,000; or 500,000-1,000,000/kg per dose, for example. The fibroblasts may be administered at a concentration of 10,000/kg per dose; 50,000/kg per dose; 100,000/kg per dose; 500,000/kg per dose; 1,000,000/kg per dose; or 2,000,000/kg per dose.

In specific embodiments, T regulatory cells (for example, 10,000-2,000,000; 10,000-1,000,000; 10,000-500,000; 10,000-250,000; 10,000-100,000; 100,000-2,000,000; 100,000-1,000,000; 100,000-500,000; 100,000-250,000; 250,000-2,000,000; 250,000-1,000,000; 250,000-500,000; 500,000-2,000,000; or 500,000-1,000,000/kg per dose) are administered with the fibroblasts. In specific cases, the fibroblasts are capable of producing at least 10, 20, 50, 100, or more pg/ml of TGF-beta, for example when cultured at a concentration of 100,000 cells per well in 96 well plates.

The multiple sclerosis may or may not be associated with a T cell attack against nervous system tissues. In some cases, rapamycin is administered together with the fibroblasts to enhance production of tolerance, for example when the fibroblasts are allogeneic or xenogeneic. In certain embodiments, anti-CD3 antibody is administered together with the fibroblasts to enhance production of tolerance, for example when the fibroblasts are allogeneic or xenogeneic. In certain embodiments, anti-CD52 antibody is administered together with the fibroblasts to enhance production of tolerance, for example when the fibroblasts are allogeneic or xenogeneic.

In one embodiment the disclosure, there is administration of fibroblasts as a means of reducing levels and/or activity of autoreactive T cells that are responsible for or at least related to the pathology in multiple sclerosis.

The disclosure provides various populations of fibroblasts that are capable of reducing autoreactive T cells through stimulation in vivo of augmented T regulatory cell numbers. These cells are an essential component of the immune system protecting the body against autoimmune attack. This is illustrated by early studies in which neonatally thymectomized mice suffered from systemic autoimmunity, which were rescued by transfer of CD4 cells. According to one embodiment of the invention, the T regulatory (Treg) phenotype is described as possessing the IL-2 receptor CD25. Peripheral blood contains a small population of T cell lymphocytes that express the T regulatory phenotype ("Treg"), i.e., positive for both CD4 and CD25 antigens. With the practice of the methods of the disclosure, several subsets of Treg cells are defined. One subset of regulatory cells develops in the thymus. Thymic derived Treg cells function by a cytokine-independent mechanism, which involves cell to cell contact. They are essential for the induction and maintenance of self-tolerance and for the prevention of autoimmunity. These regulatory cells prevent the activation and proliferation of autoreactive T cells that have escaped thymic deletion or recognize extrathymic antigens, thus they are critical for homeostasis and immune regulation, as well as for protecting the host against the development of autoimmunity. Thus, immune regulatory $CD4^+$ $CD25^+$ T cells are often referred to as "professional suppressor cells."

In one embodiment of the invention, stimulation of production of naturally arising $CD4^+CD25^+$ Treg cells is achieved through the administration of fibroblasts intravenously. It is known that the naturally occurring Treg are a distinct cell population of cells that are positively selected on high affinity ligands in the thymus and that have been shown to play an important role in the establishment and maintenance of immunological tolerance to self antigens. Deficiencies in the development and/or function of these cells have been associated with severe autoimmunity in humans and various animal models of congenital or induced autoimmunity.

In one embodiment of the disclosure, the Treg cells generated by augmentation of tolerogenic cytokines, which occurs as a result of intravenous fibroblast administration manifest their tolerogenic effects directly via cell-to-cell contact or indirectly via soluble factors. Although not wishing to be bound by theory, blockade of IL-2 expression in effector T cells (Teff), physical elimination of Teff cells, induction of tolerogenic dendritic cells (DCs) via CTLA-4/B7 axis, and inhibition of Teff cells via TGF-beta and IL-10 are some of the mechanisms that have been implicated to date. It also has been shown that reverse signaling through CTLA-4/CD80 into Teff cells plays an important role in their inhibition by Treg cells. Similarly, interactions between CTLA-4 on Treg cells and CD80 on DCs can result in reverse signaling and upregulation of the indoleamine dioxygenase enzyme that is involved in tolerance via the regulation of tryptophan metabolism.

The dose of fibroblast cells appropriate to be used in accordance with various embodiments of the invention will depend on numerous factors. It may vary considerably for different circumstances. The parameters that will determine optimal doses of fibroblast cells to be administered for primary and adjunctive therapy generally will include some or all of the following: the disease being treated and its stage; the species of the subject, their health, gender, age, weight, and metabolic rate; the subject's immunocompetence; other therapies being administered; and expected potential complications from the subject's history or genotype. The parameters may also include: whether the fibroblast cells are syngeneic, autologous, allogeneic, or xenogeneic; their potency (specific activity); the site and/or distribution that must be targeted for the fibroblast cells to be effective; and such characteristics of the site such as accessibility to fibroblast cells and/or engraftment of fibroblast cells. Additional parameters include co-administration with fibroblast cells of other factors (such as growth factors and cytokines). The optimal dose in a given situation also will take into consideration the way in which the cells are formulated, the way they are administered, and the degree to which the cells will be localized at the target sites following administration. Finally, the determination of optimal dosing necessarily will provide an effective dose that is neither below the threshold of maximal beneficial effect nor above the threshold where the deleterious effects associated with the dose of fibroblast cells outweighs the advantages of the increased dose.

The optimal dose of fibroblast cells for some embodiments will be in the range of doses used for allogeneic mesenchymal stem cells. For fairly pure preparations of fibroblast cells, optimal doses in various embodiments will range from $10^4$ to $10^8$ fibroblast cells/kg of recipient mass per administration. In some embodiments the optimal dose per administration will be between $10^5$ to $10^7$ fibroblast cells/kg. In many embodiments the optimal dose per administration will be $5\times10^5$ to $5\times10^6$ fibroblast cells/kg. By way of reference, higher doses in the foregoing are analogous to the doses of nucleated cells used in allogeneic mesenchymal stem cell transplantation. It is to be appreciated that a single dose may be delivered all at once, fractionally, or continuously over a period of time. The entire dose also may be delivered to a single location or spread fractionally over several locations. It is noted that human subjects are treated generally longer than experimental animals; but, treatment generally has a length proportional to the length of the disease process and the effectiveness of the treatment. Those skilled in the art will take this into account in using the results of other procedures carried out in humans and/or in animals, such as rats, mice, non-human primates, and the like, to determine appropriate doses for humans. Such determinations, based on these considerations and taking into account guidance provided by the present disclosure and the prior art will enable the skilled artisan to do so without undue experimentation. Suitable regimens for initial administration and further doses or for sequential administrations may all be the same or may be variable. Appropriate regiments can be ascertained by the skilled artisan, from this disclosure, the documents cited herein, and the knowledge in the art.

In one embodiment of the disclosure, fibroblasts are administered intravenously into a patient suffering from multiple sclerosis together with T regulatory cells obtained from the same (autologous) or from a different (allogeneic) person. Treg cells may be generated by means that are known in various laboratories and routinely used. Any method of cell isolation may be used according to the present teachings. One exemplary method of isolation of regulatory cells from peripheral blood comprises centrifugation, with or without a gradient (e.g. Percoll gradient). This technique separates cells based upon density. Another exemplary method which may be used comprises panning and immunomagnetic isolation, using molecules immobilized to surface or magnetic beads, respectively, as for example, antibodies that recognize and bind molecules on the cell surface (e.g. CD4, CD8, CD20, etc.). Molecules immobilized to a surface or conjugated to magnetic beads recognize and bind to one or more of the cell specific surface markers of a particular cell type. Cells that possess one or more cell surface markers are bound by the immobilized molecules or exposure of the bead-conjugated cells to a magnetic field, allowing any other cell to be washed away. In positive selection procedures the cell type of interest is retained, and in negative selection procedures cell type of interest is purged. Another isolation procedure which may used according to the present teachings includes fluorescence activated cell sorting (FACS). Antibodies with fluorescent tags may be used to bind to the cells of interest. The antibodies bind to the cell surface molecules (e.g. CD4, CD8, CD20, etc.), and a FACS sorter may then sort and collect the cells based upon the fluorescence observed. The cells that display certain fluorescence may then be isolated. Following isolation of the immune regulatory cells, the cells may be further cultured, expanded and/or stimulated. Ex vivo expansion of isolated immune regulatory cells include, for example, the protocol for T regulatory cells: cells are cultured with CD3/CD28 stimulation (e.g. anti-CD3 antibody and anti-CD28 antibody) in the presence of high IL-2 concentrations, IL-10 and stimulation/education with dendritic cells. Ex vivo expansion of the cells as described herein (i.e. with an antigen presenting cell) may also selectively enrich for antigen-specific immune regulatory cells. It will be appreciated that the immune regulatory cells may also be expanded in vivo in order to increase the number of these cells prior to isolation and ex vivo manipulation.

L. Fibroblast Mediated Treatment of Autoimmunity

This embodiment concerns means of inducing antigen-specific tolerance through genetically modifying fibroblasts to express antigens of interest in an inducible manner or constitutive manner. Prior work in the art involved administration of autoantigens in non-immunogenic routes, such as orally, intranasally, or delivered using immature dendritic cells, and these have shown some signs of clinical efficacy; however, the effect has not been robust enough to allow for human therapeutic success. In the present embodiment, there is genetic modification of fibroblasts to induce overexpression of autoantigen(s) in a regulated manner in order to generate a universal donor antigen-specific tolerogenic vaccine as a treatment, such as for autoimmunity. Fibroblasts are utilized as a foundation for induction of antigen specific tolerance based on the discovery of their previously unknown ability to: a) induce T regulatory cells; b) suppress T helper cells, T cytotoxic cells, and NK cells (for example); and c) stimulate inhibitory processes that result in diminished ability for antigen presenting cells to perform the process of antigen presentation. Given that in one embodiment of the disclosure fibroblasts would be utilized in an allogeneic manner, induction of tolerance would occur predominantly through the indirect pathway of antigen presentation, which is more amenable to tolerogenesis in the context of immune modulatory factors.

Immunological tolerance is a critical feature of the immune system, which allows for recognition and elimination of pathological threats, while selectively ignoring antigens that belong to the body. Understanding mechanisms of immunological tolerance, and having the ability to induce this process would make a major impact in autoimmune conditions, which affect approximately 8% of the U.S. population.

Major autoimmune diseases include rheumatoid arthritis, multiple sclerosis, type 1 diabetes, systemic lupus erythromatosis, and inflammatory bowel disease. Traditionally, autoimmune conditions are treated with non-specific inhibitors of inflammation such as steroids, as well as immune suppressive agents such as cyclosporine, 5-azathioprine, and methotrexate. These approaches globally suppress immune functions and have numerous undesirable side effects. Unfortunately, given the substantial decrease in quality of life observed in patients with autoimmunity, the potential of alleviation of autoimmune symptoms outweighs the side effects such as opportunistic infections and increased predisposition to neoplasia. The introduction of "biological therapies" such as anti-TNF-alpha antibodies has led to some improvements in prognosis, although side effects are still present due to the non-specific nature of the intervention. Regardless, sales of TNF-alpha inhibitors have been quite successful: Humira ($9.2B; 2012), Enbrel ($7.8B; 2011), Remicade ($6.7B; 2011). These approaches do not "cure" autoimmunity, but merely alleviate symptomology.

To "cure" autoimmunity, it is essential to delete/inactivate the T cell clone that is recognizing the autoantigen in a selective manner. This would be akin to recapitulating the natural process of tolerance induction. While thymic deletion was the original process identified as being responsible for selectively deleting autoreactive T cells, it became clear that numerous redundant mechanisms exist that are not limited to the neonatal period. Specifically, a "mirror image" immune system was demonstrated to co-exist with the conventional immune system. Conventional T cells are activated by self-antigens to die in the thymus and conventional T cells that are not activated receive a survival signal (Ramsdell and Fowlkes, 1990); the "mirror image", T regulatory (Treg) cells are actually selected to live by encounter with self-antigens, and Treg cells that do not bind self antigens are deleted (Apostolou et al., 2002; Aschenbrenner et al., 2007). Thus the self-nonself discrimination by the immune system occurs in part based on self antigens depleting autoreactive T cells, while promoting the generation of Treg cells. An important point for development of an antigen-specific tolerogenic vaccine is that in adult life, and in the periphery, autoreactive T cells are "anergized" by presentation of self-antigens in absence of danger signals, and autoreactive Treg are generated in response to self antigens. Although the process of T cell deletion in the thymus is different than induction of T cell anergy, and Treg generation in the thymus, results in a different type of Treg as compared to peripheral induced Treg, in many aspects, the end result of adult tolerogenesis is similar to that which occurs in the neonatal period. In one embodiment of the disclosure, fibroblasts are transfected with autoantigens and said transfected fibroblasts are administered in a manner in which to generate immunological tolerance towards such antigen. The administration of fibroblasts is performed in order to induce generation of T regulatory cells and to inhibit activation of autoreactive T cells. This is particularly relevant in autoimmune conditions where autoantigens are well defined.

The disclosure seeks to replicate natural processes of tolerogenesis by administration of fibroblasts that are transfected with an autoantigen. For example it is known that tolerogenesis occurs in adults in settings such as pregnancy, cancer, and oral tolerance. The invention teaches utilization of molecules, cells and processes that occur in these situations in order to modify fibroblasts as a tolerogenic mediator.

In a situation of pregnancy, studies have demonstrated selective inactivation of maternal T cell clones that recognize fetal antigens occurs through a variety of mechanisms, including FasL expression on fetal and placental cells (Vacchio and Hodes, 2005), antigen presentation in the context of PD1-L (D'Addio et al., 2011) and HLA-G interacting with immune inhibitory receptors such as ILT4 (Kuroki and Maenaka, 2007). Accordingly, the invention teaches the co-transfection of fibroblasts with autoantigens combined with death inducing molecules such as FasL, co-inhibitory molecules such as PD-L1 and immune modulatory molecules such as ILT4.

In pregnancy, "tolerogenic antigen presentation" occurs only through the indirect pathway of antigen presentation (Erlebacher et al., 2007). Other pathways of selective tolerogenesis in pregnancy include the stimulation of Treg cells, which have been demonstrated essential for successful pregnancy (Chen et al., 2013). The disclosure, in one embodiment, concerns the modification of fibroblasts by transfection with MHC or MHC-like molecules in order to create an antigen presenting cell from said fibroblasts, wherein said antigen presenting cell is capable of inducing antigen-specific tolerance when administered into a host at a therapeutically sufficient concentration and frequency.

In the context of cancer, depletion of tumor specific T cells, while sparing of T cells with specificities to other antigens has been demonstrated by the tumor itself or tumor associated cells (Harimoto et al., 2013; Ney et al., 2009; Cheung et al., 2008; Bai et al., 2008). This is the mechanism why which cancer can selectively induce a "hole in the repertoire" while allowing the host to be generally immunocompetent. Additionally, Treg cells have been demonstrated to actively suppress anti-tumor T cells, perhaps as a "back up" mechanism of tumor immune evasion (Jacobs et al., 2012; Pedroza-Gonzalez et al., 2013; Donkor et al., 2011). At a clinical level the ability of tumors to inhibit peripheral T cell activity has been associated in numerous studies with poor prognosis (Whiteside, 2004; Whiteside, 1999; Reichert et al., 2002). Accordingly, in one embodiment of the invention the utilization of molecules that stimulate generation of Treg, as well as administration of molecules that expand Tregs which have been generated, are utilized. In one embodiment, fibroblasts are transfected with autoantigen together with interleukin-2 in order to enhance Treg generation. In other embodiments, interleukin 2 is administered systemically in order to enhance in vivo proliferation of Tregs.

Another natural example of tolerance that is utilized by the invention as a template for modification of fibroblasts is oral tolerance. Oral tolerance is the process by which ingested antigens induce generation of antigen-specific TGF-beta producing cells (called "Th3" by some) (Faria and Weiner, 2005; Weiner, 2001; Fukaura et al., 1996), as well as Treg cells (Palamares et al., 2012; Yamashita et al., 2012). Ingestion of antigen, including the autoantigen collagen II (Park et al., 2009), has been shown to induce inhibition of both T and B cell responses in a specific manner (Womer et al., 2008; Faria and Weiner, 2006). It appears that induction of regulatory cells, as well as deletion/anergy of effector cells is associated with antigen presentation in a tolerogenic manner (Park et al., 2012). Remission of disease in animal models of RA (Thompson et al., 1993, multiple sclerosis (Song et al., 2004), and type I diabetes (Hanninen and Harrison, 2004), has been reported by oral administration of autoantigens. Furthermore, clinical trials have shown signals of efficacy of oral tolerance in autoimmune diseases such as rheumatoid arthritis ei et al., 2009), autoimmune uveitis (Thurau et al., 1997), and multiple sclerosis (Weiner et al., 1993). In all of these natural conditions of tolerance, common molecules and mechanisms seem to be operating. Accordingly, a natural means of inducing tolerance would be the administration of a "universal donor" cell with tolerogenic potential that generate molecules similar to those found in physiological conditions of tolerance induction. In some embodiments, oral tolerance is utilized together with the autoantigen transfected fibroblasts of the invention. For example, if a patient with type 1 diabetes is treated, the patient may be administered fibroblasts that have been transfected with a diabetes-specific autoantigen such as GAD65; additionally the fibroblasts may be transfected with tolerogenic molecules such as IL-10, and when the fibroblasts are administered, orally delivered GAD65 may be utilized in order to enhance the tolerogenic processes. In another embodiment, the disclosure concerns the transfection of fibroblasts with autoantigens combined with molecules associated with oral tolerogenesis such as TGF-beta.

In some embodiments, fibroblasts are transfected with biologically effective molecules in order to resemble the immune modulatory activities of mesenchymal stem cells. For example, it is known that these cells suppress T cell activation through inhibition of IL-2 receptor alpha (CD25) (Le Blanc et al., 2004). Accordingly in one embodiments, fibroblasts are transfected with one or more autoantigens as well as IL-2 receptors in order to "suck up" IL-2 so as to prevent T cells from being activated. In other embodiments fibroblasts are cultured under conditions used for culture of mesenchymal stem cells in order to endow said fibroblast with the properties of induction of division arrest Glennie et al., 2005; Kim et al., 2007), induction of T cell anergy directly (Zappia et al., 2005) or via immature DC (Wang et al., 2008), stimulation of apoptosis of activated T cells lumas et al., 2005; Lim et al., 2010), blockade of IL-2 signaling and induction of PGE2 production (Rasmusson et al., 2005; Xu et al., 2007; English et al., 2009; Spaggiari et al., 2009; Yanez et al., 2010; Zafranskaya et al., 2013), induction of TGF-beta (Nasef et al., 2007), production of HLA-G (Magatti et ao., 2008), expression of serine protease inhibitor 6 (El Haddad t al., 2011), stimulation of nitric oxide release (Sato et al., 2007; Oh et al., 2007; Ren et al., 2008), stimulation of indolamine 2,3 deoxygenase DelaRosa et al., 2009; Tipnis et al., 2010; Ge et al., 2010; Francois et al., 2012), expression of adenosine generating ectoenzymes such as CD39 and CD73 (Sattler et al., 2011; Saldhana-Araujo et al., 2011; Barry et al., 2001), Galectin expression (Xue et al., 2010; Gieseke et al., 2010), induction of hemoxygenase 1 (Chabannes et al., 2007; Mougiakakos et al., 2011), activation of the PD1 pathway (Xue et al., 2010; Augello et al., 2005; Sheng et al., 2008; Luz-Crawford et al., 2012), Fas ligand expression (Akiyama et al., 2012; Gu et al., 2013), CD200 expression (Najar et al., 2012), Th2 deviation (Batten et al., 2006; Lu et al., 2009; Zanone et al., 2010), inhibition of Th17 differentiation (Ko et al., 2008; Rafei et al., 2009; Tatara et al., 2011; Duffy et al., 2011; Luz-Crawford et al., 2013), TSG-6 expression (Kota et al., 2013), NOTCH-1 expression (Del Pap e al., 2013), stimulation of Treg cell generation (Maccario et al., 2005; Prevosto et al, 2007; Di Ianni et al., 2008; Casiraghi et al., 2008; Boumaza et al., 2009; Ye et al., 2008; Madec et al., 2009; Melief et al., 2013). Mechanisms of Treg generation may be direct, or may be through modulation of DC. It has been reported by us and others, that activation of T cells in the absence of costimulatory signals leads to generation of immune suppressive CD4+ CD25+ T regulatory (Treg) cells (Zhang et al., 2008; Ichim et al., 2003). Thus local activation of immunity in lymph nodes would theoretically be associated with reduced costimulatory molecule expression DC after MSC administration, which may predispose to Treg generation. Conversely, it is known that Tregs are involved in maintaining DC in the DC2 phenotype (Tiemessen et al., 2007). Indeed numerous studies have demonstrated the ability of MSC to induce Treg cells (Di Ianni et al., 2008; Casiraghi et al., 2008; Ye et al., 2008; Gonzalez-Rey et al., 2009).

Embodiments of the disclosure concern methods of treatment for autoimmunity in an individual comprising the step of administering modified fibroblast into an individual in need of therapy. In some cases, the method comprises the steps of: a) obtaining a fibroblast cell population; b) transfecting said fibroblast cell population with one or more autoantigens (a molecular entity recognized by the immune system that belongs normally to the body) of interest in order to generate modified fibroblasts; and c) administering said modified fibroblast into an individual in need of therapy. In specific cases, the fibroblast cells are adipose tissue-derived adherent cells, including those that express one or more markers selected from the group consisting of CD73, CD105, CD90, and a combination thereof. In specific cases, the fibroblast cells lack expression of one or more markers selected from the group consisting of CD14, CD34, CD45, and a combination thereof. In at least some embodiments, the autoantigen is selected from the group consisting of myelin oligodendrocyte protein; b) myelin basic protein; c) collagen II; d) myofibril protein; and e) a combination thereof. Any transfected cells may be transfected by means of plasmid DNA or a viral vector, such as lentivirus, retrovirus, or adenovirus. In specific embodiments, the fibroblast cells are selected from the group of tissue sources consisting of: a) adipose; b) omental; c) bone marrow; d) placental; e) umbilical cord; f) dermal; g) Wharton's jelly; and h) a combination thereof.

In embodiments where type 1 diabetes is treated, the autoantigen(s) may be selected from the group consisting of insulin, proinsulin, GAD65 (glutamic acid decarboxylase), IA-2 (islet antigen 2; tyrosine phosphatase), and the ZnT8 transporter (zink transporter 8, localized on the membrane of insulin secretory granules). Functional fragments derived from any autoantigen(s) may be utilized, as well as the immunomodulatory peptide DiaPep277 (derived from hsp60 protein), and other HSP60-derived peptides may be used as autoantigens.

In embodiments where multiple sclerosis is treated, the autoantigen(s) may be selected from the group consisting of myelin basic protein (MBP), myelin oligodendrocyte protein (MOG), proteolipid protein (PLP), and a combination thereof. Fragments of autoantigens may be used as autoantigens for the purpose of transfection. Examples of fragments include $BP_{13-32}$, $MBP_{83-99}$, $MBP_{111-129}$, $MBP_{146-170}$, $MOG_{1-20}$, $MOG_{35-55}$, and $PLP_{139-154}$.

III. General Embodiments

Methods that include exposure of fibroblasts to immune cells (and/or of certain agents) may in some cases share common parameters. Examples of such parameters are addressed below, although in practice one or more may be altered as appropriate.

The amount of any types of cells for administration to an individual may depend on the type of disease to be treated, of the severity and stage of the disease, and/or of the type of cells to be injected for the treatment. The cells may be prepared for administration in a pharmaceutically acceptable carrier, for example a sterile saline isotonic solution. In some embodiments, the pharmaceutically acceptable carrier may comprise one or more additional agents, such as FAS ligand, IL-2R, IL-1 Ra, IL-2, IL-4, IL-8, IL-10, IL-20, IL-35, HLA-G, PD-L1, I-309, DO, iNOS, CD200, Galectin 3, sCR1, arginase, PGE-2, aspirin, atorvastatin, fluvastatin, lovastatin, pravastatin, rosuvastatin, simvastatin, pitavastatin, n-acetylcysteine, rapamycin, IVIG, naltrexone, TGF-beta, VEGF, PDGF, CTLA-4, anti-CD45RB antibody, hydroxychloroquine, leflunomide, auranofin, dicyanogold, sulfasalazine, methotrexate, glucocorticoids, etanercept, adalimumab, abatacept, anakinra, certolizumab, Etanercept-szzs, golimumab, infliximab, rituximab, tocilizumab, cyclosporine, IFN-gamma, everolimus, rapamycin, VEGF, FGF-1, FGF-2, angiopoietin, HIF-1-alpha, or a combination thereof.

In one embodiment of the disclosure, fibroblasts are administered to a subject by any suitable route, including by injection (such as intramuscular injection), including in hypoxic areas. Suitable routes include intravenous, subcutaneous, intrathecal, oral, intrarectal, intrathecal, intraomentral, intraventricular, intrahepatic, and intrarenal.

In certain embodiments, fibroblasts may be derived from tissues comprising skin, heart, blood vessels, bone marrow, skeletal muscle, liver, pancreas, brain, adipose tissue, foreskin, placental, and/or umbilical cord. In specific embodiments, the fibroblasts are placental, fetal, neonatal or adult or mixtures thereof.

The number of administrations of cells to an individual will depend upon the factors described herein at least in part and may be optimized using routine methods in the art. In specific embodiments, a single administration is required. In other embodiments, a plurality of administration of cells is required. It should be appreciated that the system is subject to variables, such as the particular need of the individual, which may vary with time and circumstances, the rate of loss of the cellular activity as a result of loss of cells or activity of individual cells, and the like. Therefore, it is expected that each individual could be monitored for the proper dosage, and such practices of monitoring an individual are routine in the art.

In certain embodiments, IFN-gamma is utilized, and the concentration of IFN-gamma in the composition comprises, consists, or consists essentially of between 0.1-500 Units per milliliter (IU/ml), 0.5-500 IU/mL, 1-500 IU/mL, 5-500 IU/mL, 10-500 IU/mL, 15-500 IU/mL, 20-500 IU/mL, 25-500 IU/mL, 30-500 IU/mL, 35-500 IU/mL, 40-500 IU/mL, 45-500 IU/mL, 50-500 IU/mL, 60-500 IU/mL, 70-500 IU/mL, 80-500 IU/mL, 90-500 IU/mL, 100-500 IU/mL, 150-500 IU/mL, 200-500 IU/mL, 250-500 IU/mL, 300-500 IU/mL, 350-500 IU/mL, 400-500 IU/mL, 450-500 IU/mL; or 0.1-450 IU/mL, 0.5-450 IU/mL, 1-450 IU/mL, 5-450 IU/mL, 10-450 IU/mL, 15-450 IU/mL, 20-450 IU/mL, 25-450 IU/mL, 30-450 IU/mL, 35-450 IU/mL, 40-450 IU/mL, 45-450 IU/mL, 50-450 IU/mL, 60-450 IU/mL, 70-450 IU/mL, 80-450 IU/mL, 90-450 IU/mL, 100-450 IU/mL, 150-450 IU/mL, 200-450 IU/mL, 250-450 IU/mL, 300-450 IU/mL, 350-450 IU/mL, 400-450 IU/mL; or 0.1-400 IU/mL, 0.5-400 IU/mL, 1-400 IU/mL, 5-400 IU/mL, 10-400 IU/mL, 15-400 IU/mL, 20-400 IU/mL, 25-400 IU/mL, 30-400 IU/mL, 35-400 IU/mL, 40-400 IU/mL, 45-400 IU/mL, 50-400 IU/mL, 60-400 IU/mL, 70-400 IU/mL, 80-400 IU/mL, 90-400 IU/mL, 100-400 IU/mL, 150-400 IU/mL, 200-400 IU/mL, 250-400 IU/mL, 300-400 IU/mL, 350-400 IU/mL; or 0.1-350 IU/mL, 0.5-350 IU/mL, 1-350 IU/mL, 5-350 IU/mL, 10-350 IU/mL, 15-350 IU/mL, 20-350 IU/mL, 25-350 IU/mL, 30-350 IU/mL, 35-350 IU/mL, 40-350 IU/mL, 45-350 IU/mL, 50-350 IU/mL, 60-350 IU/mL, 70-350 IU/mL, 80-350 IU/mL, 90-350 IU/mL, 100-350 IU/mL, 150-350 IU/mL, 200-350 IU/mL, 250-350 IU/mL, 300-350 IU/mL; or 0.1-300 IU/mL, 0.5-300 IU/mL, 1-300 IU/mL, 5-300 IU/mL, 10-300 IU/mL, 15-300 IU/mL, 20-300 IU/mL, 25-300 IU/mL, 30-300 IU/mL, 35-300 IU/mL, 40-300 IU/mL, 45-300 IU/mL, 50-300 IU/mL, 60-300 IU/mL, 70-300 IU/mL, 80-300 IU/mL, 90-300 IU/mL, 100-300 IU/mL, 150-300 IU/mL, 200-300 IU/mL, 250-300 IU/mL; or 0.1-250 IU/mL, 0.5-250 IU/mL, 1-250 IU/mL, 5-250 IU/mL, 10-250 IU/mL, 15-250 IU/mL, 20-250 IU/mL, 25-250 IU/mL, 30-250 IU/mL, 35-250 IU/mL, 40-250 IU/mL, 45-250 IU/mL, 50-250 IU/mL, 60-250 IU/mL, 70-250 IU/mL, 80-250 IU/mL, 90-250 IU/mL, 100-250 IU/mL, 150-250 IU/mL, 200-250 IU/mL; or 0.1-200 IU/mL, 0.5-200 IU/mL, 1-200 IU/mL, 5-200 IU/mL, 10-200 IU/mL, 15-200 IU/mL, 20-200 IU/mL, 25-200 IU/mL, 30-200 IU/mL, 35-200 IU/mL, 40-200 IU/mL, 45-200 IU/mL, 50-200 IU/mL, 60-200 IU/mL, 70-200 IU/mL, 80-200 IU/mL, 90-200 IU/mL, 100-200 IU/mL, 150-200 IU/mL; or 0.1-150 IU/mL, 0.5-150 IU/mL, 1-150 IU/mL, 5-150 IU/mL, 10-150 IU/mL, 15-150 IU/mL, 20-150 IU/mL, 25-150 IU/mL, 30-150 IU/mL, 35-150 IU/mL, 40-150 IU/mL, 45-150 IU/mL, 50-150 IU/mL, 60-150 IU/mL, 70-150 IU/mL, 80-150 IU/mL, 90-150 IU/mL, 100-150 IU/mL; or 0.1-100 IU/mL, 0.5-100 IU/mL, 1-100 IU/mL, 5-100 IU/mL, 10-100 IU/mL, 15-100 IU/mL, 20-100 IU/mL, 25-100 IU/mL, 30-100 IU/mL, 35-100 IU/mL, 40-100 IU/mL, 45-100 IU/mL, 50-100 IU/mL, 60-100 IU/mL, 70-100 IU/mL, 80-100 IU/mL, 90-100 IU/mL; or 0.1-90 IU/mL, 0.5-90 IU/mL, 1-90 IU/mL, 5-90 IU/mL, 10-90 IU/mL, 15-90 IU/mL, 20-90 IU/mL, 25-90 IU/mL, 30-90 IU/mL, 35-90 IU/mL, 40-90 IU/mL, 45-90 IU/mL, 50-90 IU/mL, 60-90 IU/mL, 70-90 IU/mL, 80-90 IU/mL; or 0.1-80 IU/mL, 0.5-80 IU/mL, 1-80 IU/mL, 5-80 IU/mL, 10-80 IU/mL, 15-80 IU/mL, 20-80 IU/mL, 25-80 IU/mL, 30-80 IU/mL, 35-80 IU/mL, 40-80 IU/mL, 45-80 IU/mL, 50-80 IU/mL, 60-80 IU/mL, 70-80 IU/mL; or 0.1-70 IU/mL, 0.5-70 IU/mL, 1-70 IU/mL, 5-70 IU/mL, 10-70 IU/mL, 15-70 IU/mL, 20-70 IU/mL, 25-70 IU/mL, 30-70 IU/mL, 35-70 IU/mL, 40-70 IU/mL, 45-70 IU/mL, 50-70 IU/mL, 60-70 IU/mL; or 0.1-60 IU/mL, 0.5-60 IU/mL, 1-60 IU/mL, 5-60 IU/mL, 10-60 IU/mL, 15-60 IU/mL, 20-60 IU/mL, 25-60 IU/mL, 30-60 IU/mL, 35-60 IU/mL, 40-60 IU/mL, 45-60 IU/mL, 50-60 IU/mL; or 0.1-50 IU/mL, 0.5-50 IU/mL, 1-50 IU/mL, 5-50 IU/mL, 10-50 IU/mL, 15-50 IU/mL, 20-50 IU/mL, 25-50 IU/mL, 30-50 IU/mL, 35-50 IU/mL, 40-50 IU/mL, 45-50 IU/mL; or 0.1-45 IU/mL, 0.5-45 IU/mL, 1-45 IU/mL, 5-45 IU/mL, 10-45 IU/mL, 15-45 IU/mL, 20-45 IU/mL, 25-45 IU/mL, 30-45 IU/mL, 35-45 IU/mL, 40-45 IU/mL; or 0.1-40 IU/mL, 0.5-40 IU/mL, 1-40 IU/mL, 5-40 IU/mL, 10-40 IU/mL, 15-40 IU/mL, 20-40 IU/mL, 25-40 IU/mL, 30-40 IU/mL, 35-40 IU/mL; or 0.1-35 IU/mL, 0.5-35 IU/mL, 1-35 IU/mL, 5-35 IU/mL, 10-35 IU/mL, 15-35 IU/mL, 20-35 IU/mL, 25-35 IU/mL, 30-35 IU/mL; or 0.1-30 IU/mL, 0.5-30 IU/mL, 1-30 IU/mL, 5-30 IU/mL, 10-30 IU/mL, 15-30 IU/mL, 20-30 IU/mL, 25-30 IU/mL; or 0.1-25 IU/mL, 0.5-25 IU/mL, 1-25 IU/mL, 5-25 IU/mL, 10-25 IU/mL, 15-25 IU/mL, 20-25 IU/mL; or 0.1-20 IU/mL, 0.5-20 IU/mL, 1-20 IU/mL, 5-20 IU/mL, 10-20 IU/mL, 15-20 IU/mL; or 0.1-15 IU/mL, 0.5-15 IU/mL, 1-15 IU/mL, 5-15 IU/mL, 10-15 IU/mL; or 0.1-10 IU/mL, 0.5-10 IU/mL, 1-10 IU/mL, 5-10 IU/mL; or 0.1-5 IU/mL, 0.5-5 IU/mL, 1-5 IU/mL; or 0.1-1 IU/mL, 0.5-1 IU/mL; or 0.1-0.5 IU/mL.

Methods of the disclosure can encompass subjecting a population of cells to IFN-gamma for a defined period of time. In certain embodiments, the cells are subjected to IFN-gamma for a time ranging from about 1 hour to about 14 days. In certain embodiments, cells are subjected to IFN-gamma for a time ranging from at least about or no more than about 1 hour to 14 days, 2 hours to 14 days, 3 hours to 14 days, 4 hours to 14 days, 5 hours to 14 days, 6 hours to 14 days, 7 hours to 14 days, 8 hours to 14 days, 9 hours to 14 days, 10 hours to 14 days, 11 hours to 14 days, 12 hours to 14 days, 18 hours to 14 days, 1 day to 14 days, 2 days to 14 days, 3 days to 14 days, 4 days to 14 days, 5 days to 14 days, 6 days to 14 days, 7 days to 14 days, 8 days to 14 days, 9 days to 14 days, 10 days to 14 days, 11 days to 14 days, 12 days to 14 days, 13 days to 14 days; or 1 hour to 13 days, 2 hours to 13 days, 3 hours to 13 days, 4 hours to 13 days, 5 hours to 13 days, 6 hours to 13 days, 7 hours to 13 days, 8 hours to 13 days, 9 hours to 13 days, 10 hours to 13 days, 11 hours to 13 days, 12 hours to 13 days, 1 day to 13 days, 2 days to 13 days, 3 days to 13 days, 4 days to 13 days, 5 days to 13 days, 6 days to 13 days, 7 days to 13 days, 8 days to 13 days, 9 days to 13 days, 10 days to 13 days, 11 days to 13 days, 12 days to 13 days; or 1 hour to 12 days, 2 hours to 12 days, 3 hours to 12 days, 4 hours to 12 days, 5 hours to 12 days, 6 hours to 12 days, 7 hours to 12 days, 8 hours to 12 days, 9 hours to 12 days, 10 hours to 12 days, 11 hours to 12 days, 12 hours to 12 days, 1 day to 12 days, 2 days to 12 days, 3 days to 12 days, 4 days to 12 days, 5 days to 12 days, 6 days to 12 days, 7 days to 12 days, 8 days to 12 days, 9 days to 12 days, 10 days to 12 days, 11 days to 12 days; or 1 hour to 11 days, 2 hours to 11 days, 3 hours to 11 days, 4 hours to 11 days, 5 hours to 11 days, 6 hours to 11 days, 7 hours to 11 days, 8 hours to 11 days, 9 hours to 11 days, 10 hours to 11 days, 11 hours to 11 days, 12 hours to 11 days, 1 day to 11 days, 2 days to 11 days, 3 days to 11 days, 4 days to 11 days, 5 days to 11 days, 6 days to 11 days, 7 days to 11 days, 8 days to 11 days, 9 days to 11 days, 10 days to 11 days 11 days; or 1 hour to 10 days, 2 hours to 10 days, 3 hours to 10 days, 4 hours to 10 days, 5 hours to 10 days, 6 hours to 10 days, 7 hours to 10 days, 8 hours to 10 days, 9 hours to 10 days, 10 hours to 10 days, 11 hours to 10 days, 12 hours to 10 days, 1 day to 10 days, 2 days to 10 days, 3 days to 10 days, 4 days to 10 days, 5 days to 10 days, 6 days to 10 days, 7 days to 10 days, 8 days to 10 days, 9 days to 10 days 10 days; or 1 hour to 9 days, 2 hours to 9 days, 3 hours to 9 days, 4 hours to 9 days, 5 hours to 9 days, 6 hours to 9 days, 7 hours to 9 days, 8 hours to 9 days, 9 hours to 9 days, 10 hours to 9 days, 11 hours to 9 days, 12 hours to 9 days, 1 day to 9 days, 2 days to 9 days, 3 days to 9 days, 4 days to 9 days, 5 days to 9 days, 6 days to 9 days, 7 days to 9 days, 8 days to 9 days 9 days; or 1 hour to 8 days, 2 hours to 8 days, 3 hours to 8 days, 4 hours to 8 days, 5 hours to 8 days, 6 hours to 8 days, 7 hours to 8 days, 8 hours to 8 days, 9 hours to 8 days, 10 hours to 8 days, 11 hours to 8 days, 12 hours to 8 days, 1 day to 8 days, 2 days to 8 days, 3 days to 8 days, 4 days to 8 days, 5 days to 8 days, 6 days to 8 days, 7 days to 8 days; or 1 hour to 7 days, 2 hours to 7 days, 3 hours to 7 days, 4 hours to 7 days, 5 hours to 7 days, 6 hours to 7 days, 7 hours to 7 days, 8 hours to 7 days, 9 hours to 7 days, 10 hours to 7 days, 11 hours to 7 days, 12 hours to 7 days, 1 day to 7 days, 2 days to 7 days, 3 days to 7 days, 4 days to 7 days, 5 days to 7 days, 6 days to 7 days; or 1 hour to 6 days, 2 hours to 6 days, 3 hours to 6 days, 4 hours to 6 days, 5 hours to 6 days, 6 hours to 6 days, 7 hours to 6 days, 8 hours to 6 days, 9 hours to 6 days, 10 hours to 6 days, 11 hours to 6 days, 12 hours to 6 days, 1 day to 6 days, 2 days to 6 days, 3 days to 6 days, 4 days to 6 days, 5 days to 6 days; or 1 hour to 5 days, 2 hours to 5 days, 3 hours to 5 days, 4 hours to 5 days, 5 hours to 5 days, 6 hours to 5 days, 7 hours to 5 days, 8 hours to 5 days, 9 hours to 5 days, 10 hours to 5 days, 11 hours to 5 days, 12 hours to 5 days, 1 day to 5 days, 2 days to 5 days, 3 days to 5 days, 4 days to 5 days; or 1 hour to 4 days, 2 hours to 4 days, 3 hours to 4 days, 4 hours to 4 days, 5 hours to 4 days, 6 hours to 4 days, 7 hours to 4 days, 8 hours to 4 days, 9 hours to 4 days, 10 hours to 4 days, 11 hours to 4 days, 12 hours to 4 days, 1 day to 4 days, 2 days to 4 days, 3 days to 4 days; or 1 hour to 3 days, 2 hours to 3 days, 3 hours to 3 days, 4 hours to 3 days, 5 hours to 3 days, 6 hours to 3 days, 7 hours to 3 days, 8 hours to 3 days, 9 hours to 3 days, 10 hours to 3 days, 11 hours to 3 days, 12 hours to 3 days, 1 day to 3 days, 2 days to 3 days; or 1 hour to 2 days, 2 hours to 2 days, 3 hours to 2 days, 4 hours to 2 days, 5 hours to 2 days, 6 hours to 2 days, 7 hours to 2 days, 8 hours to 2 days, 9 hours to 2 days, 10 hours to 2 days, 11 hours to 2 days, 12 hours to 2 days, 1 day to 2 days; or 1 hour to 1 day, 2 hours to 1 day, 3 hours to 1 day, 4 hours to 1 day, 5 hours to 1 day, 6 hours to 1 day, 7 hours to 1 day, 8 hours to 1 day, 9 hours to 1 day, 10 hours to 1 day, 11 hours to 1 day, 12 hours to 1 day; or 1 hour to 12 hours, 2 hours to 12 hours, 3 hours to 12 hours, 4 hours to 12 hours, 5 hours to 12 hours, 6 hours to 12 hours, 7 hours to 12 hours, 8 hours to 12 hours, 9 hours to 12 hours, 10 hours to 12 hours, 11 hours to 12 hours; or 1 hour to 11 hours, 2 hours to 11 hours, 3 hours to 11 hours, 4 hours to 11 hours, 5 hours to 11 hours, 6 hours to 11 hours, 7 hours to 11 hours, 8 hours to 11 hours, 9 hours to 11 hours, 10 hours to 11 hours; or 1 hour to 10 hours, 2 hours to 10 hours, 3 hours to 10 hours, 4 hours to 10 hours, 5 hours to 10 hours, 6 hours to 10 hours, 7 hours to 10 hours, 8 hours to 10 hours, 9 hours to 10 hours; or 1 hour to 9 hours, 2 hours to 9 hours, 3 hours to 9 hours, 4 hours to 9 hours, 5 hours to 9 hours, 6 hours to 9 hours, 7 hours to 9 hours, 8 hours to 9 hours; or 1 hour to 8 hours, 2 hours to 8 hours, 3 hours to 8 hours, 4 hours to 8 hours, 5 hours to 8 hours, 6 hours to 8 hours, 7 hours to 8 hours; or 1 hour to 7 hours, 2 hours to 7 hours, 3 hours to 7 hours, 4 hours to 7 hours, 5 hours to 7 hours, 6 hours to 7 hours; or 1 hour to 6 hours, 2 hours to 6 hours, 3 hours to 6 hours, 4 hours to 6 hours, 5 hours to 6 hours; or 1 hour to 5 hours, 2 hours to 5 hours, 3 hours to 5 hours, 4 hours to 5 hours; or 1 hour to 4 hours, 2 hours to 4 hours, 3 hours to 4 hours; or 1 hour to 3 hours, 2 hours to 3 hours, or 1 hour to 2 hours.

In some embodiments, the cells are subjected to one or more media compositions that comprises, consists of, or consists essentially of Roswell Park Memorial Institute (RPMI-1640), Dublecco's Modified Essential Media (DMEM), Eagle's Modified Essential Media (EMEM), Optimem, Iscove's Media, or a combination thereof.

In one embodiment of the disclosure, cells (such as fibroblasts) are cultured ex vivo using means known in the art for preserving viability and proliferative ability of the cells. In specific embodiments for fibroblasts, there may be modification of known culture techniques to achieve one or more desired effects for the cells, such as to decrease visibility of fibroblasts to a recipient immune system. In one embodiment, cells (for example, fibroblasts) are cultured in conditions that lack one or more xenogeneic components, such as fetal calf serum. In specific embodiments, the disclosure encompasses the substitution of fetal calf serum with human platelet rich plasma, platelet lysate, umbilical cord blood serum, autologous serum, and/or defined cytokine mixes as an additional feature, for example to reduce the immunogenicity of the cells (such as fibroblasts).

In certain embodiments, the cells are subjected to one or more compositions that comprise, consist of, or consist essentially of human platelet rich plasma, platelet lysate, umbilical cord blood serum, autologous serum, human serum, serum replacement, or a combination thereof. In specific embodiments, the composition that has such elements is a media composition. In one embodiment serum replacement comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of volume of a composition. In another embodiment human platelet rich plasma comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of volume of a composition. In yet another embodiment platelet lysate comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of volume of a composition. In one embodiment umbilical cord blood serum comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of volume of a composition. In one embodiment autologous serum comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of volume of a composition. In another embodiment human serum comprises at least or no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% of volume of a composition.

In cases wherein recombination technology is employed, one or more types of cells are manipulated to harbor an expression vector that encodes a gene product of interest. A recombinant expression vector(s) can be introduced as one or more DNA molecules or constructs, where there may be at least one marker that will allow for selection of host cells that contain the vector(s). The vector(s) can be prepared in conventional ways, wherein the genes and regulatory regions may be isolated, as appropriate, ligated, cloned in an appropriate cloning host, and analyzed by sequencing or other convenient means. Particularly, using PCR, individual fragments including all or portions of a functional unit may be isolated, where in some cases one or more mutations may be introduced using "primer repair", ligation, in vitro mutagenesis, etc. as appropriate. The vector(s) once completed and demonstrated to have the appropriate sequences may then be introduced into the host cell by any convenient means. The constructs may be integrated and packaged into non-replicating, defective viral genomes like lentivirus, Adenovirus, Adeno-associated virus (AAV), Herpes simplex virus (HSV), or others, including retroviral vectors, for infection or transduction into cells. The vector(s) may include viral sequences for transfection, if desired. Alternatively, the construct may be introduced by fusion, electroporation, biolistics, transfection, lipofection, or the like. The host cells may be grown and expanded in culture before introduction of the vector(s), followed by the appropriate treatment for introduction of the vector(s) and integration of the vector(s). The cells are then expanded and screened by virtue of a marker present in the construct. Various markers that may be used successfully include hprt, neomycin resistance, thymidine kinase, hygromycin resistance, etc.

Any of the genes or gene products described herein, or active portions thereof, may be cloned into mammalian expression constructs comprising one or more promoter sequences enabling expression in cells such as the CMV promoter [Artuc et al., Exp. Dermatol. 1995, 4:317-21]. Examples of suitable constructs include, but are not limited to pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com), or the pSH expression vector which enables a regulated polynucleotide expression in human foreskin cells [Ventura and Villa, 1993, Biochem. Biophys. Commun. 192: 867-9]. Examples of retroviral vector and packaging systems are those sold by Clontech, San Diego, Calif., USA, including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter. After completing plasmid transfection fibroblasts are harvested by a means allowing for detachment from tissue culture plates, for example, by trypsinization and transferred to either a 6-well (Nunc, Denmark) or a 24-well plate (Nunc) for proliferation. Approximately 3 days post-transfection, the cell media is changed to media allow for proliferation and expansion of modified fibroblasts. One example is Neurobasal A (NBA) proliferation medium comprising Neurobasal-A (Invitrogen), 1% D-glucose (Sigma Aldrich), 1% Penicillin/Streptomycin/Glutamine (Invitrogen), 2% B27 supplement with Retinoic acid (Invitrogen), 0.2% EGF (Peprotech, USA), 0.08% FGF-2 (Peprotech), 0.2% Heparin (Sigma Aldrich, USA) and Valproic acid (Sigma-Aldrich) to a concentration of 1 µM. The media is then subsequently changed thrice weekly, and cells are re-plated regularly (for example, 2-8 times up to a maximum of weekly re-plating, becoming more regular as colonies began to develop) to remove non-reprogrammed cells until widespread colony formation is achieved.

In some instances, one or more agents, such as angiogenic agents or functional fragments thereof, may be introduced into the cells as an RNA molecule for transient expression. RNA can be delivered to any cells, including any modified cells, of the disclosure by various means including microinjection, electroporation, and lipid-mediated transfection, for example. In particular aspects, introduction of vector(s) into cells may occur via transposons. An example of a synthetic transposon for use is the Sleeping Beauty transposon that comprises an expression cassette including the angiogenic agent gene thereof. Alternatively, one may have a target site for homologous recombination, where it is desired that vector(s) be integrated at a particular locus using materials and methods as are known in the art for homologous recombination. For homologous recombination, one may use either OMEGA or O-vectors. See, for example, Thomas and Capecchi, 1987; Mansour, et al., 1988; and Joyner, et al., 1989.

The vector(s) may be introduced as a single DNA molecule encoding at least one agent (including one or more angiogenic agent or functional fragments thereof) and optionally another polynucleotide (such as genes), or different DNA molecules having one or more polynucleotides (such as genes). The vector(s) may be introduced simultaneously or consecutively, each with the same or different markers. In an illustrative example, one vector would contain one or more agents (such as angiogenic agent(s)) under the control of particular regulatory sequences.

Vector(s) comprising useful elements such as bacterial or yeast origins of replication, selectable and/or amplifiable markers, promoter/enhancer elements for expression in prokaryotes or eukaryotes, etc. that may be used to prepare stocks of vector DNAs and for carrying out transfections are well known in the art, and many are commercially available.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

In some situations, it may be desirable to kill the modified cells, such as when the object is to terminate the treatment, the cells become neoplastic, in research where the absence of the cells after their presence is of interest, and/or another event. For this purpose one can provide for the expression of certain gene products in which one can kill the modified cells under controlled conditions, such as a suicide gene. Suicide genes are known in the art, e.g. the iCaspase9 system in which a modified form of caspase 9 is dimerizable with a small molecule, e.g. AP1903. See, e.g., Straathof et al., *Blood* 105:4247-4254 (2005).

V. Kits of the Disclosure

Any of the cellular and/or non-cellular compositions described herein or similar thereto may be comprised in a kit. In a non-limiting example, one or more reagents for use in methods for preparing cellular therapy may be comprised in a kit. Such reagents may include cells, IFN-gamma, platelet rich plasma, platelet lysate, one or more angiogenic factors, one or more growth factors, vector(s) one or more costimulatory factors, media, enzymes, buffers, nucleotides, salts, primers, and so forth. The kit may comprise any protein listed in the disclosure. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, or may be a substrate with multiple compartments for a desired reaction.

Some components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile acceptable buffer and/or other diluent.

In specific embodiments, reagents and materials include primers for amplifying desired sequences, nucleotides, suitable buffers or buffer reagents, salt, and so forth, and in some cases the reagents include apparatus or reagents for isolation of a particular desired cell(s).

In particular embodiments, there are one or more apparatuses in the kit suitable for extracting one or more samples from an individual. The apparatus may be a syringe, fine needles, scalpel, and so forth.

EXAMPLES

The following examples are included to demonstrate particular embodiments of the invention. It should be appreciated by those of skill in the art that the techniques disclosed in the examples that follow represent techniques discovered by the inventors to function well in the practice of the methods of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Interferon Gamma Pretreatment Decreases Allostimulatory Activity of Fibroblasts

The present example characterizes the use of IFN-gamma to decrease allostimulatory activity of foreskin fibroblasts as an example of a type of fibroblasts.

Figure 2:
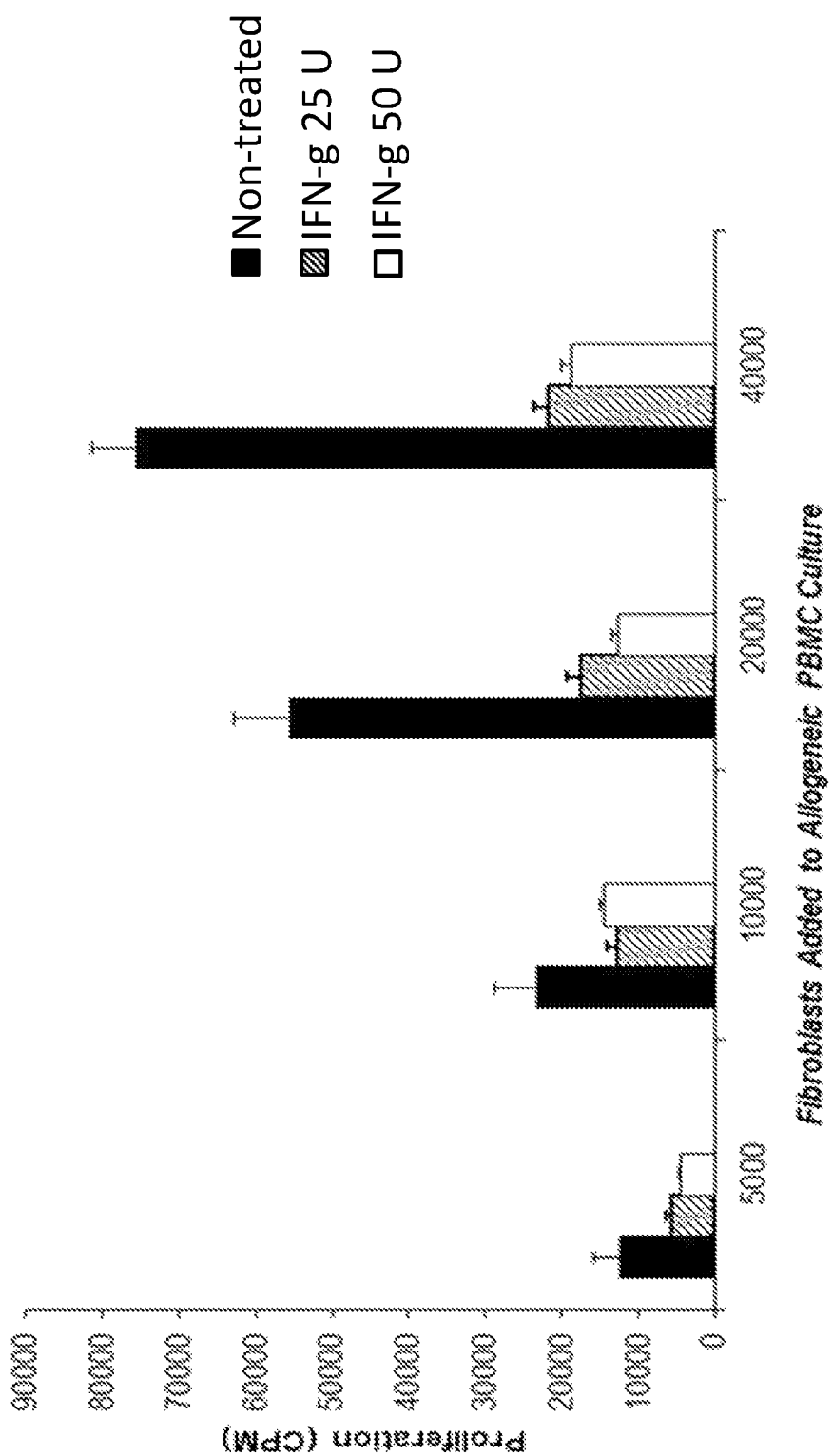
FIG. 2 shows that interferon gamma pretreatment decreases allostimulatory activity of fibroblasts.

Foreskin fibroblasts were purchased from ATCC (Manassas VA) and pretreated with the indicated concentrations of interferon gamma (25 and 50 Units) for 24 hours in a fully humidified atmosphere of 5% carbon dioxide (FIG. 2). Cells were irradiated and utilized as stimulators of mixed lymphocyte reaction (MLR). Responding cells in the MLR were peripheral blood mononuclear cells (PBMC) that were isolated from 5 ml of blood by Ficoll density gradient (Sigma-Aldrich). Cells were washed twice in phosphate buffered saline (PBS) and plated in round-bottom, 96-well plates (Nunc). In each well, 10,000, 20,000 or 100,000 PBMC where added to a total volume of 200 uL in RPMI media containing 10% fetal calf serum (Life Technologies). Cells were cultured for 48 hours and proliferation was assessed by thymidine incorporation subsequent to loading with 1 microCurie of tritiated thymidine in the last 8 hours of culture (FIG. 2).

As shown therein, exposing IFN-gamma to fibroblasts results in a decrease of allostimulatory activity for the fibroblasts.

Example 2

Figure 3:
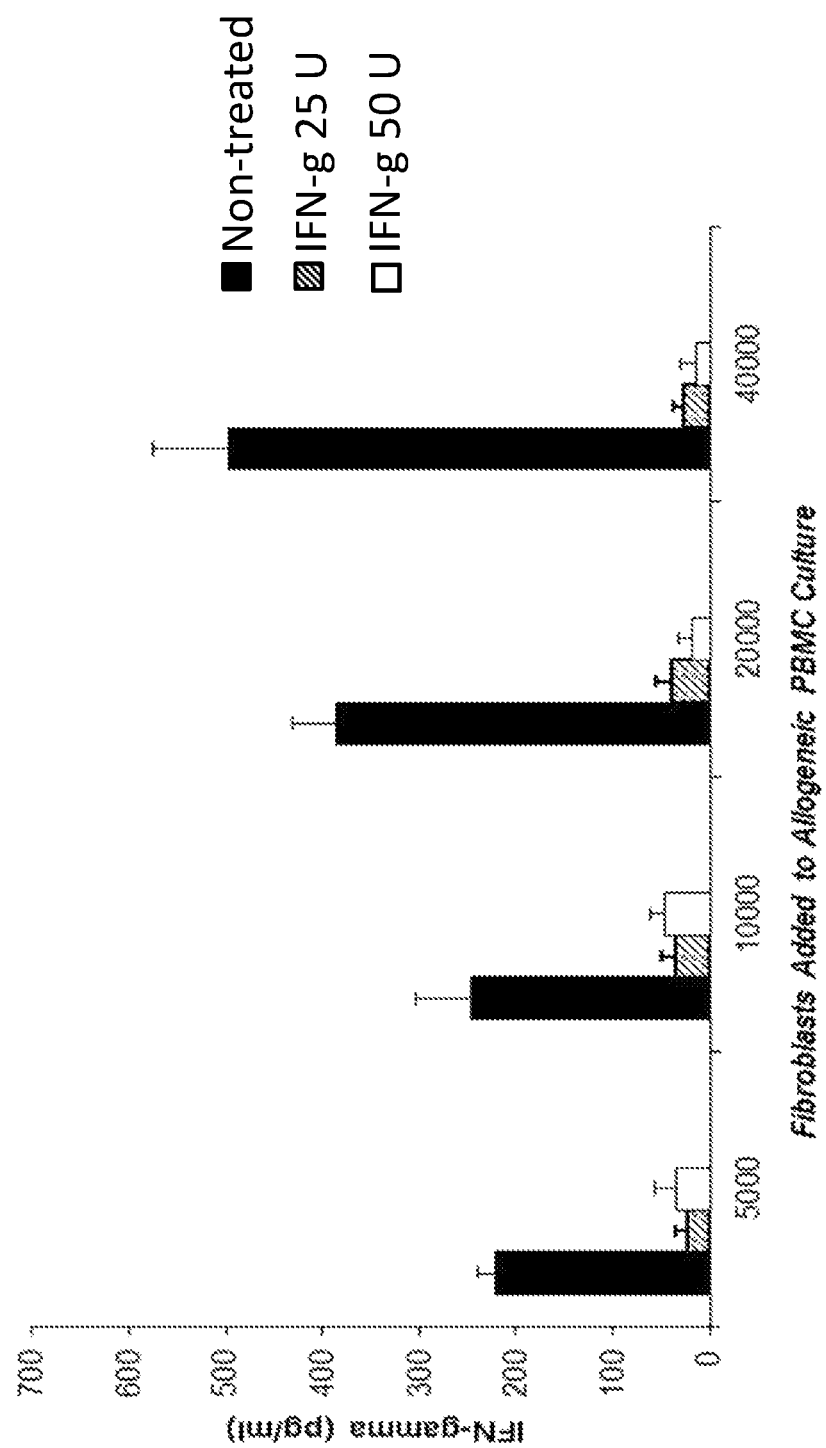
FIG. 3 demonstrates that interferon gamma treated fibroblasts inhibit interferon gamma production from allogeneic lymphocytes.

Interferon Gamma Treated Fibroblasts Inhibit Interferon Gamma Production from Allogeneic Lymphocytes Foreskin fibroblasts were treated with two concentrations of interferon gamma as described in Example 1 and were utilized to stimulate mixed lymphocyte reaction. Interferon gamma secretion was assessed after 48 hours of culture by performing ELISA assay on culture supernatant (FIG. 3). As shown therein, the treated fibroblasts inhibited production of IFN-gamma from the lymphocytes.

Example 3

Figure 4:
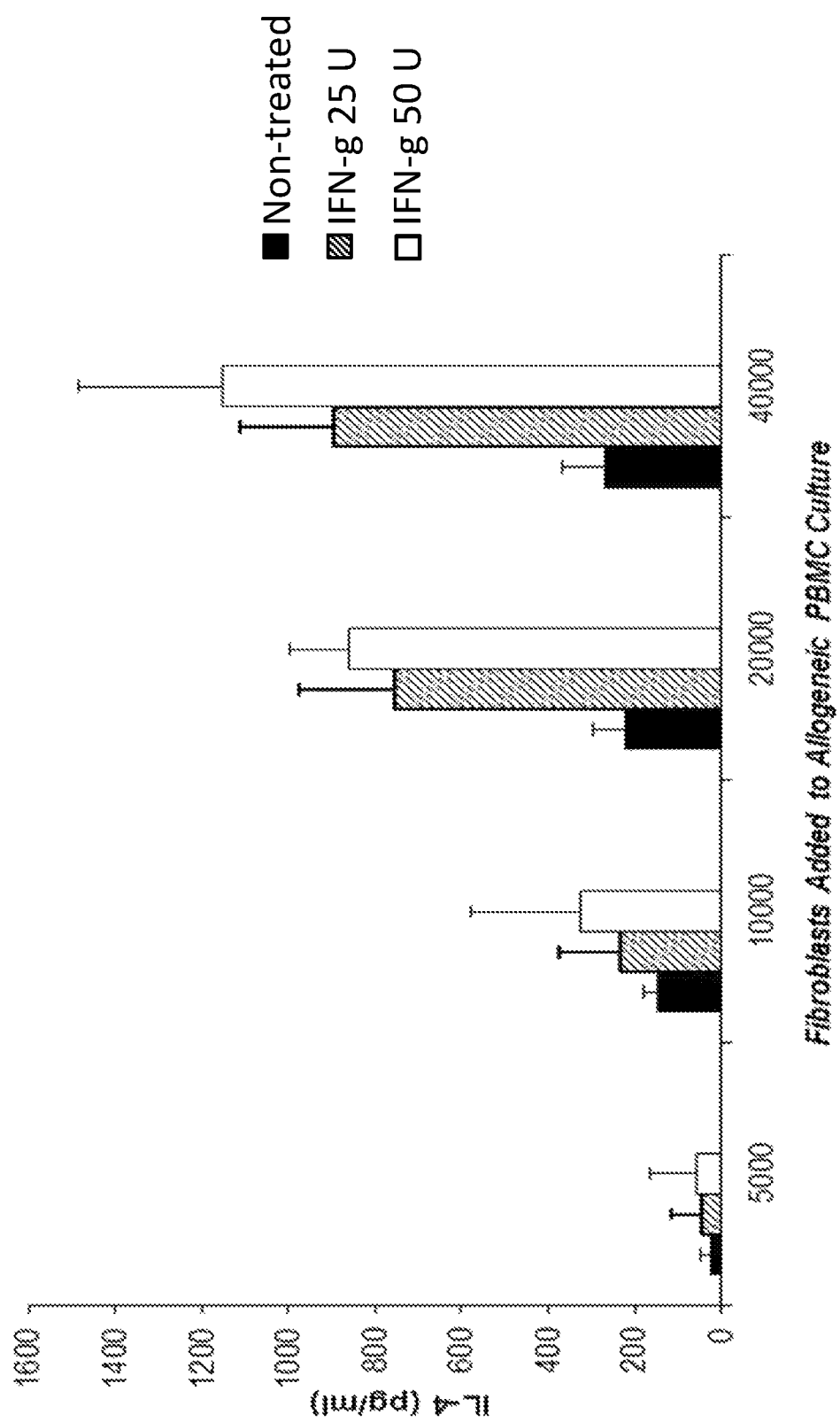
FIG. 4 demonstrates that interferon gamma treated fibroblasts stimulates interleukin-4 production from allogeneic lymphocytes.

Interferon Gamma Treated Fibroblasts Stimulates Interleukin-4 Production from Allogeneic Lymphocytes Foreskin fibroblasts were treated with interferon gamma as described in Example 1 and utilized to stimulate mixed lymphocyte reaction. Interleukin-4 secretion was assessed after 48 hours of culture by performing ELISA assay on culture supernatant (FIG. 4).

Production of IL-4 increased with IFN-gamma-treated fibroblasts compared to controls.

Example 4

Figure 5:
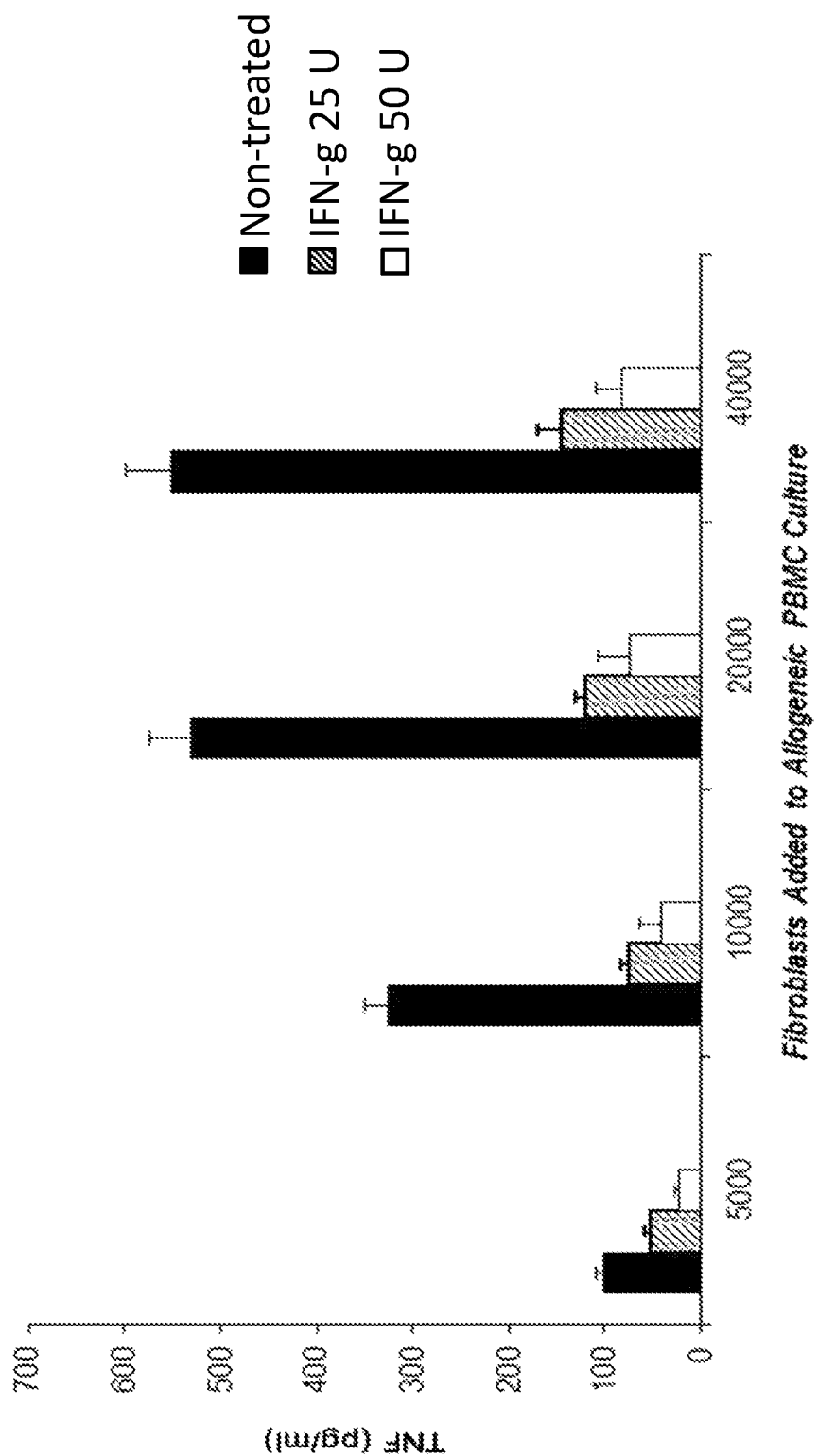
FIG. 5 shows that interferon gamma treated fibroblasts inhibits TNF-alpha production from allogeneic lymphocytes.

Interferon Gamma Treated Fibroblasts Inhibits TNF-Alpha Production from Allogeneic Lymphocytes Foreskin fibroblasts were treated with interferon gamma as described in Example 1 and utilized to stimulate mixed lymphocyte reaction. TNF-alpha secretion was assessed after 48 hours of culture by performing ELISA assay on culture supernatant (FIG. 5) and shown to be reduced for IFN-gamma-treated fibroblasts.

Example 5

Figure 6:
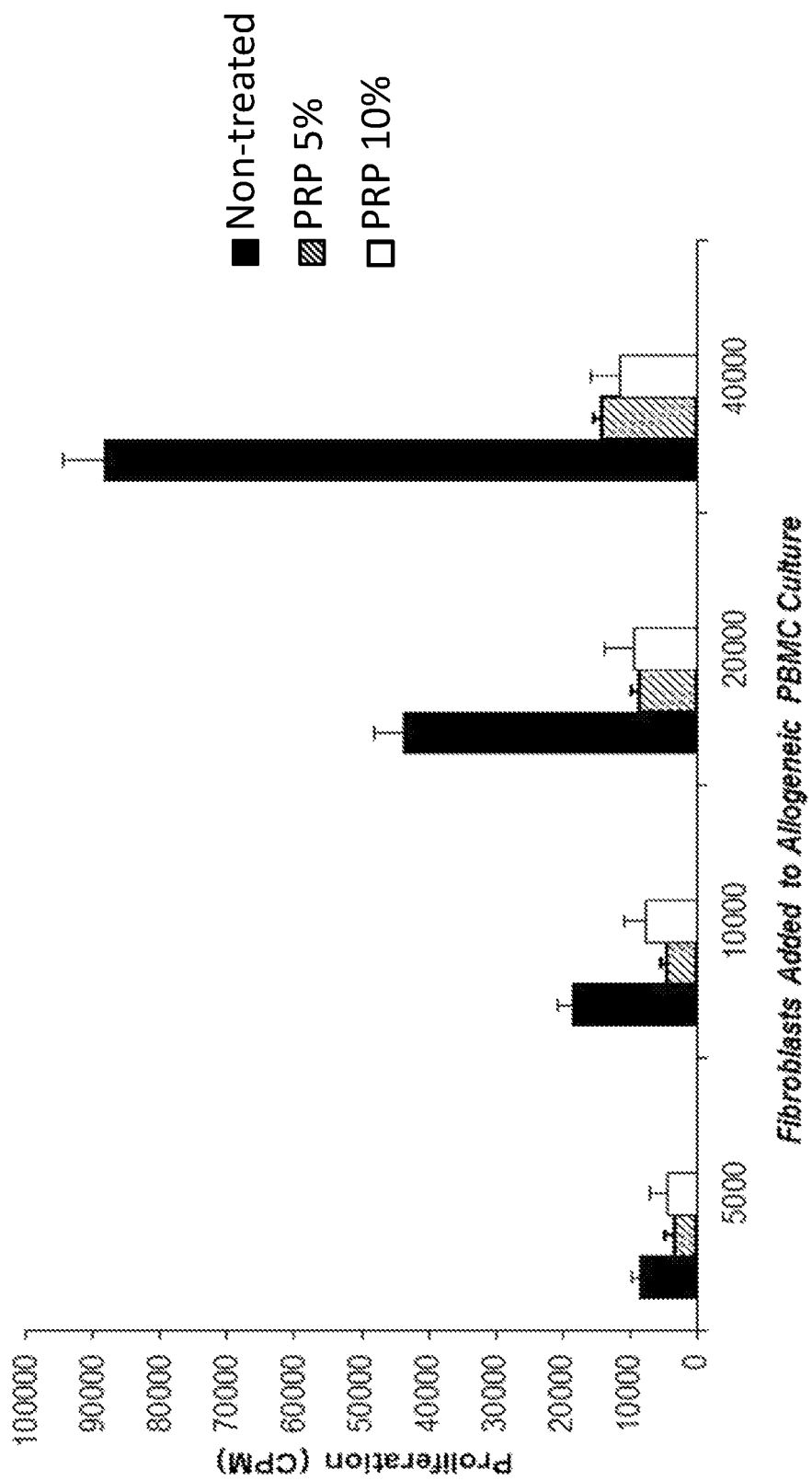
FIG. 6 exhibits that platelet rich plasma pretreatment decreases allostimulatory activity of fibroblasts.

Platelet Rich Plasma Pretreatment Decreases Allostimulatory Activity of Fibroblasts Foreskin fibroblasts were purchased from ATCC (Manassas VA) and pretreated with the indicated concentrations of platelet rich plasma (5% and 10% volume by volume) for 24 hours in a fully humidified atmosphere of 5% carbon dioxide (FIG. 6). Cells were irradiated and utilized as stimulators of mixed lymphocyte reaction (MLR). Responding cells in the MLR were peripheral blood mononuclear cells (PBMC) were isolated from 5 ml of blood by Ficoll density gradient (Sigma-Aldrich). Cells were washed twice in phosphate buffered saline (PBS) and plated in round-bottom, 96-well plates (Nunc). In each well, 10,000, 20,000 or 100,000 PBMC where added to a total volume of 200 uL in RPMI media containing 10% fetal calf serum (Life Technologies). Cells were cultured for 48 hours and proliferation was assessed by thymidine incorporation subsequent to loading with 1 microCurie of tritiated thymidine in the last 8 hours of culture (FIG. 6).

Pretreatment with platelet rich plasma results in a reduction in the allostimulatory activity of the treated fibroblasts.

Example 6

Cellular Transplantation Therapy for Immunomodulation

The present example concerns methods for immunomodulation of cellular therapy for an individual in need thereof.

Treatment of Collagen Induced Arthritis by Fibroblasts and IFN-Gamma Pretreated Fibroblasts Foreskin fibroblasts were purchased from ATCC (Manassas VA) and pretreated with the indicated concentrations of interferon gamma (25 Units) for 24 hours in a fully humidified atmosphere of 5% carbon dioxide. 5 million fibroblasts were intravenous injected into collagen induced arthritis mice, generated as described below, two times on day 7 and day 14 after the first collagen II immunization. The animals were observed for 4 wk after arthritis onset (7 d after second CII immunization). Each limb was graded on a scale from 0 to 4, and the average clinical score per affected paw was calculated.

Figure 7:
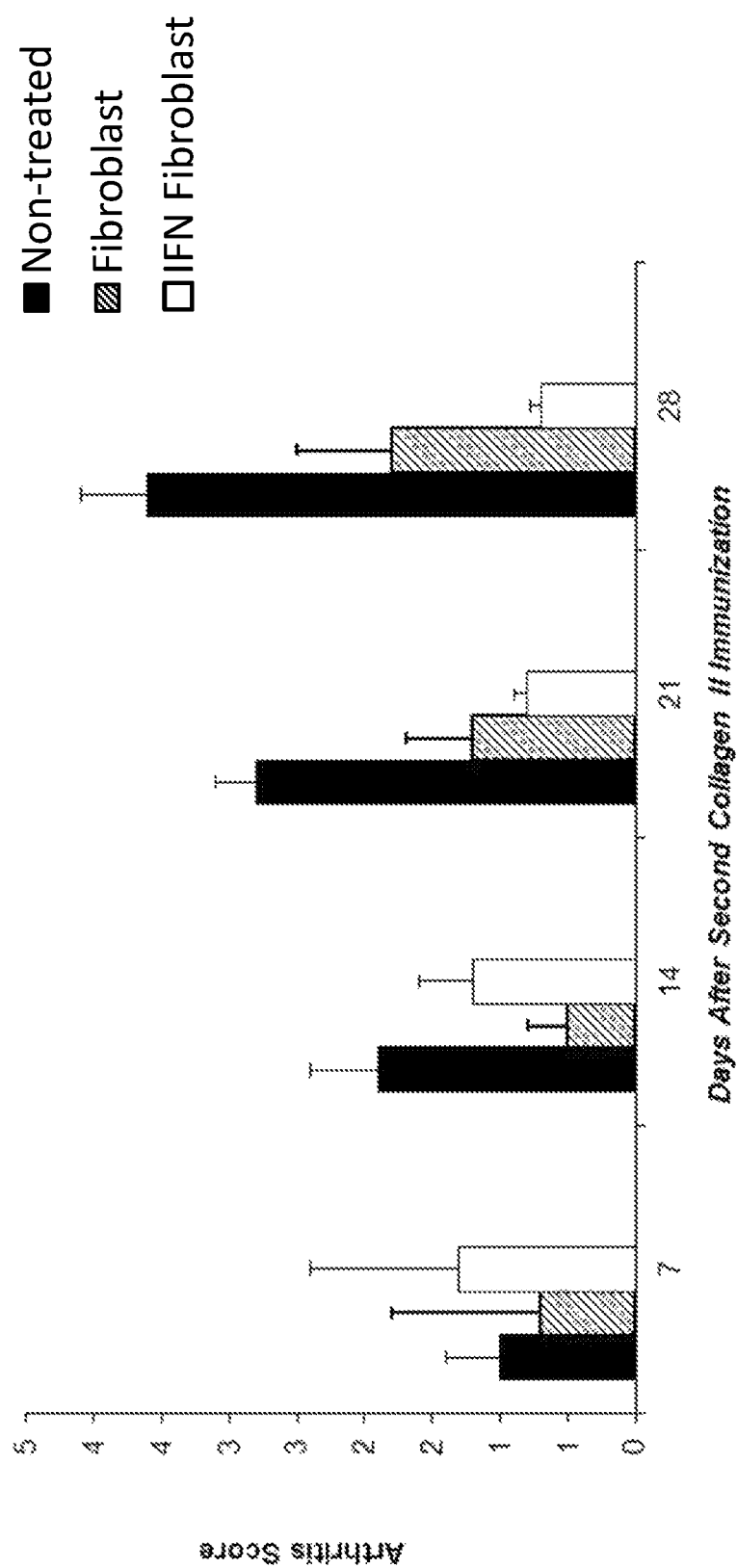
FIG. 7 shows the treatment of collagen-induced arthritis by fibroblasts vs. IFN-gamma pretreated fibroblasts.

Induction of collagen induced arthritis (CIA) was informed in DBA/1 LacJ mice, 7 wk of age, were intradermally immunized (day 0) at several sites into the base of the tail with 200 µg bovine type II collagen (CII) (Sigma-Aldrich, St. Louis, MO) dissolved in 100 µl 0.05 M acetic acid and mixed with an equal volume of CFA (Sigma-Aldrich). CII was dissolved at a concentration of 2 mg/ml by stirring overnight at 4° C. On day 21 after priming, the mice received an intraperitoneal booster injection with 200 µg CII in an equal volume (100 µl) of PBS. Mice were examined visually three times per week for the appearance of arthritis in the peripheral joints, and the arthritis score index for disease severity was given as follows: 0, no evidence of erythema and swelling; 1, erythema and mild swelling confined to the midfoot (tarsals) or ankle joint; 2, erythema and mild swelling extending from the ankle to the midfoot; 3, erythema and moderate swelling extending from the ankle to the metatarsal joints; 4, erythema and severe swelling encompassing the ankle, foot, and digits. Scoring was performed by two independent observers, without knowledge of the experimental and control groups. FIG. 7 shows reduction of arthritis score by intravenous fibroblasts or IFN-gamma treated fibroblasts.

Treatment of Collagen-Induced Arthritis by Fibroblasts and PRP-Pretreated Fibroblasts Foreskin fibroblasts were purchased from ATCC (Manassas VA) and pretreated with the indicated concentrations of PRP (5% v/v) for 24 hours in a fully humidified atmosphere of 5% carbon dioxide. 5 million fibroblasts were intravenous injected into collagen induced arthritis mice, generated as described below, two times on day 7 and day 14 after the first collagen II immunization. The animals were observed for 4 wk after arthritis onset (7 d after second CII immunization). Each limb was graded on a scale from 0 to 4, and the average clinical score per affected paw was calculated.

Figure 8:
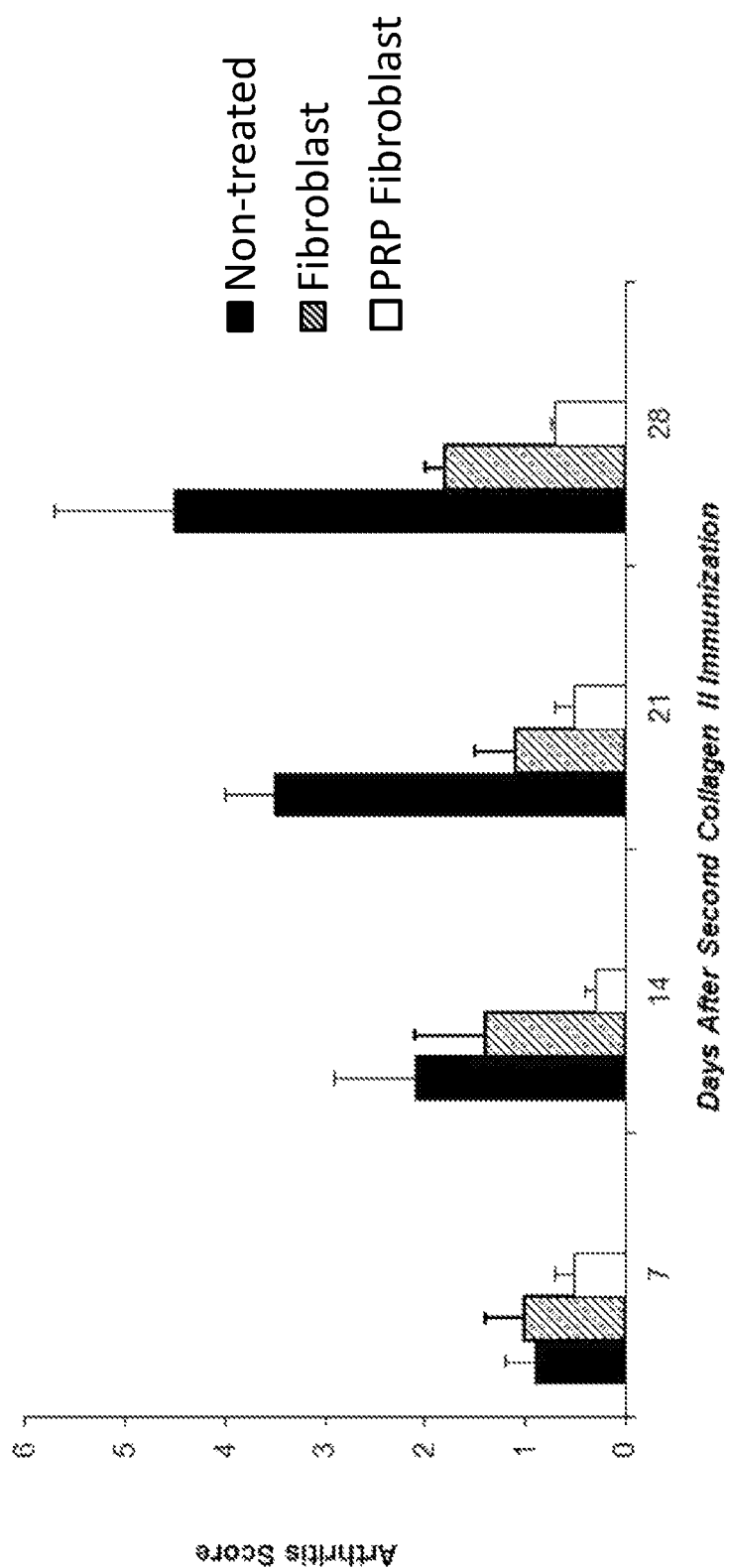
FIG. 8 illustrates the treatment of collagen-induced arthritis by fibroblasts and PRP pretreated fibroblasts.

Induction of collagen induced arthritis (CIA) was informed in DBA/1 LacJ mice, 7 wk of age, were intradermally immunized (day 0) at several sites into the base of the tail with 200 µg bovine type II collagen (CII) (Sigma-Aldrich, St. Louis, MO) dissolved in 100 µl 0.05 M acetic acid and mixed with an equal volume of CFA (Sigma-Aldrich). CII was dissolved at a concentration of 2 mg/ml by stirring overnight at 4° C. On day 21 after priming, the mice received an intraperitoneal booster injection with 200 µg CII in an equal volume (100 µl) of PBS. Mice were examined visually three times per week for the appearance of arthritis in the peripheral joints, and the arthritis score index for disease severity was given as follows: 0, no evidence of erythema and swelling; 1, erythema and mild swelling confined to the midfoot (tarsals) or ankle joint; 2, erythema and mild swelling extending from the ankle to the midfoot; 3, erythema and moderate swelling extending from the ankle to the metatarsal joints; 4, erythema and severe swelling encompassing the ankle, foot, and digits. Scoring was performed by two independent observers, without knowledge of the experimental and control groups. FIG. 8 demonstrates reduction of arthritis score by intravenous fibroblasts or PRP treated fibroblasts.

Thus, the present example concerns treatment of one or more autoimmune or inflammatory conditions in an individual. In particular embodiments, a population of cells are subjected to IFN-gamma (and optionally one or more additional agents and/or conditions) to produce a composition. In additional embodiments, an effective amount of the composition is administered to an individual to treat an autoimmune or inflammatory condition.

Example 7

Culture and Expansion of T Regulatory Cells

The present example concerns generation of T regulatory cells capable of inhibiting autoimmunity using fibroblasts in vitro and in vivo.

Figure 9:
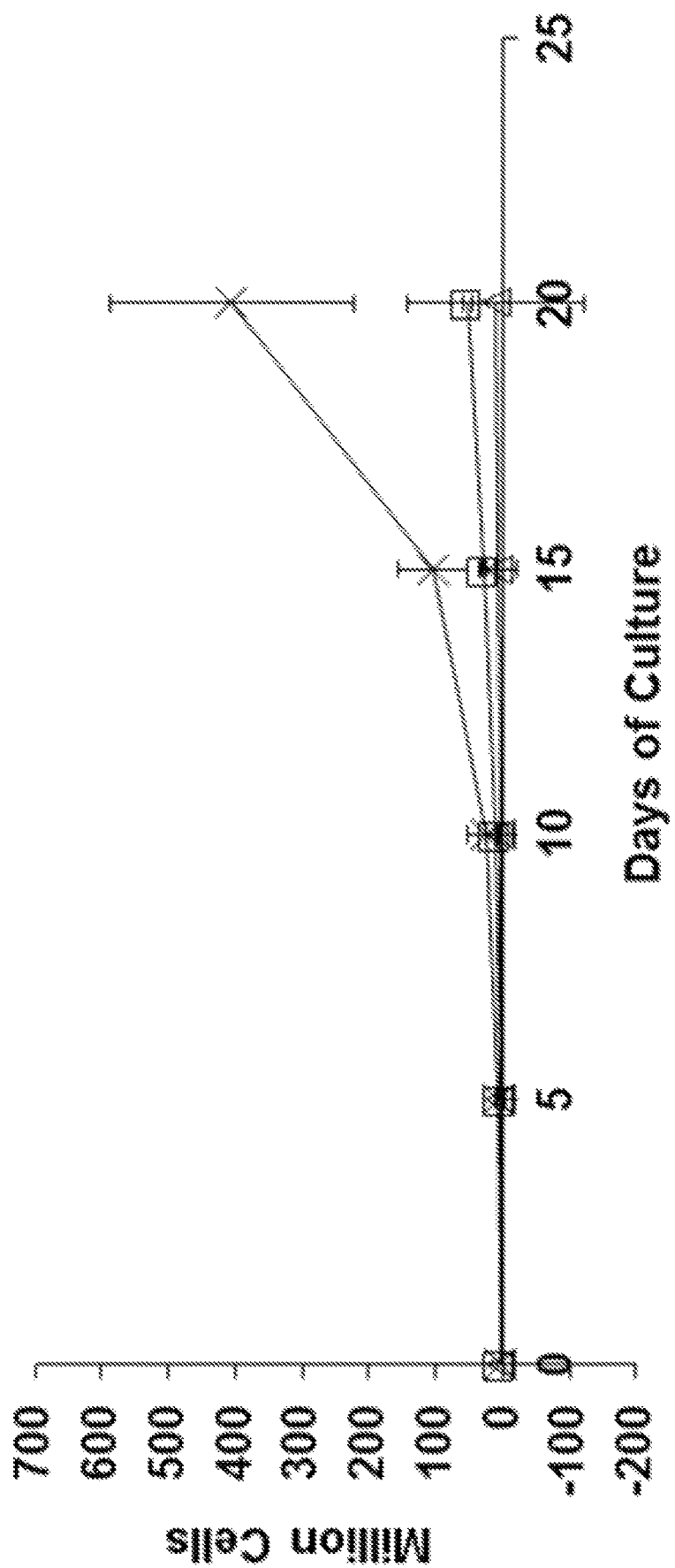
FIG. 9 demonstrates that the addition of foreskin fibroblasts accelerates regulatory T cells ("Tregs") expansion in ex vivo culture. Foreskin fibroblasts were pre-plated at 50% confluency prior to addition of cord blood cells. The "X" symbols indicate the growth of Tregs in co-culture with fibroblasts and cocktail. The square symbols indicate the growth of Tregs in co-culture with fibroblasts alone. The triangle symbols indicate the growth of Tregs in culture with cocktail alone. At initiation of culture, 50,000 Tregs were added. Counting of Tregs was performed by flow cytometry.

Embodiments of the disclosure include methods and compositions for the preparation and clinical use of certain T regulatory cells that have been and/or are being exposed to modified fibroblasts. In specific cases, the fibroblasts have been modified by exposure at least to IFN-gamma. Additional embodiments include the exposure of the fibroblasts to one or more agents, such as a CD3 ligand, a CD28 ligand, rapamycin, IL-10, TGF-beta, IL-2 or combinations thereof. Specific embodiments are demonstrated in the following studies:

Cryopreserved cord blood bags (1 unit bags) where thawed and washed in CliniMACS buffer (Miltenyi Biotec, Bergish Gladbach, Germany) containing 0.5% HSA (Baxter Healthcare, Westlake Village, CA) in order to purify mononuclear cells. Subsequently, cells CD25+ cell enrichment was performed by positive selection using magnetic activated cell sorting (MACS) according to manufacturer's instructions (Miltenyi Biotec, Bergish Gladbach, Germany). Cells were check for viability and subsequently stimulated by co-cultured with CD3/28 co-expressing Dynabeads® (ClinExVivo™ CD3/CD28, Invitrogen Dynal AS, Oslo, Norway) at a 1 cell: 3 bead ratio (Thakur et al., 2016) and re-suspended at 1×10⁶ cells/ml in X-VIVO 15 medium (Cambrex BioScience, Walkersville, MD) supplemented with 10% human AB serum (Gemini Bio-Products, Sacramento, CA), 2 mM L-glutamine (Sigma, St. Louis, MO), 1% Penicillin-Streptomycin (Gibco/Invitrogen, Grand Island, NY)] and 200 IU/ml interleukin (IL)-2 (CHIRON Corporation, Emeryville, CA). Ex vivo co-culture of the CD25+ cells and beads was performed in tissue culture flasks at 37° C. in a 5% $CO_2$-in-air atmosphere. The CB-derived CD25+ enriched T-cells were maintained at 1×10⁶ cells/ml by the addition of fresh medium and IL-2 (maintaining 200 IU/ml) every 48-72 hours. An addition of foreskin fibroblasts was provided in some cultures. In specific embodiments, the foreskin fibroblasts were pre-plated at 50% confluency prior to addition of cord blood cells, as described above. FIG. 9 demonstrates culture and expansion of T regulatory cells, where "X" indicates culture of fibroblasts and cocktail. Squares represent fibroblasts alone and triangles represent cocktail alone. At initiation of culture, 50,000 Treg cells were added. Counting of Tregs was performed by flow cytometry.

Example 8

Treatment of Liver Failure with Allogeneic Lymphocyte-Activated Fibroblasts

The present example concerns means of treatment of liver failure and augmentation of liver regeneration by utilization of fibroblast cells pretreated with allogeneic peripheral blood mononuclear cells. In one embodiment, liver failure is treated by fibroblasts that have been previously cultured with allogeneic peripheral blood mononuclear cells in order to augment production of hepatocyte growth factor.

Murine Fibroblasts BALB/c origin were cultured in DMEM media with 10% fetal calf serum and subsequent to passaging cells were "primed" by exposure to an equal amount of allogeneic C57BL/6 splenocytes for 24 hours. Fibroblasts where subsequently washed off splenocytes and utilized for experiments.

Healthy male C57BL/6 mice weighing 18 to 20 g and aged 6-8 weeks were housed under conventional experimental environment with 12-hour light-dark cycle in the Animal Care Facility. The mice had a free access to commercial standard mouse diet and water. All experiments were conducted in accordance with the protocols approved. The preparation of animal model was done as previously described (Li et al., 2014). In brief, eighteen mice were randomly assigned to the following three groups (n=6). (1) Normal control group, mice first receiving intraperitoneal (i.p.) injection of corn oil were then injected 200 ul PBS intravenously 30 min later. (2) untreated group, mice first receiving i.p. injection of a single dose of $CCl_4$ (Sigma-aldrich, St Louis, United States) for induction of acute liver injury were injected 200 µl PBS intravenously 30 min later (Fan et al., 1995). (3) activated fibroblast-treated group, mice first receiving i.p. injection of $CCl_4$ were injected 1×10⁶ activated fibroblasts at passage 4 resuspended in 200 µl of PBS intravenously 30 min later (Spiewak-Rinaudo and Thorgeirsson, 1997). Mice were sacrificed 24 h after injection of $CCl_4$, and blood was collected. Liver and spleen were then promptly removed for later analysis or stored frozen at −80° C. Serum alanine aminotransferase (ALT) and aspartate aminotransferase (AST) activities were measured by standard spectrophotometric procedures using a ChemiLab ALT and AST assay kit (IVDLab Co., Ltd., Korea), respectively. Enzyme activities were shown in international unit per liter (IU/L). Liver slices were made from part of the left lobes and fixed in 10% neutral buffered formalin, embedded in paraffin and cut into 5 μm sections. Specimens were dewaxed, hydrated and stained in the usual manner with standard hematoxylin and eosin (H&E) to examine morphology.

Figure 10:
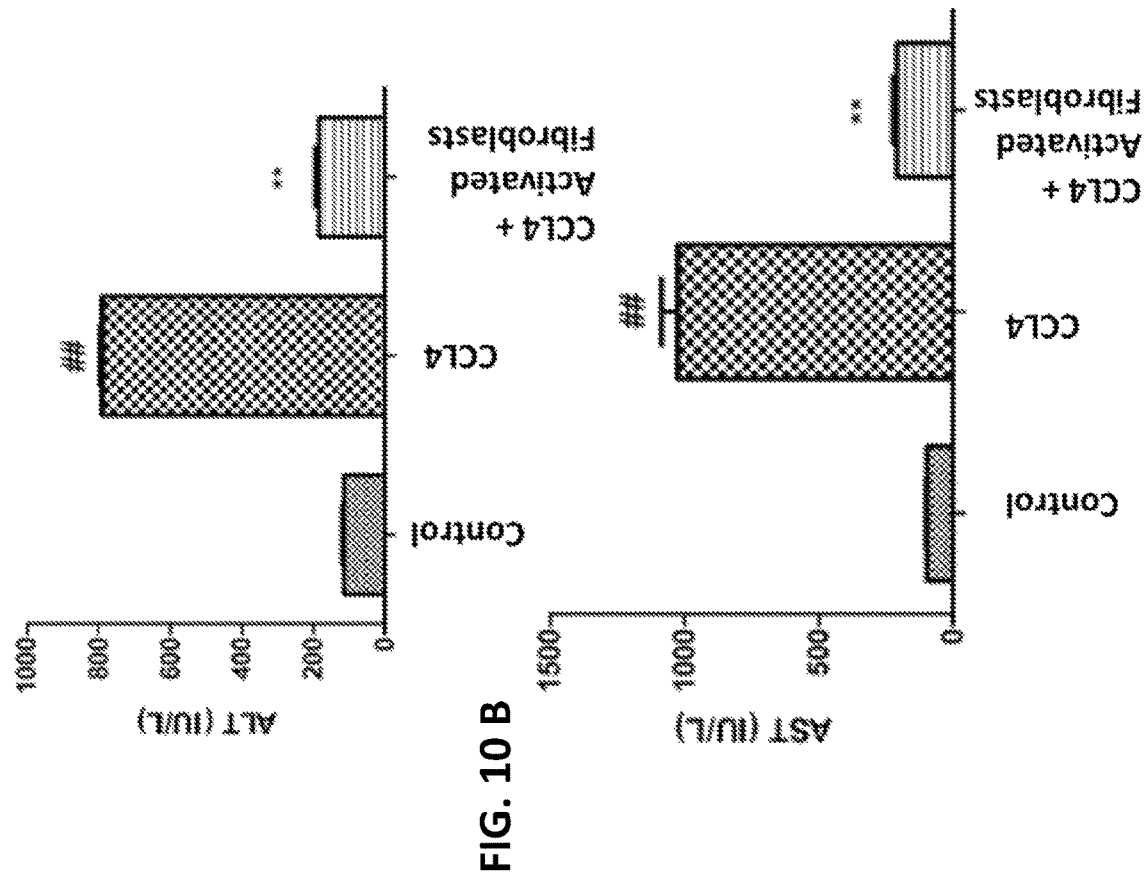
FIGS. 10A and 10B show that lymphocyte-activated fibroblasts significantly reduced levels of alanine aminotransferase (ALT.

In FIGS. 10A and 10B, serum samples were collected from mice of normal control, mice treated with Carbon Tetrachloride and carbon tetrachloride with $10^6$ lymphocyte activated fibroblasts injected intravenously. Lymphocyte activated fibroblasts significantly reduced serum levels of (FIG. 10A) ALT and (FIG. 10B) AST in comparison with those of untreated ALI group. Bar graphs represent mean±SEM of three separate experiments. P values were determined by one-way ANOVA. Data show are representative of three separate experiments performed (##p<0.01, vs. normal control group. *p<0.05 and **p<0.01 vs. untreated group, n=6).

Figure 11:
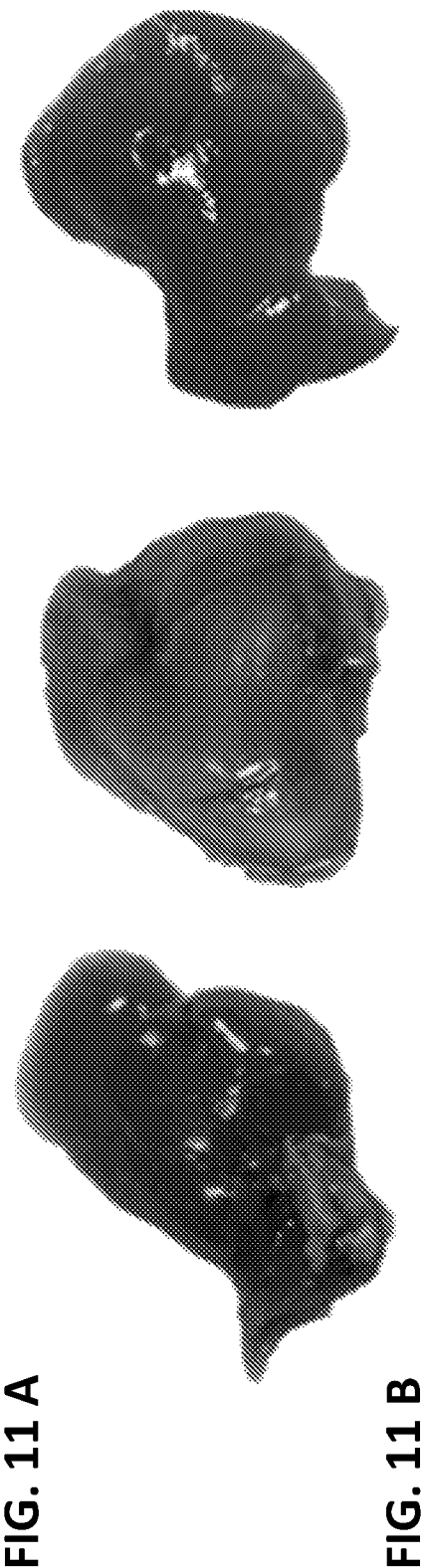
FIGS. 11A and 11B show pathological changes of livers in mice (FIG. 11A) treated with CCL4 compared to CCL4 and activated fibroblasts, including histological sections of the liver (FIG. 11B).
Figure 11:
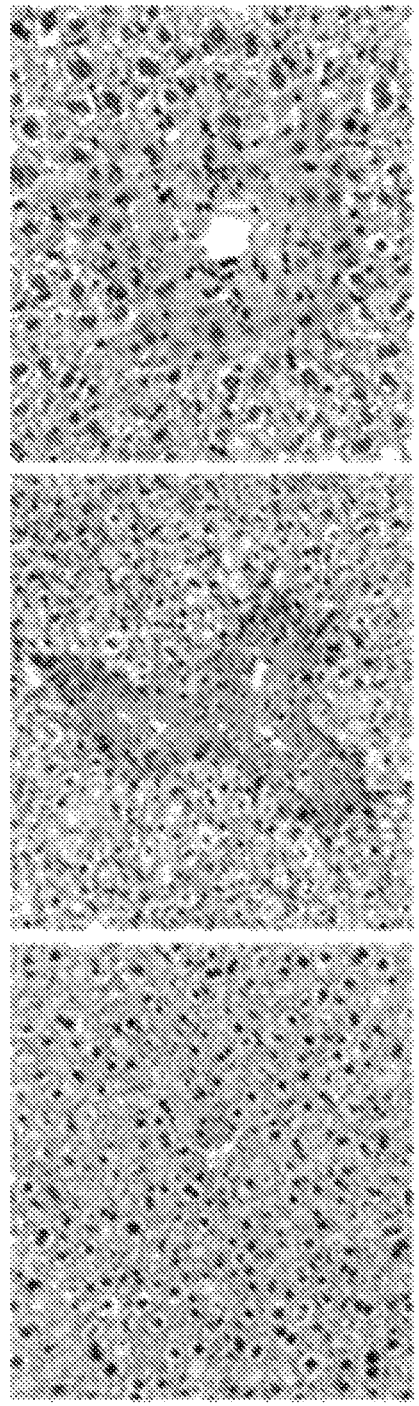

Mice were treated with $CCl_4$ (1 ml/kg body weight and 1:3 diluted in corn) to induce acute liver injury, then intravenously administered with lymphocyte activated fibroblasts ($1 \times 10^6$/0.2 ml/mouse, suspended in PBS) 30 min after $CCl_4$ injection, only once in 24 hours. Photographs of livers were taken 24 hours after $CCl_4$ injection. FIG. 11A indicates gross pathological changes of livers. FIG. 11B shows representative photomicrographs of histological sections of liver (200×, haematoxylin and eosin staining). Livers in untreated group exhibited more ballooned hepatocytes, apoptosis and necrosis than those in normal control groups, which were significantly alleviated by ppMSC treatment (n=6).

Example 9

Stimulation of VEGF Production from HUVEC Cultures by Fibroblast Reprogrammed Monocytes Macrophages are key components of the innate immune system that play a principal role in the regulation of inflammation as well as physiological processes such as tissue remodeling (van Furth and Cohn, 1968; Wynn et al., 2013). The diverse role of macrophages can be seen in conditions ranging from wound healing (Smith et al., 2017; Vannella and Wynn, 2017; Boddupalli et al., 2016; Snyder et al., 2016), to myocardial infarction (Gombozhapova et al., 2017; Hu et al., 2011; Ma et al., 2013; Lee et al., 2013; Yan et al., 2013; Fernandez-Velasco et al., 2014), to renal failure (Guiteras et al., 2016; Meng et al., 2015; Yamamoto et al., 2015; Li et al., 2015) and liver failure (Sun et al., 2017).

Differentiated macrophages and their precursors are versatile cells that can adapt to microenvironmental signals by altering their phenotype and function (Gratchev et al., 2006). Although they have been studied for many years, it has only recently been shown that these cells comprise distinct subpopulations, known as classical M1 and alternative M2 (Mills, 2012). Mirroring the nomenclature of Th1 cells, M1 macrophages are described as the pro-inflammatory subtype of macrophages induced by IFN-gamma and LPS. They produce effector molecules (e.g., reactive oxygen species) and pro-inflammatory cytokines (e.g., IL-12, TNF-alpha and IL-6) and they trigger Th1 polarized responses (Mills and Ley, 2014). M2 macrophages are further sub-divided into M2a (following exposure to IL-4 or IL-13), M2b (immunocomplexes and Toll-like receptors or IL-1b ligands) and M2c (induced by IL-10, TGF-.beta. and glucocorticoids). All three subtypes have an anti-inflammatory phenotype characterized by IL-10.sup.high (especially M2b+M2c), RELM-alpha$^{high}$ (mouse only), CD206$^{high}$ and IL-12$^{low}$ (M2a) (Mantovani et al., 2004).

During normal inflammation, macrophages undergo dynamic switching between these polarization states. Whereas M1 macrophages are more abundant during the early stages and mediate clearance and the recruitment of other effector cells, M2 macrophages predominate towards the end of inflammation, promoting vascularization and new tissue formation (Ferrante and Leibovich, 2012). The course of inflammation is strongly dependent on this appropriately-balanced ratio of M1/M2 macrophages. Failure to switch from the predominance of M1 to M2 may lead to the perpetuation and reinforcement of the pro-inflammatory environment in chronic inflammation. Therefore, M1 arrest may prevent the resolution of inflammation (Hu et al., 2011).

A disrupted M1/M2 ratio has been observed in several autoimmune and chronic inflammatory diseases, as well as metabolism-associated diseases such as diabetes and metabolic syndrome (Ma et al., 2013). Adipose tissue macrophages (ATMs) from obese individuals have been shown to undergo a phenotypic shift from M2 (CD206$^+$, CD301$^+$, Arg1$^+$) to M1 (NOS2$^+$, CD11c$^+$), producing pro-inflammatory cytokines such as IL-6, TNF-alpha, and IL-1beta (Lee et al., 2013), thus antagonizing the effects of leptin and adiponectin (Yan et al., 2013). Similar M1-associated pathology has been associated with cardiovascular diseases such as atherosclerosis (Fernandez-Velasco et al., 2014), and autoimmune diseases such as rheumatoid arthritis (de Couto et al., 2015), multiple sclerosis (Guiteras et al., 2016), systemic lupus erythematosus (Meng et al., 2015) and Crohn's disease (Yamamoto et al., 2015).

The persistence of M1 macrophages during the initial inflammatory response can also prevent the resolution of inflammation in several chronic skin diseases. Reducing the number of pro-inflammatory M1 macrophages in diabetes-associated skin ulcerations can attenuate wound inflammation and promote wound closure. In human patients with chronic venous ulcers, the persistence of M1 macrophages induces the production of reactive oxygen species which cause DNA damage and lead to defective tissue repair. Activated (presumably M1) macrophages are also associated with atopic dermatitis, another chronic skin disease that is increasing in prevalence, affecting 10-20% of children and 1-3% of adults in industrial countries with an economic impact running into billions of dollars.

Given the importance of M1 and M2 macrophages, it is useful in the field to have means and methods of generating M2 macrophages. The present disclosure addresses this need.

In order to replicate angiogenic processes in vitro, a culture of human umbilical vein endothelial cells (HUVEC) is performed in 96 well plates. HUVEC cells are plated at a concentration of 20,000 cells per well. Various concentrations of monocytes, fibroblasts, or monocytes that have previously been incubated with fibroblasts are added to the HUVEC cells.

Figure 12:
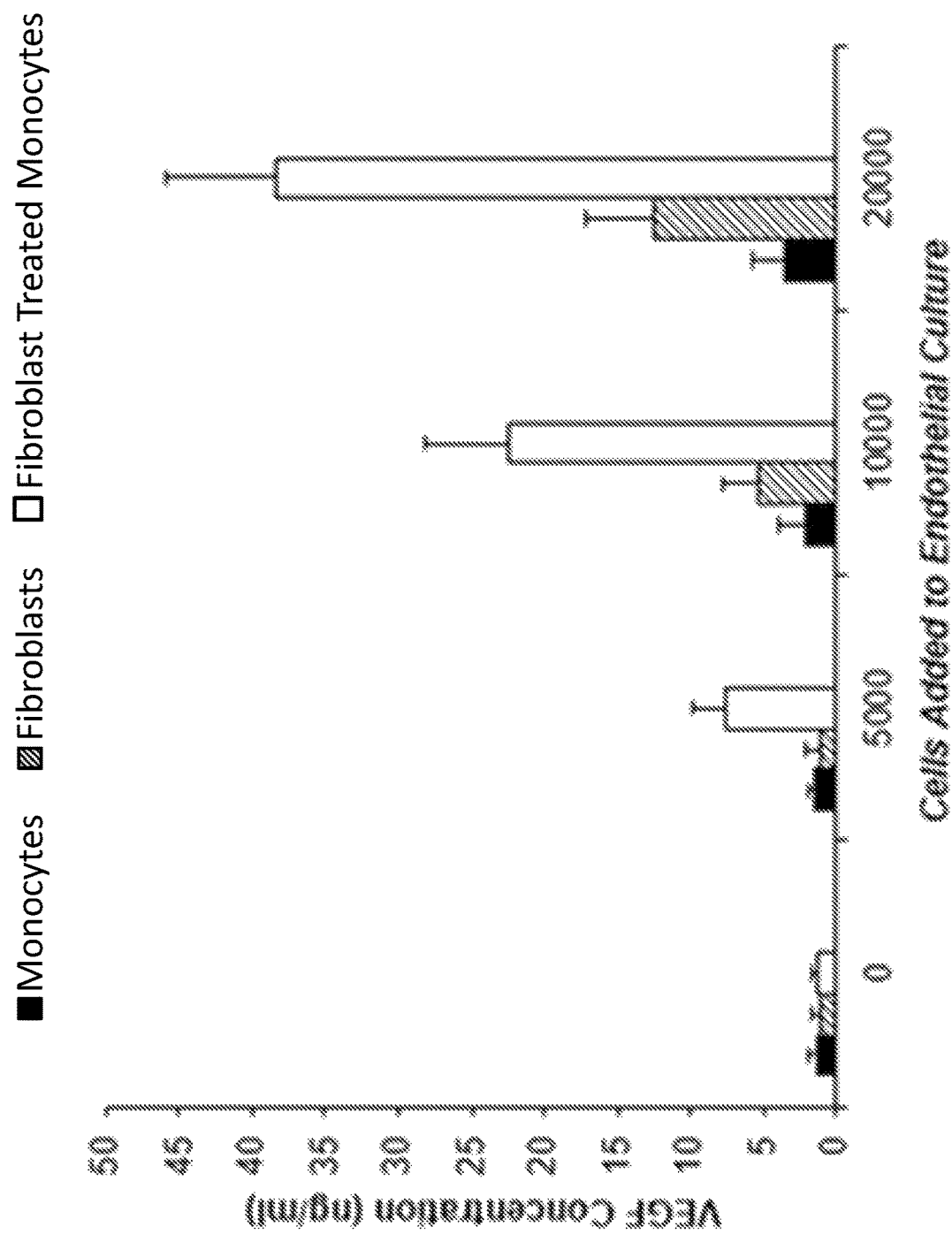
FIG. 12 shows VEGF production from HUVEC cultures following exposure to fibroblast-treated monocytes, fibroblasts alone, or monocytes alone.

Monocytes are obtained by plastic adherence of peripheral blood mononuclear cells and purified by CD14 magnetic activated separation (MACS). Fibroblasts are purchased from ATCC. For incubation of monocytes with fibroblasts, a 1 to 1 ratio of monocytes and fibroblasts is cultured for 48 hours in RMPI media with 10% fetal calf serum at 37° Celsius in a fully humidified atmosphere with 5% carbon dioxide. Subsequent to culture, cells are trypsinized and monocytes are purified by CD14 selection using MACS. Cells are subsequently incubated at the indicated ratio with HUVEC cells in a total of 200 uL of media per well. Conditioned media is extracted after 48 hours of culture and VEGF production is analyzed by ELISA (FIG. 12).

Example 10

Figure 13:
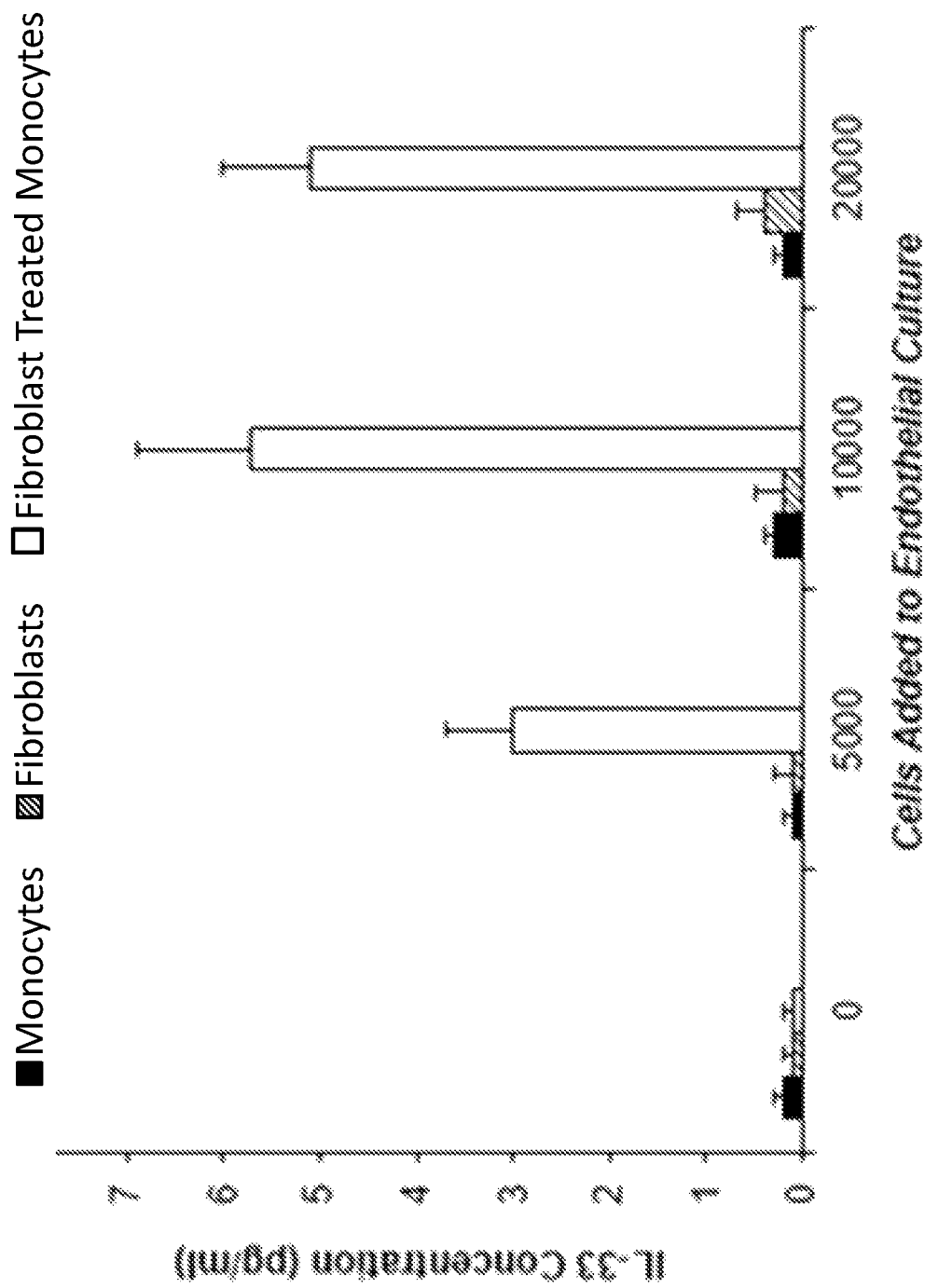
FIG. 13 shows IL-33 production from HUVEC cultures following exposure to fibroblast-treated monocytes, fibroblasts alone, or monocytes alone.

Stimulation of IL-33 Production from HUVEC Cultures by Fibroblast Reprogrammed Monocytes In order to replicate angiogenic processes in vitro, a culture of human umbilical vein endothelial cells (HUVEC) is performed in 96 well plates. HUVEC cells are plated at a concentration of 20,000 cells per well. Various concentrations of monocytes, fibroblasts, or monocytes that have previously been incubated with fibroblasts are added to the HUVEC cells. Monocytes are obtained by plastic adherence of peripheral blood mononuclear cells and purified by CD14 magnetic activated separation (MACS). Fibroblasts are purchased from ATCC. For incubation of monocytes with fibroblasts, a 1 to 1 ratio of monocytes and fibroblasts is cultured for 48 hours in RMPI media with 10% fetal calf serum at 37° Celsius in a fully humidified atmosphere with 5% carbon dioxide. Subsequent to culture, cells are trypsinized and monocytes are purified by CD14 selection using MACS. Cells are subsequently incubated at the indicated ratio with HUVEC cells in a total of 200 uL of media per well. Conditioned media is extracted after 48 hours of culture and IL-33 production is analyzed by ELISA (FIG. 13).

Example 11

Stimulation of HUVEC Proliferation by Fibroblast Reprogrammed Monocytes

In order to replicate angiogenic processes in vitro, a culture of human umbilical vein endothelial cells (HUVEC) is performed in 96 well plates. HUVEC cells are plated at a concentration of 20,000 cells per well. Various concentrations of monocytes, fibroblasts, or monocytes that have previously been incubated with fibroblasts are added to the HUVEC cells. Monocytes are obtained by plastic adherence of peripheral blood mononuclear cells and purified by CD14 magnetic activated separation (MACS). Fibroblasts are purchased from ATCC. For incubation of monocytes with fibroblasts, a 1 to 1 ratio of monocytes and fibroblasts is cultured for 48 hours in RMPI media with 10% fetal calf serum at 37° Celsius in a fully humidified atmosphere with 5% carbon dioxide. Subsequent to culture, cells are trypsinized and monocytes are purified by CD14 selection using MACS.

Figure 14:
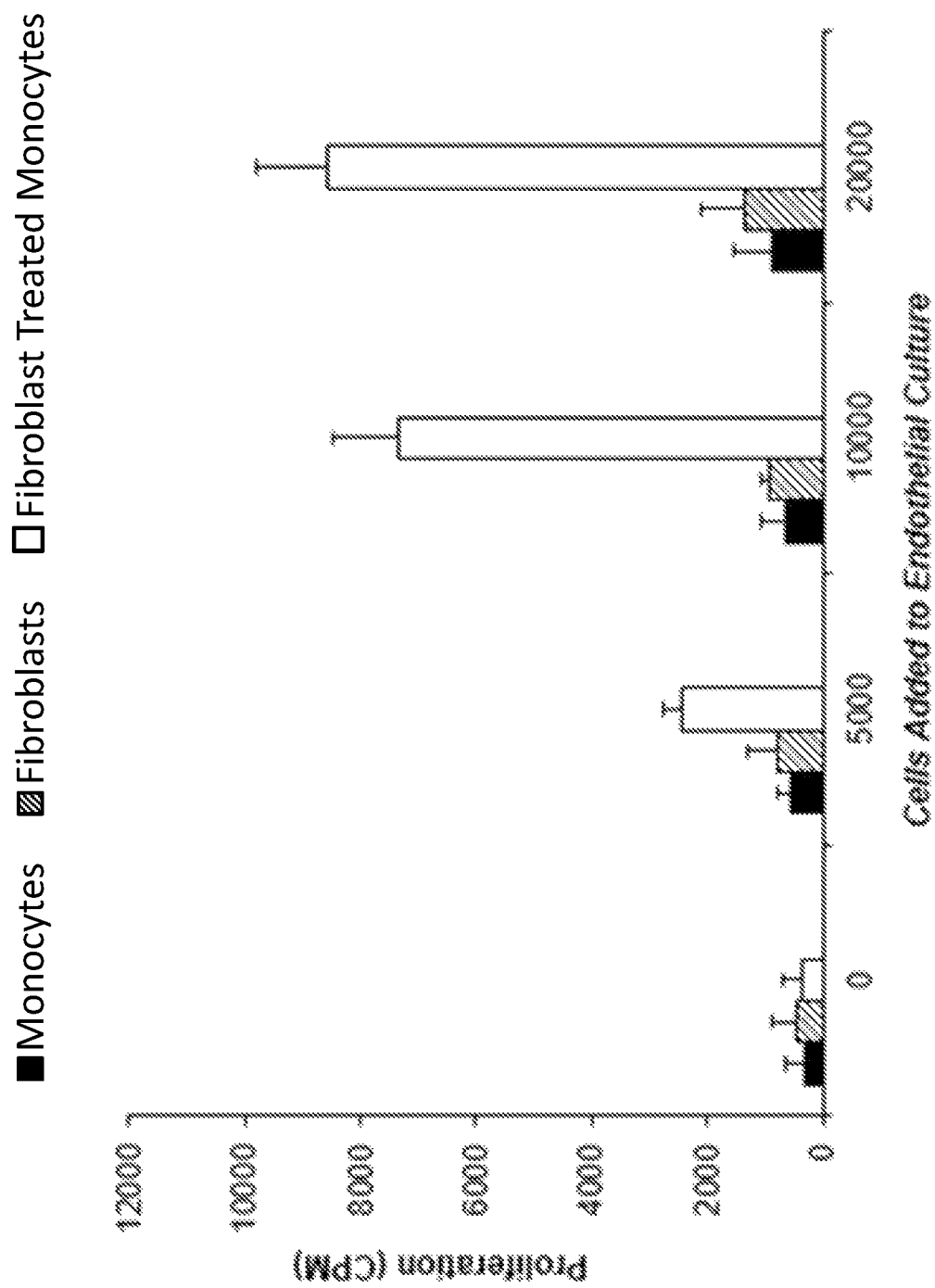
FIG. 14 shows proliferation of HUVEC cells following exposure to fibroblast-treated monocytes, fibroblasts alone, or monocytes alone.

Added cells are mitotically inactivated by incubation with mitomycin C (5 ug/ml for 12 hours). Cells are subsequently incubated at the indicated ratio with HUVEC cells in a total of 200 uL of media per well for 72 hours. 1 uCurie/ml of tritiated thymidine is added in the last 12 hours of culture and proliferation is quantified by scintillation counting. Proliferation is expressed as counts per minute (FIG. 14).

Example 12

Stimulation of Angiogenesis/Acceleration of Wound Healing Using Fibroblast Reprogrammed Autologous T Cells Ischemic disease are a cause of significant morbidity and mortality in today's society. Currently used interventions such as surgery or endovascular interventions have limited success and often require re-intervention, in part due to restenosis and inflammatory reactions. One promising means of treating ischemic diseases is through the use of angiogenesis therapy. However, while administration of angiogenic factors to patients with critical limb ischemia, for example, does induce some benefit in early trials, data from randomized trials to date do not support widespread use. The transfection of upstream transcription factors such as HIF-1 alpha is a promising approach because it mimics natural angiogenesis in that a plurality of growth factors are induced following transfection. However clinical results are too premature to draw firm conclusions. The present disclosure overcomes limitations in the use of angiogenesis therapy by reprogramming T cells using PBMCs reprogrammed by fibroblasts.

Example 13

Stimulation of HUVEC Proliferation by Fibroblast Reprogrammed Peripheral Blood Mononuclear Cells In order to replicate angiogenic processes in vitro, a culture of human umbilical vein endothelial cells (HUVEC) is performed in 96 well plates. HUVEC cells are plated at a concentration of 20,000 cells per well. Various concentrations of PBMC, fibroblasts, or PBMC that have previously been incubated with fibroblasts are added to the HUVEC cells.

Peripheral blood mononuclear cells (PBMC) are obtained by Ficoll density gradient. Fibroblasts are purchased from ATCC.

Figure 15:
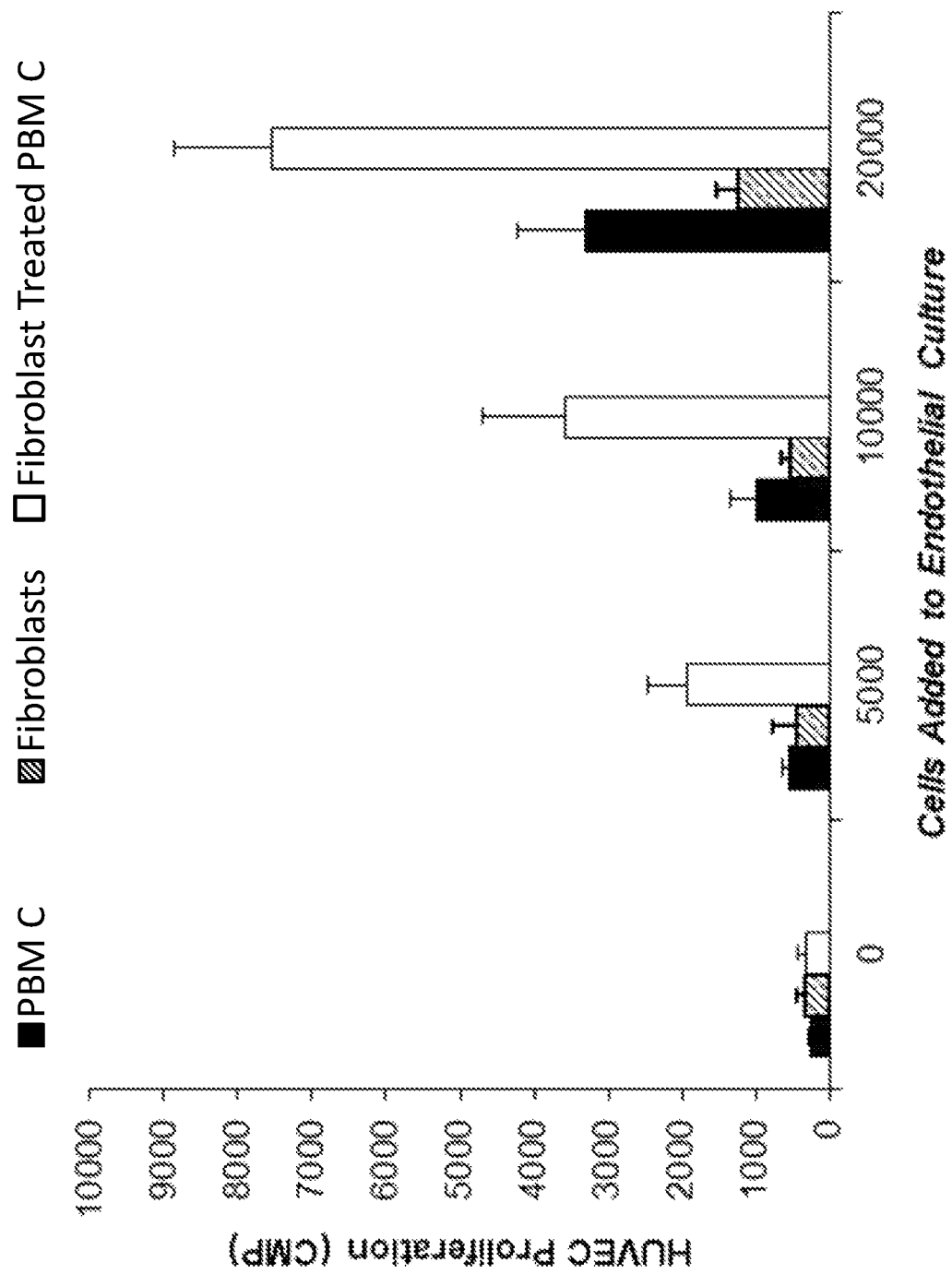
FIG. 15 shows proliferation of HUVEC cells following exposure to fibroblast-treated PBMCs, PBMCs alone, or fibroblasts alone.

For incubation of PBMC with fibroblasts, a 1 to 1 ratio of PBMC and fibroblasts is cultured for 48 hours in RMPI media with 10% fetal calf serum at 37° Celsius in a fully humidified atmosphere with 5% carbon dioxide. Subsequent to culture, non-adherent cells are harvested by pipetting. Cells are washed in phosphate buffered saline, resuspended in RPMI media and subsequently incubated at the indicated ratio with HUVEC cells in a total of 200 uL of media per well. Proliferation was assessed at 48 hours by tritiated thymidine incorporation (FIG. 15).

Example 14

Stimulation of Dendritic Cell CD80 by Stressed Fibroblasts

Peripheral blood mononuclear cells were isolated from peripheral blood by the Ficoll methodology. Briefly, blood was extracted using heparin EDTA and overlaid on Ficoll Histopaque in a 50 ml conical tube. Cells were spun at 1200 g for 30 minutes and the mononuclear cells were isolated. Said mononuclear cells were washed 2 times in phosphate buffered saline and resuspended in RPMA media with 10% fetal calf serum. Cells were plated in 6 well flasks and allowed to adhere for 2 hours. Adherent cells were used as a source of monocytes. Monocytes were cultured for 7 days in IL-4 10 ng/ml and GM-CSF 10 ng/ml in the presence of control fibroblasts, as well as stressed fibroblasts.

To produce control and stressed fibroblasts, foreskin fibroblasts where purchased from ATCC and cultured in Media 106 (Thermo Fisher) supplemented with 10% fetal calf serum and antibiotic/antimycotic mixture as per manufacturer's instructions (Thermo Fischer). Cells were cultured in T-175 flasks at 5% $CO_2$ in a fully humidified atmosphere at 37° Celsius until they reached 75% confluency. Hyperthermia was applied by heating cells in a 40° Celsius water bath for 4 hours. Control cells were placed in a 37 Celsius water bath. For serum deprivation, foreskin fibroblasts where cultured has described above and exposed to Media 106 without fetal calf serum for 24 hours.

Figure 16:
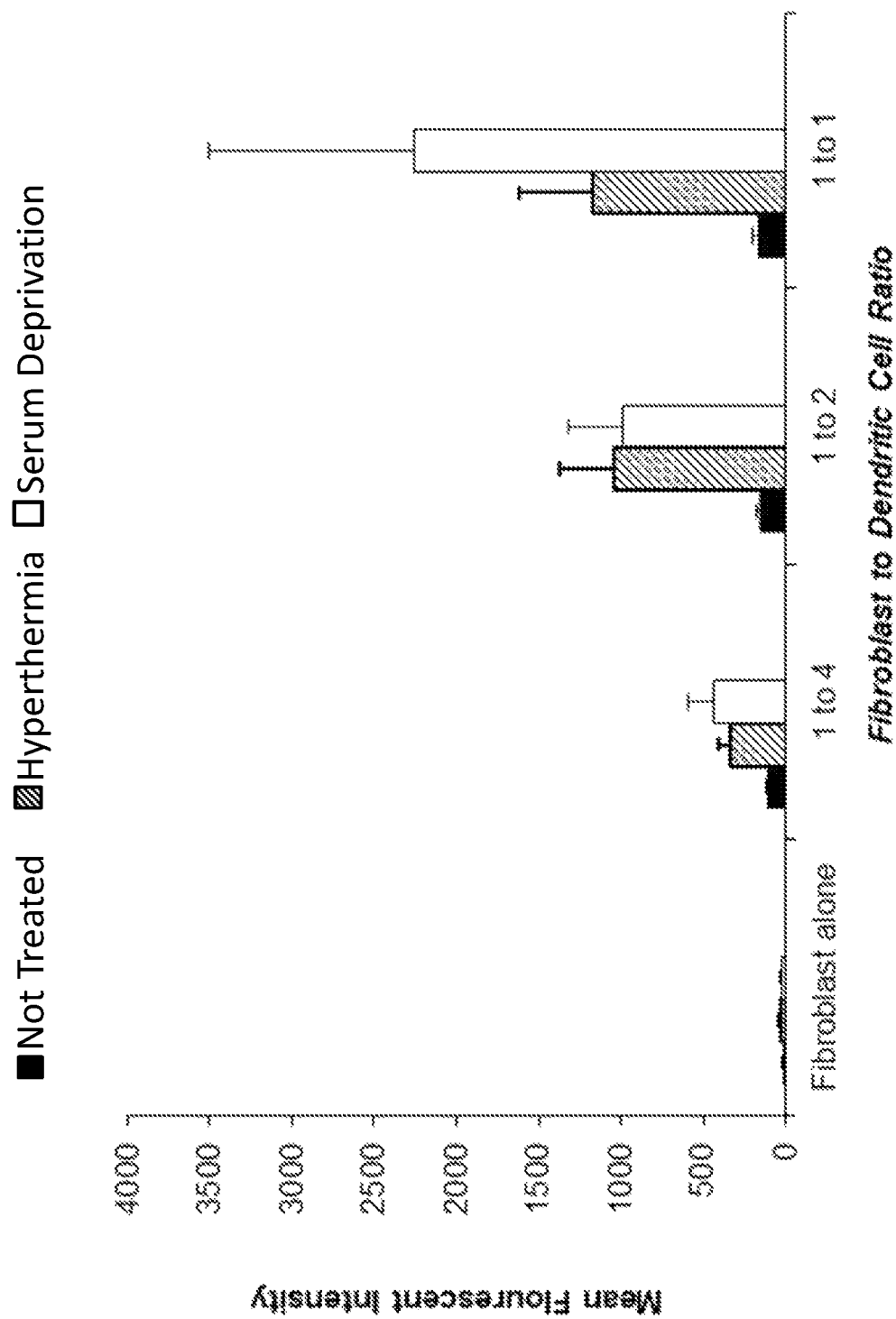
FIG. 16 demonstrates that increased expression of CD80 was observed in culture with stressed fibroblasts as compared to control fibroblasts.

Seven days after tissue culture dendritic cells were assessed for maturation markers CD80 by flow cytometry. As seen in FIG. 16, increased expression of CD80 was observed in culture with stressed fibroblasts as compared to control fibroblasts.

Example 15

Stimulation of Dendritic Cell CD86 by Stressed Fibroblasts

Peripheral blood mononuclear cells were isolated from peripheral blood by the Ficoll methodology. Briefly, blood was extracted using heparin EDTA and overlaid on Ficoll Histopaque in a 50 ml conical tube. Cells were spun at 1200 g for 30 minutes and the mononuclear cells were isolated. Said mononuclear cells were washed 2 times in phosphate buffered saline and resuspended in RPMA media with 10% fetal calf serum. Cells were plated in 6 well flasks and allowed to adhere for 2 hours. Adherent cells were used as a source of monocytes. Monocytes were cultured for 7 days in IL-4 10 ng/ml and GM-CSF 10 ng/ml in the presence of control fibroblasts, as well as stressed fibroblasts.

To produce control and stressed fibroblasts, foreskin fibroblasts where purchased from ATCC and cultured in Media 106 (Thermo Fisher) supplemented with 10% fetal calf serum and antibiotic/antimycotic mixture as per manufacturer's instructions (Thermo Fischer). Cells were cultured in T-175 flasks at 5% $CO_2$ in a fully humidified atmosphere at 37° Celsius until they reached 75% confluency. Hyperthermia was applied by heating cells in a 40° Celsius water bath for 4 hours. Control cells were placed in a 37° Celsius water bath. For serum deprivation, foreskin fibroblasts where cultured has described above and exposed to Media 106 without fetal calf serum for 24 hours.

Figure 17:
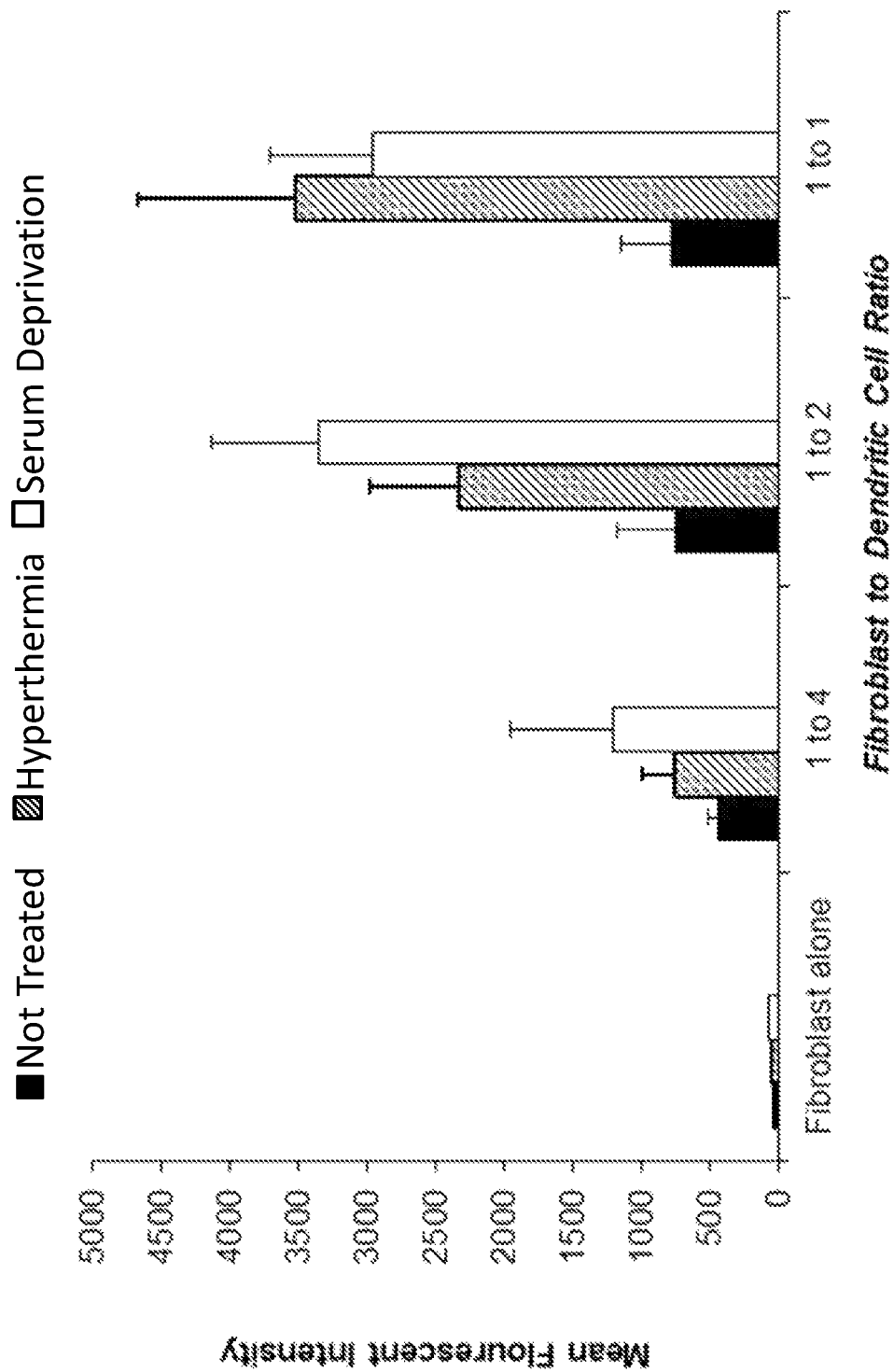
FIG. 17 shows that increased expression of CD86 was observed in culture with stressed fibroblasts as compared to control fibroblasts.

Seven days after tissue culture dendritic cells were assessed for maturation marker CD86 by flow cytometry. As seen in FIG. 17, increased expression of CD86 was observed in culture with stressed fibroblasts as compared to control fibroblasts.

Example 16

Augmentation of CD8 Proliferation by Culture on Hyperthermia or Serum Deprived Fibroblasts Foreskin fibroblasts where purchased from ATCC and cultured in Media 106 (Thermo Fisher) supplemented with 10% fetal calf serum and antibiotic/antimycotic mixture as per manufacturer's instructions (Thermo Fischer). Cells were cultured in T-175 flasks at 5% $CO_2$ in a fully humidified atmosphere at 37 Celsius until they reached 75% confluency. Hyperthermia was applied by heating cells in a 40 Celsius water bath for 4 hours. Control cells were placed in a 37 Celsius water bath.

For serum deprivation, foreskin fibroblasts where cultured has described above and exposed to Media 106 without fetal calf serum for 24 hours.

Cells where subsequently trypsinized and plated on T-175 flasks at 50% confluency with Magnetic Activated Cell Sorting (MACS) isolated CD8 cells. Peripheral blood mononuclear cells from healthy donors were used as source of T cells for isolation. Culture of CD8 cells and fibroblasts were established at the indicated ratios.

Figure 18:
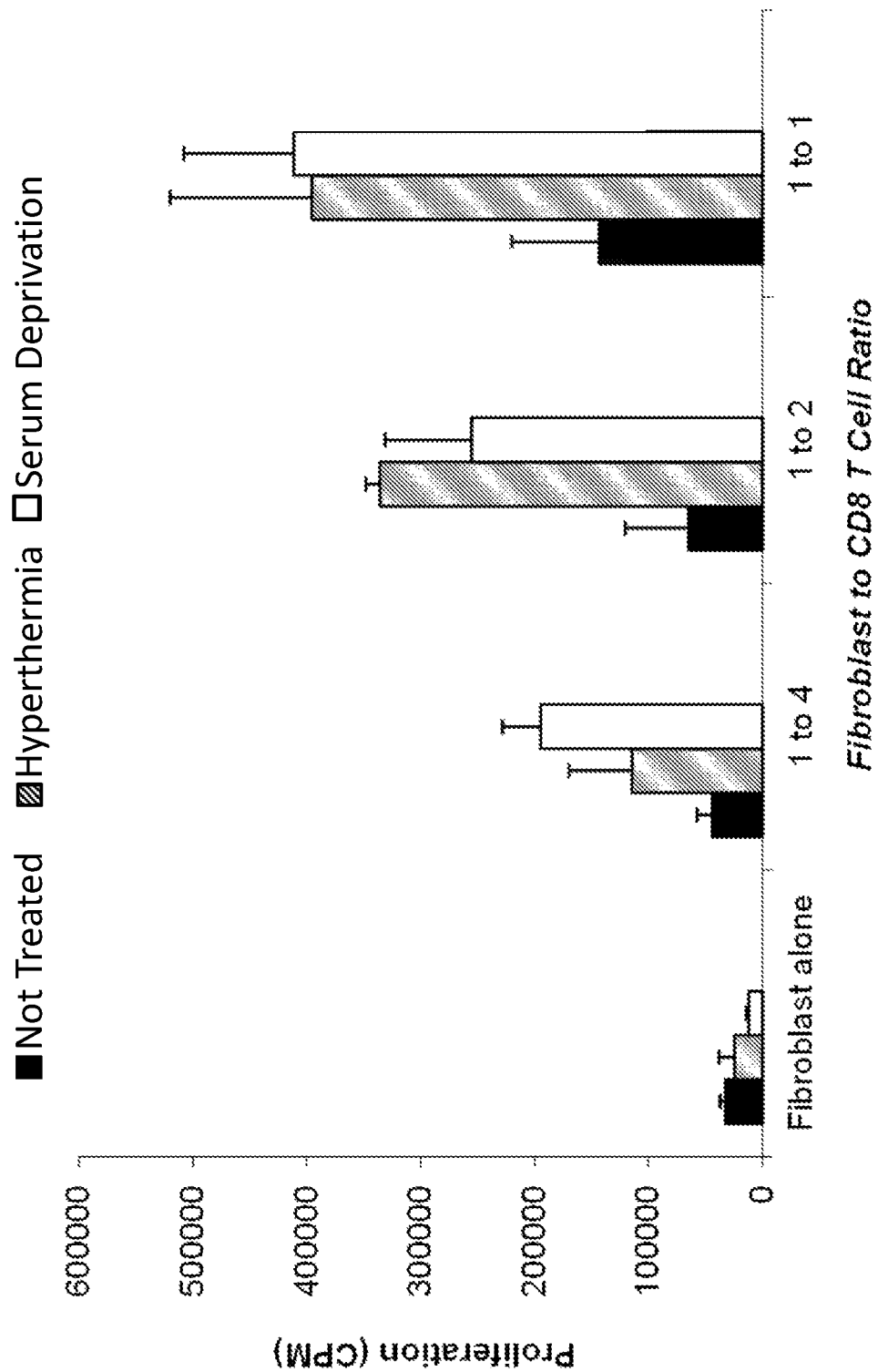
FIG. 18 shows augmentation of CD8 proliferation by culture on hyperthermia or serum-deprived fibroblasts.

After 48 hour incubation, non-adherent cells were isolated by washing and stimulated with phytohaemagglutinin (5 ug/ml) for 24 hours. Proliferation was assessed by tritiated thymidine incorporation by pulsing for 12 hours with 1 microCurie per ml of tritiated thymidine. Proliferation was expressed as counts per minute by scintillation counting (FIG. 18).

Example 17

Preservation of End Diastolic Volume by Administration of Fibroblast and Monocytes Cultured in PGE2

Figure 19:
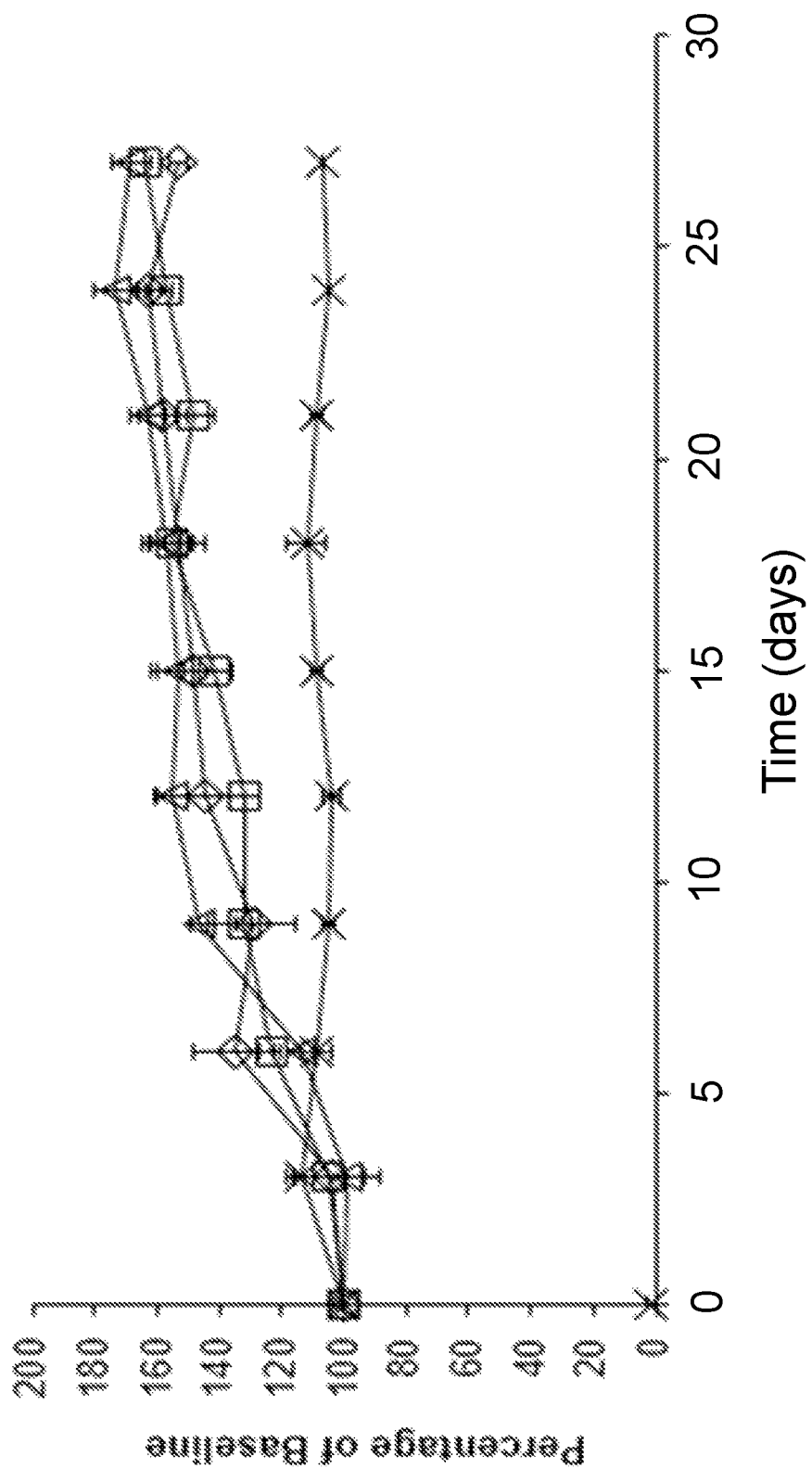
FIG. 19 shows treatment of cardiac infarct mouse model using cultured cells. Diamonds reflect monocytes, squares are fibroblasts, triangles are saline, and "x" is a combination of monocyte and fibroblast.

C57BL/6 mice were subjected to left anterior descending artery ligation to mimic a coronary infarct. Mice were treated on day 1 with either human monocytes, human fibroblasts, or the combination. Combination of human monocyte and fibroblast cultures were performed by 36 hour culture in 100 ng/ml PGE-2. Cells were dissociated with trypsinization, washed, and administered intravenously. Administration was performed of 1 million cells. End diastolic volume was measured with echocardiogram. Ten mice per group were used. A significant preservation of ventricular volume was observed in the combination treated animals (FIG. 19). Diamonds are monocytes, squares are fibroblasts, triangles are saline, "x" is a combination of monocyte and fibroblast.

Example 18

Treatment of Graft Versus Host Disease by Fibroblasts and Populations Thereof

Example A: Preclinical Study 8-12 week female B6 mice were treated with intraperitoneal injection of 150 mg/kg 5-FU (Sigma Chemical Corp., St. Louis, MO) on day 0 to induce a state of hematopoietic injury capable of allowing allogeneic reconstitution.

Groups of 10 mice per treatment were administered phosphate buffered saline (PBS) control or 15,000; 30,000; or 60,000 bone marrow mononuclear cells from BALB/c mice on day 1 after administration of 5-FU.

Mice were concurrently treated with placebo (saline) and fibroblasts of recipient origin (B6), donor origin (BALB/c), or third party control (C3H) intravenously at a concentration of 100,000 cells per mouse intravenously via tail vein.

GVHD was experienced in all control B6 mice receiving 30,000; or 60,000 bone marrow mononuclear cells from BALB/c mice based on clinical pathology. Mice receiving fibroblasts from allogeneic, recipient, or donor sources did not experience GVHD or possessed marked reduction compared to control.

Example B: Clinical Reduction of Inflammatory Markers

Figure 20A:
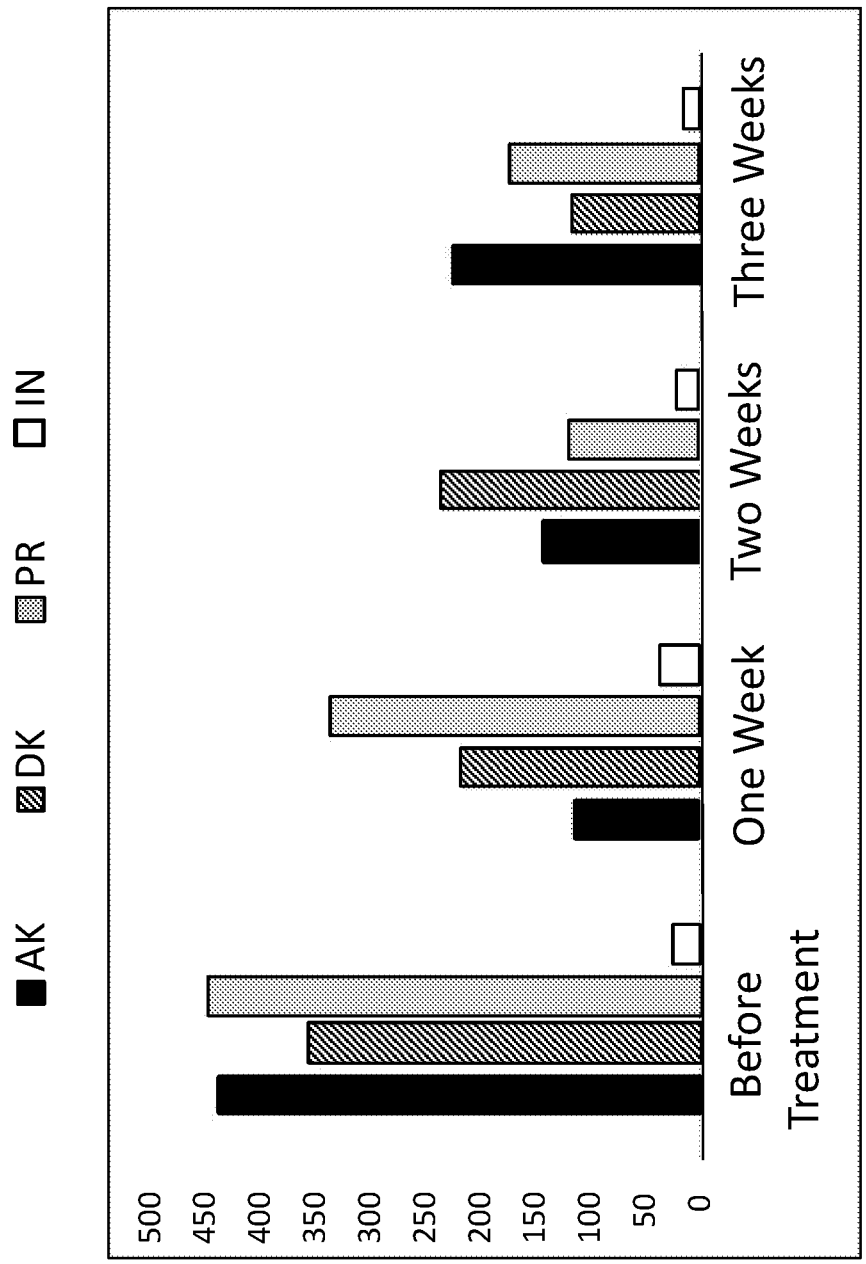
FIGS. 20A-20C show reduction in C-reactive protein following exposure of an individual with GVHD to an effective amount of fibroblasts.
Figure 20B:
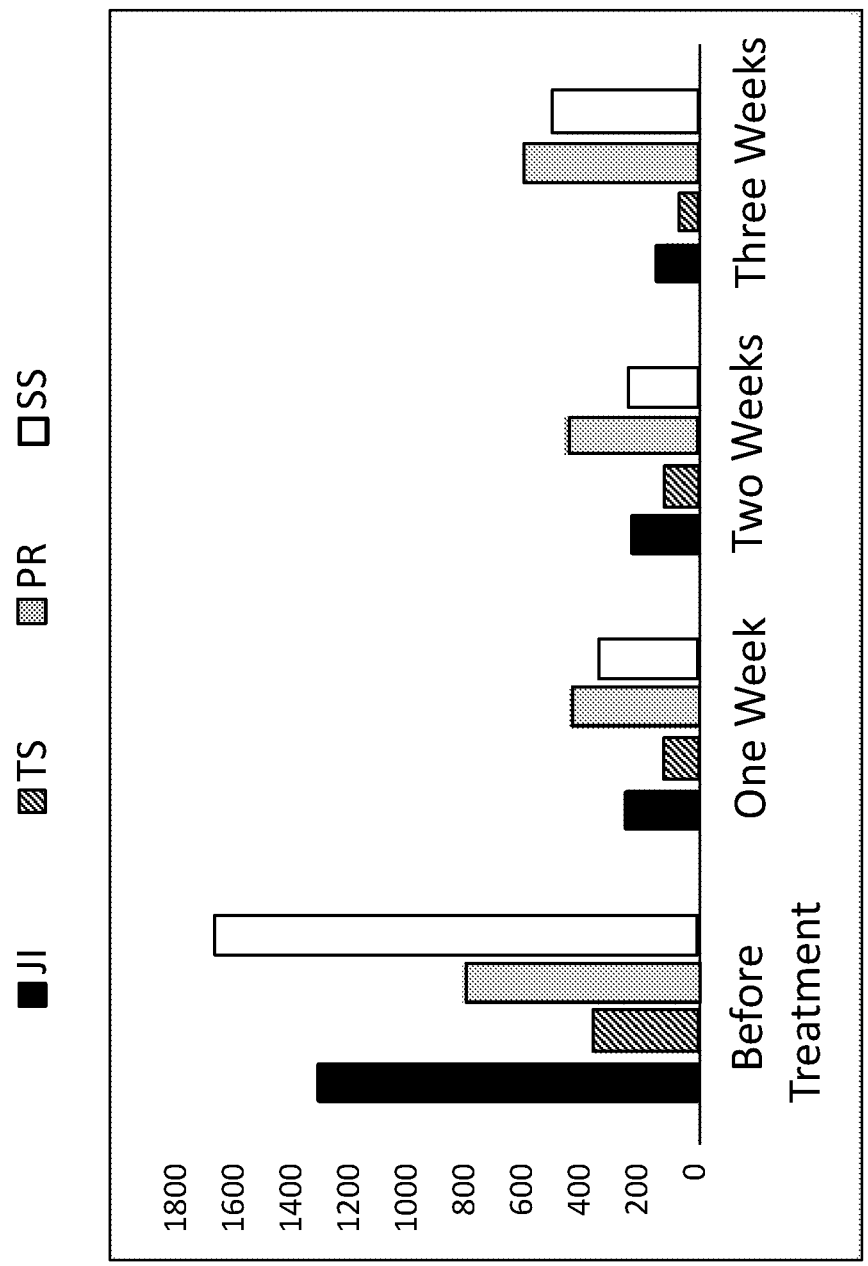
Figure 20C:
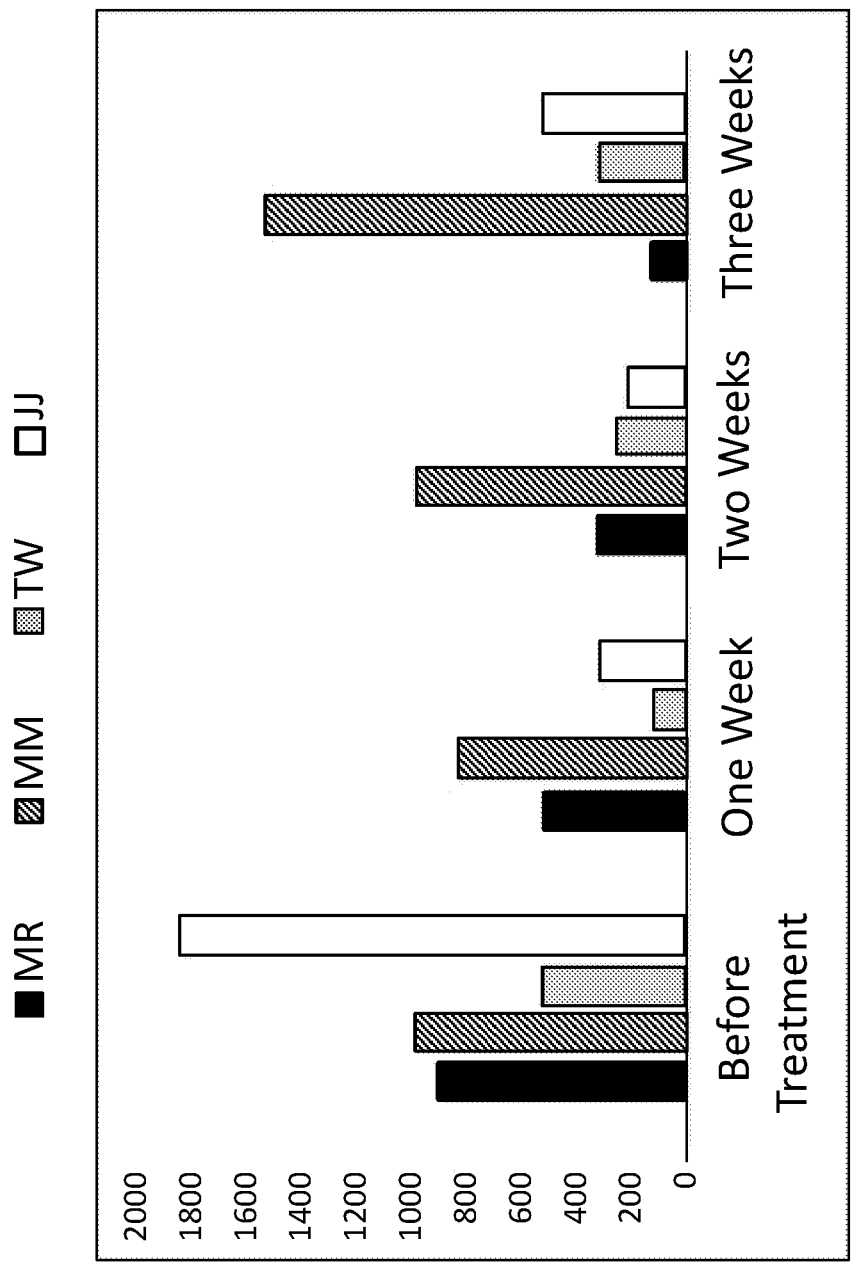
Figure 21A:
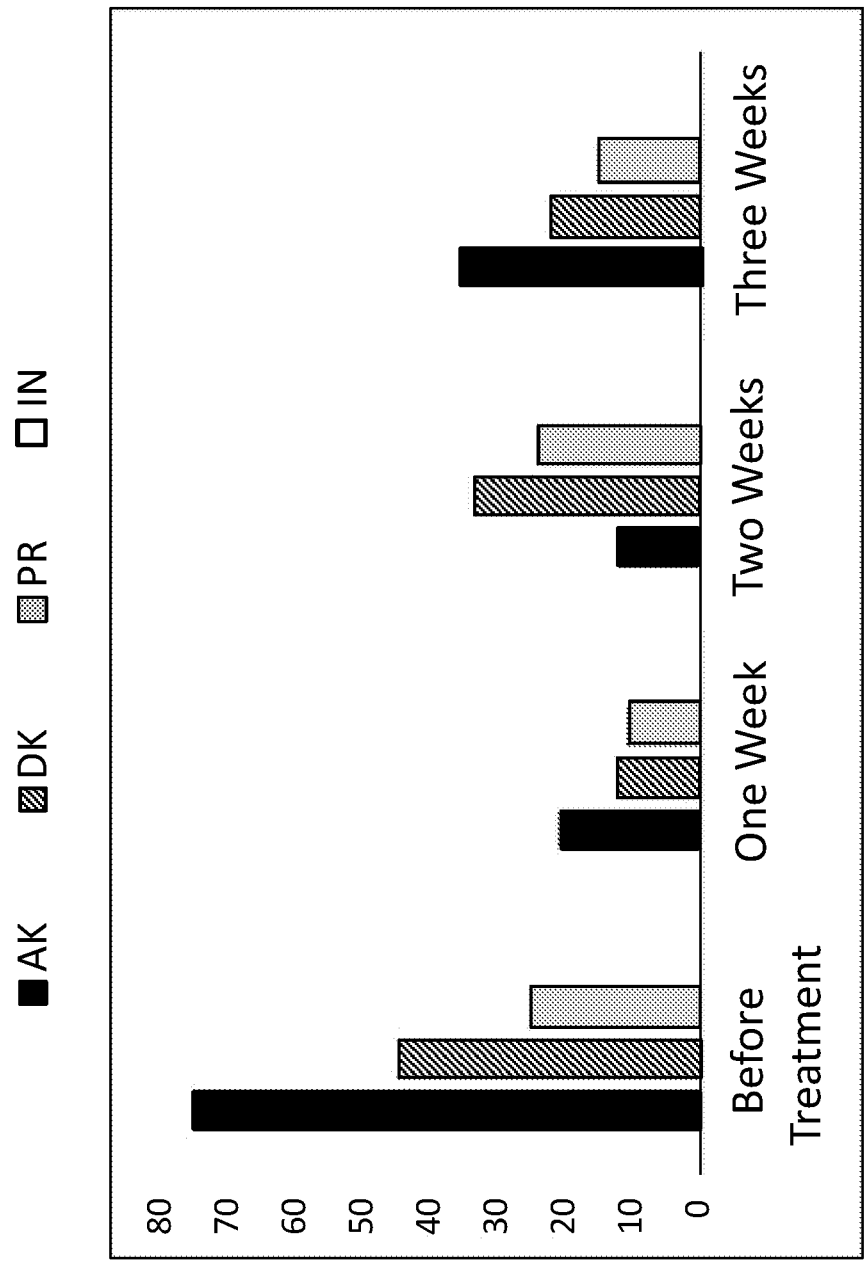
FIGS. 21A-21C show reduction in TNF alpha following exposure of an individual with GVHD to an effective amount of fibroblasts.
Figure 21B:
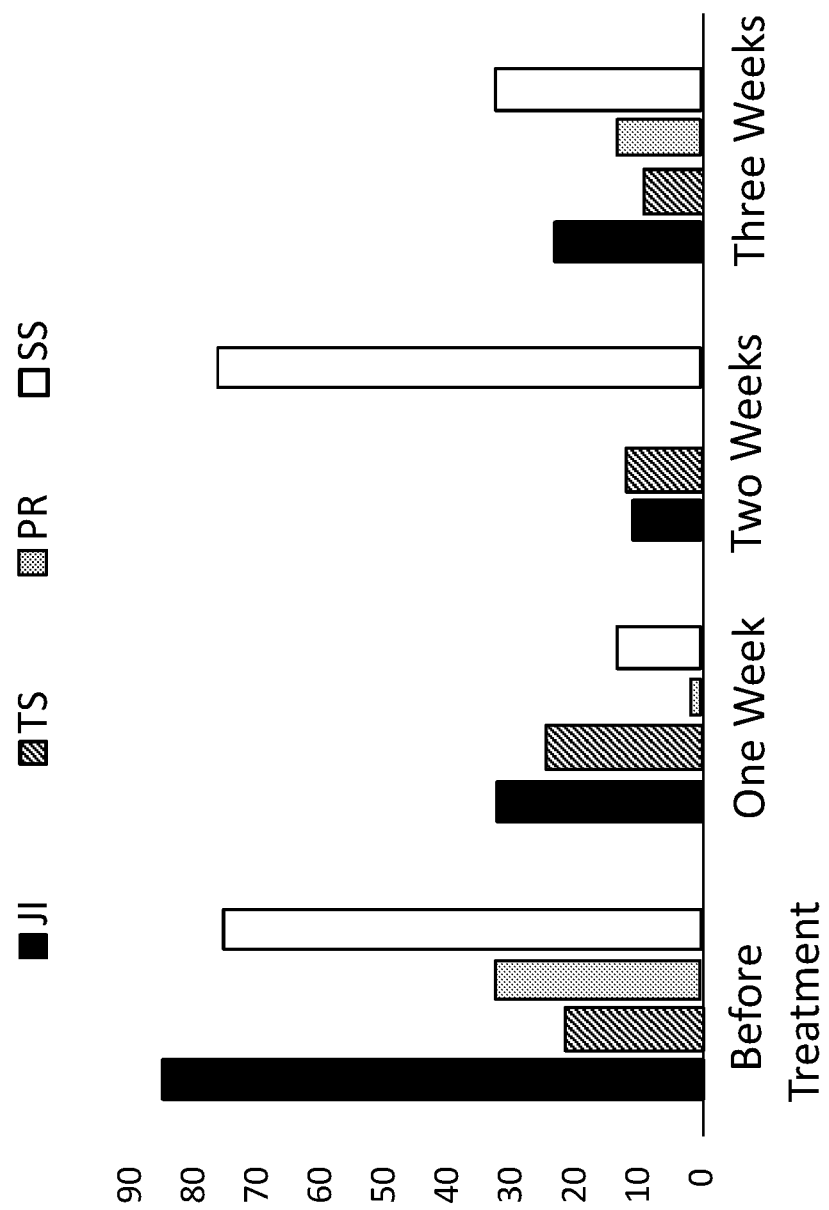
Figure 21C:
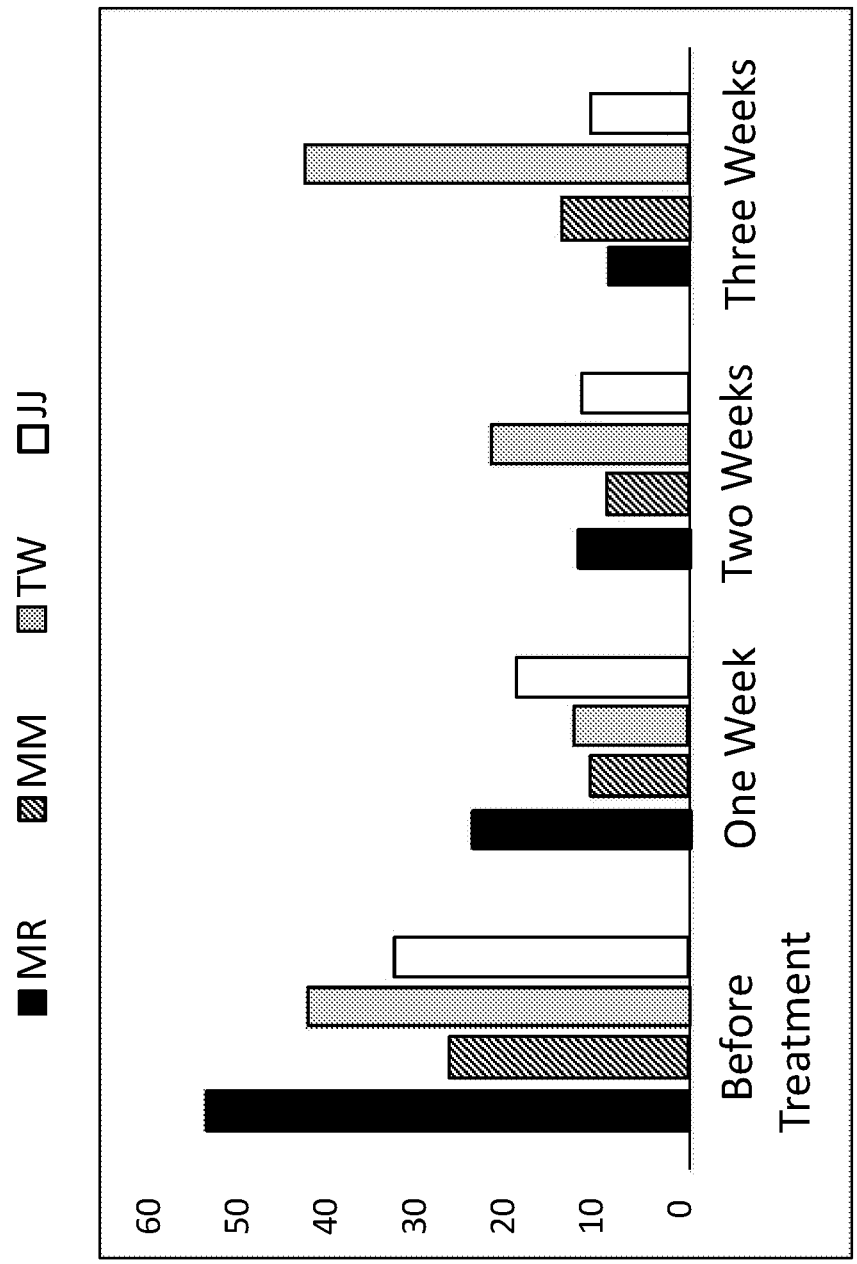
Figure 22A:
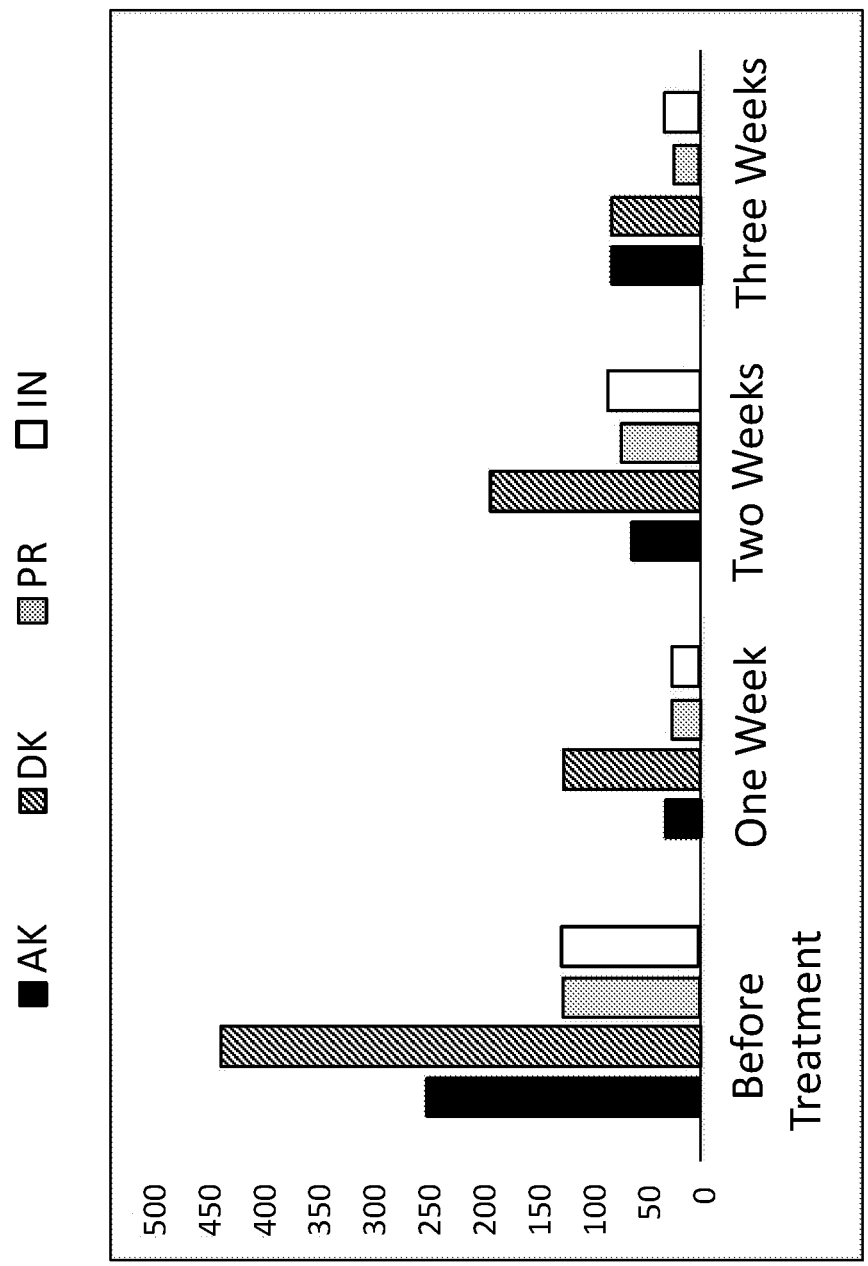
FIGS. 22A-22C show reduction in IL-6 following exposure of an individual with GVHD to an effective amount of fibroblasts.
Figure 22B:
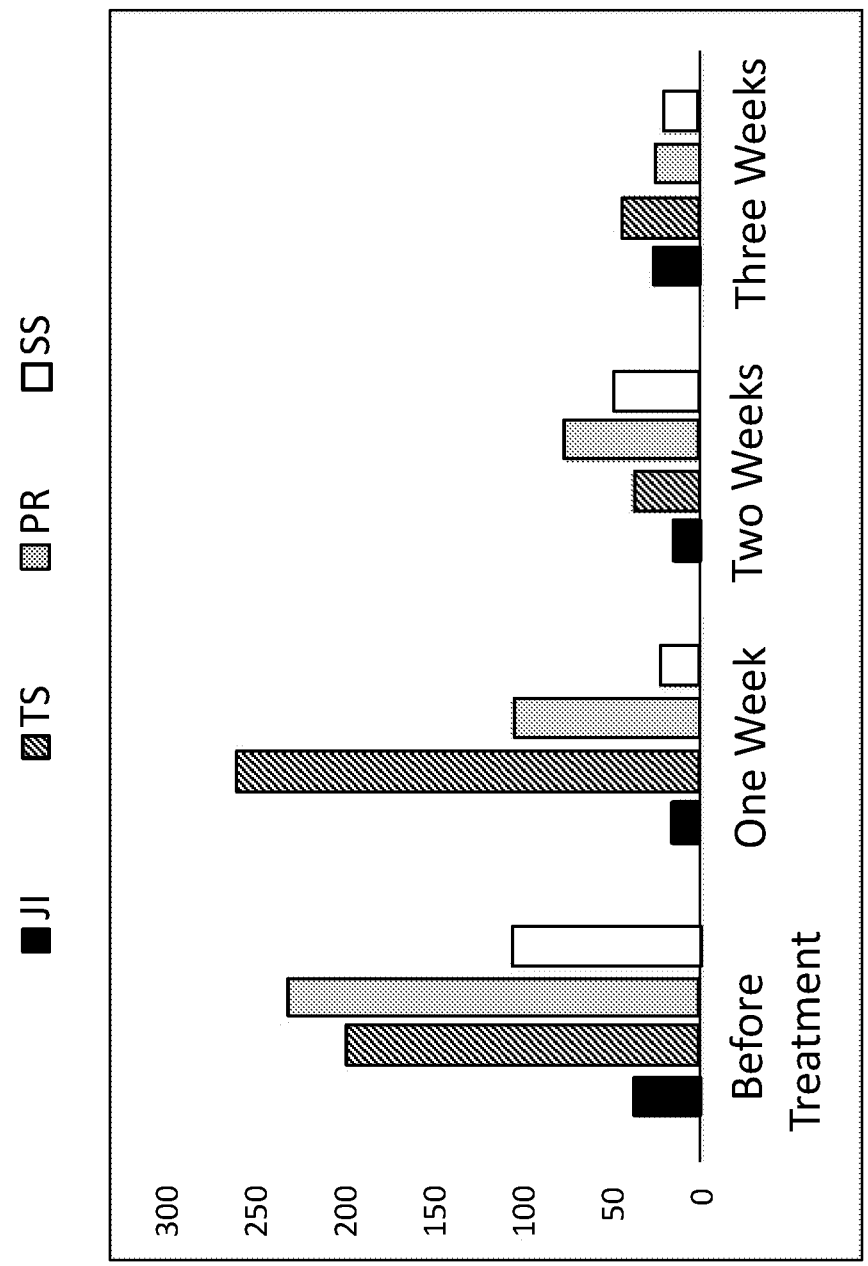
Figure 22C:
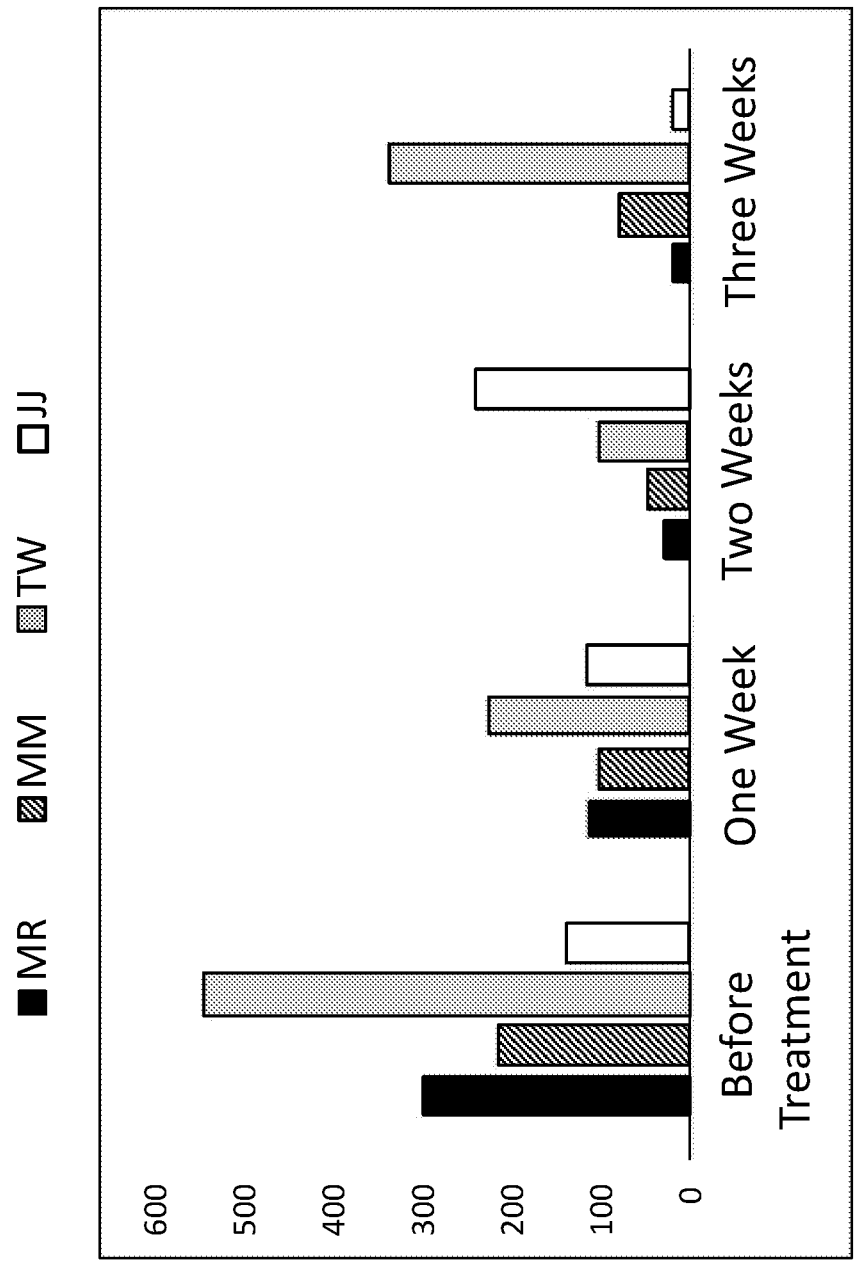

Twelve patients suffering from GVHD with C reactive protein (CRP) elevated beyond normal are administered intravenously 20 million fibroblasts derived from dermal sources expressing >80% CD73 and >80% CD105. Levels of CRP (FIGS. 20A-20C), TNF alpha (FIGS. 21A-21C), and IL-6 (FIGS. 22A-22C) were measured prior to cell administration and at week 1, 2, and 3.

Figure 23A:
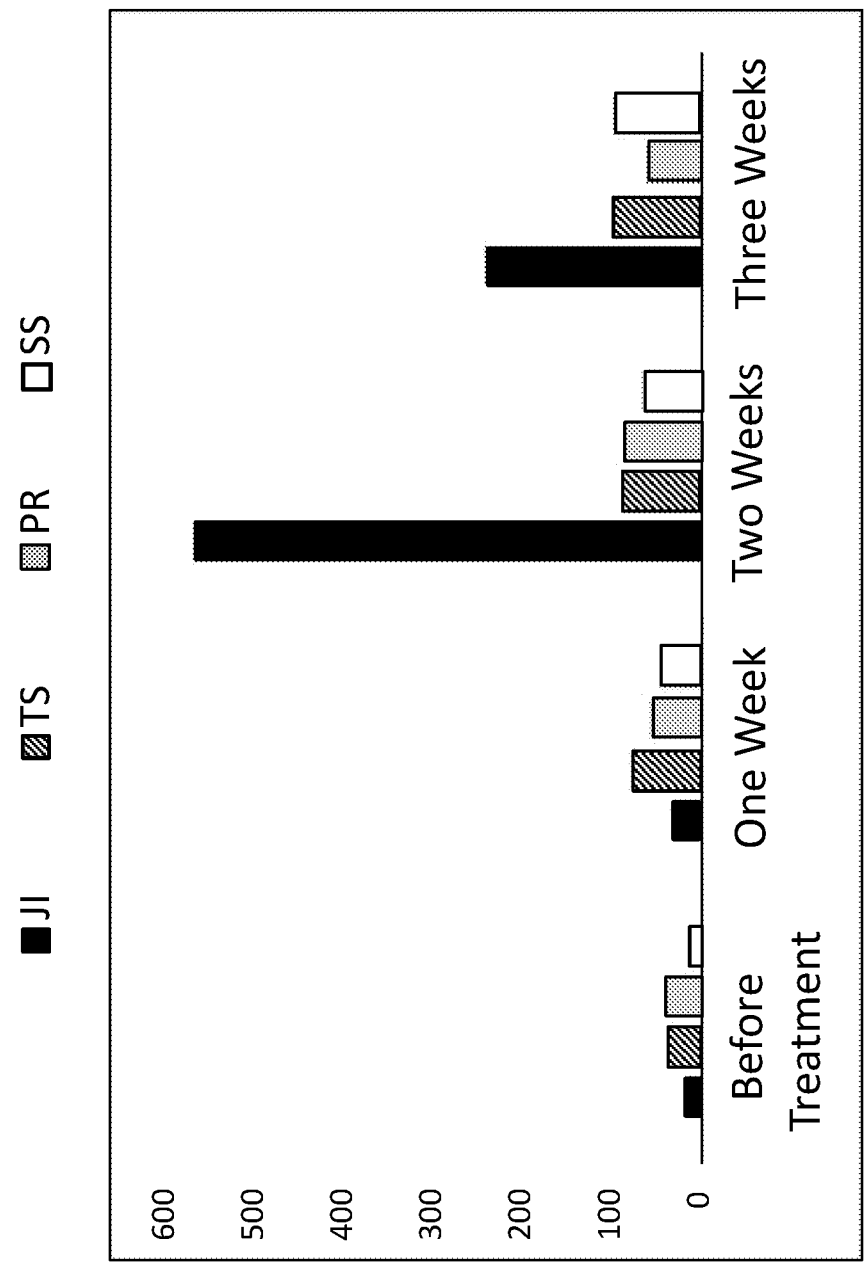
FIGS. 23A-23C show augmentation of IFNγ production following exposure of an individual with GVHD to an effective amount of fibroblasts.
Figure 23B:
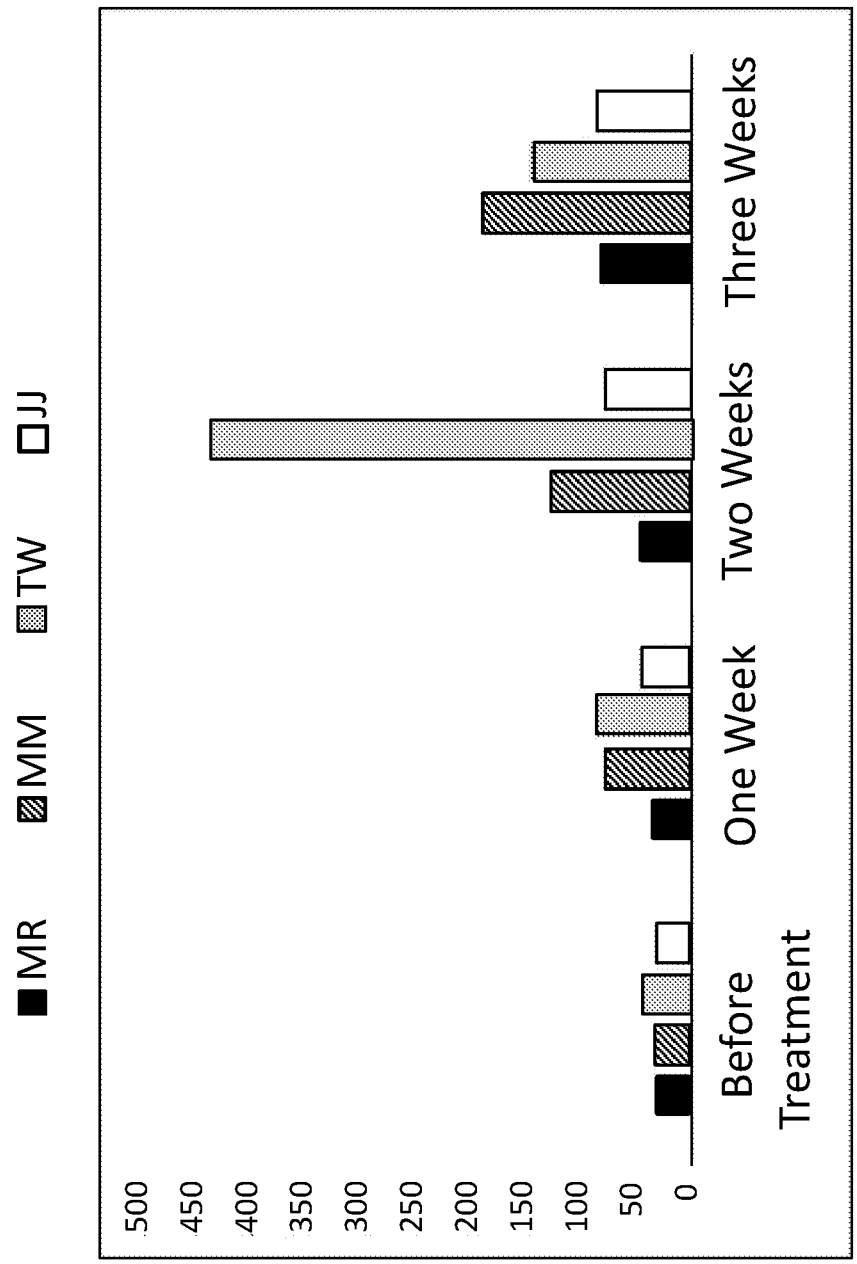
Figure 23C:
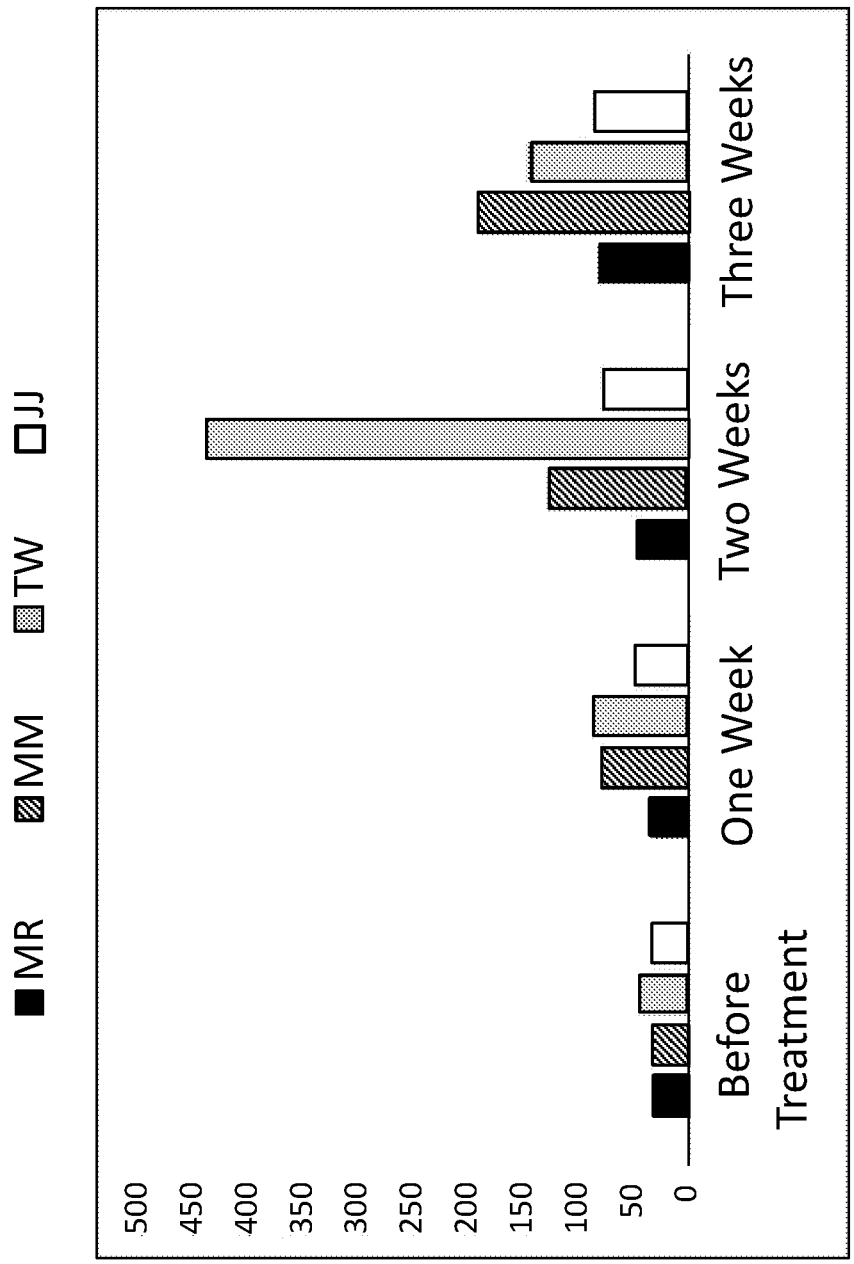
Figure 24A:
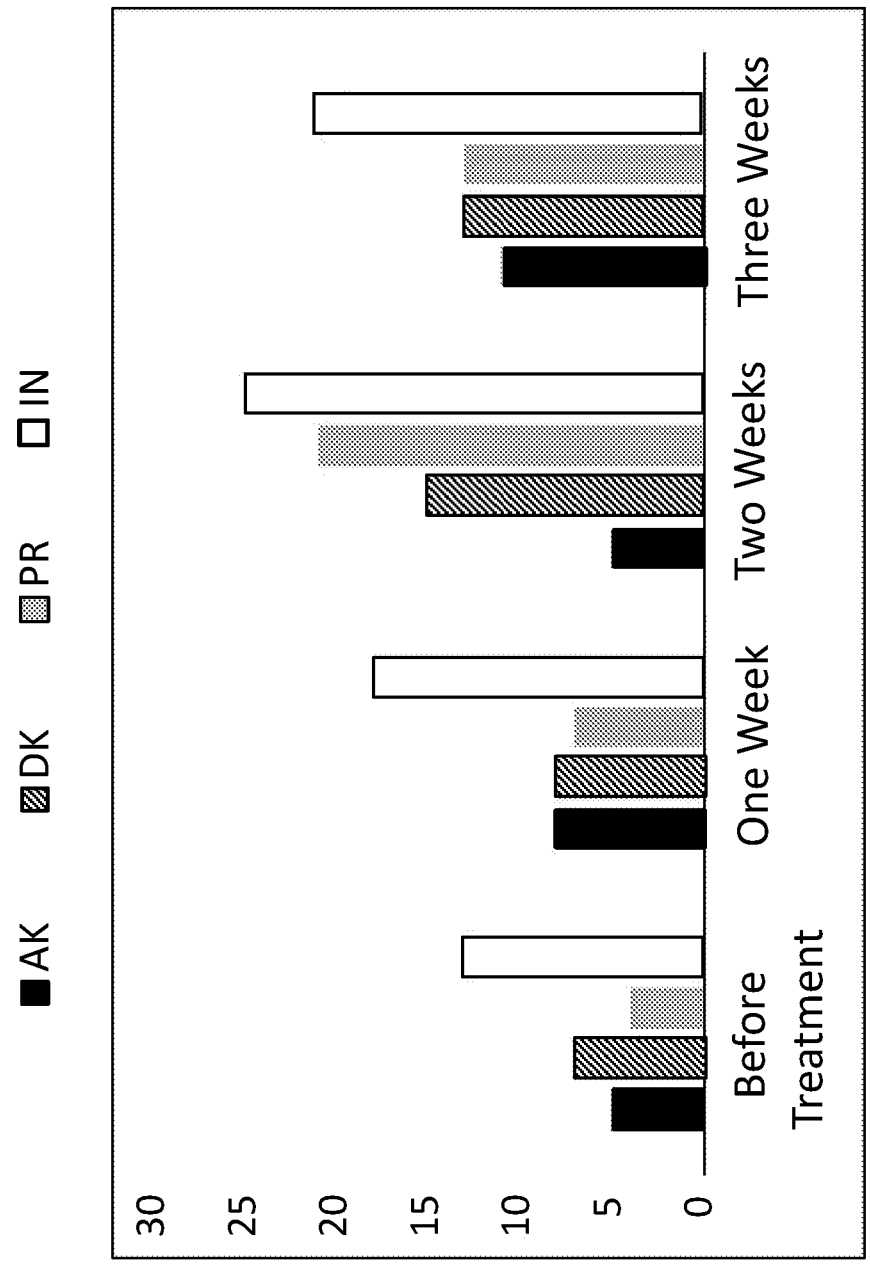
FIGS. 24A-24C show augmentation of Natural Killer NK) activity following exposure of an individual with GVHD to an effective amount of fibroblasts
Figure 24B:
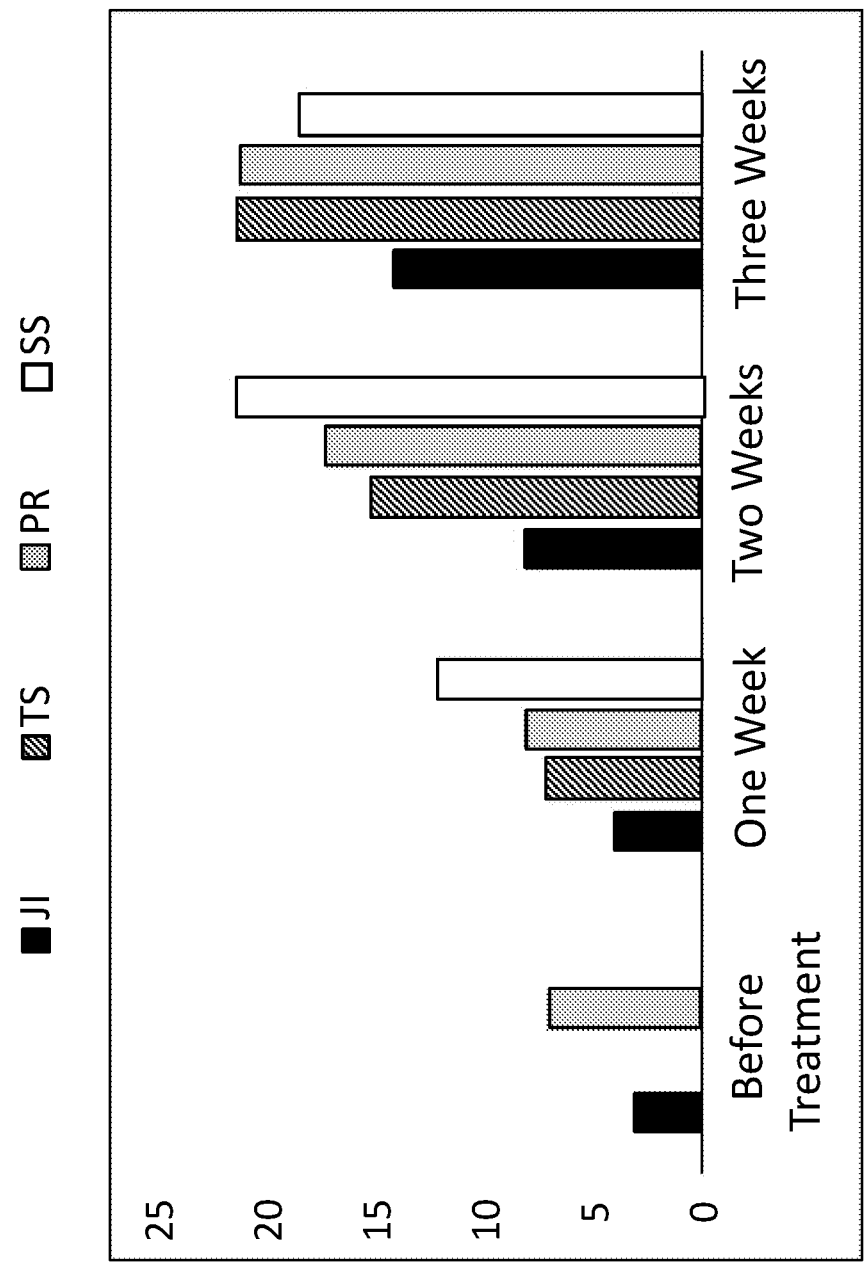
Figure 24C:
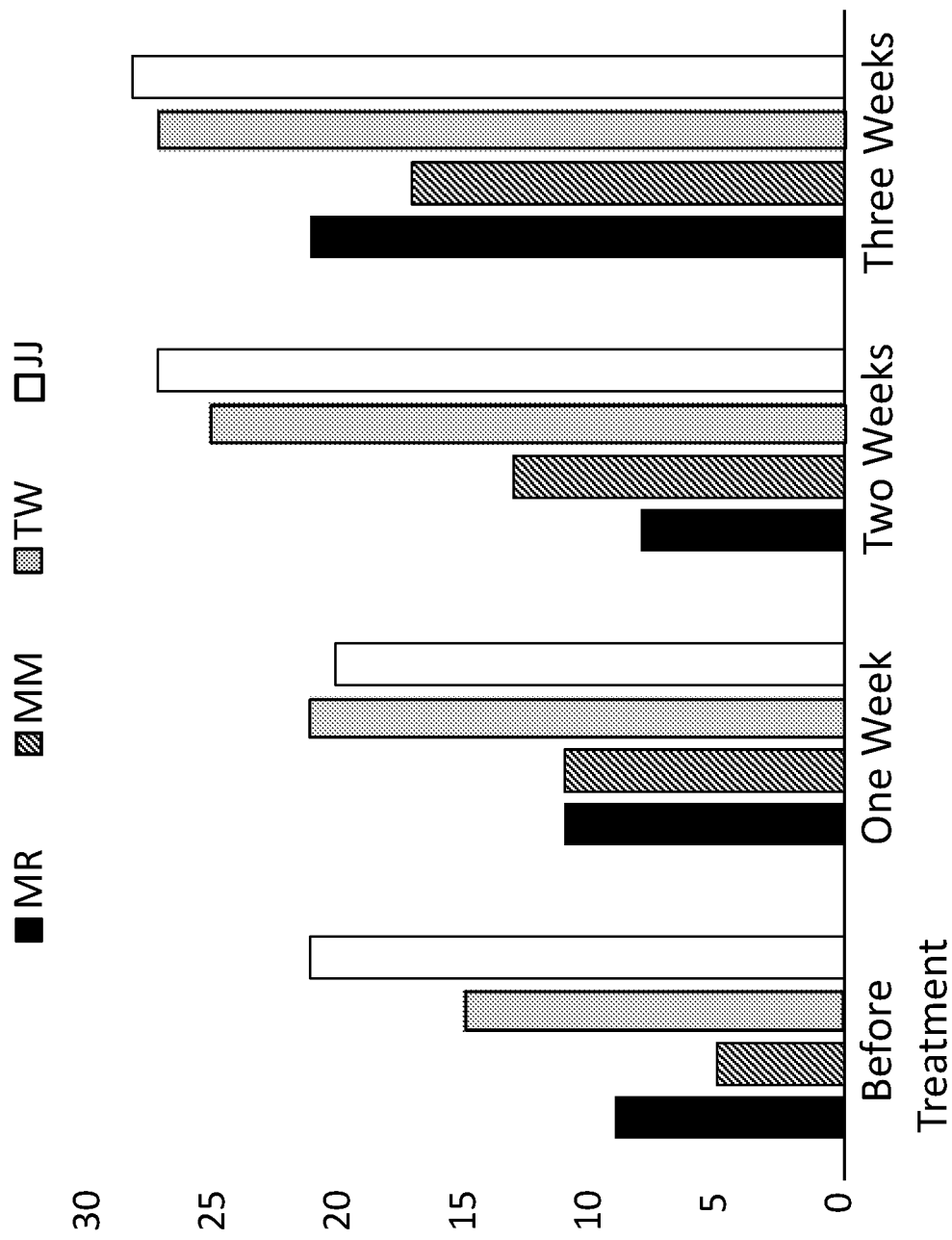

Concentrations are expressed in picograms per ml. Importantly, administration of fibroblasts was associated with augmentation of IFN-gamma production (FIGS. 23A-23C) and NK activity (FIGS. 24A-24C), indicating a selective anticancer effect while reducing inflammation.

Example 19

Clinical Trial of Fibroblast Cells in Patients with Multiple Sclerosis

A clinical trial is conducted to determine safety of intravenously administered fibroblast cells in patients with treatment-resistant secondary progressive MS. Safety is be defined as lack of treatment associated adverse events. Efficacy parameters comprise endpoints of changes in: a) EDSS; b) Scripps neurological rating scale (NRS); c) Paced auditory serial addition test (PASAT); d) Nine-hole peg test; e) 25-foot walking time; f) Short-form 36 (SF-36) QoL Questionnaire; g) Gadolinium MRI and; e) Changes in T regulatory (Treg) cell as defined by CD4, CD25 and FoxP3 expression.

Patients are randomized to receive 25, 50, or 100 million fibroblast cells intravenously on day 0 in a volume of 50 ml suspended in Isolyte. The reason that fibroblasts are administered to patients with multiple sclerosis is because of previous studies showing efficacy of these cells in suppression of animal models of multiple sclerosis, as well as demonstration of superior immune modulatory activity in comparison to bone marrow mesenchymal stem cells which have previously been clinically utilized in MS animal models. Specifically, fibroblasts have been demonstrated to augment expression of IL-4, IL-10, indolamine 2,3 deoxygenase (IDO), and HLA-G, while inhibiting TNF-alpha, IFN-gamma, IL-12, and IL-17 expression.

The following visit schedule may be utilized, in specific embodiments.

Visit 1: Screening Visit and Baseline Assessments (1 Week Before Infusion)
 Informed Consent
 History
 Physical Exam
 MS diagnosis according to McDonald and Poser criteria.
 Labs—chemistries and CBC
 EDSS
 Scripps neurological rating scale (NRS)
 Paced auditory serial addition test (PASAT)
 Nine-hole peg test
 25-foot walking time
 Short-form 36 (SF-36) QoL Questionnaire
 Gadolinium MRI
 Treg assessment
Visit 2: Day 0, First Infusion (ERC-124 Administration)
 Intravenous JD-001 injection
 Injection site assessment
 EKG
Visit 3: Day 7 Telephone Call
 Adverse events.
Visit 4: Day 30 Assessment
 EKG
 Adverse Event Assessment
 Labs—chemistries and CBC
 EDSS
 Scripps neurological rating scale (NRS)
 Paced auditory serial addition test (PASAT)
 Nine-hole peg test
 25-foot walking time
 Short-form 36 (SF-36) QoL Questionnaire
 Gadolinium MIll
 Treg assessment
Visit 5: Day 90Assessment
 Labs—chemistries and CBC
 EDSS
 Scripps neurological rating scale (NRS)
 Paced auditory serial addition test (PASAT)
 Nine-hole peg test
 25-foot walking time
 Short-form 36 (SF-36) QoL Questionnaire
 Treg assessment
Visit 6: Day 180 Assessment
 Labs—chemistries and CBC
 EDSS
 Scripps neurological rating scale (NRS)
 Paced auditory serial addition test (PASAT)
 Nine-hole peg test
 25-foot walking time
 Short-form 36 (SF-36) QoL Questionnaire
 Gadolinium MIll
 Treg assessment Subjects must have a screening visit with baseline evaluations performed within 7 days prior to cell dosing and must meet all inclusion and exclusion criteria. Results of all baseline evaluations, which assure that all inclusion and exclusion criteria have been satisfied, must be reviewed by the Principal Investigator or his/her designee prior to enrollment of that subject. The subject must be informed about all aspects of the study and written informed consent must be obtained from the subject prior to study initiation.

Inclusion Criteria:
 18-65 years with clinically definite secondary progressive MS according to the McDonald and Poser criteria
 Expanded disability status scale (EDSS) score of 2.0-6.5
 Steady progression rather than relapse must be the major cause of increasing disability in the preceding 2 years. Progression can be evident from either an increase of at least one point in EDSS or clinical documentation of increasing disability in patients notes
 Ability to undergo gadolinium MRI
Exclusion Criteria:
 Bleeding disorder
 Received interferon beta or glatiramer acetate within 6 months of trial entry,
 Patients with unstable cardiovascular status
 Patients with active infections, unless treatment is not judged necessary by the investigators
 Patients with serological evidence of infection with HIV, hepatitis B or hepatitis C.
 Sexually active females who are not a) postmenopausal, b) surgically sterile or c) using an acceptable method of contraception: oral contraceptives, Norplant, Depo-provera and barrier devices combined with spermicidal gel are acceptable.
 Patients with known or previous malignancy. Patient with any condition or any circumstance that in the opinion of the investigator would make it unsafe to undergo treatment with fibroblasts.
 Patients with retinopathy
 Patients with allergy to bovine products
 Fibroblasts will be provided with a certificate of analysis for each batch certifying purity and lack of contaminants according to WHO blood banking regulations and 21CFR1271 Subpart C donor regulations for allogeneic products. Charter CF-50 bags will be filled with cellular product from cell bank that has been generated and tested. Filling of the bags will be performed by General BioTechnology with cells previously expanded from the working cell bank at passage 9. Cells are resuspended in 50 mL of Isolyte S Multi-Electrolyte Solution (B. Braun Medical) containing 10% DMSO. Each Charter CF-50 bag will contain 25, 50 or 100 million cells in a volume of 50 ml. Approximately 25, 50, or 100 million cells are needed per clinical dose.

Patients receiving fibroblasts undergo a dose dependent reduction in EDSS score and resolution of plaques on gadolinium MRI All patents and publications mentioned in the specification are indicative of the level of those skilled in the art to which the disclosure pertains. All patents and publications are herein incorporated by reference to the same extent as if each individual publication was specifically and individually indicated to be incorporated by reference.

U.S. PATENTS

U.S. Pat. No. 9,637,721
U.S. Pat. No. 9,580,687
U.S. Pat. No. 7,709,229
U.S. Pat. No. 6,162,643
U.S. Pat. No. 6,103,529
U.S. Pat. No. 6,048,728
U.S. Pat. No. 5,324,666
U.S. Pat. No. 4,560,655

PUBLICATIONS

Akiyama, K., et al., Mesenchymal-stem-cell-induced immunoregulation involves FAS-ligand-/FAS-mediated T cell apoptosis. Cell Stem Cell, 2012. 10(5): p. 544-55.

Aliotta, J. M., et al., Bone marrow production of lung cells: The impact of G-CSF, cardiotoxin, graded doses of irradiation, and subpopulation phenotype. Exp Hematol, 2006. 34(2): p. 230-41.

Andre-Schmutz, I., et al., IL-7 effect on immunological reconstitution after HSCT depends on MHC incompatibility. Br J Haematol, 2004. 126(6): p. 844-51.

Apostolou, I., et al., Origin of regulatory T cells with known specificity for antigen. Nat Immunol, 2002. 3(8): p. 756-63.

Aschenbrenner, K., et al., Selection of Foxp3+ regulatory T cells specific for self antigen expressed and presented by Aire+ medullary thymic epithelial cells. Nat Immunol, 2007. 8(4): p. 351-8.

Atarashi, K., et al., Treg induction by a rationally selected mixture of Clostridia strains from the human microbiota. Nature, 2013. 500(7461): p. 232-6.

Atkins, M. B., et al., High-dose recombinant interleukin 2 therapy for patients with metastatic melanoma: analysis of 270 patients treated between 1985 and 1993. J Clin Oncol, 1999. 17(7): p. 2105-16.

Augello, A., et al., Bone marrow mesenchymal progenitor cells inhibit lymphocyte proliferation by activation of the programmed death 1 pathway. Eur J Immunol, 2005. 35(5): p. 1482-90.

Avradopoulos, K., et al., Interleukin-10 as a possible mediator of immunosuppressive effect in patients with squamous cell carcinoma of the head and neck. Ann Surg Oncol, 1997. 4(2): p. 184-90.

Babon, J. A., et al., Analysis of self-antigen specificity of islet-infiltrating T cells from human donors with type 1 diabetes. Nat Med, 2016. 22(12): p. 1482-1487.

Bai, A., et al., Rapid tolerization of virus-activated tumor-specific CD8+ T cells in prostate tumors of TRAMP mice. Proc Natl Acad Sci USA, 2008. 105(35): p. 13003-8.

Bai, L., et al., Hepatocyte growth factor mediates mesenchymal stem cell-induced recovery in multiple sclerosis models. Nat Neurosci, 2012. 15(6): p. 862-70.

Banchereau, J. and R. M. Steinman, Dendritic cells and the control of immunity. Nature, 1998. 392(6673): p. 245-52.

Bansard, C., et al., Can rheumatoid arthritis responsiveness to methotrexate and biologics be predicted? Rheumatology (Oxford), 2009. 48(9): p. 1021-8.

Barbay, V., et al., Role of M2-like macrophage recruitment during angiogenic growth factor therapy. Angiogenesis, 2015. 18(2): p. 191-200.

Barrou, B., et al., Vaccination of prostatectomized prostate cancer patients in biochemical relapse, with autologous dendritic cells pulsed with recombinant human PSA. Cancer Immunol Immunother, 2004. 53(5): p. 453-60.

Barry, F., et al., The SH-3 and SH-4 antibodies recognize distinct epitopes on CD73 from human mesenchymal stem cells. Biochem Biophys Res Commun, 2001. 289(2): p. 519-24.

Barletta, B., et al., Probiotic VSL #3-induced TGF-beta ameliorates food allergy inflammation in a mouse model of peanut sensitization through the induction of regulatory T cells in the gut mucosa. Mol Nutr Food Res, 2013. 57(12): p. 2233-44.

Batten, P., et al., Human mesenchymal stem cells induce T cell anergy and downregulate T cell allo-responses via the TH2 pathway: relevance to tissue engineering human heart valves. Tissue Eng, 2006. 12(8): p. 2263-73.

Bellayr, I. H., X. Mu, and Y. Li, Biochemical insights into the role of matrix metalloproteinases in regeneration: challenges and recent developments. Future Med Chem, 2009. 1(6): p. 1095-1111.

Ben-Mordechai, T., et al., Macrophage subpopulations are essential for infarct repair with and without stem cell therapy. J Am Coll Cardiol, 2013. 62(20): p. 1890-901.

Ben-Mordechai, T., et al., Macrophage subpopulations are essential for infarct repair with and without stem cell therapy. J Am Coll Cardiol, 2013. 62(20): p. 1890-901.

Bieback K, Hecker A, Kocaomer A, Lannert H, Schallmoser K, Strunk D et al (2009) Human alternatives to fetal bovine serum for the expansion of mesenchymal stromal cells from bone marrow. Stem Cells 27(9):2331-2341

Bijlsma, J. W., et al., Are glucocorticoids DMARDs? Ann N Y Acad Sci, 2006. 1069: p. 268-74.

Boddupalli, A., L. Zhu, and K. M. Bratlie, Methods for Implant Acceptance and Wound Healing: Material Selection and Implant Location Modulate Macrophage and Fibroblast Phenotypes. Adv Healthc Mater, 2016. 5(20): p. 2575-2594.

Bohmer, R. M., IL-3-dependent early erythropoiesis is stimulated by autocrine transforming growth factor beta. Stem Cells, 2004. 22(2): p. 216-24.

Boumaza, I., et al., Autologous bone marrow-derived rat mesenchymal stem cells promote PDX-1 and insulin expression in the islets, alter T cell cytokine pattern and preserve regulatory T cells in the periphery and induce sustained normoglycemia. J Autoimmun, 2009. 32(1): p. 33-42. Bracci-Laudiero, L., et al., CD34-positive cells in human umbilical cord blood express nerve growth factor and its specific receptor TrkA. J Neuroimmunol, 2003. 136(1-2): p. 130-9.

Brentjens, R. J., et al., Safety and persistence of adoptively transferred autologous CD19-targeted T cells in patients with relapsed or chemotherapy refractory B-cell leukemias. Blood, 2011. 118(18): p. 4817-28.

Brentjens, R. J., et al., CD19-targeted T cells rapidly induce molecular remissions in adults with chemotherapy-refractory acute lymphoblastic leukemia. Sci Transl Med, 2013. 5(177): p. 177ra38.

Bruton, J. K. and J. M. Koeller, Recombinant interleukin-2. Pharmacotherapy, 1994. 14(6): p. 635-56.

Cahill, E. F., et al., Jagged-1 is required for the expansion of CD4+ CD25+ FoxP3+ regulatory T cells and tolerogenic dendritic cells by murine mesenchymal stromal cells. Stem Cell Res Ther, 2015. 6: p. 19.

Cancedda, C., et al., Specific T-cell deletion by transfected human monocytes expressing Fas ligand and antigen. Transplant Proc, 2001. 33(1-2): p. 165-6.

Capelli C, Domenghini M, Borleri G, Bellavita P, Poma R, Carobbio A et al (2007) Human platelet lysate allows expansion and clinical grade production of mesenchymal stromal cells from small samples of bone marrow aspirates or marrow filter washouts. Bone Marrow Transpl 40(8):785-791.

Carrancio S, Lopez-Holgado N, Sanchez-Guijo F M, Villaron E, Barbado V, Tabera S et al (2008) Optimization of mesenchymal stem cell expansion procedures by cell separation and culture conditions modification. Experimental Hematol 36(8):1014-1021

Casiraghi, F., et al., Pretransplant infusion of mesenchymal stem cells prolongs the survival of a semiallogeneic heart transplant through the generation of regulatory T cells. J Immunol, 2008. 181(6): p. 3933-46.

Caux, C., et al., Activation of human dendritic cells through CD40 cross-linking. J Exp Med, 1994. 180(4): p. 1263-72.

Cerdan, C., A. Rouleau, and M. Bhatia, VEGF-A165 augments erythropoietic development from human embryonic stem cells. Blood, 2004. 103(7): p. 2504-12.

Chabannes, D., et al., A role for heme oxygenase-1 in the immunosuppressive effect of adult rat and human mesenchymal stem cells. Blood, 2007. 110(10): p. 3691-4.

Chadwick, K., et al., Cytokines and BMP-4 promote hematopoietic differentiation of human embryonic stem cells. Blood, 2003. 102(3): p. 906-15.

Cheema, A. R. and E. M. Hersh, Local tumor immunotherapy with in vitro activated autochithonous lymphocytes. Cancer, 1972. 29(4): p. 982-6.

Chen, C., et al., Mesenchymal stem cells upregulate Treg cells via sHLA-G in SLE patients. Int Immunopharmacol, 2017. 44: p. 234-241.

Chen, T., et al., Self-specific memory regulatory T cells protect embryos at implantation in mice. J Immunol, 2013. 191(5): p. 2273-81.

Cheung, A. F., et al., Regulated expression of a tumor-associated antigen reveals multiple levels of T-cell tolerance in a mouse model of lung cancer. Cancer Res, 2008. 68(22): p. 9459-68.

Cho, D. I., et al., Mesenchymal stem cells reciprocally regulate the M1/M2 balance in mouse bone marrow-derived macrophages. Exp Mol Med, 2014. 46: p. e70.

Chodorowska, G., A. Glowacka, and M. Tomczyk, Leukemia inhibitory factor (LIF) and its biological activity. Ann Univ Mariae Curie Sklodowska [Med], 2004. 59(2): p. 189-93.

Chong, A. S., et al., In vivo activity of leflunomide: pharmacokinetic analyses and mechanism of immunosuppression. Transplantation, 1999. 68(1): p. 100-9.

Courties, G., et al., In vivo silencing of the transcription factor IRF5 reprograms the macrophage phenotype and improves infarct healing. J Am Coll Cardiol, 2014. 63(15): p. 1556-66.

Coutu, D. L., M. Francois, and J. Galipeau, Inhibition of cellular senescence by developmentally regulated FGF receptors in mesenchymal stem cells. Blood, 2011. 117 (25): p. 6801-12.

Crcareva, A., et al., Hematopoietic stem cells expanded by fibroblast growth factor-1 are excellent targets for retrovirus-mediated gene delivery. Exp Hematol, 2005. 33(12): p. 1459-69.

Cruz, C. R., et al., Infusion of donor-derived CD19-redirected virus-specific T cells for B-cell malignancies relapsed after allogeneic stem cell transplant: a phase 1 study. Blood, 2013. 122(17): p. 2965-73.

Davila, M. L. and R. Brentjens, Chimeric antigen receptor therapy for chronic lymphocytic leukemia: what are the challenges? Hematol Oncol Clin North Am, 2013. 27(2): p. 341-53.

Dayan, V., et al., Mesenchymal stromal cells mediate a switch to alternatively activated monocytes/macrophages after acute myocardial infarction. Basic Res Cardiol, 2011. 106(6): p. 1299-310.

de Couto, G., et al., Macrophages mediate cardioprotective cellular postconditioning in acute myocardial infarction. J Clin Invest, 2015. 125(8): p. 3147-62.

de Haan, G., et al., In vitro generation of long-term repopulating hematopoietic stem cells by fibroblast growth factor-1. Dev Cell, 2003. 4(2): p. 241-51.

de Jesus, E. R., et al., Adoptive Transfer of Dendritic Cells Expressing Fas Ligand Modulates Intestinal Inflammation in a Model of Inflammatory Bowel Disease. J Clin Cell Immunol, 2016. 7(2).

de Roock, S., et al., Lactic acid bacteria differ in their ability to induce functional regulatory T cells in humans. Clin Exp Allergy, 2010. 40(1): p. 103-10.

De Waele, M., et al., Growth factor receptor profile of CD34 cells in normal bone marrow, cord blood and mobilized peripheral blood. Eur J Haematol, 2004. 72(3): p. 193-202.

DelaRosa, O., et al., Requirement of IFN-gamma-mediated indoleamine 2,3-dioxygenase expression in the modulation of lymphocyte proliferation by human adipose-derived stem cells. Tissue Eng Part A, 2009. 15(10): p. 2795-806.

Del Papa, B., et al., Notch1 modulates mesenchymal stem cells mediated regulatory T-cell induction. Eur J Immunol, 2013. 43(1): p. 182-7.

D'Addio, F., et al., The link between the PDL1 costimulatory pathway and Th17 in fetomaternal tolerance. J Immunol, 2011. 187(9): p. 4530-41.

Di Filippo, C., et al., Involvement of proteasome and macrophages M2 in the protection afforded by telmisartan against the acute myocardial infarction in Zucker diabetic fatty rats with metabolic syndrome. Mediators Inflamm, 2014. 2014: p. 972761.

Di Ianni, M., et al., Mesenchymal cells recruit and regulate T regulatory cells. Exp Hematol, 2008. 36(3): p. 309-18.

Dimitrova, P., et al., Restriction of de novo pyrimidine biosynthesis inhibits Th1 cell activation and promotes Th2 cell differentiation. J Immunol, 2002. 169(6): p. 3392-9.

Donkor, M. K., et al., T cell surveillance of oncogene-induced prostate cancer is impeded by T cell-derived TGF-beta1 cytokine. Immunity, 2011. 35(1): p. 123-34.

Dormady, S. P., et al., Immortalized multipotential mesenchymal cells and the hematopoietic microenvironment. J Hematother Stem Cell Res, 2001. 10(1): p. 125-40.

Du Bois, J. S., J. E. Udelson, and M. B. Atkins, Severe reversible global and regional ventricular dysfunction associated with high-dose interleukin-2 immunotherapy. J Immunother Emphasis Tumor Immunol, 1995. 18(2): p. 119-23.

Duffy, M. M., et al., Mesenchymal stem cell inhibition of T-helper 17 cell-differentiation is triggered by cell-cell contact and mediated by prostaglandin E2 via the EP4 receptor. Eur J Immunol, 2011. 41(10): p. 2840-51.

Dugdale and Siddall (1969) J. Med. Lab. Technol. 26: 31-5

Edwards, M. J., D. L. Abney, and F. N. Miller, Pentoxifylline inhibits interleukin-2-induced leukocyte-endothelial adherence and reduces systemic toxicity. Surgery, 1991. 110(2): p. 199-204.

El Haddad, N., et al., Mesenchymal stem cells express serine protease inhibitor to evade the host immune response. Blood, 2011. 117(4): p. 1176-83.

Elder, D. E., et al., Neoplastic progression and prognosis in melanoma. Semin Cutan Med Surg, 1996. 15(4): p. 336-48.

Erlebacher, A., et al., Constraints in antigen presentation severely restrict T cell recognition of the allogeneic fetus. J Clin Invest, 2007. 117(5): p. 1399-411.

Engela, A. U., et al., Human adipose-tissue derived mesenchymal stem cells induce functional de-novo regulatory T cells with methylated FOXP3 gene DNA. Clin Exp Immunol, 2013. 173(2): p. 343-54.

English, K., et al., Cell contact, prostaglandin E(2) and transforming growth factor beta 1 play non-redundant roles in human mesenchymal stem cell induction of CD4+CD25(High) forkhead box P3+ regulatory T cells. Clin Exp Immunol, 2009. 156(1): p. 149-60.

Erkers, T., et al., Decidual stromal cells promote regulatory T cells and suppress alloreactivity in a cell contact-dependent manner. Stem Cells Dev, 2013. 22(19): p. 2596-605.

Faria, A. M. and H. L. Weiner, Oral tolerance. Immunol Rev, 2005. 206: p. 232-59.

Faria, A. M. and H. L. Weiner, Oral tolerance: therapeutic implications for autoimmune diseases. Clin Dev Immunol, 2006. 13(2-4): p. 143-57.

Fausto, N., J. S. Campbell, and K. J. Riehle, Liver regeneration. Hepatology, 2006. 43(2 Suppl 1): p. S45-53.

Feleszko, W., et al., Probiotic-induced suppression of allergic sensitization and airway inflammation is associated with an increase of T regulatory-dependent mechanisms in a murine model of asthma. Clin Exp Allergy, 2007. 37(4): p. 498-505.

Fernandez-Velasco, M., S. Gonzalez-Ramos, and L. Bosca, Involvement of monocytes/macrophages as key factors in the development and progression of cardiovascular diseases. Biochem J, 2014. 458(2): p. 187-93.

Ferrante, C. J. and S. J. Leibovich, Regulation of Macrophage Polarization and Wound Healing. Adv Wound Care (New Rochelle), 2012. 1(1): p. 10-16.

Feugier, P., et al., Ex vivo expansion of stem and progenitor cells in co-culture of mobilized peripheral blood CD34+ cells on human endothelium transfected with adenovectors expressing thrombopoietin, c-kit ligand, and Flt-3 ligand. J Hematother Stem Cell Res, 2002. 11(1): p. 127-38.

Ficara, F., et al., IL-3 or IL-7 increases ex vivo gene transfer efficiency in ADA-SCID BM CD34+ cells while maintaining in vivo lymphoid potential. Mol Ther, 2004. 10(6): p. 1096-108.

Filgueira, L., et al., Effects of different culture protocols on the expression of discrete T-cell receptor variable regions in human tumour infiltrating lymphocytes. Eur J Cancer, 1993. 29A(12): p. 1754-60.

Fink, L. N., Induction of regulatory T cells by probiotics: potential for treatment of allergy? Clin Exp Allergy, 2010. 40(1): p. 5-8.

Fong, C. Y., et al., Human umbilical cord Wharton's jelly stem cells and its conditioned medium support hematopoietic stem cell expansion ex vivo. J Cell Biochem, 2012. 113(2): p. 658-68.

Forni, G. and I. Green, Heterologous sera: a target for in vitro cell-mediated cytotoxicity. J Immunol, 1976. 116(6): p. 1561-5.

Francois, M., et al., Human MSC suppression correlates with cytokine induction of indoleamine 2,3-dioxygenase and bystander M2 macrophage differentiation. Mol Ther, 2012. 20(1): p. 187-95.

Frasca, L., et al., Human anergic CD4+ T cells can act as suppressor cells by affecting autologous dendritic cell conditioning and survival. J Immunol, 2002. 168(3): p. 1060-8.

Fuchs, Y. F., et al., CD8+ T cells specific for the islet autoantigen IGRP are restricted in their T cell receptor chain usage. Sci Rep, 2017. 7: p. 44661.

Fukaura, H., et al., Induction of circulating myelin basic protein and proteolipid protein-specific transforming growth factor-beta1-secreting Th3 T cells by oral administration of myelin in multiple sclerosis patients. J Clin Invest, 1996. 98(1): p. 70-7.

Ge, W., et al., Regulatory T-cell generation and kidney allograft tolerance induced by mesenchymal stem cells associated with indoleamine 2,3-dioxygenase expression. Transplantation, 2010. 90(12): p. 1312-20.

Glennie, S., et al., Bone marrow mesenchymal stem cells induce division arrest anergy of activated T cells. Blood, 2005. 105(7): p. 2821-7.

Gieseke, F., et al., Human multipotent mesenchymal stromal cells use galectin-1 to inhibit immune effector cells. Blood, 2010. 116(19): p. 3770-9.

Gonzalez-Rey, E., et al., Human adipose-derived mesenchymal stem cells reduce inflammatory and T-cell responses and induce regulatory T cells in vitro in rheumatoid arthritis. Ann Rheum Dis, 2009. Gangenahalli, G. U., et al., Stem cell fate specification: role of master regulatory switch transcription factor PU.1 in differential hematopoiesis. Stem Cells Dev, 2005. 14(2): p. 140-52.

Garovoy, M. R., et al., Derect lymphocyte-mediated cytotoxicity as an assay of presensitisation. Lancet, 1973. 1(7803): p. 573-6.

Glassman, A. B., Interleukin-2 and lymphokine activated killer cells: promises and cautions. Ann Clin Lab Sci, 1989. 19(1): p. 51-5.

Gombozhapova, A., et al., Macrophage activation and polarization in post-infarction cardiac remodeling. J Biomed Sci, 2017. 24(1): p. 13.

Gomella, L. G., F. Gelpi-Hammerschmidt, and C. Kundavram, Practical guide to immunotherapy in castration resistant prostate cancer: the use of sipuleucel-T immunotherapy. Can J Urol, 2014. 21(2 Supp 1): p. 48-56.

Gondek, D. C., et al., Cutting edge: contact-mediated suppression by CD4+CD25+ regulatory cells involves a granzyme B-dependent, perforin-independent mechanism. J Immunol, 2005. 174(4): p. 1783-6.
Gratchev, A., et al., Mphi1 and Mphi2 can be re-polarized by Th2 or Th1 cytokines, respectively, and respond to exogenous danger signals. Immunobiology, 2006. 211(6-8): p. 473-86.
Grimm, E. A., Human lymphokine-activated killer cells (LAK cells) as a potential immunotherapeutic modality. Biochim Biophys Acta, 1986. 865(3): p. 267-79.
Gross, L., et al., FDG-PET reveals improved cardiac regeneration and attenuated adverse remodelling following Sitagliptin+G-CSF therapy after acute myocardial infarction. Eur Heart J Cardiovasc Imaging, 2016. 17(2): p. 136-45.
Grothe, C., et al., Fibroblast growth factor-20 promotes the differentiation of Nurr1-overexpressing neural stem cells into tyrosine hydroxylase-positive neurons. Neurobiol Dis, 2004. 17(2): p. 163-70.
Gu, Y. Z., et al., Different roles of PD-L1 and FasL in immunomodulation mediated by human placenta-derived mesenchymal stem cells. Hum Immunol, 2013. 74(3): p. 267-76
Guerra, L. L., et al., Novel prokaryotic expression of thioredoxin-fused insulinoma associated protein tyrosine phosphatase 2 (IA-2), its characterization and immunodiagnostic application. BMC Biotechnol, 2016. 16(1): p. 84.
Guillot, C., et al., Active suppression of allogeneic proliferative responses by dendritic cells after induction of long-term allograft survival by CTLA4Ig. Blood, 2003. 101(8): p. 3325-33.
Guiteras, R., M. Flaquer, and J. M. Cruzado, Macrophage in chronic kidney disease. Clin Kidney J, 2016. 9(6): p. 765-771.
Guo, Y., B. Graham-Evans, and H. E. Broxmeyer, Murine Embryonic Stem Cells Secrete Cytokines/Growth Modulators that Enhance Cell Survival/Anti-Apoptosis and Stimulate Colony Formation of Murine Hematopoietic Progenitor Cells. Stem Cells, 2005.
Haileselassie, Y., et al., Postbiotic Modulation of Retinoic Acid Imprinted Mucosal-like Dendritic Cells by Probiotic *Lactobacillus reuteri* 17938 In vitro. Front Immunol, 2016. 7: p. 96.
Hall, J. L. and L. N. Wei, Could silencing IRF5 improve healing of a myocardial infarct through the reprogramming of the macrophage population? J Am Coll Cardiol, 2014. 63(15): p. 1567-8.
Han, S., et al., Auranofin, an immunosuppressive drug, inhibits MHC class I and MHC class II pathways of antigen presentation in dendritic cells. Arch Pharm Res, 2008. 31(3): p. 370-6.
Hanninen, A. and L. C. Harrison, Mucosal tolerance to prevent type 1 diabetes: can the outcome be improved in humans? Rev Diabet Stud, 2004. 1(3): p. 113-21.
He, S., et al., Lp-PLA2 Antagonizes Left Ventricular Healing After Myocardial Infarction by Impairing the Appearance of Reparative Macrophages. Circ Heart Fail, 2015. 8(5): p. 980-7.
He, B., et al., Resetting microbiota by *Lactobacillus reuteri* inhibits T reg deficiency-induced autoimmunity via adenosine A2A receptors. J Exp Med, 2017. 214(1): p. 107-123.
He, S., et al., Lp-PLA2 Antagonizes Left Ventricular Healing After Myocardial Infarction by Impairing the Appearance of Reparative Macrophages. Circ Heart Fail, 2015. 8(5): p. 980-7.
Harimoto, H., et al., Inactivation of tumor-specific CD8(+) CTLs by tumor-infiltrating tolerogenic dendritic cells. Immunol Cell Biol, 2013. 91(9): p. 545-55.
Hofmann, U., et al., Interleukin-13 deficiency aggravates healing and remodeling in male mice after experimental myocardial infarction. Circ Heart Fail, 2014. 7(5): p. 822-30.
Hori, S., T. Takahashi, and S. Sakaguchi, Control of autoimmunity by naturally arising regulatory CD4+ T cells. Adv Immunol, 2003. 81: p. 331-71.
Hrdy, J., et al., The effect of a probiotic *Escherichia coli* strain on regulatory T-cells in six year-old children. Benef Microbes, 2016. 7(5): p. 639-648.
Hu, Y., et al., Class A scavenger receptor attenuates myocardial infarction-induced cardiomyocyte necrosis through suppressing M1 macrophage subset polarization. Basic Res Cardiol, 2011. 106(6): p. 1311-28.
Huang, Y., et al., Histone deacetylase inhibitor significantly improved the cloning efficiency of porcine somatic cell nuclear transfer embryos. Cell Reprogram, 2011. 13(6): p. 513-20.
Ichim, T. E., R. Zhong, and W. P. Min, *Prevention of allograft rejection by in vitro generated tolerogenic dendritic cells*. Transpl Immunol, 2003. 11(3-4): p. 295-306.
Igarashi, T., et al., Effect of tumor-infiltrating lymphocyte subsets on prognosis and susceptibility to interferon therapy in patients with renal cell carcinoma. Urol Int, 2002. 69(1): p. 51-6.
Igarashi, T., D. Rodrigues, and C. C. Ting, Studies of the mechanisms for the induction of in vivo tumor immunity. IV. Enhancement of the in vitro generation of secondary cell-mediated cytotoxic response by normal peritoneal macrophages and their culture supernatants. J Immunol, 1979. 122(4): p. 1519-27.
Inderbitzin, D., et al., Interleukin-3 induces hepatocyte-specific metabolic activity in bone marrow-derived liver stem cells. J Gastrointest Surg, 2005. 9(1): p. 69-74.
Irie, R. F., K. Irie, and D. L. Morton, Natural antibody in human serum to a neoantigen in human cultured cells grown in fetal bovine serum. J Natl Cancer Inst, 1974. 52(4): p. 1051-8.
Ishikawa, T., et al., Stem cells for hepatic regeneration: the role of adipose tissue derived mesenchymal stem cells. Curr Stem Cell Res Ther, 2010. 5(2): p. 182-9.
Itano, A. A. and M. K. Jenkins, Antigen presentation to naive CD4 T cells in the lymph node. Nat Immunol, 2003. 4(8): p. 733-9.
Ivanovic, Z., Interleukin-3 and ex vivo maintenance of hematopoietic stem cells: facts and controversies. Eur Cytokine Netw, 2004. 15(1): p. 6-13.
Jacobs, J. F., et al., Regulatory T cells in melanoma: the final hurdle towards effective immunotherapy? Lancet Oncol, 2012. 13(1): p. e32-42.
Jang, S. O., et al., Asthma Prevention by *Lactobacillus Rhamnosus* in a Mouse Model is Associated With CD4 (+)CD25(+)Foxp3(+) T Cells. Allergy Asthma Immunol Res, 2012. 4(3): p. 150-6.
Jay, K. E., et al., Identification of a novel population of human cord blood cells with hema-topoietic and chondrocytic potential. Cell Res, 2004. 14(4): p. 268-82.
Jeon, S. G., et al., Probiotic *Bifidobacterium breve* induces IL-10-producing Tr1 cells in the colon. PLoS Pathog, 2012. 8(5): p. e1002714.
Jung, K. H., et al., Granulocyte colony-stimulating factor stimulates neurogenesis via vascular endothelial growth factor with STAT activation. Brain Res, 2006.

Kadri, N., et al., Fetal calf serum-primed dendritic cells induce a strong anti-fetal calf serum immune response and diabetes protection in the non-obese diabetic mouse. Immunol Lett, 2007. 108(2): p. 129-36.

Kalos, M., et al., T cells with chimeric antigen receptors have potent antitumor effects and can establish memory in patients with advanced leukemia. Sci Transl Med, 2011. 3(95): p. 95ra73.

Kandalaft, L. E., D. J. Powell, Jr., and G. Coukos, A phase I clinical trial of adoptive transfer of folate receptor-alpha redirected autologous T cells for recurrent ovarian cancer. J Transl Med, 2012. 10: p. 157.

Kang, H. B., et al., Basic fibroblast growth factor activates ERK and induces c-fos in human embryonic stem cell line MizhES1. Stem Cells Dev, 2005. 14(4): p. 395-401.

Karimi, K., et al., *Lactobacillus reuteri*-induced regulatory T cells protect against an allergic airway response in mice. Am J Respir Crit Care Med, 2009. 179(3): p. 186-93.

Kawada, H., et al., Rapid ex vivo expansion of human umbilical cord hematopoietic progenitors using a novel culture system. Exp Hematol, 1999. 27(5): p. 904-15.

Kawata, A., et al., Tumor-infiltrating lymphocytes and prognosis of hepatocellular carcinoma. Jpn J Clin Oncol, 1992. 22(4): p. 256-63.

Kawai, K., et al., Matrix metalloproteinase-9 contributes to the mobilization of bone marrow cells in the injured liver. Cell Transplant, 2012. 21(2-3): p. 453-64.

Kebriaei, P., et al., Infusing CD19-directed T cells to augment disease control in patients undergoing autologous hematopoietic stem-cell transplantation for advanced B-lymphoid malignancies. Hum Gene Ther, 2012. 23(5): p. 444-50.

Kershaw, M. H., et al., A phase I study on adoptive immunotherapy using gene-modified T cells for ovarian cancer. Clin Cancer Res, 2006. 12(20 Pt 1): p. 6106-15.

Kim, H. J., et al., Effects of *Lactobacillus rhamnosus* on allergic march model by suppressing Th2, Th17, and TSLP responses via CD4(+)CD25(+)Foxp3(+) Tregs. Clin Immunol, 2014. 153(1): p. 178-86.

Kim, T. S., et al., Inhibition of interleukin-12 production by auranofin, an anti-rheumatic gold compound, deviates CD4(+) T cells from the Th1 to the Th2 pathway. Br J Pharmacol, 2001. 134(3): p. 571-8.

Kim, J. A., et al., The inhibition of T-cells proliferation by mouse mesenchymal stem cells through the induction of p16INK4A-cyclin D1/cdk4 and p21waf1, p27kip1-cyclin E/cdk2 pathways. Cell Immunol, 2007. 245(1): p. 16-23.

Kinnaird, T., et al., Local delivery of marrow-derived stromal cells augments collateral perfusion through paracrine mechanisms. Circulation, 2004. 109(12): p. 1543-9.

Kinnaird, T., et al., Marrow-derived stromal cells express genes encoding a broad spectrum of arteriogenic cytokines and promote in vitro and in vivo arteriogenesis through paracrine mechanisms. Circ Res, 2004. 94(5): p. 678-85.

Kingsley et al., 2002 J. Immunol. 168: 1080

Kirsch, B. M., et al., The active metabolite of leflunomide, A77 1726, interferes with dendritic cell function. Arthritis Res Ther, 2005. 7(3): p. R694-703.

Kjaergaard, J., et al., Augmentation versus inhibition: effects of conjunctional OX-40 receptor monoclonal antibody and IL-2 treatment on adoptive immunotherapy of advanced tumor. J Immunol, 2001. 167(11): p. 6669-77.

Ko, E., et al., Mesenchymal stem cells inhibit the differentiation of CD4+ T cells into interleukin-17-secreting T cells. Acta Haematol, 2008. 120(3): p. 165-7.

Kochenderfer, J. N. and S. A. Rosenberg, Treating B-cell cancer with T cells expressing anti-CD19 chimeric antigen receptors. Nat Rev Clin Oncol, 2013. 10(5): p. 267-76.

Kochenderfer, J. N., et al., Donor-derived CD19-targeted T cells cause regression of malignancy persisting after allogeneic hematopoietic stem cell transplantation. Blood, 2013. 122(25): p. 4129-39.

Kota, D. J., et al., TSG-6 produced by hMSCs delays the onset of autoimmune diabetes by suppressing Th1 development and enhancing tolerogenicity. Diabetes, 2013. 62(6): p. 2048-58.

Kochenderfer, J. N., et al., Eradication of B-lineage cells and regression of lymphoma in a patient treated with autologous T cells genetically engineered to recognize CD19. Blood, 2010. 116(20): p. 4099-102.

Kochenderfer, J. N., et al., B-cell depletion and remissions of malignancy along with cytokine-associated toxicity in a clinical trial of anti-CD19 chimeric-antigen-receptor-transduced T cells. Blood, 2012. 119(12): p. 2709-20.

Kogler, G., et al., Cytokine production and hematopoiesis supporting activity of cord blood-derived unrestricted somatic stem cells. Exp Hematol, 2005. 33(5): p. 573-83.

Koppi, T. A. and W. J. Halliday, Cellular origin of blocking factors from cultured spleen cells of tumor-bearing mice. Cell Immunol, 1983. 76(1): p. 29-38.

Krawczenko, A., C. Kieda, and D. Dus, The biological role and potential therapeutic application of interleukin 7. Arch Immunol Ther Exp (Warsz), 2005. 53(6): p. 518-25.

Kuroki, K. and K. Maenaka, Immune modulation of HLA-G dimer in maternal-fetal interface. Eur J Immunol, 2007. 37(7): p. 1727-9.

Kwon, M. S., et al., The immunomodulatory effects of human mesenchymal stem cells on peripheral blood mononuclear cells in ALS patients. J Neurochem, 2014. 131(2): p. 206-18.

Kwon, H. M., et al., Multiple paracrine factors secreted by mesenchymal stem cells contribute to angiogenesis. Vascul Pharmacol, 2014. 63(1): p. 19-28.

Lai, W. T., V. Krishnappa, and D. G. Phinney, Fibroblast growth factor 2 (Fgf2) inhibits differentiation of mesenchymal stem cells by inducing Twist2 and Spry4, blocking extracellular regulated kinase activation, and altering Fgf receptor expression levels. Stem Cells, 2011. 29(7): p. 1102-11.

Lamers, C. H., et al., Treatment of metastatic renal cell carcinoma with CAIX CAR-engineered T cells: clinical evaluation and management of on-target toxicity. Mol Ther, 2013. 21(4): p. 904-12.

Lange C, Cakiroglu F, Spiess A N, Cappallo-Obermann H, Dierlamm J, Zander A R (2007) Accelerated and safe expansion of human mesenchymal stromal cells in animal serum-free medium for transplantation and regenerative medicine. J Cellular Physiol 213(1):18-26.

Lauer, S. J., et al., In vitro enhancement of peripheral blood mononuclear cell natural killer activity following short term incubation with fetal calf serum. J Clin Lab Immunol, 1983. 12(2): p. 105-10.

Lavasani, S., et al., A novel probiotic mixture exerts a therapeutic effect on experimental autoimmune encephalomyelitis mediated by IL-10 producing regulatory T cells. PLoS One, 2010. 5(2): p. e9009.

Le Blanc, K., et al., Mesenchymal stem cells inhibit the expression of CD25 (interleukin-2 receptor) and CD38 on phytohaemagglutinin-activated lymphocytes. Scand J Immunol, 2004. 60(3): p. 307-15.

Leblond, A. L., et al., Systemic and Cardiac Depletion of M2 Macrophage through CSF-1R Signaling Inhibition Alters Cardiac Function Post Myocardial Infarction. PLoS One, 2015. 10(9): p. e0137515

Lee, C. W., et al., Macrophage heterogeneity of culprit coronary plaques in patients with acute myocardial infarction or stable angina. Am J Clin Pathol, 2013. 139(3): p. 317-22.

Lee, E. S., et al., Adoptive Transfer of Treg Cells Combined with Mesenchymal Stem Cells Facilitates Repopulation of Endogenous Treg Cells in a Murine Acute GVHD Model. PLoS One, 2015. 10(9): p. e0138846.

Levac, K., F. Karanu, and M. Bhatia, Identification of growth factor conditions that reduce ex vivo cord blood progenitor expansion but do not alter human repopulating cell function in vivo. Haematologica, 2005. 90(2): p. 166-72.

Li, C., et al., Enhanced M1 and Impaired M2 Macrophage Polarization and Reduced Mitochondrial Biogenesis via Inhibition of AMP Kinase in Chronic Kidney Disease. Cell Physiol Biochem, 2015. 36(1): p. 358-72.

Li, K., et al., Preclinical ex vivo expansion of G-CSF-mobilized peripheral blood stem cells: effects of serum-free media, cytokine combinations and chemotherapy. Eur J Haematol, 2005. 74(2): p. 128-35.

Li, X., et al., Reversine Increases the Plasticity of Long-Term Cryopreserved Fibroblasts to Multipotent Progenitor Cells through Activation of Oct4. Int J Biol Sci, 2016. 12(1): p. 53-62.

Li, Y., et al., Costimulation of tumor-reactive CD4+ and CD8+ T lymphocytes by B7, a natural ligand for CD28, can be used to treat established mouse melanoma. J Immunol, 1994. 153(1): p. 421-8.

Li, Y., R. B. Jalili, and A. Ghahary, Accelerating skin wound healing by M-CSF through generating SSEA-1 and -3 stem cells in the injured sites. Sci Rep, 2016. 6: p. 28979.

Lim, J. H., et al., Immunomodulation of delayed-type hypersensitivity responses by mesenchymal stem cells is associated with bystander T cell apoptosis in the draining lymph node. J Immunol, 2010. 185(7): p. 4022-9.

Lindemann, A., et al., Lymphokine activated killer cells. Blut, 1989. 59(4): p. 375-84.

Lipponen, P. K., et al., Tumour infiltrating lymphocytes as an independent prognostic factor in transitional cell bladder cancer. Eur J Cancer, 1992. 29A(1): p. 69-75.

Lissoni, P., et al., Prevention of cytokine-induced hypotension in cancer patients by the pineal hormone melatonin. Support Care Cancer, 1996. 4(4): p. 313-6.

Liu, W., et al., Activation in M1 but not M2 Macrophages Contributes to Cardiac Remodeling after Myocardial Infarction in Rats: a Critical Role of the Calcium Sensing Receptor/NRLP3 Inflammasome. Cell Physiol Biochem, 2015. 35(6): p. 2483-500.

Liu, Y., et al., *Lactobacillus reuteri* DSM 17938 changes the frequency of Foxp3+ regulatory T cells in the intestine and mesenteric lymph node in experimental necrotizing enterocolitis. PLoS One, 2013. 8(2): p. e56547.

Liu, Y., et al., *Lactobacillus reuteri* DSM 17938 differentially modulates effector memory T cells and Foxp3+ regulatory T cells in a mouse model of necrotizing enterocolitis. Am J Physiol Gastrointest Liver Physiol, 2014. 307(2): p. G177-86.

Lopez, P., et al., Interaction of *Bifidobacterium bifidum* LMG13195 with HT29 cells influences regulatory-T-cell-associated chemokine receptor expression. Appl Environ Microbiol, 2012. 78(8): p. 2850-7.

Lopez, P., et al., Treg-inducing membrane vesicles from *Bifidobacterium bifidum* LMG13195 as potential adjuvants in immunotherapy. Vaccine, 2012. 30(5): p. 825-9.

Lotze, M. T., et al., High-dose recombinant interleukin 2 in the treatment of patients with disseminated cancer. Responses, treatment-related morbidity, and histologic findings. JAMA, 1986. 256(22): p. 3117-24.

Louis, C. U., et al., Antitumor activity and long-term fate of chimeric antigen receptor-positive T cells in patients with neuroblastoma. Blood, 2011. 118(23): p. 6050-6.

Lu, X., et al., Immunomodulatory effects of mesenchymal stem cells involved in favoring type 2 T cell subsets. Transpl Immunol, 2009. 22(1-2): p. 55-61.

Luz-Crawford, P., et al., Mesenchymal stem cells repress Th17 molecular program through the PD-1 pathway. PLoS One, 2012. 7(9): p. e45272.

Luz-Crawford, P., et al., Mesenchymal stem cells generate a CD4+CD25+Foxp3+ regulatory T cell population during the differentiation process of Th1 and Th17 cells. Stem Cell Res Ther, 2013. 4(3): p. 65.

Lu, L. L., et al., [Effect of Tpo and/or IL-11 gene modified stromal cells on the expansion of CD34+CD38− hematopoietic primitive progenitor cells]. Zhonghua Xue Ye Xue Za Zhi, 2003. 24(11): p. 589-92.

Lu, S. J., et al., CD34+CD38− hematopoietic precursors derived from human embryonic stem cells exhibit an embryonic gene expression pattern. Blood, 2004. 103 (11): p. 4134-41.

Lucarelli, E., et al., Platelet-derived growth factors enhance proliferation of human stromal stem cells. Biomaterials, 2003. 24(18): p. 3095-100.

Lutz, M. B., et al., Culture of bone marrow cells in GM-CSF plus high doses of lipopolysaccharide generates exclusively immature dendritic cells which induce alloantigen-specific CD4 T cell anergy in vitro. Eur J Immunol, 2000. 30(4): p. 1048-52.

Luz-Crawford, P., et al., Mesenchymal stem cells generate a CD4+CD25+Foxp3+ regulatory T cell population during the differentiation process of Th1 and Th17 cells. Stem Cell Res Ther, 2013. 4(3): p. 65.

Lyons, A., et al., Bacterial strain-specific induction of Foxp3+ T regulatory cells is protective in murine allergy models. Clin Exp Allergy, 2010. 40(5): p. 811-9.

Ma, D. and M. J. Gu, Immune effect of tumor-infiltrating lymphocytes and its relation to the survival rate of patients with ovarian malignancies. J Tongji Med Univ, 1991. 11(4): p. 235-9.

Ma, Y., et al., Matrix metalloproteinase-28 deletion exacerbates cardiac dysfunction and rupture after myocardial infarction in mice by inhibiting M2 macrophage activation. Circ Res, 2013. 112(4): p. 675-88.

Macy, E., et al., Anaphylaxis to infusion of autologous bone marrow: an apparent reaction to self, mediated by IgE antibody to bovine serum albumin. J Allergy Clin Immunol, 1989. 83(5): p. 871-5.

Maccario, R., et al., Interaction of human mesenchymal stem cells with cells involved in alloantigen-specific immune response favors the differentiation of CD4+ T-cell subsets expressing a regulatory/suppressive phenotype. Haematologica, 2005. 90(4): p. 516-25.

Mackensen, A., et al., Presence of IgE antibodies to bovine serum albumin in a patient developing anaphylaxis after vaccination with human peptide-pulsed dendritic cells. Cancer Immunol Immunother, 2000. 49(3): p. 152-6.

Madec, A. M., et al., Mesenchymal stem cells protect NOD mice from diabetes by inducing regulatory T cells. Diabetologia, 2009. 52(7): p. 1391-9.

Magatti, M., et al., Human amnion mesenchyme harbors cells with allogeneic T-cell suppression and stimulation capabilities. Stem Cells, 2008. 26(1): p. 182-92.

Malemud, C. J., Matrix metalloproteinases (MMPs) in health and disease: an overview. Front Biosci, 2006. 11: p. 1696-701.

Mantovani, A., et al., The chemokine system in diverse forms of macrophage activation and polarization. Trends Immunol, 2004. 25(12): p. 677-86.

Maurer, A. M., et al., Ex vivo expansion of megakaryocytic cells. Int J Hematol, 2000. 71(3): p. 203-10.

McDevitt, T. C., M. A. Laflamme, and C. E. Murry, Proliferation of cardiomyocytes derived from human embryonic stem cells is mediated via the IGF/PI 3-kinase/Akt signaling pathway. J Mol Cell Cardiol, 2005. 39(6): p. 865-73.

McGuckin, C. P., et al., Thrombopoietin, flt3-ligand and c-kit-ligand modulate HOX gene expression in expanding cord blood CD133 cells. Cell Prolif, 2004. 37(4): p. 295-306.

Medoff, J. R., V. D. Clack, and J. K. Roche, Characterization of an immunosuppressive factor from malignant ascites that resembles a factor induced in vitro by carcinoembryonic antigen. J Immunol, 1986. 137(6): p. 2057-64.

Melief, S. M., et al., Multipotent stromal cells induce human regulatory T cells through a novel pathway involving skewing of monocytes toward anti-inflammatory macrophages. Stem Cells, 2013. 31(9): p. 1980-91.

Meng, X. M., et al., Macrophage Phenotype in Kidney Injury and Repair. Kidney Dis (Basel), 2015. 1(2): p. 138-46.

Mercadante, A. C., et al., Oral combined therapy with probiotics and alloantigen induces B cell-dependent long-lasting specific tolerance. J Immunol, 2014. 192(4): p. 1928-37.

Mertens, W. C., et al., Sustained oral indomethacin and ranitidine with intermittent continuous infusion interleukin-2 in advanced renal cell carcinoma. Cancer Biother, 1993. 8(3): p. 229-33.

Mier, J. W., et al., Inhibition of interleukin-2-induced tumor necrosis factor release by dexamethasone: prevention of an acquired neutrophil chemotaxis defect and differential suppression of interleukin-2-associated side effects. Blood, 1990. 76(10): p. 1933-40.

Milkiewicz, M., C. W. Pugh, and S. Egginton, Inhibition of endogenous HIF inactivation induces angiogenesis in ischaemic skeletal muscles of mice. J Physiol, 2004. 560(Pt 1): p. 21-6.

Mills, C. D., M1 and M2 Macrophages: Oracles of Health and Disease. Crit Rev Immunol, 2012. 32(6): p. 463-88.

Mills, C. D. and K. Ley, M1 and M2 macrophages: the chicken and the egg of immunity. J Innate Immun, 2014. 6(6): p. 716-26.

Min, W., et al., Fas ligand-transfected dendritic cells induce apoptosis of antigen-specific T cells. Transplant Proc, 2001. 33(1-2): p. 234.

Miyaoka, Y. and A. Miyajima, To divide or not to divide: revisiting liver regeneration. Cell Div, 2013. 8(1): p. 8.

Miyara, M. and S. Sakaguchi, Natural regulatory T cells: mechanisms of suppression. Trends Mol Med, 2007. 13(3): p. 108-16.

Miyazaki, M., et al., Propagation of adult rat bone marrow-derived hepatocyte-like cells by serial passages in vitro. Cell Transplant, 2004. 13(4): p. 385-91.

Miwa, H., Identification and prognostic implications of tumor infiltrating lymphocytes—a review. Acta Med Okayama, 1984. 38(3): p. 215-8.

Mobest, D., R. Mertelsmann, and R. Henschler, Serum-free ex vivo expansion of CD34(+) hematopoietic progenitor cells. Biotechnol Bioeng, 1998. 60(3): p. 341-7.

Momose, K., et al., Effects of interleukin-11 on the hematopoietic action of granulocyte colony-stimulating factor. Arzneimittelforschung, 2002. 52(11): p. 857-61.

Montes, R., et al., Feeder-free maintenance of hESCs in mesenchymal stem cell-conditioned media: distinct requirements for TGF-beta and IGF-II. Cell Res, 2009. 19(6): p. 698-709.

Mosna, F., L. Sensebe, and M. Krampera, Human bone marrow and adipose tissue mesenchymal stem cells: a user's guide. Stem Cells Dev, 2010. 19(10): p. 1449-70.

Moon, J. H., et al., Induction of neural stem cell-like cells (NSCLCs) from mouse astrocytes by Bmi1. Biochem Biophys Res Commun, 2008. 371(2): p. 267-72.

Mougiakakos, D., et al., The impact of inflammatory licensing on heme oxygenase-1-mediated induction of regulatory T cells by human mesenchymal stem cells. Blood, 2011. 117(18): p. 4826-35.

Mule, J. J., et al., Selective localization of radiolabeled immune lymphocytes into syngeneic tumors. J Immunol, 1979. 123(2): p. 600-6.

Musaro, A., Growth factor enhancement of muscle regeneration: a central role of IGF-1. Arch Ital Biol, 2005. 143(3-4): p. 243-8.

Narushima, S., et al., Characterization of the 17 strains of regulatory T cell-inducing human-derived Clostridia. Gut Microbes, 2014. 5(3): p. 333-9.

Nakamura, M., et al., Role of IL-6 in spinal cord injury in a mouse model. Clin Rev Allergy Immunol, 2005. 28(3): p. 197-204.

Nakamura et al., 2001 J. Exp. Med. 194: 629-644

Najar, M., et al., Characterization and functionality of the CD200-CD200R system during mesenchymal stromal cell interactions with T-lymphocytes. Immunol Lett, 2012. 146(1-2): p. 50-6.

Nasef, A., et al., Identification of IL-10 and TGF-beta transcripts involved in the inhibition of T-lymphocyte proliferation during cell contact with human mesenchymal stem cells. Gene Expr, 2007. 13(4-5): p. 217-26.

Ney, J. T., et al., Autochthonous liver tumors induce systemic T cell tolerance associated with T cell receptor down-modulation. Hepatology, 2009. 49(2): p. 471-81.

O'Mahony, A. M., et al., An immune suppressive factor derived from esophageal squamous carcinoma induces apoptosis in normal and transformed cells of lymphoid lineage. J Immunol, 1993. 151(9): p. 4847-56.

Oh, I., et al., Interferon-gamma and NF-kappaB mediate nitric oxide production by mesenchymal stromal cells. Biochem Biophys Res Commun, 2007. 355(4): p. 956-62.

Okajima, Y., et al., Insulin-like growth factor-I augments erythropoietin-induced proliferation through enhanced tyrosine phosphorylation of STATS. J Biol Chem, 1998. 273(36): p. 22877-83.

Onishi, Y., et al., Foxp3+ natural regulatory T cells preferentially form aggregates on dendritic cells in vitro and actively inhibit their maturation. Proc Natl Acad Sci USA, 2008. 105(29): p. 10113-8.

Otani, T., et al., Erythroblasts derived in vitro from embryonic stem cells in the presence of erythropoietin do not express the TER-119 antigen. Exp Hematol, 2004. 32(7): p. 607-13.

Palomares, O., et al., Induction and maintenance of allergen-specific FOXP3+ Treg cells in human tonsils as potential first-line organs of oral tolerance. J Allergy Clin Immunol, 2012. 129(2): p. 510-20, 520 e1-9.

Park, M. J., et al., A distinct tolerogenic subset of splenic IDO(+)CD11b(+) dendritic cells from orally tolerized mice is responsible for induction of systemic immune tolerance and suppression of collagen-induced arthritis. Cell Immunol, 2012. 278(1-2): p. 45-54.

Park, J. H. and R. J. Brentjens, Adoptive immunotherapy for B-cell malignancies with autologous chimeric antigen receptor modified tumor targeted T cells. Discov Med, 2010. 9(47): p. 277-88.

Park, J. R., et al., Adoptive transfer of chimeric antigen receptor re-directed cytolytic T lymphocyte clones in patients with neuroblastoma. Mol Ther, 2007. 15(4): p. 825-33.

Park, K. S., et al., Type II collagen oral tolerance; mechanism and role in collagen-induced arthritis and rheumatoid arthritis. Mod Rheumatol, 2009.

Pedroza-Gonzalez, A., et al., Activated tumor-infiltrating CD4+ regulatory T cells restrain antitumor immunity in patients with primary or metastatic liver cancer. Hepatology, 2013. 57(1): p. 183-94.

Peng, L., S. Shu, and J. C. Krauss, Treatment of subcutaneous tumor with adoptively transferred T cells. Cell Immunol, 1997. 178(1): p. 24-32.

Peng, L., et al., Helper-independent, L-selectin low CD8+ T cells with broad anti-tumor efficacy are naturally sensitized during tumor progression. J Immunol, 2000. 165 (10): p. 5738-49.

Peschle, C., et al., Stringently purified human hematopoietic progenitors/stem cells: analysis of cellular/molecular mechanisms underlying early hematopoiesis. Stem Cells, 1993. 11(5): p. 356-70.

Phelps, E. A., et al., Aberrant Accumulation of the Diabetes Autoantigen GAD65 in Golgi Membranes in Conditions of ER Stress and Autoimmunity. Diabetes, 2016. 65(9): p. 2686-99.

Pillay, D. J., M. Karmazyn, and B. L. Pope, Activation of suppressor cells by low molecular weight factors secreted by spleen cells of tumor-bearing mice: modulatory role of prostaglandins. Int J Immunopharmacol, 1986. 8(2): p. 227-35.

Pletinckx, K., et al., Role of dendritic cell maturity/costimulation for generation, homeostasis, and suppressive activity of regulatory T cells. Front Immunol, 2011. 2: p. 39.

Ploemacher, R. E., et al., Bone morphogenetic protein 9 is a potent synergistic factor for murine hemopoietic progenitor cell generation and colony formation in serum-free cultures. Leukemia, 1999. 13(3): p. 428-37.

Plumas, J., et al., Mesenchymal stem cells induce apoptosis of activated T cells. Leukemia, 2005. 19(9): p. 1597-604.

Pope, B. L., The effect of indomethacin on the activation and effector function of suppressor cells from tumor-bearing mice. Cancer Immunol Immunother, 1985. 19(2): p. 101-8.

Pope, B. L., Activation of suppressor T cells by low-molecular-weight factors secreted by spleen cells from tumor-bearing mice. Cell Immunol, 1985. 93(2): p. 364-74.

Porter, D. L., et al., Chimeric antigen receptor-modified T cells in chronic lymphoid leukemia. N Engl J Med, 2011. 365(8): p. 725-33.

Prevosto, C., et al., Generation of CD4+ or CD8+ regulatory T cells upon mesenchymal stem cell-lymphocyte interaction. Haematologica, 2007. 92(7): p. 881-8.

Pulendran, B., K. Palucka, and J. Banchereau, Sensing pathogens and tuning immune responses. Science, 2001. 293(5528): p. 253-6.

Puglisi, M. A., et al., Adipose tissue-derived mesenchymal stem cells and hepatic differentiation: old concepts and future perspectives. Eur Rev Med Pharmacol Sci, 2011. 15(4): p. 355-64.

Qiu, X., et al., *Faecalibacterium prausnitzii* upregulates regulatory T cells and anti-inflammatory cytokines in treating TNBS-induced colitis. J Crohns Colitis, 2013. 7(11): p. e558-68.

Quesenberry, P., et al., Long-term marrow cultures: human and murine systems. J Cell Biochem, 1991. 45(3): p. 273-8.

Quito, F. L., et al., Effects of fibroblast growth factor-4 (k-FGF) on long-term cultures of human bone marrow cells. Blood, 1996. 87(4): p. 1282-91.

Rafei, M., et al., Mesenchymal stromal cells ameliorate experimental autoimmune encephalomyelitis by inhibiting CD4 Th17 T cells in a CC chemokine ligand 2-dependent manner. J Immunol, 2009. 182(10): p. 5994-6002.

Rafatian, N., et al., Cardiac macrophages and apoptosis after myocardial infarction: effects of central MR blockade. Am J Physiol Regul Integr Comp Physiol, 2014. 307(7): p. R879-87.

Ramsdell, F. and B. J. Fowlkes, Clonal deletion versus clonal anergy: the role of the thymus in inducing self tolerance. Science, 1990. 248(4961): p. 1342-8

Rasmusson, I., et al., Mesenchymal stem cells inhibit lymphocyte proliferation by mitogens and alloantigens by different mechanisms. Exp Cell Res, 2005. 305(1): p. 33-41.

Ratajczak, M. Z., et al., Effect of basic (FGF-2) and acidic (FGF-1) fibroblast growth factors on early haemopoietic cell development. Br J Haematol, 1996. 93(4): p. 772-82.

Reichert, T. E., et al., Signaling abnormalities, apoptosis, and reduced proliferation of circulating and tumor-infiltrating lymphocytes in patients with oral carcinoma. Clin Cancer Res, 2002. 8(10): p. 3137-45.

Ren, G., et al., Mesenchymal stem cell-mediated immunosuppression occurs via concerted action of chemokines and nitric oxide. Cell Stem Cell, 2008. 2(2): p. 141-50.

Richards, J. M., et al., Phase I study of weekly 24-hour infusions of recombinant human interleukin-2. J Natl Cancer Inst, 1988. 80(16): p. 1325-8.

Riordan et al. J Transl Med. 2015 Jul. 17; 13:232

Riordan, N. H., et al., Scalable efficient expansion of mesenchymal stem cells in xeno free media using commercially available reagents. J Transl Med, 2015. 13: p. 232.

Rodrigues, D. and C. C. Ting, Studies of the mechanisms for the induction of in vivo tumor immunity. V. A comparison of the generation of the primary cell-mediated cytotoxic response using in vitro mixed-lymphocyte—tumor cell culture and an in vivo technique. Cell Immunol, 1981. 59(1): p. 127-37.

Roelofs-Haarhuis, K., et al., Infectious nickel tolerance: a reciprocal interplay of tolerogenic APCs and T suppressor cells that is driven by immunization. J Immunol, 2003. 171(6): p. 2863-72.

Ropponen, K. M., et al., Prognostic value of tumour-infiltrating lymphocytes (TILs) in colorectal cancer. J Pathol, 1997. 182(3): p. 318-24.

Rosenberg, S. A., et al., A progress report on the treatment of 157 patients with advanced cancer using lymphokine-activated killer cells and interleukin-2 or high-dose interleukin-2 alone. N Engl J Med, 1987. 316(15): p. 889-97.

Rosenberg, S. A., et al., A new approach to the therapy of cancer based on the systemic administration of autologous lymphokine-activated killer cells and recombinant interleukin-2. Surgery, 1986. 100(2): p. 262-72.

Rosenberg, S. A., et al., The development of gene therapy for the treatment of cancer. Ann Surg, 1993. 218(4): p. 455-63; discussion 463-4.

Rubin, J. T., et al., Immunohistochemical correlates of response to recombinant interleukin-2-based immunotherapy in humans. Cancer Res, 1989. 49(24 Pt 1): p. 7086-92.

Salvade A, Della Mina P, Gaddi D, Gatto F, Villa A, Bigoni M et al (2010) Characterization of platelet lysate cultured mesenchymal stromal cells and their potential use in tissue-engineered osteogenic devices for the treatment of bone defects. Tissue Eng Part C 16(2):201-214.

Sakaguchi, S., et al., Regulatory T cells: how do they suppress immune responses? Int Immunol, 2009. 21(10): p. 1105-11.

Saldanha-Araujo, F., et al., Mesenchymal stromal cells upregulate CD39 and increase adenosine production to suppress activated T-lymphocytes. Stem Cell Res, 2011. 7(1): p. 66-74.

Sato, K., et al., Nitric oxide plays a critical role in suppression of T-cell proliferation by mesenchymal stem cells. Blood, 2007. 109(1): p. 228-34.

Sattler, C, et al., Inhibition of T-cell Proliferation by murin multipotent mesenchymal stromal cells is mediated by CD39 expression and adenosine generation. Cell Transplant, 2011. 20(8): p. 1221-30.

Schallmoser K, Bartmann C, Rohde E, Reinisch A, Kashofer K, Stadelmeyer E et al (2007) Human platelet lysate can replace fetal bovine serum for clinical-scale expansion of functional mesenchymal stromal cells. Transfusion 47(8): 1436-1446.

Scheding, S., et al., Effective ex vivo generation of granulopoietic postprogenitor cells from mobilized peripheral blood CD34(+) cells. Exp Hematol, 2000. 28(4): p. 460-70.

Schuberth, P. C., et al., Treatment of malignant pleural mesothelioma by fibroblast activation protein-specific redirected T cells. J Transl Med, 2013. 11: p. 187.

Schwartz, R. E., et al., Defined conditions for development of functional hepatic cells from human embryonic stem cells. Stem Cells Dev, 2005. 14(6): p. 643-55.

Selvaggi, T. A., R. E. Walker, and T. A. Fleisher, Development of antibodies to fetal calf serum with arthus-like reactions in human immunodeficiency virus-infected patients given syngeneic lymphocyte infusions. Blood, 1997. 89(3): p. 776-9.

Shav-Tal, Y. and D. Zipori, The role of activin a in regulation of hemopoiesis. Stem Cells, 2002. 20(6): p. 493-500.

Shen, C., et al., Conditioned medium from umbilical cord mesenchymal stem cells induces migration and angiogenesis. Mol Med Rep, 2015. 12(1): p. 20-30.

Sheng, H., et al., A critical role of IFNgamma in priming MSC-mediated suppression of T cell proliferation through up-regulation of B7-H1. Cell Res, 2008. 18(8): p. 846-57.

Shevach, E. M., Regulatory T cells in autoimmmunity*. Annu Rev Immunol, 2000. 18: p. 423-49.

Shulman, K. L., W. M. Stadler, and N. J. Vogelzang, High-dose continuous intravenous infusion of interleukin-2 therapy for metastatic renal cell carcinoma: the University of Chicago experience. Urology, 1996. 47(2): p. 194-7.

Silva Dos Santos, D., et al., Human Menstrual Blood-Derived Mesenchymal Cells as New Human Feeder Layer System for Human Embryonic Stem Cells. Cell Med, 2014. 7(1): p. 25-35.

Simone, M. D., et al., Nerve growth factor: a survey of activity on immune and hematopoietic cells. Hematol Oncol, 1999. 17(1): p. 1-10.

Singla, D. K., et al., Fibroblast growth factor-9 enhances M2 macrophage differentiation and attenuates adverse cardiac remodeling in the infarcted diabetic heart. PLoS One, 2015. 10(3): p. e0120739.

Smelt, M. J., et al., The impact of *Lactobacillus plantarum* WCFS1 teichoic acid D-alanylation on the generation of effector and regulatory T-cells in healthy mice. PLoS One, 2013. 8(4): p. e63099.

Smelt, M. J., et al., Probiotics can generate FoxP3 T-cell responses in the small intestine and simultaneously inducing CD4 and CD8 T cell activation in the large intestine. PLoS One, 2013. 8(7): p. e68952.

Smith, T. D., et al., Harnessing macrophage plasticity for tissue regeneration. Adv Drug Deliv Rev, 2017.

Snyder, R. J., et al., Macrophages: A review of their role in wound healing and their therapeutic use. Wound Repair Regen, 2016. 24(4): p. 613-29.

Song, F., et al., The thymus plays a role in oral tolerance induction in experimental autoimmune encephalomyelitis. Ann N Y Acad Sci, 2004. 1029: p. 402-4.

Spaggiari, G. M., et al., MSCs inhibit monocyte-derived DC maturation and function by selectively interfering with the generation of immature DCs: central role of MSC-derived prostaglandin E2. Blood, 2009. 113(26): p. 6576-83.

Spellman, J. E., et al., Cytokine production by human soft tissue sarcomas: implications for immunosuppression within the tumour bed. Surg Oncol, 1996. 5(5-6): p. 237-44.

Spiess, P. J., J. C. Yang, and S. A. Rosenberg, In vivo antitumor activity of tumor-infiltrating lymphocytes expanded in recombinant interleukin-2. J Natl Cancer Inst, 1987. 79(5): p. 1067-75.

Steinman, R. M. and Z. A. Cohn, Identification of a novel cell type in peripheral lymphoid organs of mice. I. Morphology, quantitation, tissue distribution. J Exp Med, 1973. 137(5): p. 1142-62.

Sternberg, C. N., et al., Progress in the treatment of advanced prostate cancer. Am Soc Clin Oncol Educ Book, 2014: p. 117-31.

Stratton, J. A. and P. J. DiSaia, Effect of immunomodulating factors present in ascitic fluids and sera from cancer patients on the responses of cultured mononuclear cells from normal subjects. Am J Reprod Immunol, 1982. 2(1): p. 50-3.

Streeter, P. R., L. Z. Dudley, and W. H. Fleming, Activation of the G-CSF and Flt-3 receptors protects hematopoietic stem cells from lethal irradiation. Exp Hematol, 2003. 31(11): p. 1119-25.

Strioga, M., et al., Same or not the same? Comparison of adipose tissue-derived versus bone marrow-derived mesenchymal stem and stromal cells. Stem Cells Dev, 2012. 21(14): p. 2724-52.

Su, R. J., et al., Platelet-derived growth factor enhances expansion of umbilical cord blood CD34+ cells in contact with hematopoietic stroma. Stem Cells Dev, 2005. 14(2): p. 223-30.

Sun, S., et al., TLR7/9 antagonists as therapeutics for immune-mediated inflammatory disorders. Inflamm Allergy Drug Targets, 2007. 6(4): p. 223-35.

Sun, Y. Y., et al., Macrophage Phenotype in Liver Injury and Repair. Scand J Immunol, 2017. 85(3): p. 166-174.

Taga, T. and S. Fukuda, Role of IL-6 in the neural stem cell differentiation. Clin Rev Allergy Immunol, 2005. 28(3): p. 249-56.

Taggart, A. J., Sulphasalazine in arthritis—an old drug rediscovered. Clin Rheumatol, 1987. 6(3): p. 378-83.

Takeichi, N. and C. W. Boone, Local adoptive transfer of the antitumor cellular immune response in syngeneic and allogeneic mice studied with a rapid radioisotopic footpad assay. J Natl Cancer Inst, 1975. 55(1): p. 183-7.

Tatara, R., et al., Mesenchymal stromal cells inhibit Th17 but not regulatory T-cell differentiation. Cytotherapy, 2011. 13(6): p. 686-94.

Tepperman, K., et al., Dicyanogold effects on lymphokine production. Met Based Drugs, 1999. 6(4-5): p. 301-9.

Thakur, B. K., et al., Live and heat-killed probiotic *Lactobacillus casei* Lbs2 protects from experimental colitis through Toll-like receptor 2-dependent induction of T-regulatory response. Int Immunopharmacol, 2016. 36: p. 39-50.

Thompson, H. S., et al., Suppression of collagen induced arthritis by oral administration of type II collagen: changes in immune and arthritic responses mediated by active peripheral suppression. Autoimmunity, 1993. 16(3): p. 189-99.

Thurau, S. R., et al., Molecular mimicry as a therapeutic approach for an autoimmune disease: oral treatment of uveitis-patients with an MHC-peptide crossreactive with autoantigen—first results. Immunol Lett, 1997. 57(1-3): p. 193-201.

Tian, Y., et al., Adenosine 2B Receptor Activation Reduces Myocardial Reperfusion Injury by Promoting Anti-Inflammatory Macrophages Differentiation via PI3K/Akt Pathway. Oxid Med Cell Longev, 2015. 2015: p. 585297.

Tiemessen, M. M., et al., CD4+CD25+Foxp3+ regulatory T cells induce alternative activation of human monocytes/macrophages. Proc Natl Acad Sci USA, 2007. 104(49): p. 19446-51.

Till, B. G., et al., CD20-specific adoptive immunotherapy for lymphoma using a chimeric antigen receptor with both CD28 and 4-1BB domains: pilot clinical trial results. Blood, 2012. 119(17): p. 3940-50.

Timonen, T. and T. S. Helander, Natural killer cell-target cell interactions. Curr Opin Cell Biol, 1997. 9(5): p. 667-73.

Ting, C. C., Studies of the mechanisms for the induction of in vivo tumor immunity. I. Induction of primary and secondary cell-mediated cytotoxic responses by adoptive transfer of lymphocytes. Cell Immunol, 1976. 27(1): p. 71-81.

Ting, C. C., Studies of the mechanisms for the induction of in vivo tumor immunity. II. Distribution and homing of cytotoxic effector and precursor cells. J Natl Cancer Inst, 1978. 60(2): p. 437-44.

Ting, C. C., D. Rodrigues, and T. Igarashi, Studies of the mechanisms for the induction of in vivo tumor immunity. III. Recruitment of host helper cells by donor T cells in adoptive transfer of cell-mediated immunity. J Immunol, 1979. 122(4): p. 1510-8.

Tipnis, S., C. Viswanathan, and A. S. Majumdar, Immunosuppressive properties of human umbilical cord-derived mesenchymal stem cells: role of B7-H1 and IDO. Immunol Cell Biol, 2010. 88(8): p. 795-806.

Tomsova, M., et al., Prognostic significance of CD3+ tumor-infiltrating lymphocytes in ovarian carcinoma. Gynecol Oncol, 2008. 108(2): p. 415-20.

Tomov, B., et al., Therapeutic response of untreatable hepatocellular carcinoma after application of the immune modulators IL-2, BCG and melatonin. Anticancer Res, 2013. 33(10): p. 4531-5.

Topalian, S. L., et al., Immunotherapy of patients with advanced cancer using tumor-infiltrating lymphocytes and recombinant interleukin-2: a pilot study. J Clin Oncol, 1988. 6(5): p. 839-53.

Treacy, O., et al., Mesenchymal stem cell therapy promotes corneal allograft survival in rats by local and systemic immunomodulation. Am J Transplant, 2014. 14(9): p. 2023-36.

Trombetta, E. S. and I. Mellman, Cell biology of antigen processing in vitro and in vivo. Annu Rev Immunol, 2005. 23: p. 975-1028.

Turnquist, H. R. and A. W. Thomson, Taming the lions: manipulating dendritic cells for use as negative cellular vaccines in organ transplantation. Curr Opin Organ Transplant, 2008. 13(4): p. 350-7.

Van der Meeren, A., et al., Administration of recombinant human IL11 after supralethal radiation exposure promotes survival in mice: interactive effect with thrombopoietin. Radiat Res, 2002. 157(6): p. 642-9.

van Furth, R. and Z. A. Cohn, The origin and kinetics of mononuclear phagocytes. J Exp Med, 1968. 128(3): p. 415-35.

van Schalk k, M. C., et al., Design of a phase I clinical trial to evaluate intratumoral delivery of ErbB-targeted chimeric antigen receptor T-cells in locally advanced or recurrent head and neck cancer. Hum Gene Ther Clin Dev, 2013. 24(3): p. 134-42.

Vacchio, M. S. and R. J. Hodes, Fetal expression of Fas ligand is necessary and sufficient for induction of CD8 T cell tolerance to the fetal antigen H-Y during pregnancy. J Immunol, 2005. 174(8): p. 4657-61.

Vannella, K. M. and T. A. Wynn, Mechanisms of Organ Injury and Repair by Macrophages. Annu Rev Physiol, 2017. 79: p. 593-617.

Veldhoen, M., et al., Modulation of dendritic cell function by naive and regulatory CD4+ T cells. J Immunol, 2006. 176(10): p. 6202-10.

Vendetti, S., et al., Anergic T cells inhibit the antigen-presenting function of dendritic cells. J Immunol, 2000. 165(3): p. 1175-81.

von Ruden, T. and E. F. Wagner, Expression of functional human EGF receptor on murine bone marrow cells. Embo J, 1988. 7(9): p. 2749-56.

Waeckerle-Men, Y., et al., Dendritic cell-based multi-epitope immunotherapy of hormone-refractory prostate carcinoma. Cancer Immunol Immunother, 2006. 55(12): p. 1524-33.

Walenda, T., et al., Synergistic effects of growth factors and mesenchymal stromal cells for expansion of hematopoietic stem and progenitor cells. Exp Hematol, 2011. 39(6): p. 617-28.

Wan, F., et al., Calpastatin overexpression impairs postinfarct scar healing in mice by compromising reparative immune cell recruitment and activation. Am J Physiol Heart Circ Physiol, 2015. 309(11): p. H1883-9.

Wang, J., et al., In vitro hematopoietic differentiation of human embryonic stem cells induced by co-culture with human bone marrow stromal cells and low dose cytokines. Cell Biol Int, 2005. 29(8): p. 654-61.

Wang, Y. and J. Adjaye, A cyclic AMP analog, 8-Br-cAMP, enhances the induction of pluripotency in human fibroblast cells. Stem Cell Rev, 2011. 7(2): p. 331-41.

Wang, Y., et al., Dendritic cell co-transfected with FasL and allergen genes induces T cell tolerance and decreases airway inflammation in allergen induced murine model. Mol Biol Rep, 2011. 38(2): p. 809-17.

Wang, Q., et al., Murine bone marrow mesenchymal stem cells cause mature dendritic cells to promote T-cell tolerance. Scand J Immunol, 2008. 68(6): p. 607-15.

Wang, Z., et al., Thrombopoietin regulates differentiation of rhesus monkey embryonic stem cells to hematopoietic cells. Ann N Y Acad Sci, 2005. 1044: p. 29-40.

Wang, Z. X., et al., Mesenchymal stem cells alleviate atherosclerosis by elevating number and function of CD4 (+)CD25 (+)FOXP3 (+) regulatory T-cells and inhibiting macrophage foam cell formation. Mol Cell Biochem, 2015. 400(1-2): p. 163-72.

Wei, W., et al., A multicenter, double-blind, randomized, controlled phase III clinical trial of chicken type II collagen in rheumatoid arthritis. Arthritis Res Ther, 2009. 11(6): p. R180

Weiner, H. L., et al., Double-blind pilot trial of oral tolerization with myelin antigens in multiple sclerosis. Science, 1993. 259(5099): p. 1321-4.

Weiner, H. L., Induction and mechanism of action of transforming growth factor-beta-secreting Th3 regulatory cells. Immunol Rev, 2001. 182: p. 207-14.

Weirather, J., et al., Foxp3+CD4+ T cells improve healing after myocardial infarction by modulating monocyte/macrophage differentiation. Circ Res, 2014. 115(1): p. 55-67.

Whiteside, T. L., Down-regulation of zeta-chain expression in T cells: a biomarker of prognosis in cancer? Cancer Immunol Immunother, 2004. 53(10): p. 865-78.

Whiteside, T. L., Signaling defects in T lymphocytes of patients with malignancy. Cancer Immunol Immunother, 1999. 48(7): p. 346-52.

Whiteside, T. L., Cancer therapy with tumor-infiltrating lymphocytes: evaluation of potential and limitations. In Vivo, 1991. 5(6): p. 553-9.

Whitney, R. B., J. G. Levy, and A. G. Smith, Studies on the effector cell of anti-tumour immunity in a chemically induced mouse tumour system. Br J Cancer, 1975. 31(2): p. 157-63.

Wile, A. G., et al., Soluble suppressor factors elaborated in experimental malignant ascites. Cell Immunol, 1984. 86(2): p. 347-53.

Willems, R., et al., Establishment of serum-free pre-colony forming unit assays for differentiation of primitive hematopoietic progenitors: serum induces early macrophage differentiation and inhibits early erythroid differentiation of CD34++CD38− cells. Ann Hematol, 2001. 80(1): p. 17-25.

Won, J. H., et al., Thrombopoietin is synergistic with other cytokines for expansion of cord blood progenitor cells. J Hematother Stem Cell Res, 2000. 9(4): p. 465-73.

Womer, K. L., et al., A pilot study on the immunological effects of oral administration of donor major histocompatibility complex class II peptides in renal transplant recipients. Clin Transplant, 2008. 22(6): p. 754-9.

Wu, R., et al., Adoptive T-cell therapy using autologous tumor-infiltrating lymphocytes for metastatic melanoma: current status and future outlook. Cancer J, 2012. 18(2): p. 160-75.

Wynn, T. A., A. Chawla, and J. W. Pollard, Macrophage biology in development, homeostasis and disease. Nature, 2013. 496(7446): p. 445-55.

Xie, X., et al., Thrombopoietin promotes mixed lineage and megakaryocytic colony-forming cell growth but inhibits primitive and definitive erythropoiesis in cells isolated from early murine yolk sacs. Blood, 2003. 101(4): p. 1329-35.

Xiong, X. R., et al., Cellular extract facilitates nuclear reprogramming by altering DNA methylation and pluripotency gene expression. Cell Reprogram, 2014. 16(3): p. 215-22.

Xu, G., et al., Immunosuppressive properties of cloned bone marrow mesenchymal stem cells. Cell Res, 2007. 17(3): p. 240-8.

Xue, Q., et al., The negative co-signaling molecule b7-h4 is expressed by human bone marrow-derived mesenchymal stem cells and mediates its T-cell modulatory activity. Stem Cells Dev, 2010. 19(1): p. 27-38.

Yabluchanskiy, A., et al., Myocardial Infarction Superimposed on Aging: MMP-9 Deletion Promotes M2 Macrophage Polarization. J Gerontol A Biol Sci Med Sci, 2016. 71(4): p. 475-83.

Yamashita, H., et al., Overcoming food allergy through acquired tolerance conferred by transfer of Tregs in a murine model. Allergy, 2012. 67(2): p. 201-9.

Yamamoto, S., et al., Atherosclerosis following renal injury is ameliorated by pioglitazone and losartan via macrophage phenotype. Atherosclerosis, 2015. 242(1): p. 56-64.

Yan, X., et al., Temporal dynamics of cardiac immune cell accumulation following acute myocardial infarction. J Mol Cell Cardiol, 2013. 62: p. 24-35.

Yang, J. C., D. Perry-Lalley, and S. A. Rosenberg, An improved method for growing murine tumor-infiltrating lymphocytes with in vivo antitumor activity. J Biol Response Mod, 1990. 9(2): p. 149-59.

Yang, M., C. N. Chesterman, and B. H. Chong, Recombinant PDGF enhances megakaryocytopoiesis in vitro. Br J Haematol, 1995. 91(2): p. 285-9.

Yanez, R., et al., Prostaglandin E2 plays a key role in the immunosuppressive properties of adipose and bone marrow tissue-derived mesenchymal stromal cells. Exp Cell Res, 2010. 316(19): p. 3109-23.

Yao, M., et al., Ex vivo expansion of CD34-positive peripheral blood progenitor cells from patients with non-Hodgkin's lymphoma: no evidence of concomitant expansion of contaminating bcl2/JH-positive lymphoma cells. Bone Marrow Transplant, 2000. 26(5): p. 497-503.

Ye, Z., et al., Immunosuppressive effects of rat mesenchymal stem cells: involvement of CD4+CD25+ regulatory T cells. Hepatobiliary Pancreat Dis Int, 2008. 7(6): p. 608-14.

Yi, T. and S. U. Song, Immunomodulatory properties of mesenchymal stem cells and their therapeutic applications. Arch Pharm Res, 2012. 35(2): p. 213-21.

Yoshida, T., et al., An increased number of CD4+CD25+ cells induced by an oral administration of *Lactobacillus plantarum* NRIC0380 are involved in antiallergic activity. Int Arch Allergy Immunol, 2013. 162(4): p. 283-9.

Young, M. R., M. A. Wright, and R. Pandit, Myeloid differentiation treatment to diminish the presence of immune-suppressive CD34+ cells within human head and neck squamous cell carcinomas. J Immunol, 1997. 159 (2): p. 990-6.

Zafranskaya, M., et al., PGE2 Contributes to In vitro MSC-Mediated Inhibition of Non-Specific and Antigen-Specific T Cell Proliferation in MS Patients. Scand J Immunol, 2013. 78(5): p. 455-62.

Zanone, M. M., et al., Human mesenchymal stem cells modulate cellular immune response to islet antigen glutamic acid decarboxylase in type 1 diabetes. J Clin Endocrinol Metab, 2010. 95(8): p. 3788-97.

Zappia, E., et al., Mesenchymal stem cells ameliorate experimental autoimmune encephalomyelitis inducing T-cell anergy. Blood, 2005. 106(5): p. 1755-61.

Zhang, Y., et al., Cardiac Repair With a Novel Population of Mesenchymal Stem Cells Resident in the Human Heart. Stem Cells, 2015. 33(10): p. 3100-13. Zhang, J. and L. Li, BMP signaling and stem cell regulation. Dev Biol, 2005. 284(1): p. 1-11.

Zhang, X., et al., Generation of therapeutic dendritic cells and regulatory T cells for preventing allogeneic cardiac graft rejection. Clin Immunol, 2008. 127(3): p. 313-21.

Zhang, P. L., et al., Increased myelinating capacity of embryonic stem cell derived oligodendrocyte precursors after treatment by interleukin-6/soluble interleukin-6 receptor fusion protein. Mol Cell Neurosci, 2005.

Zhang, Y., et al., Cardiac Repair With a Novel Population of Mesenchymal Stem Cells Resident in the Human Heart. Stem Cells, 2015. 33(10): p. 3100-13.

Zhao, A., et al., Adoptive transfer of mFas ligand into dendritic cells influences the spontaneous resorption rate in the CBA/J×DBA/2 mouse model. Fertil Steril, 2010. 93(5): p. 1700-5.

Zhao, H. M., et al., Probiotics increase T regulatory cells and reduce severity of experimental colitis in mice. World J Gastroenterol, 2013. 19(5): p. 742-9.

Zhou, L. S., et al., Silencing collapsin response mediator protein-2 reprograms macrophage phenotype and improves infarct healing in experimental myocardial infarction model. J Inflamm (Lond), 2015. 12: p. 11.

Zou, Q., et al., Development of a Xeno-Free Feeder-Layer System from Human Umbilical Cord Mesenchymal Stem Cells for Prolonged Expansion of Human Induced Pluripotent Stem Cells in Culture. PLoS One, 2016. 11(2): p. e0149023.

Zumkeller, W. and S. Burdach, The insulin-like growth factor system in normal and malignant hematopoietic cells. Blood, 1999. 94(11): p. 3653-7.

Although the present disclosure and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for generating and using a population of regulatory T cells for cell therapy, comprising the steps of:
    exposing a composition comprising activated fibroblast cells and transforming growth factor (TGF)-beta to cluster of differentiation (CD) 25$^+$ regulatory T cells and
    administering the regulatory T cells to an individual with an effective amount of one or more immunomodulatory agents.

2. The method of claim 1, wherein the one or more immunomodulatory agents are inosine, FAS ligand, interleukin (IL)-2R, IL-1 Ra, IL-2, IL-4, IL-8, IL-10, IL-20, IL-35, human leukocyte antigen (HLA)-G, Programmed death-ligand 1 (PD-L1), 1-309, Indoleaminepyrrole 2,3-dioxygenase (1DO), Inducible nitric oxide synthase (iNOS), cluster of differentiation (CD) 200, Galectin 3, soluble complement receptor 1 (sCR1), arginase, Prostaglandin E2 (PGE-2), aspirin, atorvastatin, fluvastatin, lovastatin, pravastatin, rosuvastatin, simvastatin, pitavastatin, n-acetyl-cysteine, rapamycin, Intravenous immunoglobulin (IVIG), Vascular endothelial growth factor (VEGF), Platelet-derived growth factor (PDGF), cytotoxic T-lymphocyte-associated protein 4 (CTLA-4), anti-CD45RB antibody, hydroxychloroquine, leflunomide, auranofin, dicyanogold, sulfasalazine, methotrexate, glucocorticoids, etanercept, adalimumab, abatacept, anakinra, certolizumab, Etanercept-szzs, golimumab, infliximab, rituximab, tocilizumab, cyclosporine, interferon (IFN)-gamma, everolimus, or a combination thereof.

3. The method of claim 1, wherein the activated fibroblast cells have been exposed to interferon (IFN)-gamma.

4. The method of claim 1, wherein the cluster of differentiation (CD) 25+ regulatory T cells are isolated from the thymus, peripheral blood, cord blood, Granulocyte colony-stimulating factor (G-CSF) mobilized peripheral blood, adipose tissue, and placenta, or a combination thereof.

5. The method of claim 1, wherein the ratio of fibroblast to T cell in a culture comprises 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, 2:1, 3:1, 4:1, 5:1, 6:1, 7:1, 8:1, 9:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

6. The method of claim 1, wherein the composition comprises an additional agent, wherein the additional agent comprises a cluster of differentiation (CD) 3 ligand, a CD28 ligand, rapamycin, interleukin (IL)-10, IL-2 or a combination thereof.

7. The method of claim 1, wherein:
    (a) the TGF-beta is soluble in the composition;
    (b) in the composition the TGF-beta is attached to the surface of the fibroblast cells;
    (c) in the composition the TGF-beta is immobilized on a bead;
    (d) in the composition the TGF-beta may be immobilized on the surface of an engineered cell; or
    (e) in the composition the TGF-beta is expressed by the fibroblasts.

8. The method of claim 7 (e), wherein the composition comprises one or more additional agents, wherein the additional agents comprise interleukin (IL)-2 and/or IL-12.

9. The method of claim 1, wherein the cluster of differentiation (CD) 25$^+$ regulatory T cells are derived from allogeneic naive CD4$^+$ T cells.

10. The method of claim 1, wherein the composition comprises an additional agent, wherein the additional agent comprises human platelet rich plasma.

11. The method of claim 1, wherein the population of regulatory T cells are maintained in culture under selection.

12. The method of claim 1, wherein an effective amount of the regulatory T cells are administered to an individual to treat one or more autoimmune or inflammatory condition.

13. The method of claim 12, wherein the one or more autoimmune or inflammatory condition comprises Acute Disseminated Encephalomyelitis, Acute necrotizing hemorrhagic leukoencephalitis, Addison's disease, adhesive capsulitis, Agammaglobulinemia, Alopecia areata, Amyloidosis, Ankylosing spondylitis, Anti-glomerular basement membrane (Anti-GBM) nephritis, Antiphospholipid syndrome (APS), Anti-Tubular Basement-Membrane (Anti- TBM) nephritis, arthofibrosis, atrial fibrosis, autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune neutropenia, autoimmune oophoritis, autoimmune pancreatitis, autoimmune retinopathy, autoimmune thrombocytopenia purpura (ATP), autoimmune thyroid disease, autoimmune urticarial, axonal and neuronal neuropathies, Balo disease, Behcet's disease, benign mucosal pemphigold, bullous pemphigoid, cardiomyopathy, Castleman disease, Celiac disease, Chagas disease, chronic fatigue syndrome, Chronic inflammatory demyelinating polyneuropathy (CIDP), chronic Lyme disease, Chronic recurrent multifocal ostomyelitis (CRMO), Churg-Strauss syndrome, cicatricial pemphigold, cirrhosis, Cogans syndrome, cold agglutinin disease, congenital heart block, Coxsackie myocarditis, calcinosis, Raynaud phenomenon, esophageal dysmotility, sclerodactyly, and telangiectasia) syndrome (CREST disease), Crohn's disease, Cystic Fibrosis, deficiency of the interleukin-I receptor antagonist, demyelinating neuropathies, dermatitis herpetiformis, dermatomyosis, Devic's disease (neuromyelitis optica), discoid lupus, Dressler's syndrome, Dupuytren's contracture, endometriosis, endomyocardial fibrosis, eosinophilic esophagitis, eosinophilic fasciitis, erythema nodosum, essential mixed cryoglobulinemia, Evans syndrome, experimental allergic encephalomyelitis, Familial Mediterranean Fever, Fibromyalgia Fibrosing alveolitis, Giant cell arteritis, giant cell myocarditis, glomerulonephritis, Glomerulonephritis, Goodpasture's syndrome, Graft-versus-host disease (GVHD), granulomatosus with polyangitis, Graves' disease, GuillainBarre syndrome, Hashimoto's encephalitis, Hashimoto's thyroiditis, hemolytic anemia, Henoch-Schonlein purpura, hepatitis, herpes gestationis, hypogammaglobulinemia, idiopathic pulmonary fibrosis, Idiopathic thrombocytopenia purpura (ITP), IgA nephropathy, IgG4-related sclerosing disease, inclusion body myositis, inflammatory bowel disorders, interstitial cystitis, juvenile arthritis, Juvenile diabetes (Type 1 diabetes), juvenile myositis, Kawasaki syndrome, keloid, Lambert-Eaton syndrome, leukocytoclastic vasculitis, lichen planus, lichen sclerosis, ligneous conjunctivitis, linear IgA disease, Lupus, Lyme disease, mediastinal fibrosis, Meniere's disease, microscopic polyangitis, Mixed connective tissue disease (MCTD), Mooren's ulcer, Mucha-Habermann disease, Multiple Sclerosis (MS), Myasthenia gravis, myelofibrosis, Myositis, narcolepsy, Neonatal Onset Multisystem Inflammatory Disease, nephrogenic systemic fibrosis, Neuromyelitis optica (Devic's), neutropenia, nonalcoholic fatty liver disease, nonalcoholic steatohepatitis (NASH), ocular-cicatricial pemphigold, optic neuritis, palindromic rheumatism, paraneoplastic cerebellar degeneration, Paroxysmal nocturnal hemoglobinuria (PNH), Parry Romberg syndrome, Pars planitis, Parsonnage-Turner syndrome, Pediatric Autoimmune Neuropsychiatric Disorders Associated with *Streptococcus* (PANDAS), Pemphigus, Peripheral neuropathy, Perivenous encephalomyelitis, Pernicious anemia, Peyronie's disease, (Polyneuropathy, Organomegaly, Endocrinopathy, Monoclonal protein, Skin changes) POEMS syndrome, polyarteritis nodosa, polymyalgia rhematica, polymyositis, postmyocardial infarction syndrome, postpericardiotomy syndrome, primary biliary cirrhosis, primary sclerosing cholangitis, progesterone dermatitis, progressive massive fibrosis, psoriasis, psoriatic arthritis, pure red cell aplasia, pyoderma gangrenosum, Raynauds phenomenon, reactic arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome, subacute bacterial endocarditis, Susac's syndrome, sympathetic ophthalmia, systemic lupus erythematosus (SLE), Takayasu's arteritis, temporal arteritis, Thrombocytopeniaurpura (TTP), Tolosa-Hunt syndrome, transverse myelitis, Tumor Necrosis Factor Receptor-associated Periodic Syndrome, Type 1 diabetes, Type I autoimmune polyglandular syndrome, Type II autoimmune polyglandular syndrome, Type III autoimmune polyglandular syndrome, ulcerative colitis, undifferentiated connective tissue disease, uveitis, vasculitis, vesiculobullous dermatosis, Vitiligo, or Wegener's granulomatosis (now termed Granulomatosis with Polyangitis (GPA)).

\* \* \* \* \*

UNITED STATES PATENT AND TRADEMARK OFFICE
CERTIFICATE OF CORRECTION

PATENT NO. : 12,233,094 B2
APPLICATION NO. : 16/765060
DATED : February 25, 2025
INVENTOR(S) : Pete O'Heeron et al.

Page 1 of 1

It is certified that error appears in the above-identified patent and that said Letters Patent is hereby corrected as shown below:

In the Claims

Column 111, Line 7-8 Claim 13:
Delete "thrombocytopenia" and replace with --thrombocytopenic--

Column 111, Line 37 Claim 13:
Delete "thrombocytopenia" and replace with --thrombocytopenic--

Column 112, Line 32-33 Claim 13:
Delete "Thrombocytopeniaurpura" and replace with --Thrombocytopenic purpura--

Signed and Sealed this
Second Day of September, 2025

Coke Morgan Stewart
*Acting Director of the United States Patent and Trademark Office*